(12) United States Patent
Machida et al.

(10) Patent No.: US 11,311,002 B2
(45) Date of Patent: Apr. 26, 2022

(54) BIOTINYLATED AND OXIDIZED LDL RECEPTOR AND ADVANCED GLYCATION END PRODUCT RECEPTOR PRODUCED USING GENETICALLY ENGINEERED SILKWORM

(71) Applicant: National Agriculture and Food Research Organization, Tsukuba (JP)

(72) Inventors: Sachiko Machida, Tsukuba (JP); Miyuki Kuramochi, Tsukuba (JP); Mayumi Kameyama, Tsukuba (JP); Mari Yamamoto, Tsukuba (JP); Toshiro Kobori, Tsukuba (JP); Hideki Sezutsu, Tsukuba (JP); Ken-ichiro Tatematsu, Tsukuba (JP)

(73) Assignee: National Agriculture and Food Research Organization, Tsukuba (JP)

( * ) Notice: Subject to any disclaimer, the term of this patent is extended or adjusted under 35 U.S.C. 154(b) by 410 days.

(21) Appl. No.: 15/515,998

(22) PCT Filed: Oct. 1, 2015

(86) PCT No.: PCT/JP2015/005017
§ 371 (c)(1),
(2) Date: Mar. 30, 2017

(87) PCT Pub. No.: WO2016/051808
PCT Pub. Date: Apr. 7, 2016

(65) Prior Publication Data
US 2017/0354129 A1  Dec. 14, 2017

(30) Foreign Application Priority Data

Oct. 1, 2014 (JP) .............. JP2014-203282
May 15, 2015 (JP) .............. JP2015-100546
May 15, 2015 (JP) .............. JP2015-100547

(51) Int. Cl.
| | | |
|---|---|---|
| A01K 67/027 | (2006.01) |
| C07K 16/18 | (2006.01) |
| C07K 14/705 | (2006.01) |
| A01K 67/033 | (2006.01) |
| C07K 16/00 | (2006.01) |
| C07K 14/47 | (2006.01) |
| C12N 9/00 | (2006.01) |
| G01N 33/92 | (2006.01) |

(52) U.S. Cl.
CPC ...... *A01K 67/0275* (2013.01); *A01K 67/0339* (2013.01); *C07K 14/4726* (2013.01); *C07K 14/705* (2013.01); *C07K 14/70503* (2013.01); *C07K 16/00* (2013.01); *C07K 16/005* (2013.01); *C07K 16/18* (2013.01); *C12N 9/93* (2013.01); *C12Y 603/04015* (2013.01); *G01N 33/92* (2013.01); *A01K 2227/706* (2013.01); *A01K 2267/01* (2013.01); *C07K 2317/21* (2013.01); *C07K 2317/622* (2013.01); *C07K 2319/20* (2013.01); *G01N 2333/705* (2013.01); *G01N 2440/00* (2013.01); *G01N 2800/323* (2013.01)

(58) Field of Classification Search
CPC ............................... A01K 67/0275
See application file for complete search history.

(56) References Cited

FOREIGN PATENT DOCUMENTS

| | | |
|---|---|---|
| CN | 103319594 A | 9/2013 |
| CN | 103517991 A | 1/2014 |
| EP | 1 903 058 A2 | 3/2008 |
| JP | 2005-97203 A | 4/2005 |
| JP | 2009-536201 A | 10/2009 |
| JP | 2012-122994 A | 6/2012 |
| WO | 2007/130302 A2 | 11/2007 |
| WO | 2012/055408 A1 | 5/2012 |

OTHER PUBLICATIONS

Hwang et al. (2014, Appl. Microbiol. Biotechmol., vol. 98, pp. 8201-8209) (Year: 2014).*
Tomita, "Protein production in transgenic silkworm cocoons," *Analysis of Biological Reagents* 37(3), 12 pages, 2014.

* cited by examiner

*Primary Examiner* — Thaian N. Ton
*Assistant Examiner* — David A Montanari
(74) *Attorney, Agent, or Firm* — Seed IP Law Group LLP

(57) ABSTRACT

The present invention pertains to a silkworm-type biotinylated CTLD14 or sRAGE and a method for manufacturing the same. One embodiment of the present invention provides a method for manufacturing biotinylated proteins, wherein the method includes A) a step for inserting a nucleic acid molecule for coding biotin ligase and protein in a coexpressable manner into a silkworm or a living organism that imparts sugar chains that are the same as the sugar chains of the silkworm, B) a step for causing the biotin ligase and protein to be expressed by disposing the silkworm or the living organism that imparts sugar chains that are the same as the sugar chains of the silkworm to conditions with which the nucleic acid molecule will carry out expression, and C) a step for administering biotin to the living organism and obtaining the biotinylated protein.

6 Claims, 59 Drawing Sheets

Specification includes a Sequence Listing.

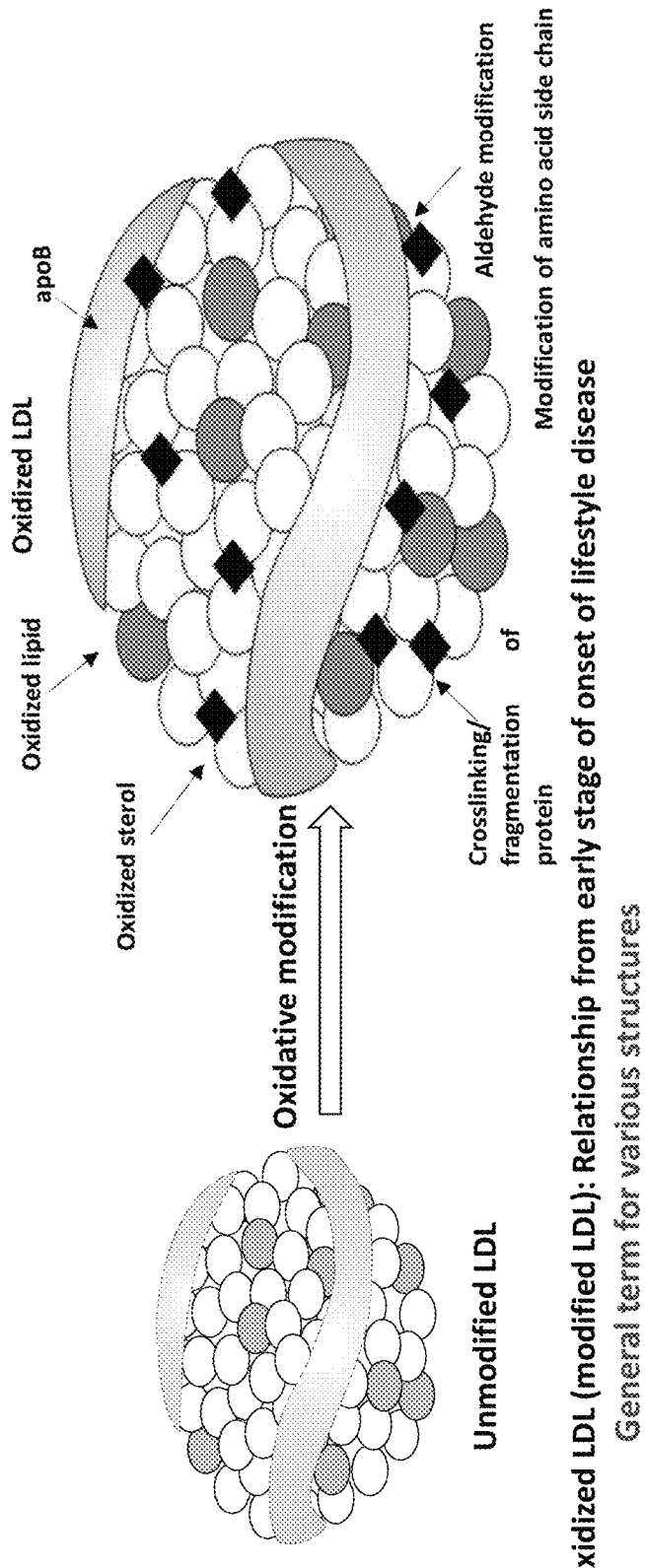

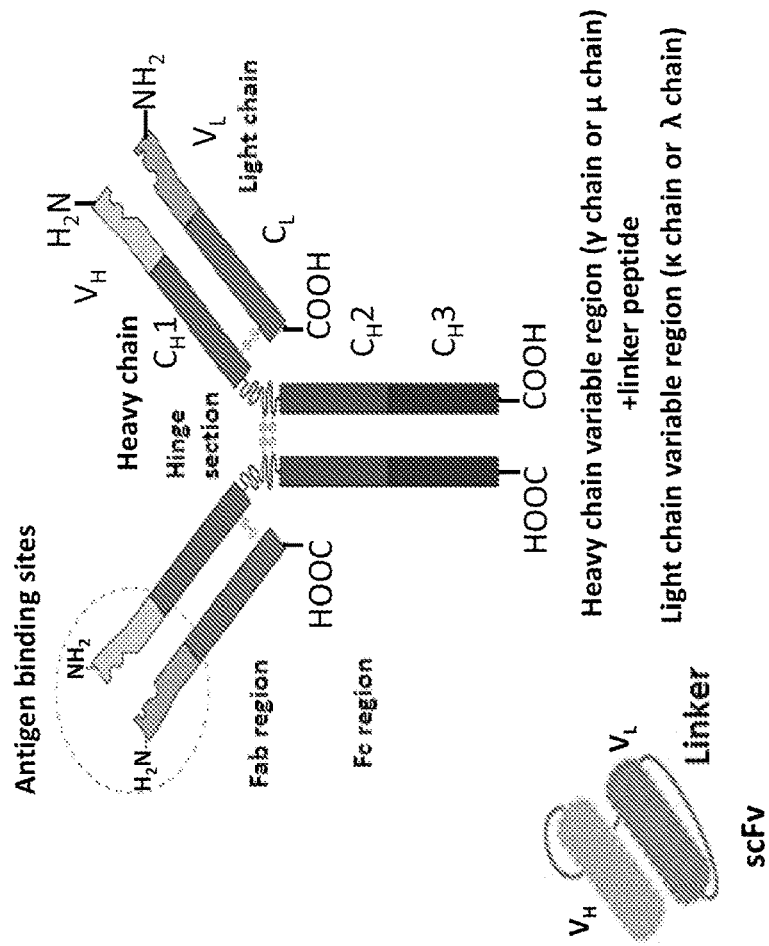
Fig. 2  Creation and utilization of single chain antibody

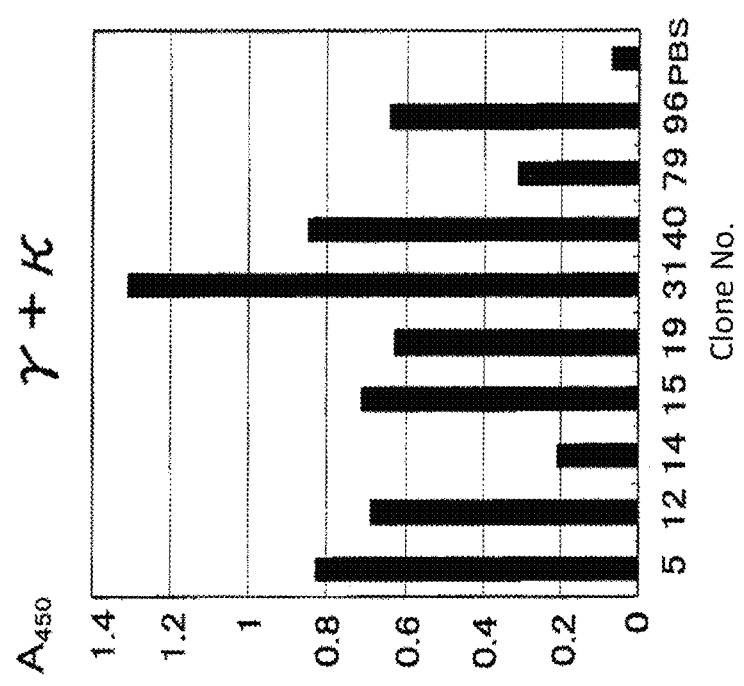

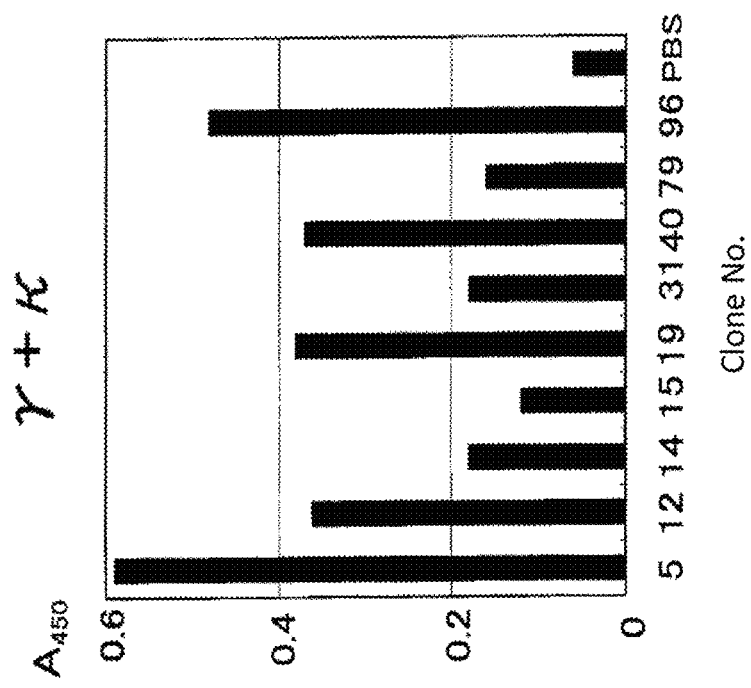

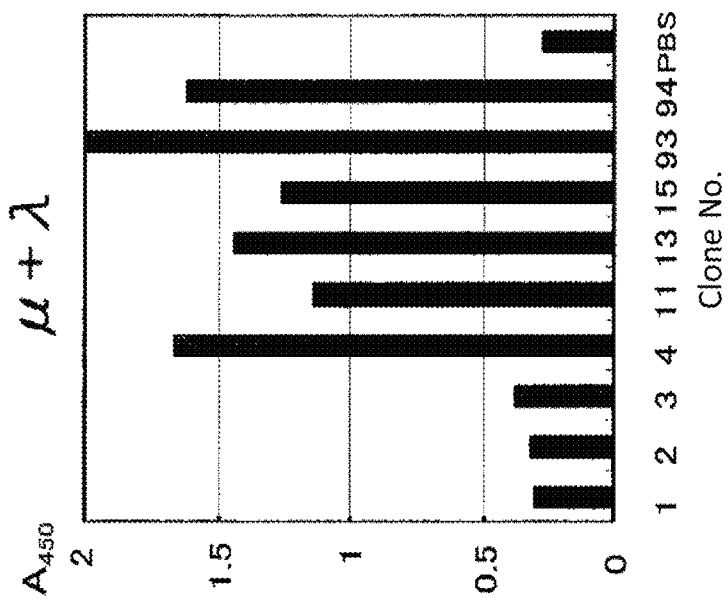

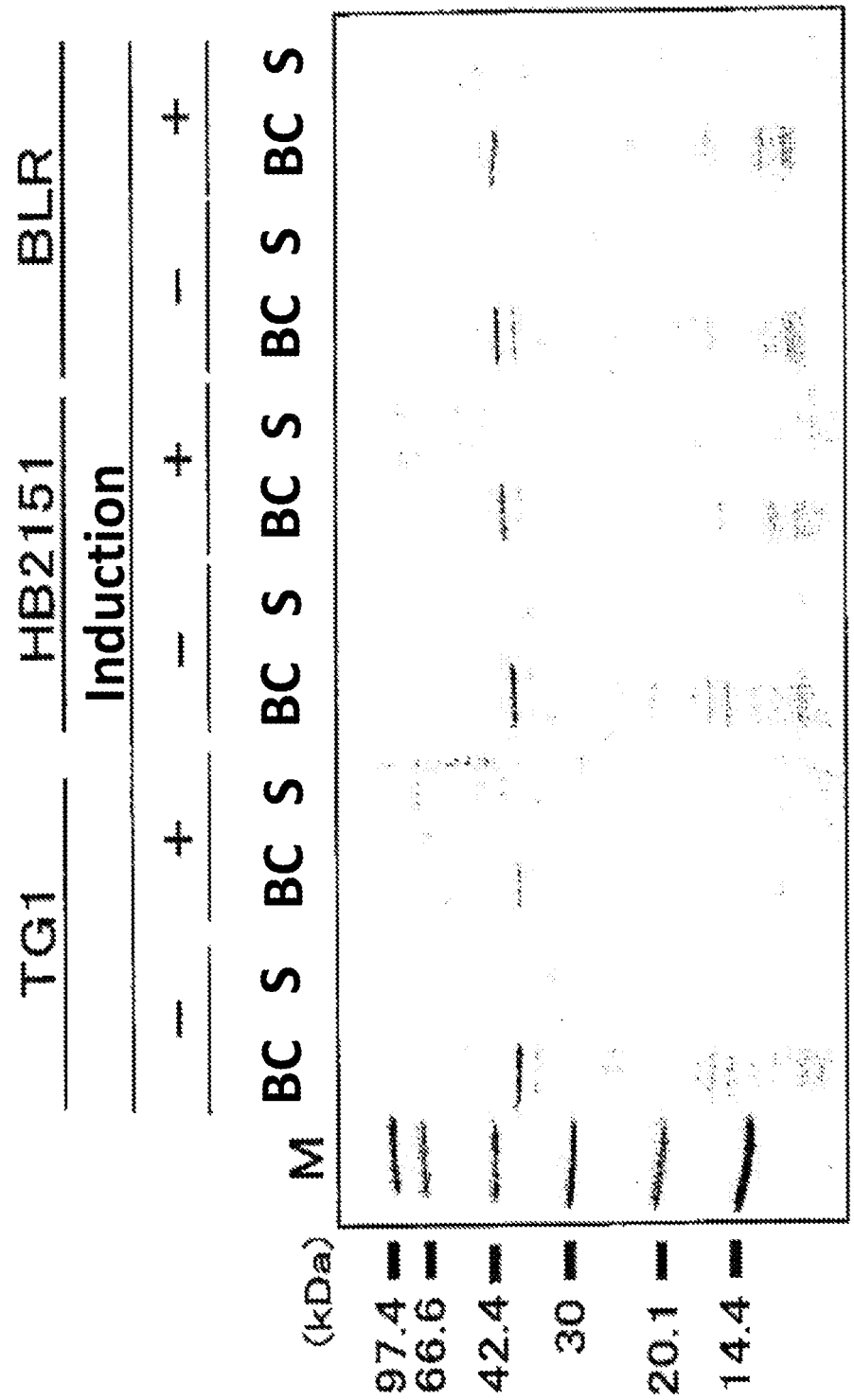

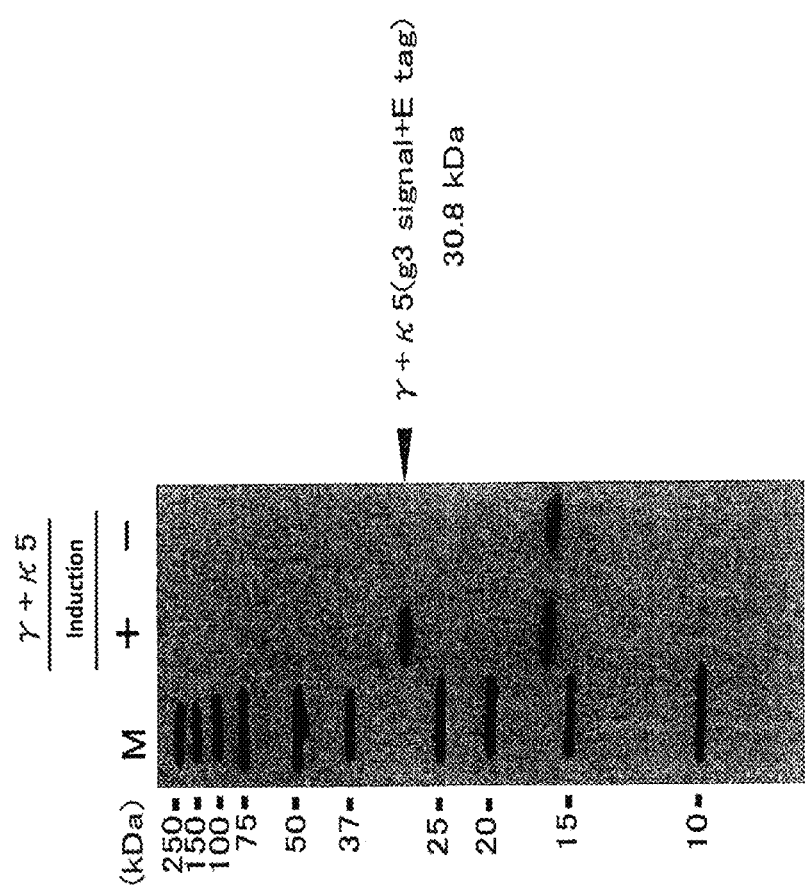

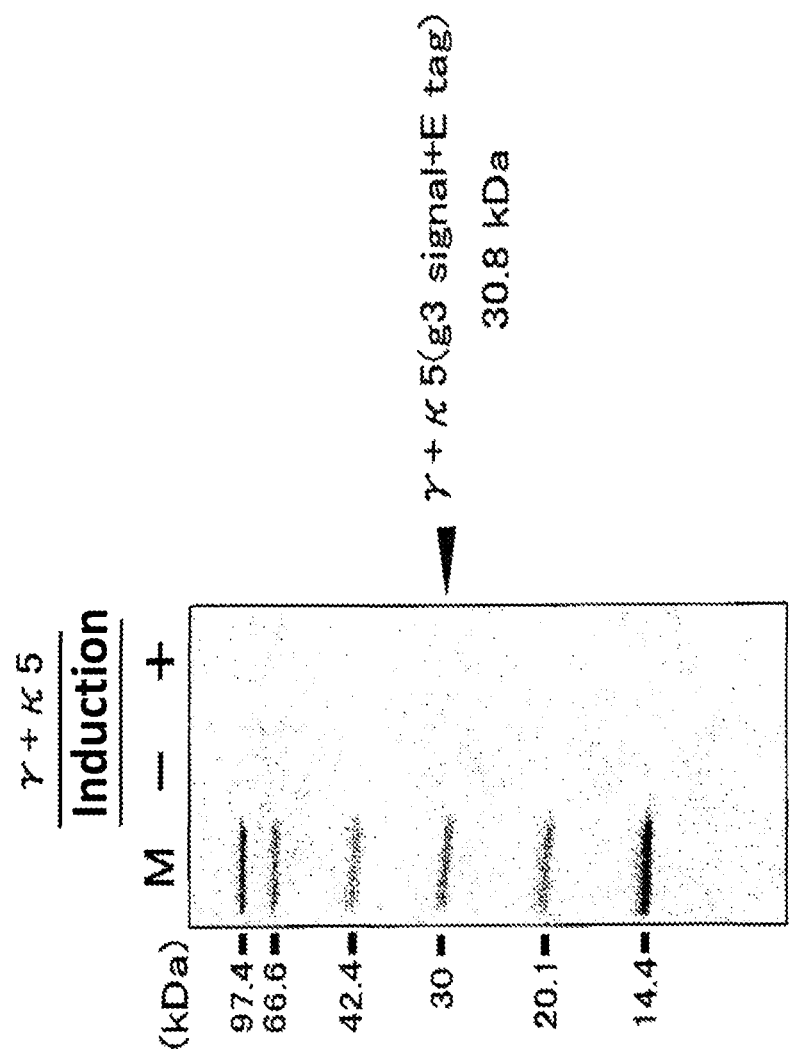

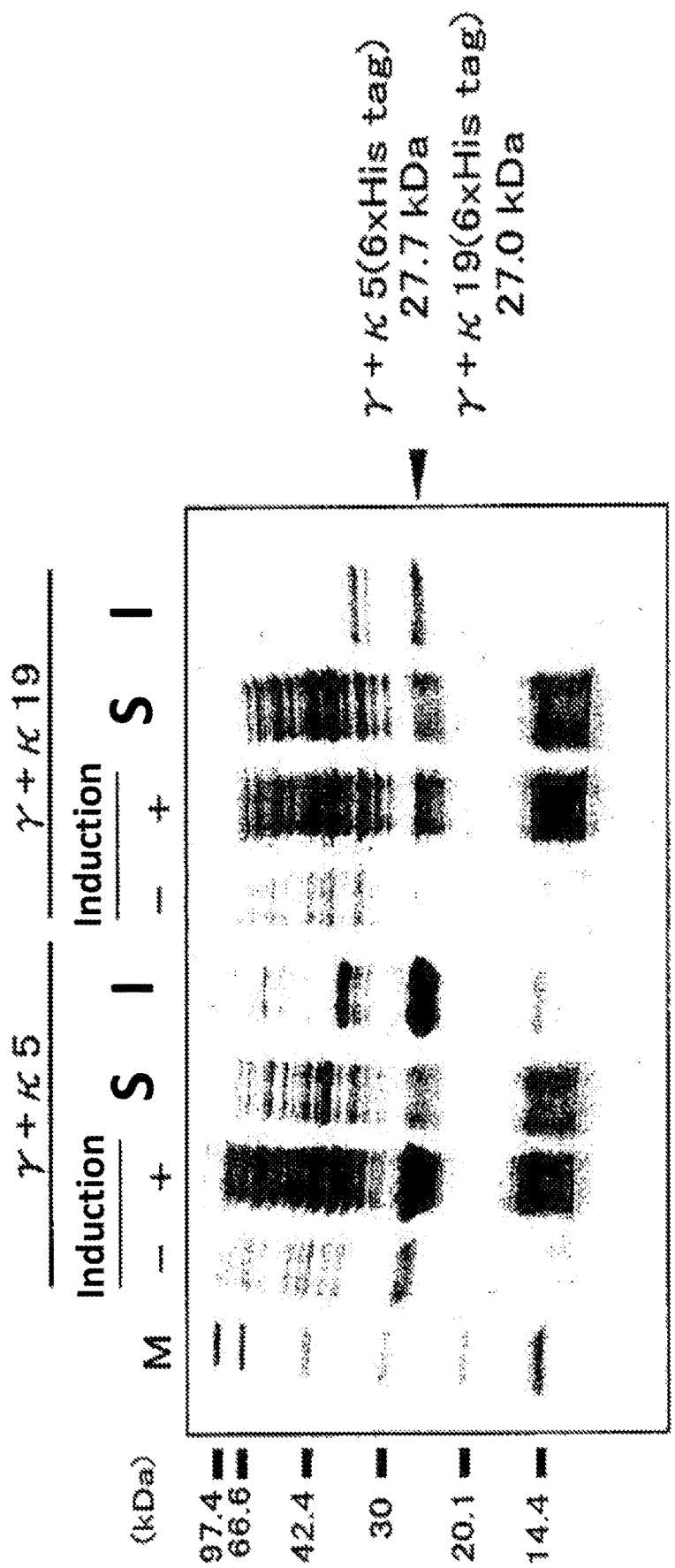

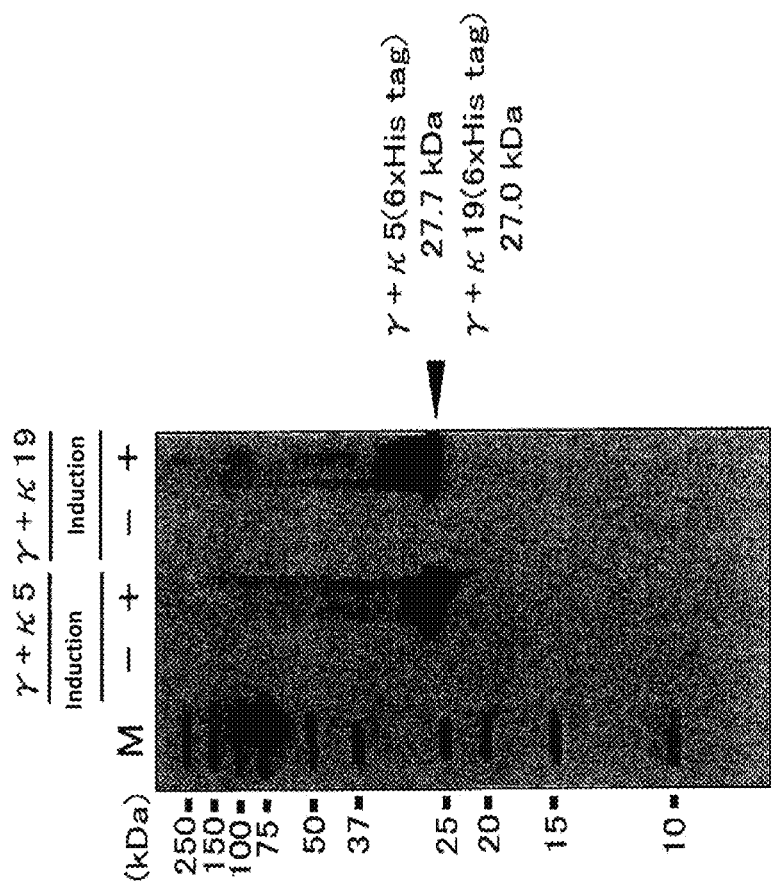

Construction of single chain antibody expression system

E.coli HB2151
↓
(Phage is infected)
↓
Single chain antibody production
Low expression Host: Change vector system
pET system
BL21(DE3)
↓
Check expression
Clone No. γ+κ 5
Clone No. γ+κ 19

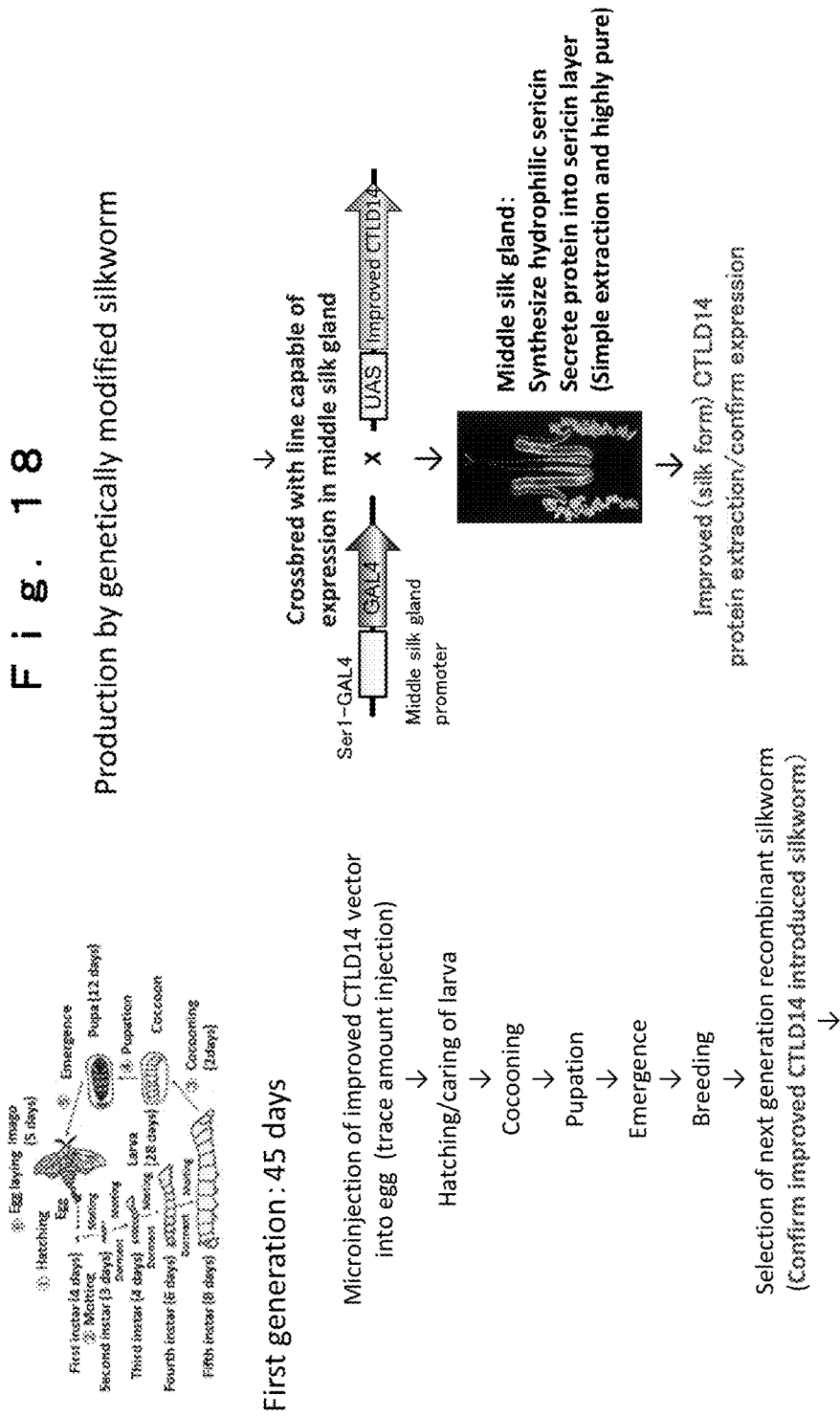

Fig. 19

Improved CTLD14 (silkworm glycosylation biotinylated CTLD14)

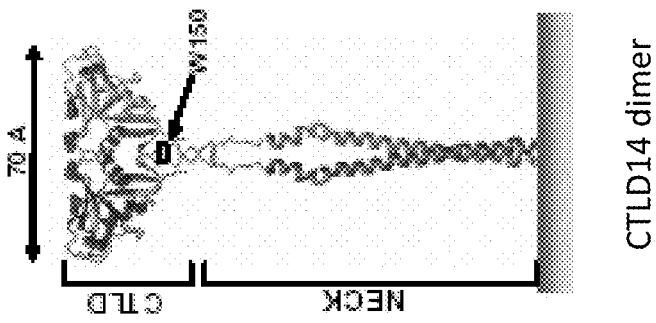

BioEaseTag-CTLD14 (251 aa)

<u>GAGTPVTAPLAGTIWKVLASEGQTVAAGEVLLILEAM</u>K<u>METEIRAAQAGTVRGIAVKAGDAVAVGDTLMT
LAGSGSDLYDDDKVHQTSLYKKAGSEFA</u>LNLQETLKRVA<u>NCS</u>APCPQDWIWHGENCYLFSSGSFNWEK
SQEKCLSLDAKLLK|NST|ADLDFIQQAISYSSFPFWMGLSRRNPSYPWLWEDGSPLMPHLFRVRGAVSQ
TYPSGTCAYIQRGAVYAENCILAAFSICQKKANLRAQHHHHHH    SEQ ID NO:110

1(Gly)-72(Ala): BioEase tag     SEQ ID NO:111
    Klebsiella pneumoniae oxaloacetate carboxy-lyases α subunit
38(Lys)(K): Biotin binding site
80(Asp)-84(Lys)(DDDDK): Entherokinase recognition site    SEQ ID NO:89

101(Asn)-245(Gln): CTLD14(129Asn-273Gln on LOX-1)    SEQ ID NO:84
Putative glycosylation site: N-X-S/T
Determination of glycosylation site: NCS(111N) and/or NST(155N)
Mass number of sugar chain part: 892 × 2+720 ≈ (203×2 + 162×2)

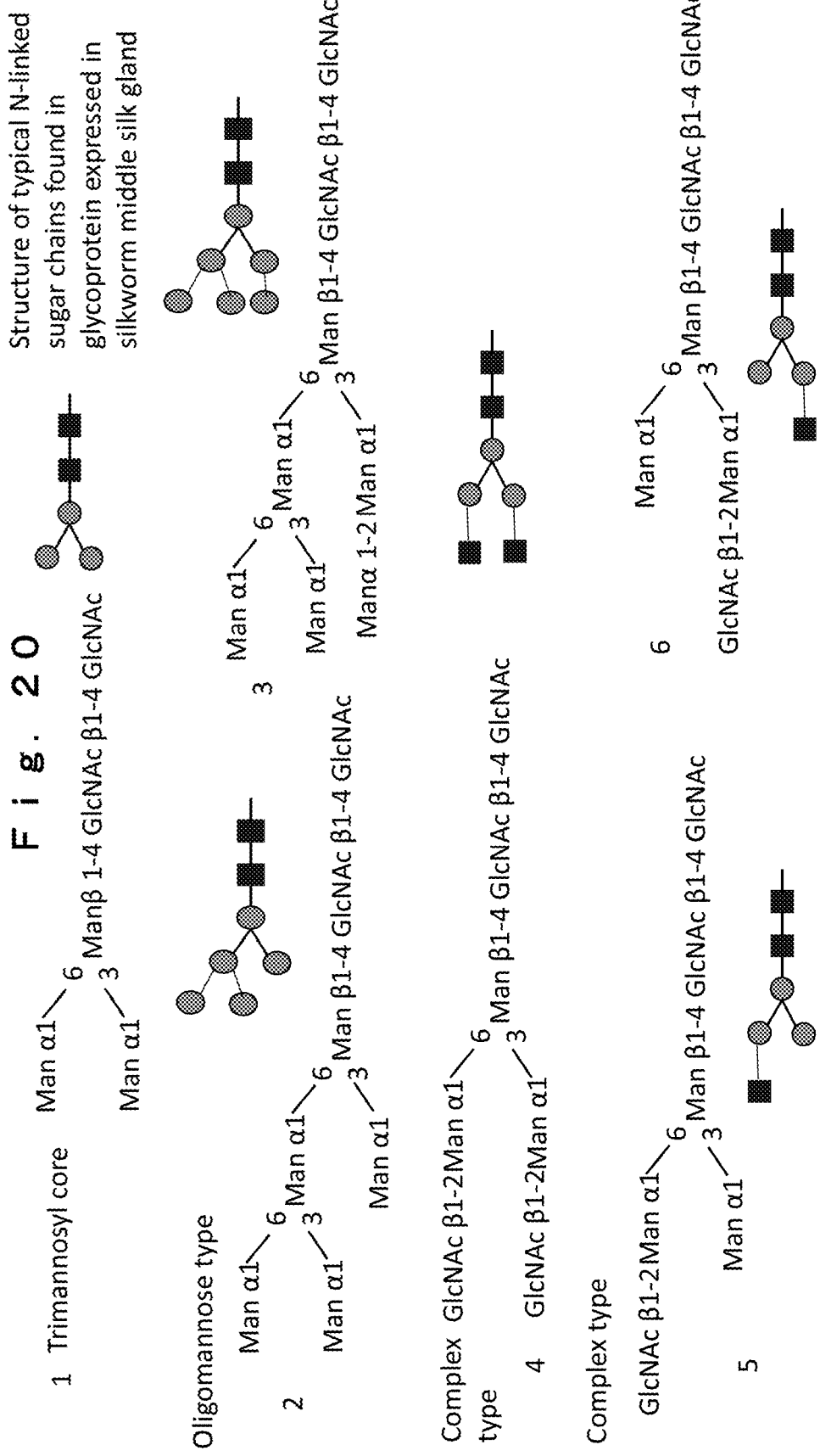

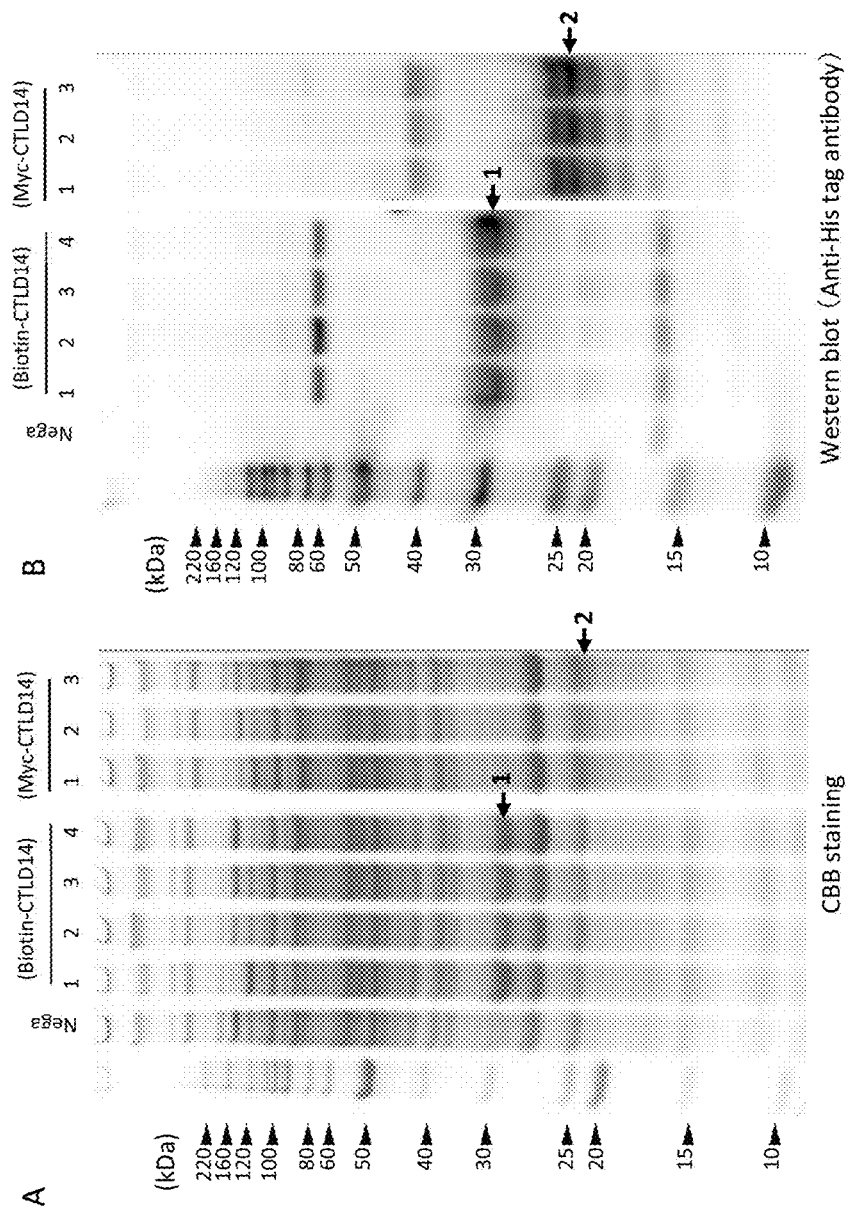

Purification of CTLD14 produced in genetically modified silkworm

Purification of Biotin-CTLD14
Ni-NTA→TALON

Lane 1: Ni-NTA purify, 2:TALON Flow through, 3:wash, 4:TALON bound, 5:50mM imidazole Eluation, 6:100mM, 7:200mM, 8,9:500mM, 10: 1M, 11: remain, 12: post-dialysis Fig. 29 Results of LC-ESIMS on CTLD14 trypsin digestion product Fig. 30 Results of LC-ESIMS on trypsin digestion product of specimen without PNGase treatment of silkworm form CTLD14

Fig. 31 Expanded diagram of mass spectrum near 13.1 minutes

Fig. 32

Difference in mass of peptide and ion observed in mass spectrum near 13.1 minutes delta (obsrvd.-calcd.peptide)

| NCS | NST | NPS | M (obsrvd) | 4475.88 | 4489.88 | 4637.92 | 4651.92 | 4787 | 4798 | 4841 | 4855 | 4962.04 | 4976.04 | 5044.08 | 5058.08 | 5389.83 |
|---|---|---|---|---|---|---|---|---|---|---|---|---|---|---|---|---|
| 3745.58 | 3093.49 | 2441.16 | | | | | | | | | | | | | | |
| 730.3 | 1382.39 | 2034.72 | 4475.88 | 0 | -14 | -162 | -176 | -311 | -322 | -365 | -379 | -486 | -500 | -568 | -582 | -914 |
| 744.3 | 1396.39 | 2048.72 | 4489.88 | 14 | 0 | -148 | -162 | -297 | -308 | -351 | -365 | -472 | -486 | -554 | -568 | -900 |
| 892.34 | 1544.43 | 2196.76 | 4637.92 | 162 | 148 | 0 | -14 | -149 | -160 | -203 | -217 | -324 | -338 | -406 | -420 | -752 |
| 906.34 | 1558.43 | 2210.76 | 4651.92 | 176 | 162 | 14 | 0 | -135 | -146 | -189 | -203 | -310 | -324 | -392 | -406 | -738 |
| 1041.42 | 1693.51 | 2345.84 | 4787 | 311 | 297 | 149 | 135 | 0 | -11 | -54 | -68 | -175 | -189 | -257 | -271 | -603 |
| 1052.42 | 1704.51 | 2356.84 | 4798 | 322 | 308 | 160 | 146 | 11 | 0 | -43 | -57 | -164 | -178 | -246 | -260 | -592 |
| 1095.42 | 1747.51 | 2399.84 | 4841 | 365 | 351 | 203 | 189 | 54 | 43 | 0 | -14 | -121 | -135 | -203 | -217 | -549 |
| 1109.42 | 1761.51 | 2413.84 | 4855 | 379 | 365 | 217 | 203 | 68 | 57 | 14 | 0 | -107 | -121 | -189 | -203 | -535 |
| 1216.46 | 1868.55 | 2520.88 | 4962.04 | 486 | 472 | 324 | 310 | 175 | 164 | 121 | 107 | 0 | -14 | -82 | -96 | -428 |
| 1230.46 | 1882.55 | 2534.88 | 4976.04 | 500 | 486 | 338 | 324 | 189 | 178 | 135 | 121 | 14 | 0 | -68 | -82 | -414 |
| 1298.5 | 1950.59 | 2602.92 | 5044.08 | 568 | 554 | 406 | 392 | 257 | 246 | 203 | 189 | 82 | 68 | 0 | -14 | -346 |
| 1312.5 | 1964.59 | 2616.92 | 5058.08 | 582 | 568 | 420 | 406 | 271 | 260 | 217 | 203 | 96 | 82 | 14 | 0 | -332 |
| 1644.25 | 2296.34 | 2948.67 | 5389.83 | 914 | 900 | 752 | 738 | 603 | 592 | 549 | 535 | 428 | 414 | 346 | 332 | 0 | corresponds to sugar chain

FIG 34

GHHHHHHHHSSGHIDDDDKHMAQ<u>NIT</u>ARIGEPLVLKCKGAPKKPPQRLEWKLN
      His tag                                   RAGE extracellular domain
TGRTEAWKVLSPQGGGPWDSVARVLP<u>NGS</u>FLPAVGIQDEGIFRCQAMNRNGKETK
SNYRVRVYQIPGKPEIVDSASELTAGVPNKVGTCVSEGSYPAGTLSWHLDGKPLVPNE
KGVSVKEQTRRHPETGLFTLQSELMVTPARGGDPRPTFSCSFSPGLPRHRALRTAPIQP
RVWEPVPLEEVQLVVEPEGGAVAPGGTVTLTCEVPAQPSPQJHWMKDGVPLPLPPS
PVLILPEIGPQDQGTYSCVATHSSHGPQESRAVSISIIEPGEEGPTAGSRSGAGTPVTAP
LAGTIWKVLASEGQTVAAGEVLILEAM<u>K</u>METEIRAAQAGTVRGIAVKAGDAVAVG
DTLMTLAGTKLGPEQKLISEEDLNSAVDHHHHHH AQ··· <u>AGS RAGE extracellular domain</u>
<u>BioEASE-tag & linker & FLAG(bold)</u>
BioEase tag: biotin binds to K
(Enables biotinylated protein production in silkworm body)

Putative glycosylation site: <u>N-X-S/T</u>

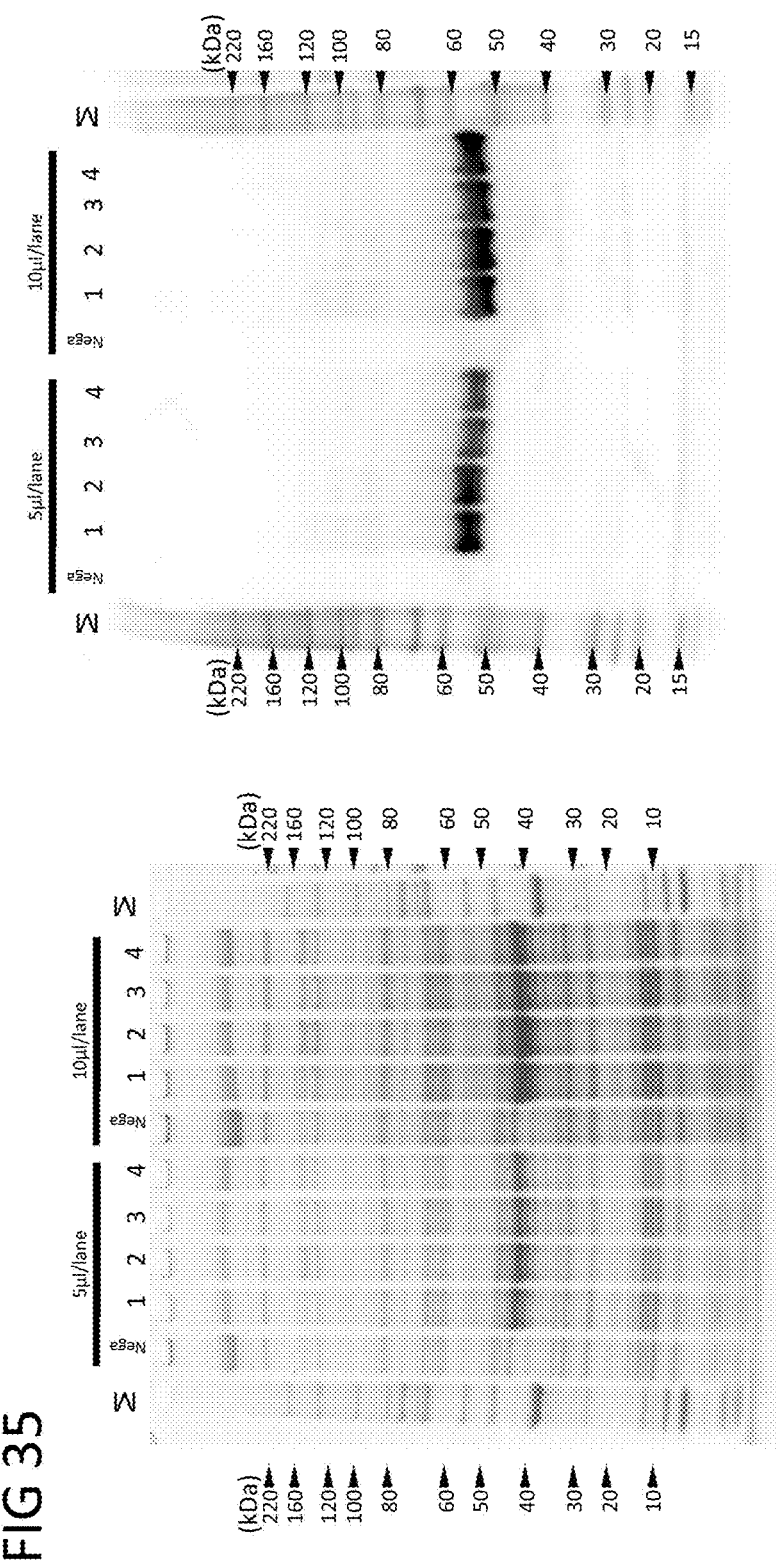

Stability of silkworm form sRAGE

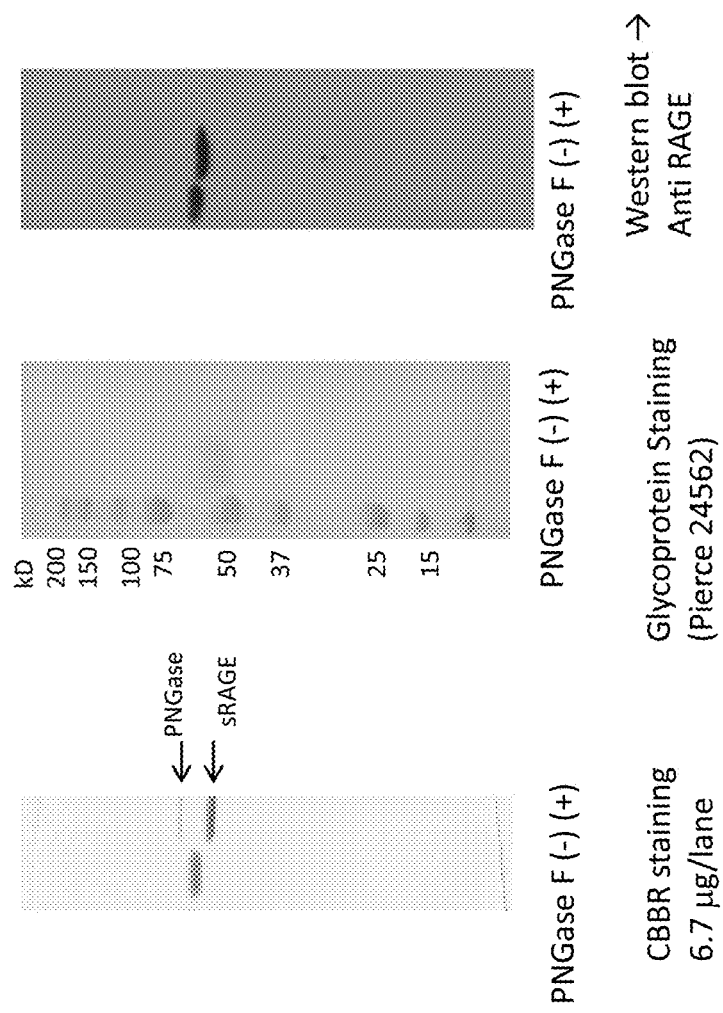

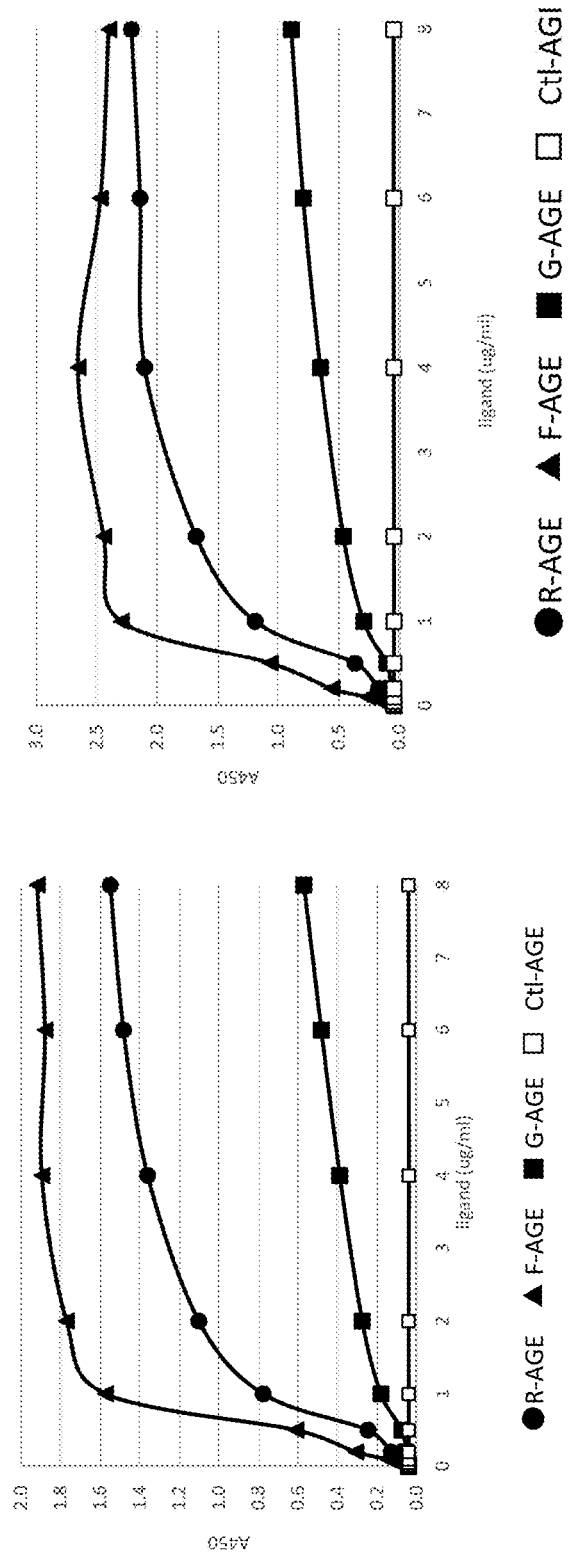

FIG 41

Confirmed amino acids from results of mass spectrometry of silkworm form sRAGE (underlined)

With PNGase treatment (no N-type sugar chain)

GHHHHHHHHHSSGHIDDDDKHMAQNITARIGEPLVLKC
KGAPKKPPQRLEWKLNTGRTEAWKVLSPQGGGPWDSVARV
LPNGSLFLPAVGIQDEGIFRCQAMNRNGKETKSNYRVRV
YQIPGKPEIVDSASELTAGVPNKVGTCVSEGSYPAGTLSW
HLDGKPLVPNEKGVSVKEQTRRHPETGLFTLQSELMVTPA
RGGDPRPTFSCSFSPGLPRHRALRTAPIQPRVWEPVPLEE
VQLVVEPEGGAVAPGGTVTLTCEVPAQPSPQIHWMKDGVP
LPLPPSPVLILPEIGPQDQGTYSCVATHSSHGPQESRAVS
ISIIEPGEEGPTAGSRSGAGTPVTAPLAGTIWKVLASEGQ
TVAAGEVLLILEAMKMETEIRAAQAGTVRGTAVKAGDAVA
VGDTLMTLAGTKLGPEQKLISEEDLNSAVDHHHHHH

Ion corresponding to HMAQNITARIGEPLVLK was observed at 7.37 minutes as m/z 521.76 (corresponding to [M+2H]²⁺).
Ion corresponding to GHHHHHHHHHSSGHIDDDDKHMAQNITARIGEPLVLK (m/z 3539.5) was not observed.
For VLSPQGGGPWDSVARVLPNGSLFLPAVGIQDEGIFR, m/z 1122.11 (corresponding to [M+2H]²⁺) and m/z 748.40 (corresponding to [M+3H]³⁺) were observed.

Without PNGase treatment (with N-type sugar chain)

GHHHHHHHHHSSGHIDDDDKHMAQNITARIGEPLVLKC
KGAPKKPPQRLEWKLNTGRTEAWKVLSPQGGGPWDSVARV
LPNGSLFLPAVGIQDEGIFRCQAMNRNGKETKSNYRVRV
YQIPGKPEIVDSASELTAGVPNKVGTCVSEGSYPAGTLSW
HLDGKPLVPNEKGVSVKEQTRRHPETGLFTLQSELMVTPA
RGGDPRPTFSCSFSPGLPRHRALRTAPIQPRVWEPVPLEE
VQLVVEPEGGAVAPGGTVTLTCEVPAQPSPQIHWMKDGVP
LPLPPSPVLILPEIGPQDQGTYSCVATHSSHGPQESRAVS
ISIIEPGEEGPTAGSRSGAGTPVTAPLAGTIWKVLASEGQ
TVAAGEVLLILEAMKMETEIRAAQAGTVRGTAVKAGDAVA
VGDTLMTLAGTKLGPEQKLISEEDLNSAVDHHHHHH

Ion corresponding to HMAQNITARIGEPLVLK was not observed, but instead observed as GHHHHHHHHHSSGHIDDDDKHMAQNITARIGEPLVLK (m/z 3539.5) by MALDI-TOFMS.
For VLSPQGGGPWDSVARVLPNGSLFLPAVGIQDEGIFR, ions corresponding to M5 type glycosylation (+1216) (m/z 1153.55 (corresponding to [M+2H]²⁺) and m/z 867.44 (corresponding to [M+3H]³⁺)) were observed in addition to non-glycosylated ion.

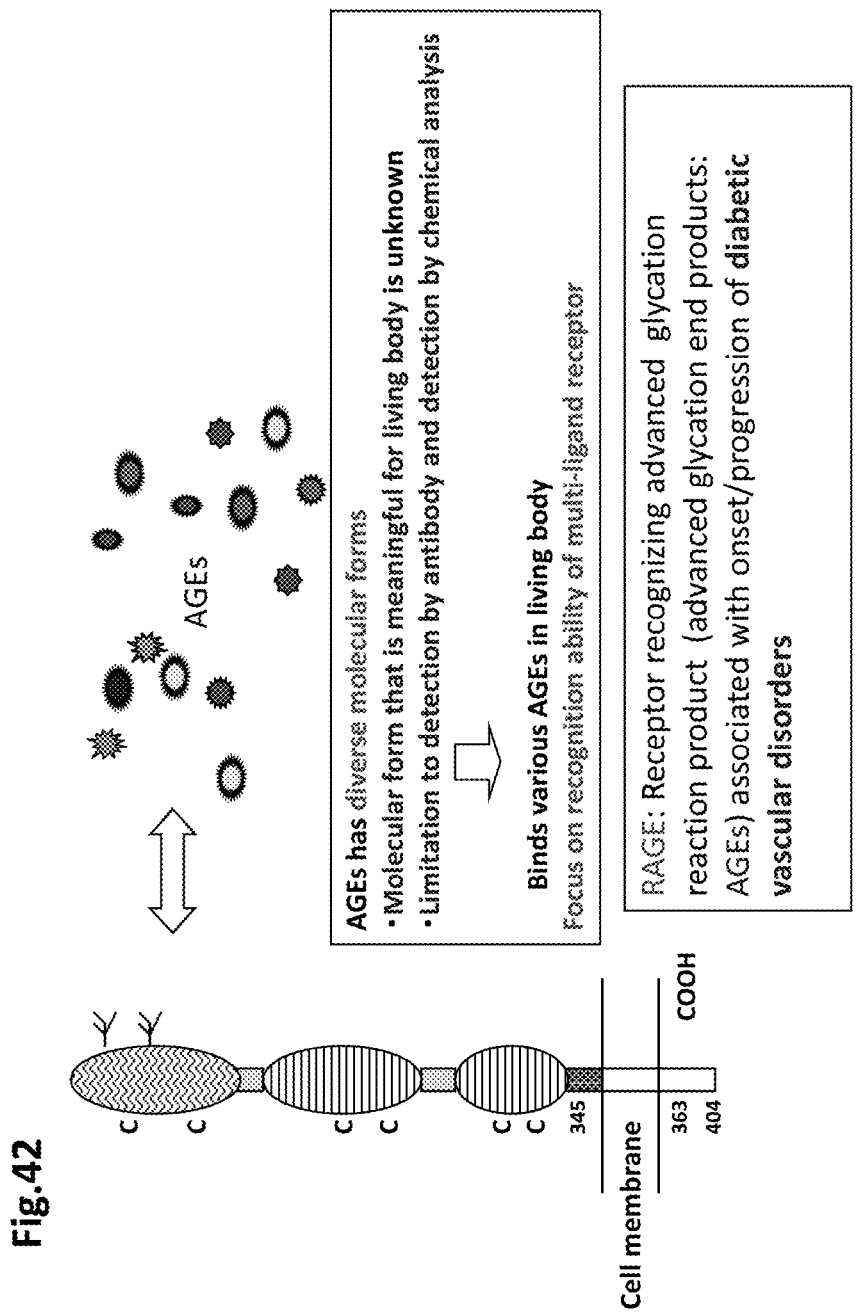

| | PBS(-) | PB | PB (pH7.4/6.0) | PB (pH7.4) |
|---|---|---|---|---|
| E.coli form | ○ | × | × | △ |
| Silkworm form | ○ | ○ | ○ | ○ |

Fig.48

Fig.49 Detection of oxidized LDL in human plasma

Fig.50 Examination of immunochromatographic condition by simple half strip

Fig.53

Stability of silkworm form sRAGE

E.coli form | Silkworm form
1 day | 40 days | 1 day | 1.5 months | 11 months

GHHHHHHHHSSGHIDDDDKHMAQNTARIGEPLVLKCKGAPKKPPQRLEWKLN
TGRTEAWKVLSPQGGGPWDSVARVTPTGSLFLPAVGIQDEGIFRCQAMNRNGKET
KSNYRVRVYQIPGKPEIVDSASELTAGVPNKVGTCVSEGSYPAGTLSWHLDGKPLVPN
EKGVSVKEQTRRHPETGLFTLQSELMVTPARGGDPRPTFSCSFSPGLPRHRALRTAPI
QPRVWEPVPLEEVQLVPEGGAVAPGGTVTLTCEVPAQPSPQIHWMKDGVPLPL
PPSPVLILPEIGPQDQGTYSCVATHSSHGPQESRAVSISIIEPGEEGPTAGSRSGAGTPV
TAPLAGTIWKVLASEGQTVAAGEVLLILEAMKMETEIRAAQAGTVRGIAVKAGDA
VAVGDTLMTLAGTKLGPEQKLISEEDLNSAVDHHHHHH

AQ・・・AGS RAGE extracellular domain
BioEASE-tag & linker & FLAG (bold)
BioEase tag: biotin binds to K
(Enables biotinylated protein production in silkworm body)

Putative glycosylation site: N-X-S/T

Fig.54

| | Sugar chain structure |
|---|---|
| N1 | Manα1-2Manα1-6⟩Manα1-6⟩Manβ1-4GlcNAcβ1-4GlcNAc-PA<br>Manα1-3⟩<br>Manα1-2Manα1-3⟩ Sugar chain M7.2 |
| N2 | Manα1-6⟩Manα1-6⟩Manβ1-4GlcNAcβ1-4GlcNAc-PA<br>Manα1-3⟩<br>Manα1-2Manα1-3⟩ Sugar chain M6.1 |
| N3 | Manα1-6⟩Manα1-6⟩Manβ1-4GlcNAcβ1-4GlcNAc-PA<br>Manα1-3⟩<br>Manα1-3⟩ Sugar chain M5.1 |
| N4-1 | Manα1-6⟩Manα1-6⟩Manβ1-4GlcNAcβ1-4GlcNAc-PA<br>Manα1-3⟩ Sugar chain 000.1 |
| N4-2 | Manα1-6⟩Manα1-6⟩Manβ1-4GlcNAcβ1-4GlcNAc-PA<br>GlcNAcβ1-2Manα1-3⟩ Sugar chain 100.2 |
| N4-3 | Manα1-3⟩Manα1-6⟩Manβ1-4GlcNAcβ1-4GlcNAc-PA<br>GlcNAcβ1-2Manα1-3⟩ Sugar chain H4.11 |

Sugar chain cut out
↓
Separation by ODS chromatography
MALDI-TOF-MS
determined estimated sugar composition of
6 types of sugar chain
↓
Separation by Amide chromatography
↓
Narrow down candidate sugar chain by GALAXY search
↓
Identification of sugar chain structure
by standard product co-injection N1, N2, N3, N4-1: oligomannose type
N4-2: complex type
N4-3: hybrid type

Fig.55

| ODS peak No. | Sugar chain | Composition ratio (%) | Quantified value (pmol/mg) | Sugar composition |
|---|---|---|---|---|
| N1+N1' | N1 | 27.5 | 3145 | (Man)7(GlcNAc)2(PA)1 |
| N2 | N2 | 10.8 | 1231 | (Man)6(GlcNAc)2(PA)1 |
| N3+N3' | N3 | 51.4 | 5872 | (Man)5(GlcNAc)2(PA)1 |
| N4 | N4-1 | 2.8 | 315 | (Man)3(GlcNAc)2(PA)1 |
|  | N4-2 | 4.6 | 525 | (Man)3(GlcNAc)3(PA)1 |
|  | N4-3 | 2.5 | 291 | (Man)4(GlcNAc)3(PA)1 |

SEQUENCE LISTING

```
<160> NUMBER OF SEQ ID NOS: 111

<210> SEQ ID NO 1
<211> LENGTH: 16
<212> TYPE: DNA
<213> ORGANISM: artificial sequence
<220> FEATURE:
<223> OTHER INFORMATION: M13forward primer

<400> SEQUENCE: 1
gtaaaacgac ggccag                                                  16

<210> SEQ ID NO 2
<211> LENGTH: 17
<212> TYPE: DNA
<213> ORGANISM: artificial sequence
<220> FEATURE:
<223> OTHER INFORMATION: M13reverse primer

<400> SEQUENCE: 2
caggaaacag ctatgac                                                 17

<210> SEQ ID NO 3
<211> LENGTH: 24
<212> TYPE: DNA
<213> ORGANISM: artificial sequence
<220> FEATURE:
<223> OTHER INFORMATION: pCANTAB5-S1 primer

<400> SEQUENCE: 3
caacgtgaaa aaattattat tcgc                                         24

<210> SEQ ID NO 4
<211> LENGTH: 23
<212> TYPE: DNA
<213> ORGANISM: artificial sequence
<220> FEATURE:
<223> OTHER INFORMATION: pCANTAB5-S6 primer

<400> SEQUENCE: 4
gtaaatgaat tttctgtatg agg                                          23

<210> SEQ ID NO 5
<211> LENGTH: 19
<212> TYPE: DNA
<213> ORGANISM: artificial sequence
<220> FEATURE:
<223> OTHER INFORMATION: T7promoter primer

<400> SEQUENCE: 5
taatacgact cactatagg                                               19
```

<210> SEQ ID NO 6
<211> LENGTH: 19
<212> TYPE: DNA
<213> ORGANISM: artificial sequence
<220> FEATURE:
<223> OTHER INFORMATION: T7terminator primer

<400> SEQUENCE: 6
gctagttatt gctcagcgg                                              19

<210> SEQ ID NO 7
<211> LENGTH: 24
<212> TYPE: DNA
<213> ORGANISM: artificial sequence
<220> FEATURE:
<223> OTHER INFORMATION: HIgG(gamma) primer

<400> SEQUENCE: 7
gtccaccttg gtgttgctgg gctt                                        24

<210> SEQ ID NO 8
<211> LENGTH: 24
<212> TYPE: DNA
<213> ORGANISM: artificial sequence
<220> FEATURE:
<223> OTHER INFORMATION: HIgM(mu) primer

<400> SEQUENCE: 8
tggaagaggc acgttctttt cttt                                        24

<210> SEQ ID NO 9
<211> LENGTH: 24
<212> TYPE: DNA
<213> ORGANISM: artificial sequence
<220> FEATURE:
<223> OTHER INFORMATION: Hkappa primer

<400> SEQUENCE: 9
agactctccc ctgttgaagc tctt                                        24

<210> SEQ ID NO 10
<211> LENGTH: 27
<212> TYPE: DNA
<213> ORGANISM: artificial sequence
<220> FEATURE:
<223> OTHER INFORMATION: Hlambda primer

<400> SEQUENCE: 10
tgaagattct gtaggggcca ctgtctt                                     27

<210> SEQ ID NO 11
<211> LENGTH: 23
<212> TYPE: DNA
<213> ORGANISM: artificial sequence
<220> FEATURE:
<223> OTHER INFORMATION: HVH1REV primer

<400> SEQUENCE: 11
caggtgcagc tggtgcagtc tgg                                         23

<210> SEQ ID NO 12
<211> LENGTH: 23
<212> TYPE: DNA
<213> ORGANISM: artificial sequence
<220> FEATURE:

```
<223> OTHER INFORMATION: HVH2REV primer

<400> SEQUENCE: 12
caggtcaact taagggagtc tgg                                          23

<210> SEQ ID NO 13
<211> LENGTH: 23
<212> TYPE: DNA
<213> ORGANISM: artificial sequence
<220> FEATURE:
<223> OTHER INFORMATION: HVH3REV primer

<400> SEQUENCE: 13
gaggtgcagc tggtggagtc tgg                                          23

<210> SEQ ID NO 14
<211> LENGTH: 23
<212> TYPE: DNA
<213> ORGANISM: artificial sequence
<220> FEATURE:
<223> OTHER INFORMATION: HVH4REV primer

<400> SEQUENCE: 14
caggtgcagc tgcaggagtc ggg                                          23

<210> SEQ ID NO 15
<211> LENGTH: 23
<212> TYPE: DNA
<213> ORGANISM: artificial sequence
<220> FEATURE:
<223> OTHER INFORMATION: HVH5REV primer

<400> SEQUENCE: 15
gaggtgcagc tgttgcagtc tgc                                          23

<210> SEQ ID NO 16
<211> LENGTH: 23
<212> TYPE: DNA
<213> ORGANISM: artificial sequence
<220> FEATURE:
<223> OTHER INFORMATION: HVH6REV primer

<400> SEQUENCE: 16
caggtacagc tgcagcagtc agg                                          23

<210> SEQ ID NO 17
<211> LENGTH: 24
<212> TYPE: DNA
<213> ORGANISM: artificial sequence
<220> FEATURE:
<223> OTHER INFORMATION: HJH12FOR primer

<400> SEQUENCE: 17
tgaggagacg gtgaccaggg tgcc                                         24

<210> SEQ ID NO 18
<211> LENGTH: 23
<212> TYPE: DNA
<213> ORGANISM: artificial sequence
<220> FEATURE:
<223> OTHER INFORMATION: HJH3 FOR primer

<400> SEQUENCE: 18
tgaagagagg tgaccattgt ccc                                          23
```

```
<210> SEQ ID NO 19
<211> LENGTH: 24
<212> TYPE: DNA
<213> ORGANISM: artificial sequence
<220> FEATURE:
<223> OTHER INFORMATION: HJH45FOR primer

<400> SEQUENCE: 19
tgaggagacg gtgaccaggg ttcc                                              24

<210> SEQ ID NO 20
<211> LENGTH: 24
<212> TYPE: DNA
<213> ORGANISM: artificial sequence
<220> FEATURE:
<223> OTHER INFORMATION: HJH6 FOR primer

<400> SEQUENCE: 20
tgaggagacg gtgaccgtgg tccc                                              24

<210> SEQ ID NO 21
<211> LENGTH: 23
<212> TYPE: DNA
<213> ORGANISM: artificial sequence
<220> FEATURE:
<223> OTHER INFORMATION: HVK1REV primer

<400> SEQUENCE: 21
gacatccaga tgacccagtc tcc                                               23

<210> SEQ ID NO 22
<211> LENGTH: 23
<212> TYPE: DNA
<213> ORGANISM: artificial sequence
<220> FEATURE:
<223> OTHER INFORMATION: HVK2REV primer

<400> SEQUENCE: 22
gatgttgtga tgactcagtc tcc                                               23

<210> SEQ ID NO 23
<211> LENGTH: 23
<212> TYPE: DNA
<213> ORGANISM: artificial sequence
<220> FEATURE:
<223> OTHER INFORMATION: HVK3REV primer

<400> SEQUENCE: 23
gaaattgtgt tgacgcagtc tcc                                               23

<210> SEQ ID NO 24
<211> LENGTH: 23
<212> TYPE: DNA
<213> ORGANISM: artificial sequence
<220> FEATURE:
<223> OTHER INFORMATION: HVK4REV primer

<400> SEQUENCE: 24
gacatcgtga tgacccagtc tcc                                               23

<210> SEQ ID NO 25
<211> LENGTH: 23
<212> TYPE: DNA
<213> ORGANISM: artificial sequence
<220> FEATURE:
<223> OTHER INFORMATION: HVK5REV primer
```

```
<400> SEQUENCE: 25
gaaacgacac tcacgcagtc tcc                                         23

<210> SEQ ID NO 26
<211> LENGTH: 23
<212> TYPE: DNA
<213> ORGANISM: artificial sequence
<220> FEATURE:
<223> OTHER INFORMATION: HVK6REV primer

<400> SEQUENCE: 26
gaaattgtgc tgactcagtc tcc                                         23

<210> SEQ ID NO 27
<211> LENGTH: 24
<212> TYPE: DNA
<213> ORGANISM: artificial sequence
<220> FEATURE:
<223> OTHER INFORMATION: HJK1FOR primer

<400> SEQUENCE: 27
acgtttgatt tccaccttgg tccc                                        24

<210> SEQ ID NO 28
<211> LENGTH: 24
<212> TYPE: DNA
<213> ORGANISM: artificial sequence
<220> FEATURE:
<223> OTHER INFORMATION: HJK2FOR primer

<400> SEQUENCE: 28
acgtttgatc tccagcttgg tccc                                        24

<210> SEQ ID NO 29
<211> LENGTH: 24
<212> TYPE: DNA
<213> ORGANISM: artificial sequence
<220> FEATURE:
<223> OTHER INFORMATION: HJK3FOR primer

<400> SEQUENCE: 29
acgtttgata tccactttgg tccc                                        24

<210> SEQ ID NO 30
<211> LENGTH: 24
<212> TYPE: DNA
<213> ORGANISM: artificial sequence
<220> FEATURE:
<223> OTHER INFORMATION: HJK4FOR primer

<400> SEQUENCE: 30
acgtttgatc tccaccttgg tccc                                        24

<210> SEQ ID NO 31
<211> LENGTH: 24
<212> TYPE: DNA
<213> ORGANISM: artificial sequence
<220> FEATURE:
<223> OTHER INFORMATION: HJK5FOR primer

<400> SEQUENCE: 31
acgtttaatc tccagtcgtg tccc                                        24

<210> SEQ ID NO 32
<211> LENGTH: 23
```

```
<212> TYPE: DNA
<213> ORGANISM: artificial sequence
<220> FEATURE:
<223> OTHER INFORMATION: HVlambda1REV primer

<400> SEQUENCE: 32
cagtctgtgt tgacgcagcc gcc                                        23

<210> SEQ ID NO 33
<211> LENGTH: 23
<212> TYPE: DNA
<213> ORGANISM: artificial sequence
<220> FEATURE:
<223> OTHER INFORMATION: HVlambda2REV primer

<400> SEQUENCE: 33
cagtctgccc tgactcagcc tgc                                        23

<210> SEQ ID NO 34
<211> LENGTH: 23
<212> TYPE: DNA
<213> ORGANISM: artificial sequence
<220> FEATURE:
<223> OTHER INFORMATION: HVlambda3aREV primer

<400> SEQUENCE: 34
tcctatgtgc tgactcagcc acc                                        23

<210> SEQ ID NO 35
<211> LENGTH: 23
<212> TYPE: DNA
<213> ORGANISM: artificial sequence
<220> FEATURE:
<223> OTHER INFORMATION: HVlambda3bREV primer

<400> SEQUENCE: 35
tcttctgagc tgactcagga ccc                                        23

<210> SEQ ID NO 36
<211> LENGTH: 23
<212> TYPE: DNA
<213> ORGANISM: artificial sequence
<220> FEATURE:
<223> OTHER INFORMATION: HVlambda4REV primer

<400> SEQUENCE: 36
cacgttatac tgactcaacc gcc                                        23

<210> SEQ ID NO 37
<211> LENGTH: 23
<212> TYPE: DNA
<213> ORGANISM: artificial sequence
<220> FEATURE:
<223> OTHER INFORMATION: HVlambda5REV primer

<400> SEQUENCE: 37
caggctgtgc tcactcagcc gtc                                        23

<210> SEQ ID NO 38
<211> LENGTH: 23
<212> TYPE: DNA
<213> ORGANISM: artificial sequence
<220> FEATURE:
<223> OTHER INFORMATION: HVlambda6REV primer

<400> SEQUENCE: 38
```
aattttatgc tgactcagcc cca                                          23

<210> SEQ ID NO 39
<211> LENGTH: 24
<212> TYPE: DNA
<213> ORGANISM: artificial sequence
<220> FEATURE:
<223> OTHER INFORMATION: HJlambda1FOR primer

<400> SEQUENCE: 39
acctaggacg gtgaccttgg tccc                                         24

<210> SEQ ID NO 40
<211> LENGTH: 24
<212> TYPE: DNA
<213> ORGANISM: artificial sequence
<220> FEATURE:
<223> OTHER INFORMATION: HJlambda2-3FOR primer

<400> SEQUENCE: 40
acctaggacg gtcagcttgg tccc                                         24

<210> SEQ ID NO 41
<211> LENGTH: 24
<212> TYPE: DNA
<213> ORGANISM: artificial sequence
<220> FEATURE:
<223> OTHER INFORMATION: HJlambda4-5FOR primer

<400> SEQUENCE: 41
acctaaaacg gtgagctggg tccc                                         24

<210> SEQ ID NO 42
<211> LENGTH: 50
<212> TYPE: DNA
<213> ORGANISM: artificial sequence
<220> FEATURE:
<223> OTHER INFORMATION: HJH12FORLK primer

<400> SEQUENCE: 42
agagccacct ccgcctgaac cgcctccacc tgaggagacg gtgaccaggg             50

<210> SEQ ID NO 43
<211> LENGTH: 50
<212> TYPE: DNA
<213> ORGANISM: artificial sequence
<220> FEATURE:
<223> OTHER INFORMATION: HJH3 FORLK primer

<400> SEQUENCE: 43
agagccacct ccgcctgaac cgcctccacc tgaagagacg gtgaccattg             50

<210> SEQ ID NO 44
<211> LENGTH: 50
<212> TYPE: DNA
<213> ORGANISM: artificial sequence
<220> FEATURE:
<223> OTHER INFORMATION: HJH45FORLK primer

<400> SEQUENCE: 44
agagccacct ccgcctgaac cgcctccacc tgaggagacg gtgaccaggg             50

<210> SEQ ID NO 45
<211> LENGTH: 50
<212> TYPE: DNA
<213> ORGANISM: artificial sequence -continued

```
<220> FEATURE:
<223> OTHER INFORMATION: HJH6 FORLK primer

<400> SEQUENCE: 45
agagccacct ccgcctgaac cgcctccacc tgaggagacg gtgaccgtgg          50

<210> SEQ ID NO 46
<211> LENGTH: 48
<212> TYPE: DNA
<213> ORGANISM: artificial sequence
<220> FEATURE:
<223> OTHER INFORMATION: HVK1REVLK primer

<400> SEQUENCE: 46
ggcggaggtg gctctggcgg tggcggatcg gacatccaga tgacccag            48

<210> SEQ ID NO 47
<211> LENGTH: 49
<212> TYPE: DNA
<213> ORGANISM: artificial sequence
<220> FEATURE:
<223> OTHER INFORMATION: HVK2REVLK primer

<400> SEQUENCE: 47
ggcggaggtg gctctggcgg tggcggatcg gatgttgtga tgactcagt           49

<210> SEQ ID NO 48
<211> LENGTH: 49
<212> TYPE: DNA
<213> ORGANISM: artificial sequence
<220> FEATURE:
<223> OTHER INFORMATION: HVK3REVLK primer

<400> SEQUENCE: 48
ggcggaggtg gctctggcgg tggcggatcg gaaattgtgt tgacgcagt           49

<210> SEQ ID NO 49
<211> LENGTH: 48
<212> TYPE: DNA
<213> ORGANISM: artificial sequence
<220> FEATURE:
<223> OTHER INFORMATION: HVK4REVLK primer

<400> SEQUENCE: 49
ggcggaggtg gctctggcgg tggcggatcg gacatcgtga tgacccag            48

<210> SEQ ID NO 50
<211> LENGTH: 49
<212> TYPE: DNA
<213> ORGANISM: artificial sequence
<220> FEATURE:
<223> OTHER INFORMATION: HVK5REVLK primer

<400> SEQUENCE: 50
ggcggaggtg gctctggcgg tggcggatcg gaaacgacac tcacgcagt           49

<210> SEQ ID NO 51
<211> LENGTH: 49
<212> TYPE: DNA
<213> ORGANISM: artificial sequence
<220> FEATURE:
<223> OTHER INFORMATION: HVK6REVLK primer

<400> SEQUENCE: 51
ggcggaggtg gctctggcgg tggcggatcg gaaattgtgc tgactcagt           49
```

<210> SEQ ID NO 52
<211> LENGTH: 48
<212> TYPE: DNA
<213> ORGANISM: artificial sequence
<220> FEATURE:
<223> OTHER INFORMATION: HVlambda1REVLK primer

<400> SEQUENCE: 52
ggcggaggtg gctctggcgg tggcggatcg cagtctgtgt tgacgcag        48

<210> SEQ ID NO 53
<211> LENGTH: 48
<212> TYPE: DNA
<213> ORGANISM: artificial sequence
<220> FEATURE:
<223> OTHER INFORMATION: HVlambda2REVLK primer

<400> SEQUENCE: 53
ggcggaggtg gctctggcgg tggcggatcg cagtctgccc tgactcag        48

<210> SEQ ID NO 54
<211> LENGTH: 48
<212> TYPE: DNA
<213> ORGANISM: artificial sequence
<220> FEATURE:
<223> OTHER INFORMATION: HVlambda3aREVLK primer

<400> SEQUENCE: 54
ggcggaggtg gctctggcgg tggcggatcg tcctatgtgc tgactcag        48

<210> SEQ ID NO 55
<211> LENGTH: 48
<212> TYPE: DNA
<213> ORGANISM: artificial sequence
<220> FEATURE:
<223> OTHER INFORMATION: HVlambda3bREVLK primer

<400> SEQUENCE: 55
ggcggaggtg gctctggcgg tggcggatcg tcttctgagc tgactcag        48

<210> SEQ ID NO 56
<211> LENGTH: 49
<212> TYPE: DNA
<213> ORGANISM: artificial sequence
<220> FEATURE:
<223> OTHER INFORMATION: HVlambda4REVLK primer

<400> SEQUENCE: 56
ggcggaggtg gctctggcgg tggcggatcg cacgttatac tgactcaac       49

<210> SEQ ID NO 57
<211> LENGTH: 48
<212> TYPE: DNA
<213> ORGANISM: artificial sequence
<220> FEATURE:
<223> OTHER INFORMATION: HVlambda5REVLK primer

<400> SEQUENCE: 57
ggcggaggtg gctctggcgg tggcggatcg caggctgtgc tcactcag        48

<210> SEQ ID NO 58
<211> LENGTH: 48
<212> TYPE: DNA
<213> ORGANISM: artificial sequence
<220> FEATURE:
<223> OTHER INFORMATION: HVlambda6REVLK primer

```
<400> SEQUENCE: 58
ggcggaggtg gctctggcgg tggcggatcg aatttatgc tgactcag        48

<210> SEQ ID NO 59
<211> LENGTH: 41
<212> TYPE: DNA
<213> ORGANISM: artificial sequence
<220> FEATURE:
<223> OTHER INFORMATION: HVH1REVSfiI primer

<400> SEQUENCE: 59
tcgcggccca gccggccatg gcccaggtgc agctggtgca g             41

<210> SEQ ID NO 60
<211> LENGTH: 41
<212> TYPE: DNA
<213> ORGANISM: artificial sequence
<220> FEATURE:
<223> OTHER INFORMATION: HVH2REVSfiI primer

<400> SEQUENCE: 60
tcgcggccca gccggccatg gcccaggtca acttaaggga g             41

<210> SEQ ID NO 61
<211> LENGTH: 41
<212> TYPE: DNA
<213> ORGANISM: artificial sequence
<220> FEATURE:
<223> OTHER INFORMATION: HVH3REVSfiI primer

<400> SEQUENCE: 61
tcgcggccca gccggccatg gccgaggtgc agctggtgga g             41

<210> SEQ ID NO 62
<211> LENGTH: 41
<212> TYPE: DNA
<213> ORGANISM: artificial sequence
<220> FEATURE:
<223> OTHER INFORMATION: HVH4REVSfiI primer

<400> SEQUENCE: 62
tcgcggccca gccggccatg gcccaggtgc agctgcagga g             41

<210> SEQ ID NO 63
<211> LENGTH: 41
<212> TYPE: DNA
<213> ORGANISM: artificial sequence
<220> FEATURE:
<223> OTHER INFORMATION: HVH5REVSfiI primer

<400> SEQUENCE: 63
tcgcggccca gccggccatg gcccaggtgc agctgttgca g             41

<210> SEQ ID NO 64
<211> LENGTH: 41
<212> TYPE: DNA
<213> ORGANISM: artificial sequence
<220> FEATURE:
<223> OTHER INFORMATION: HVH6REVSfiI primer

<400> SEQUENCE: 64
tcgcggccca gccggccatg gccgaggtac agctgcagca g             41

<210> SEQ ID NO 65
```

-continued

<210> SEQ ID NO 65
<211> LENGTH: 41
<212> TYPE: DNA
<213> ORGANISM: artificial sequence
<220> FEATURE:
<223> OTHER INFORMATION: HJK1FORNotI primer

<400> SEQUENCE: 65
gatatgagat actgcggccg cacgtttgat ttccaccttg g        41

<210> SEQ ID NO 66
<211> LENGTH: 41
<212> TYPE: DNA
<213> ORGANISM: artificial sequence
<220> FEATURE:
<223> OTHER INFORMATION: HJK2FORNotI primer

<400> SEQUENCE: 66
gatatgagat actgcggccg cacgtttgat ctccagcttg g        41

<210> SEQ ID NO 67
<211> LENGTH: 41
<212> TYPE: DNA
<213> ORGANISM: artificial sequence
<220> FEATURE:
<223> OTHER INFORMATION: HJK3FORNotI primer

<400> SEQUENCE: 67
gatatgagat actgcggccg cacgtttgat atccactttg g        41

<210> SEQ ID NO 68
<211> LENGTH: 41
<212> TYPE: DNA
<213> ORGANISM: artificial sequence
<220> FEATURE:
<223> OTHER INFORMATION: HJK4FORNotI primer

<400> SEQUENCE: 68
gatatgagat actgcggccg cacgtttgat ctccaccttg g        41

<210> SEQ ID NO 69
<211> LENGTH: 41
<212> TYPE: DNA
<213> ORGANISM: artificial sequence
<220> FEATURE:
<223> OTHER INFORMATION: HJK5FORNotI primer

<400> SEQUENCE: 69
gatatgagat actgcggccg cacgtttaat ctccagtcgt g        41

<210> SEQ ID NO 70
<211> LENGTH: 41
<212> TYPE: DNA
<213> ORGANISM: artificial sequence
<220> FEATURE:
<223> OTHER INFORMATION: HJlambda1FORNotI primer

<400> SEQUENCE: 70
gatatgagat actgcggccg cacctaggac ggtgaccttg g        41

<210> SEQ ID NO 71
<211> LENGTH: 41
<212> TYPE: DNA
<213> ORGANISM: artificial sequence
<220> FEATURE:
<223> OTHER INFORMATION: HJlambda2-3FORNotI primer

<400> SEQUENCE: 71

```
gatatgagat actgcggccg cacctaggac ggtcagcttg g         41
```

<210> SEQ ID NO 72
<211> LENGTH: 41
<212> TYPE: DNA
<213> ORGANISM: artificial sequence
<220> FEATURE:
<223> OTHER INFORMATION: HJlambda4-5FORNotI primer

<400> SEQUENCE: 72

```
gatatgagat actgcggccg cacctaaaac ggtgagctgg g         41
```

<210> SEQ ID NO 73
<211> LENGTH: 41
<212> TYPE: DNA
<213> ORGANISM: artificial sequence
<220> FEATURE:
<223> OTHER INFORMATION: g+k aREV

<400> SEQUENCE: 73

```
gtcgaccata tgccatggca ggtacagctg cagcagtcag g         41
```

<210> SEQ ID NO 74
<211> LENGTH: 41
<212> TYPE: DNA
<213> ORGANISM: artificial sequence
<220> FEATURE:
<223> OTHER INFORMATION: g+k bREV

<400> SEQUENCE: 74

```
gtcgaccata tgccatggga ggtgcagctg gtggagtctg g         41
```

<210> SEQ ID NO 75
<211> LENGTH: 21
<212> TYPE: DNA
<213> ORGANISM: artificial sequence
<220> FEATURE:
<223> OTHER INFORMATION: g+k aFOR

<400> SEQUENCE: 75

```
ctcgagacgt ttgatctcca g                              21
```

<210> SEQ ID NO 76
<211> LENGTH: 250
<212> TYPE: PRT
<213> ORGANISM: artificial sequence
<220> FEATURE:
<223> OTHER INFORMATION: gamma+kappa 5

<400> SEQUENCE: 76

Met Ala Gln Val Gln Leu Gln Gln Ser Gly Pro Gly Leu Val Lys Pro
1               5                   10                  15

Ser Gln Thr Leu Ser Leu Thr Cys Ala Ile Ser Gly Asp Ser Val Ser
            20                  25                  30

Ser Arg Asp Ala Ala Trp Asn Trp Ile Arg Gln Ser Pro Ser Arg Gly
        35                  40                  45

Leu Glu Trp Leu Gly Arg Thr Tyr Tyr Arg Ser Glu Trp Tyr Thr Asp
    50                  55                  60

Tyr Ala Val Ser Leu Glu Ser Arg Leu Thr Val Asn Pro Asp Thr Ser
65                  70                  75                  80

Arg Asn Gln Phe Ser Leu Gln Leu Asn Ser Val Thr Pro Glu Asp Thr
                85                  90                  95

```
Ala Val Tyr Leu Cys Ala Arg Gly Ser Ser Trp Gly His Ala Pro Ala
                100                 105                 110

Phe Phe Asp Tyr Trp Gly Gln Gly Thr Leu Val Thr Val Ser Ser Gly
            115                 120                 125

Gly Gly Gly Ser Gly Gly Gly Ser Gly Gly Gly Ser Asp Ile
    130                 135                 140

Gln Met Thr Gln Ser Pro Ser Ser Leu Ser Ala Ser Val Glu Asp Arg
145                 150                 155                 160

Val Ala Ile Thr Cys Arg Ala Ser Gln Ser Val Ser Tyr Val Ala
                165                 170                 175

Trp Tyr Gln Gln Lys Pro Gly Lys Ala Pro Lys Leu Leu Ile Ser Gln
                180                 185                 190

Ala Ser Ser Leu Glu Asn Gly Val Pro Ser Arg Phe Ser Gly Ser Gly
                195                 200                 205

Ser Gly Thr Asp Phe Thr Leu Thr Ile Ser Ser Leu Gln Pro Glu Asp
            210                 215                 220

Phe Ala Thr Tyr Tyr Cys Gln Gln Tyr Thr Thr Tyr Pro Tyr Thr Phe
225                 230                 235                 240

Gly Gln Gly Thr Lys Leu Glu Ile Lys Arg
                245                 250

<210> SEQ ID NO 77
<211> LENGTH: 251
<212> TYPE: PRT
<213> ORGANISM: artificial sequence
<220> FEATURE:
<223> OTHER INFORMATION: gamma+kappa 12

<400> SEQUENCE: 77

Met Ala Gln Val Gln Leu Gln Gln Ser Gly Pro Gly Leu Val Lys Pro
1               5                   10                  15

Ser Gln Thr Leu Ser Leu Thr Cys Asp Ile Ser Gly Asp Ser Ile Ser
                20                  25                  30

Thr Asn Gly Ala Ala Trp Asn Trp Ile Arg Gln Ser Pro Ser Arg Gly
            35                  40                  45

Leu Glu Trp Leu Gly Arg Thr Phe Tyr Arg Ser Lys Trp Tyr Asn Asp
        50                  55                  60

Tyr Ala Val Ser Val Lys Ser Arg Met Ile Ile Asn Pro Asp Thr Ser
65                  70                  75                  80

Lys Asn Gln Phe Ser Leu Gln Leu Ser Ser Val Thr Pro Glu Asp Thr
                85                  90                  95

Ala Val Tyr Tyr Cys Ala Arg Val Ala Cys Ser Gly Gly Thr Cys Leu
                100                 105                 110

Asp Gly Ile Asp Val Trp Gly Gln Gly Thr Thr Val Thr Val Ser Ser
            115                 120                 125

Gly Gly Gly Gly Ser Gly Gly Gly Ser Gly Gly Gly Gly Ser Asp
            130                 135                 140

Ile Val Met Thr Gln Ser Pro Ser Ser Leu Ser Ala Ser Val Gly Glu
145                 150                 155                 160

Arg Val Thr Ile Thr Cys Arg Ala Ser Gln Ala Ile Arg Asn Asp Leu
                165                 170                 175

Gly Trp Tyr Gln Gln Lys Pro Gly Lys Ala Pro Lys Leu Leu Val Tyr
            180                 185                 190

Ser Ala Ser Asn Leu Gln Ser Gly Val Pro Ser Arg Phe Ser Gly Ser
            195                 200                 205
```

-continued

Gly Ser Gly Thr Asp Phe Thr Leu Thr Ile Ser Ser Leu Gln Pro Glu
            210                 215                 220

Asp Phe Ala Thr Tyr Tyr Cys Gln Gln Tyr His Ser Tyr Pro Arg Thr
225                 230                 235                 240

Phe Ser Gln Gly Thr Lys Leu Glu Ile Lys Arg
                245                 250

<210> SEQ ID NO 78
<211> LENGTH: 244
<212> TYPE: PRT
<213> ORGANISM: artificial sequence
<220> FEATURE:
<223> OTHER INFORMATION: gamma+kappa 19

<400> SEQUENCE: 78

Met Ala Glu Val Gln Leu Val Glu Ser Gly Ala Glu Val Lys Asn Pro
1               5                   10                  15

Gly Ala Ser Val Lys Val Ser Cys Lys Ala Ser Gly Tyr Thr Leu Thr
                20                  25                  30

Gly Tyr Tyr Met His Trp Val Arg Gln Ala Pro Gly Gln Gly Leu Glu
            35                  40                  45

Trp Met Gly Gly Ile Ile Pro Met Tyr Gly Thr Pro Thr Tyr Ala Pro
    50                  55                  60

Arg Phe Gln Gly Arg Val Thr Phe Thr Ala Asp Tyr Ser Thr Asn Thr
65                  70                  75                  80

Val Tyr Met Glu Leu Arg Ser Leu Arg Ser Glu Asp Thr Ala Val Phe
                85                  90                  95

Tyr Cys Ala Arg Gln Ala Asp Ser Ala Ser Tyr Leu Asp Tyr Trp Gly
            100                 105                 110

Gln Gly Thr Leu Val Thr Val Ser Ser Gly Gly Gly Ser Gly Gly
            115                 120                 125

Gly Gly Ser Gly Gly Gly Ser Asp Val Val Met Thr Gln Ser Pro
        130                 135                 140

Gly Thr Leu Ser Leu Ser Pro Gly Glu Arg Ala Thr Leu Ser Cys Arg
145                 150                 155                 160

Ala Ser Gln Ser Leu Asp Ser Ser Tyr Leu Ala Trp Tyr Gln Gln Lys
                165                 170                 175

Pro Gly Arg Ala Pro Arg Leu Leu Ile Tyr Gly Ala Ser Asp Arg Asp
            180                 185                 190

Thr Gly Ile Pro Asp Arg Phe Ser Gly Ser Gly Ser Gly Thr Asp Phe
        195                 200                 205

Thr Leu Thr Ile Ser Arg Leu Glu Pro Glu Asp Phe Ala Val Tyr Tyr
    210                 215                 220

Cys Gln Gln Tyr Gly Arg Ser Arg Thr Phe Gly Gln Gly Thr Lys Leu
225                 230                 235                 240

Glu Ile Lys Arg

<210> SEQ ID NO 79
<211> LENGTH: 244
<212> TYPE: PRT
<213> ORGANISM: artificial sequence
<220> FEATURE:
<223> OTHER INFORMATION: gamma+kappa 40

<400> SEQUENCE: 79

Met Ala Gln Val Gln Leu Val Gln Ser Gly Val Glu Leu Arg Lys Pro
1               5                   10                  15

Gly Asp Ser Val Lys Val Ser Cys Lys Ala Ser Gly Tyr Ser Val Asn
            20                  25                  30

Thr His Gly Met Ser Trp Val Arg Gln Ala Pro Gly Gln Gly Leu Glu
        35                  40                  45

Trp Leu Gly Arg Ile Ser Ser Tyr Ile Gly Leu Thr Lys Phe Ala Gln
    50                  55                  60

Lys Phe Gln Asp Arg Val Thr Leu Thr Thr Asp Thr Ser Thr Asn Thr
65                  70                  75                  80

Ala Tyr Leu Glu Met Arg Ser Leu Lys Ser Asp Asp Thr Ala Val Tyr
                85                  90                  95

Phe Cys Gly Arg Asp Asp Tyr Glu Tyr Asp Ala Phe Asp Val Trp Gly
            100                 105                 110

Gln Gly Thr Met Val Thr Val Ser Ser Gly Gly Gly Ser Gly Gly
        115                 120                 125

Gly Gly Ser Ser Gly Gly Gly Ser Glu Ile Val Leu Thr Gln Ser Pro
130                 135                 140

Ala Thr Leu Ser Val Ser Pro Gly Glu Arg Ala Thr Leu Ser Cys Arg
145                 150                 155                 160

Thr Thr Glu Ser Val Thr Asp Ser Gln Leu Ala Trp Tyr Gln Gln Lys
                165                 170                 175

Pro Gly Gln Ala Pro Arg Leu Leu Ile Tyr Gly Pro Ser Thr Arg Ala
            180                 185                 190

Thr Gly Ile Pro Asp Arg Phe Ser Gly Ser Gly Ser Gly Thr Asp Phe
        195                 200                 205

Thr Leu Thr Ile Ser Gly Leu Glu Pro Glu Asp Phe Ala Val Tyr Tyr
    210                 215                 220

Cys Gln Gln Arg Asn Ser Trp Tyr Thr Phe Gly Gln Gly Thr Lys Leu
225                 230                 235                 240

Glu Ile Lys Arg

<210> SEQ ID NO 80
<211> LENGTH: 241
<212> TYPE: PRT
<213> ORGANISM: artificial sequence
<220> FEATURE:
<223> OTHER INFORMATION: gamma+kappa 96

<400> SEQUENCE: 80

Met Ala Glu Val Gln Leu Val Glu Ser Gly Ala Glu Ala Lys Lys Pro
1               5                   10                  15

Gly Glu Ser Leu Lys Ile Ser Cys Lys Gly Ser Gly Tyr Ser Phe Thr
            20                  25                  30

Thr Asn Trp Ile Gly Trp Val Arg Gln Leu Pro Gly Lys Gly Leu Asp
        35                  40                  45

Trp Met Gly Ile Ile Tyr Pro Asp Asp Ser Asp Thr Arg Tyr Ser Pro
    50                  55                  60

Ser Phe Gln Gly Gln Val Thr Ile Ser Ala Asp Lys Ser Ile Ser Thr
65                  70                  75                  80

Ala Tyr Leu Gln Trp Asn Ser Leu Lys Ala Ser Asp Thr Ala Met Tyr
                85                  90                  95

Tyr Cys Ala Arg Arg Gln Trp Gly Ser Phe Asp Leu Trp Gly Gln Gly
            100                 105                 110

Thr Met Val Thr Val Ser Ser Gly Gly Gly Gly Ser Gly Gly Gly Gly
        115                 120                 125

Ser Gly Gly Gly Gly Ser Glu Ile Val Leu Thr Gln Ser Pro Ala Thr

```
                    130                 135                 140
Leu Ser Leu Ser Pro Gly Glu Arg Ala Thr Leu Ser Cys Arg Ala Ser
145                 150                 155                 160

Gln Ser Val Ser Ser Phe Leu Ala Trp Tyr Gln Gln Lys Pro Gly Gln
                165                 170                 175

Ala Pro Arg Leu Leu Ile Tyr Gly Ala Ser Ser Arg Ala Thr Gly Ile
            180                 185                 190

Pro Asp Arg Phe Ser Gly Ser Gly Ser Gly Thr Asp Phe Thr Leu Thr
        195                 200                 205

Ile Asn Arg Leu Glu Pro Glu Asp Phe Ala Val Tyr Tyr Cys Gln Tyr
    210                 215                 220

Tyr Gly Ser Ser Gly Thr Phe Gly Gln Gly Thr Lys Val Glu Ile Lys
225                 230                 235                 240

Arg

<210> SEQ ID NO 81
<211> LENGTH: 822
<212> TYPE: DNA
<213> ORGANISM: Homo sapiens
<220> FEATURE:
<221> NAME/KEY: CDS
<222> LOCATION: (1)..(822)
<220> FEATURE:
<221> NAME/KEY: misc_feature
<222> LOCATION: (232)..(232)
<223> OTHER INFORMATION: The 'Xaa' at location 232 stands for Gly, or
      Arg.
<220> FEATURE:
<221> NAME/KEY: misc_feature
<222> LOCATION: (249)..(249)
<223> OTHER INFORMATION: The 'Xaa' at location 249 stands for Gly, or
      Ala.

<400> SEQUENCE: 81 atg act ttt gat gac cta aag atc cag act gtg aag gac cag cct gat       48
Met Thr Phe Asp Asp Leu Lys Ile Gln Thr Val Lys Asp Gln Pro Asp
1               5                   10                  15 gag aag tca aat gga aaa aaa gct aaa ggt ctt cag ttt ctt tac tct       96
Glu Lys Ser Asn Gly Lys Lys Ala Lys Gly Leu Gln Phe Leu Tyr Ser
                20                  25                  30 cca tgg tgg tgc ctg gct gct gcg act cta ggg gtc ctt tgc ctg gga      144
Pro Trp Trp Cys Leu Ala Ala Ala Thr Leu Gly Val Leu Cys Leu Gly
            35                  40                  45 tta gta gtg acc att atg gtg ctg ggc atg caa tta tcc cag gtg tct      192
Leu Val Val Thr Ile Met Val Leu Gly Met Gln Leu Ser Gln Val Ser
50                  55                  60 gac ctc cta aca caa gag caa gca aac cta act cac cag aaa aag aaa      240
Asp Leu Leu Thr Gln Glu Gln Ala Asn Leu Thr His Gln Lys Lys Lys
65                  70                  75                  80 ctg gag gga cag atc tca gcc cgg caa caa gca gaa gaa gct tca cag      288
Leu Glu Gly Gln Ile Ser Ala Arg Gln Gln Ala Glu Glu Ala Ser Gln
                85                  90                  95 gag tca gaa aac gaa ctc aag gaa atg ata gaa acc ctt gct cgg aag      336
Glu Ser Glu Asn Glu Leu Lys Glu Met Ile Glu Thr Leu Ala Arg Lys
                100                 105                 110 ctg aat gag aaa tcc aaa gag caa atg gaa ctt cac cac cag aat ctg      384
Leu Asn Glu Lys Ser Lys Glu Gln Met Glu Leu His His Gln Asn Leu
            115                 120                 125 aat ctc caa gaa aca ctg aag aga gta gca aat tgt tca gct cct tgt      432
Asn Leu Gln Glu Thr Leu Lys Arg Val Ala Asn Cys Ser Ala Pro Cys
        130                 135                 140
```

```
ccg caa gac tgg atc tgg cat gga gaa aac tgt tac cta ttt tcc tcg    480
Pro Gln Asp Trp Ile Trp His Gly Glu Asn Cys Tyr Leu Phe Ser Ser
145                 150                 155                 160 ggc tca ttt aac tgg gaa aag agc caa gag aag tgc ttg tct ttg gat    528
Gly Ser Phe Asn Trp Glu Lys Ser Gln Glu Lys Cys Leu Ser Leu Asp
                165                 170                 175 gcc aag ttg ctg aaa att aat agc aca gct gat ctg gac ttc atc cag    576
Ala Lys Leu Leu Lys Ile Asn Ser Thr Ala Asp Leu Asp Phe Ile Gln
            180                 185                 190 caa gca att tcc tat tcc agt ttt cca ttc tgg atg ggg ctg tct cgg    624
Gln Ala Ile Ser Tyr Ser Ser Phe Pro Phe Trp Met Gly Leu Ser Arg
        195                 200                 205 agg aac ccc agc tac cca tgg ctc tgg gag gac ggt tct cct ttg atg    672
Arg Asn Pro Ser Tyr Pro Trp Leu Trp Glu Asp Gly Ser Pro Leu Met
    210                 215                 220 ccc cac tta ttt aga gtc cga sgc gct gtc tcc cag aca tac cct tca    720
Pro His Leu Phe Arg Val Arg Xaa Ala Val Ser Gln Thr Tyr Pro Ser
225                 230                 235                 240 ggt acc tgt gca tat ata caa cga gsa gct gtt tat gcg gaa aac tgc    768
Gly Thr Cys Ala Tyr Ile Gln Arg Xaa Ala Val Tyr Ala Glu Asn Cys
                245                 250                 255 att tta gct gcc ttc agt ata tgt cag aag aag gca aac cta aga gca    816
Ile Leu Ala Ala Phe Ser Ile Cys Gln Lys Lys Ala Asn Leu Arg Ala
            260                 265                 270 cag tga                                                            822
Gln

<210> SEQ ID NO 82
<211> LENGTH: 273
<212> TYPE: PRT
<213> ORGANISM: Homo sapiens
<220> FEATURE:
<221> NAME/KEY: misc_feature
<222> LOCATION: (232)..(232)
<223> OTHER INFORMATION: The 'Xaa' at location 232 stands for Gly, or
      Arg.
<220> FEATURE:
<221> NAME/KEY: misc_feature
<222> LOCATION: (249)..(249)
<223> OTHER INFORMATION: The 'Xaa' at location 249 stands for Gly, or
      Ala.

<400> SEQUENCE: 82

Met Thr Phe Asp Asp Leu Lys Ile Gln Thr Val Lys Asp Gln Pro Asp
1               5                   10                  15

Glu Lys Ser Asn Gly Lys Lys Ala Lys Gly Leu Gln Phe Leu Tyr Ser
            20                  25                  30

Pro Trp Trp Cys Leu Ala Ala Ala Thr Leu Gly Val Leu Cys Leu Gly
        35                  40                  45

Leu Val Val Thr Ile Met Val Leu Gly Met Gln Leu Ser Gln Val Ser
    50                  55                  60

Asp Leu Leu Thr Gln Glu Gln Ala Asn Leu Thr His Gln Lys Lys Lys
65                  70                  75                  80

Leu Glu Gly Gln Ile Ser Ala Arg Gln Gln Ala Glu Glu Ala Ser Gln
                85                  90                  95

Glu Ser Glu Asn Glu Leu Lys Glu Met Ile Glu Thr Leu Ala Arg Lys
            100                 105                 110

Leu Asn Glu Lys Ser Lys Glu Gln Met Glu Leu His His Gln Asn Leu
        115                 120                 125

Asn Leu Gln Glu Thr Leu Lys Arg Val Ala Asn Cys Ser Ala Pro Cys
    130                 135                 140
```

```
Pro Gln Asp Trp Ile Trp His Gly Glu Asn Cys Tyr Leu Phe Ser Ser
145                 150                 155                 160

Gly Ser Phe Asn Trp Glu Lys Ser Gln Glu Lys Cys Leu Ser Leu Asp
            165                 170                 175

Ala Lys Leu Leu Lys Ile Asn Ser Thr Ala Asp Leu Asp Phe Ile Gln
        180                 185                 190

Gln Ala Ile Ser Tyr Ser Ser Phe Pro Phe Trp Met Gly Leu Ser Arg
    195                 200                 205

Arg Asn Pro Ser Tyr Pro Trp Leu Trp Glu Asp Gly Ser Pro Leu Met
210                 215                 220

Pro His Leu Phe Arg Val Arg Xaa Ala Val Ser Gln Thr Tyr Pro Ser
225                 230                 235                 240

Gly Thr Cys Ala Tyr Ile Gln Arg Xaa Ala Val Tyr Ala Glu Asn Cys
            245                 250                 255

Ile Leu Ala Ala Phe Ser Ile Cys Gln Lys Lys Ala Asn Leu Arg Ala
        260                 265                 270

Gln
```

<210> SEQ ID NO 83
<211> LENGTH: 435
<212> TYPE: DNA
<213> ORGANISM: Homo sapiens
<220> FEATURE:
<221> NAME/KEY: CDS
<222> LOCATION: (1)..(435)
<220> FEATURE:
<221> NAME/KEY: misc_feature
<222> LOCATION: (104)..(104)
<223> OTHER INFORMATION: The 'Xaa' at location 104 stands for Gly, or
      Ala.
<220> FEATURE:
<221> NAME/KEY: misc_feature
<222> LOCATION: (121)..(121)
<223> OTHER INFORMATION: The 'Xaa' at location 121 stands for Gly, or
      Ala.

<400> SEQUENCE: 83

```
aat ctc caa gaa aca ctg aag aga gta gca aat tgt tca gct cct tgt      48
Asn Leu Gln Glu Thr Leu Lys Arg Val Ala Asn Cys Ser Ala Pro Cys
1               5                   10                  15 ccg caa gac tgg atc tgg cat gga gaa aac tgt tac cta ttt tcc tcg     96
Pro Gln Asp Trp Ile Trp His Gly Glu Asn Cys Tyr Leu Phe Ser Ser
            20                  25                  30 ggc tca ttt aac tgg gaa aag agc caa gag aag tgc ttg tct ttg gat    144
Gly Ser Phe Asn Trp Glu Lys Ser Gln Glu Lys Cys Leu Ser Leu Asp
        35                  40                  45 gcc aag ttg ctg aaa att aat agc aca gct gat ctg gac ttc atc cag    192
Ala Lys Leu Leu Lys Ile Asn Ser Thr Ala Asp Leu Asp Phe Ile Gln
    50                  55                  60 caa gca att tcc tat tcc agt ttt cca ttc tgg atg ggg ctg tct cgg    240
Gln Ala Ile Ser Tyr Ser Ser Phe Pro Phe Trp Met Gly Leu Ser Arg
65                  70                  75                  80 agg aac ccc agc tac cca tgg ctc tgg gag gac ggt tct cct ttg atg    288
Arg Asn Pro Ser Tyr Pro Trp Leu Trp Glu Asp Gly Ser Pro Leu Met
                85                  90                  95 ccc cac tta ttt aga gtc cga gsc gct gtc cag aca tac cct tca        336
Pro His Leu Phe Arg Val Arg Xaa Ala Val Ser Gln Thr Tyr Pro Ser
            100                 105                 110 ggt acc tgt gca tat ata caa cga gsa gct gtt tat gcg gaa aac tgc    384
Gly Thr Cys Ala Tyr Ile Gln Arg Xaa Ala Val Tyr Ala Glu Asn Cys
        115                 120                 125
```

```
att tta gct gcc ttc agt ata tgt cag aag aag gca aac cta aga gca      432
Ile Leu Ala Ala Phe Ser Ile Cys Gln Lys Lys Ala Asn Leu Arg Ala
    130                 135                 140 cag                                                                   435
Gln
145

<210> SEQ ID NO 84
<211> LENGTH: 145
<212> TYPE: PRT
<213> ORGANISM: Homo sapiens
<220> FEATURE:
<221> NAME/KEY: misc_feature
<222> LOCATION: (104)..(104)
<223> OTHER INFORMATION: The 'Xaa' at location 104 stands for Gly, or
      Ala.
<220> FEATURE:
<221> NAME/KEY: misc_feature
<222> LOCATION: (121)..(121)
<223> OTHER INFORMATION: The 'Xaa' at location 121 stands for Gly, or
      Ala.

<400> SEQUENCE: 84

Asn Leu Gln Glu Thr Leu Lys Arg Val Ala Asn Cys Ser Ala Pro Cys
1               5                   10                  15

Pro Gln Asp Trp Ile Trp His Gly Glu Asn Cys Tyr Leu Phe Ser Ser
                20                  25                  30

Gly Ser Phe Asn Trp Glu Lys Ser Gln Glu Lys Cys Leu Ser Leu Asp
            35                  40                  45

Ala Lys Leu Leu Lys Ile Asn Ser Thr Ala Asp Leu Asp Phe Ile Gln
    50                  55                  60

Gln Ala Ile Ser Tyr Ser Ser Phe Pro Phe Trp Met Gly Leu Ser Arg
65                  70                  75                  80

Arg Asn Pro Ser Tyr Pro Trp Leu Trp Glu Asp Gly Ser Pro Leu Met
                85                  90                  95

Pro His Leu Phe Arg Val Arg Xaa Ala Val Ser Gln Thr Tyr Pro Ser
                100                 105                 110

Gly Thr Cys Ala Tyr Ile Gln Arg Xaa Ala Val Tyr Ala Glu Asn Cys
            115                 120                 125

Ile Leu Ala Ala Phe Ser Ile Cys Gln Lys Lys Ala Asn Leu Arg Ala
    130                 135                 140

Gln
145

<210> SEQ ID NO 85
<211> LENGTH: 1790
<212> TYPE: DNA
<213> ORGANISM: artificial sequence
<220> FEATURE:
<223> OTHER INFORMATION: Biotin-CTLD14-His
<220> FEATURE:
<221> NAME/KEY: CDS
<222> LOCATION: (1)..(42)
<220> FEATURE:
<221> NAME/KEY: CDS
<222> LOCATION: (1014)..(1787)

<400> SEQUENCE: 85 atg aga gtc aaa acc ttt gtg atc ttg tgc tgc gct ctg cag            42
Met Arg Val Lys Thr Phe Val Ile Leu Cys Cys Ala Leu Gln
1               5                   10 gtgagttaat tattttacta ttatttcaga aggtggccag acgatatcac gggccacctg    102
```

```
ataataagtg gtcgccaaaa cgcacagata tcgtaaattg tgccatttga tttgtcacgc    162 ccggggggc tacggaataa actacattta tttatttaaa aaatgaacct tagattatgt    222
aacttgtgat ttatttgcgt caaaagtagg caagatgaat ctatgtaaat acctgggcag    282
acttgcaata tcctatttca ccggtaaatc agcattgcaa tatgcaatgc atattcaaca    342
atatgtaaaa caattcgtaa agcatcatta gaaaatagac gaaagaaatt gcataaaatt    402
ataaccgcat tattaattta ttatgatatc tattaacaat tgctattgcc ttttttcgc    462 aaattataat cattttcata acctcgaggt agcattctgt tacattttaa tacattggta    522
tgtgattata acacgagctg ctcactgagt ttctcgccag atcttctcag tgggtcgcgt    582
taccgatcac gtgatagatt ctatgaagca ctgctcttgt tagggctagt gttagcaaat    642
tctttcaggt tgagtctgag agctcaccta cccatcggag cgtagctgga ataggctacc    702
agctaatagg tagggaaaac aaagctcgaa acaagctcaa gtaataacaa cataatgtga    762
ccataaaatc tcgtggtgta tgagatacaa ttatgtactt tcccacaaat gtttacataa    822
ttagaatgtt gttcaacttg cctaacgccc cagctagaac attcaattat tactattacc    882
actactaagg cagtatgtcc taactcgttc cagatcagcg ctaacttcga ttgaatgtgc    942
gaaatttata gctcaatatt ttagcactta tcgtattgat ttaagaaaaa attgttaaca   1002
ttttgtttca g tat gtc gct tat aca aat gca ggc gcc ggc acc ccg gtg   1052
             Tyr Val Ala Tyr Thr Asn Ala Gly Ala Gly Thr Pro Val
              15                  20                  25 acc gcc ccg ctg gcg ggc act atc tgg aag gtg ctg gcc agc gaa ggc   1100
Thr Ala Pro Leu Ala Gly Thr Ile Trp Lys Val Leu Ala Ser Glu Gly
         30                  35                  40 cag acg gtg gcc gca ggc gag gtg ctg ctg att ctg gaa gcc atg aag   1148
Gln Thr Val Ala Ala Gly Glu Val Leu Leu Ile Leu Glu Ala Met Lys
     45                  50                  55 atg gaa acc gaa atc cgc gcc gcg cag gcc ggg acc gtg cgc ggt atc   1196
Met Glu Thr Glu Ile Arg Ala Ala Gln Ala Gly Thr Val Arg Gly Ile
 60                  65                  70                  75 gcg gtg aaa gcc ggc gac gcg gtg gcg gtc ggc gac acc ctg atg acc   1244
Ala Val Lys Ala Gly Asp Ala Val Ala Val Gly Asp Thr Leu Met Thr
                 80                  85                  90 ctg gcg ggc tct gga tcc gat ctg tac gat gat gac gat aag gta cat   1292
Leu Ala Gly Ser Gly Ser Asp Leu Tyr Asp Asp Asp Asp Lys Val His
             95                 100                 105 caa aca agt ttg tac aaa aaa gca ggc tcc gaa ttc gcc ctt aat ctc   1340
Gln Thr Ser Leu Tyr Lys Lys Ala Gly Ser Glu Phe Ala Leu Asn Leu
         110                 115                 120 caa gaa aca ctg aag aga gta gca aat tgt tca gct cct tgt ccg caa   1388
Gln Glu Thr Leu Lys Arg Val Ala Asn Cys Ser Ala Pro Cys Pro Gln
     125                 130                 135 gac tgg atc tgg cat gga gaa aac tgt tac cta ttt tcc tcg ggc tca   1436
Asp Trp Ile Trp His Gly Glu Asn Cys Tyr Leu Phe Ser Ser Gly Ser
140                 145                 150                 155 ttt aac tgg gaa aag agc caa gag aag tgc ttg tct ttg gat gcc aag   1484
Phe Asn Trp Glu Lys Ser Gln Glu Lys Cys Leu Ser Leu Asp Ala Lys
                 160                 165                 170 ttg ctg aaa att aat agc aca gct gat ctg gac ttc atc cag caa gca   1532
Leu Leu Lys Ile Asn Ser Thr Ala Asp Leu Asp Phe Ile Gln Gln Ala
             175                 180                 185 att tcc tat tcc agt ttt cca ttc tgg atg ggg ctg tct cgg agg aac   1580
Ile Ser Tyr Ser Ser Phe Pro Phe Trp Met Gly Leu Ser Arg Arg Asn
         190                 195                 200 ccc agc tac cca tgg ctc tgg gag gac ggt tct cct ttg atg ccc cac   1628
```

-continued

```
Pro Ser Tyr Pro Trp Leu Trp Glu Asp Gly Ser Pro Leu Met Pro His
    205                 210                 215 tta ttt aga gtc cga ggc gct gtc tcc cag aca tac cct tca ggt acc      1676
Leu Phe Arg Val Arg Gly Ala Val Ser Gln Thr Tyr Pro Ser Gly Thr
220             225                 230                 235 tgt gca tat ata caa cga gga gct gtt tat gcg gaa aac tgc att tta      1724
Cys Ala Tyr Ile Gln Arg Gly Ala Val Tyr Ala Glu Asn Cys Ile Leu
            240                 245                 250 gct gcc ttc agt ata tgt cag aag aag gca aac cta aga gca cag cat      1772
Ala Ala Phe Ser Ile Cys Gln Lys Lys Ala Asn Leu Arg Ala Gln His
                255                 260                 265 cac cat cat cat cac taa                                              1790
His His His His His
        270
```

<210> SEQ ID NO 86
<211> LENGTH: 272
<212> TYPE: PRT
<213> ORGANISM: artificial sequence
<220> FEATURE:
<223> OTHER INFORMATION: Synthetic Construct

<400> SEQUENCE: 86

```
Met Arg Val Lys Thr Phe Val Ile Leu Cys Cys Ala Leu Gln Tyr Val
1               5                   10                  15

Ala Tyr Thr Asn Ala Gly Ala Gly Thr Pro Val Thr Ala Pro Leu Ala
            20                  25                  30

Gly Thr Ile Trp Lys Val Leu Ala Ser Glu Gly Gln Thr Val Ala Ala
        35                  40                  45

Gly Glu Val Leu Leu Ile Leu Glu Ala Met Lys Met Glu Thr Glu Ile
    50                  55                  60

Arg Ala Ala Gln Ala Gly Thr Val Arg Gly Ile Ala Val Lys Ala Gly
65                  70                  75                  80

Asp Ala Val Ala Val Gly Asp Thr Leu Met Thr Leu Ala Gly Ser Gly
                85                  90                  95

Ser Asp Leu Tyr Asp Asp Asp Lys Val His Gln Thr Ser Leu Tyr
            100                 105                 110

Lys Lys Ala Gly Ser Glu Phe Ala Leu Asn Leu Gln Glu Thr Leu Lys
        115                 120                 125

Arg Val Ala Asn Cys Ser Ala Pro Cys Pro Gln Asp Trp Ile Trp His
    130                 135                 140

Gly Glu Asn Cys Tyr Leu Phe Ser Ser Gly Ser Phe Asn Trp Glu Lys
145                 150                 155                 160

Ser Gln Glu Lys Cys Leu Ser Leu Asp Ala Lys Leu Leu Lys Ile Asn
                165                 170                 175

Ser Thr Ala Asp Leu Asp Phe Ile Gln Gln Ala Ile Ser Tyr Ser Ser
            180                 185                 190

Phe Pro Phe Trp Met Gly Leu Ser Arg Arg Asn Pro Ser Tyr Pro Trp
        195                 200                 205

Leu Trp Glu Asp Gly Ser Pro Leu Met Pro His Leu Phe Arg Val Arg
    210                 215                 220

Gly Ala Val Ser Gln Thr Tyr Pro Ser Gly Thr Cys Ala Tyr Ile Gln
225                 230                 235                 240

Arg Gly Ala Val Tyr Ala Glu Asn Cys Ile Leu Ala Ala Phe Ser Ile
                245                 250                 255

Cys Gln Lys Lys Ala Asn Leu Arg Ala Gln His His His His His His
            260                 265                 270
```

-continued

<210> SEQ ID NO 87
<211> LENGTH: 21
<212> TYPE: DNA
<213> ORGANISM: artificial sequence
<220> FEATURE:
<223> OTHER INFORMATION: CTLD14-F

<400> SEQUENCE: 87
aatctccaag aaacactgaa g                                          21

<210> SEQ ID NO 88
<211> LENGTH: 21
<212> TYPE: DNA
<213> ORGANISM: artificial sequence
<220> FEATURE:
<223> OTHER INFORMATION: CTLD14s-R

<400> SEQUENCE: 88
tcactgtgct cttaggtttg c                                          21

<210> SEQ ID NO 89
<211> LENGTH: 5
<212> TYPE: PRT
<213> ORGANISM: artificial sequence
<220> FEATURE:
<223> OTHER INFORMATION: enterokinase recognition site

<400> SEQUENCE: 89

Asp Asp Asp Asp Lys
1               5

<210> SEQ ID NO 90
<211> LENGTH: 31
<212> TYPE: PRT
<213> ORGANISM: artificial sequence
<220> FEATURE:
<223> OTHER INFORMATION: partial sequence 1

<400> SEQUENCE: 90

Val Ala Asn Cys Ser Ala Pro Cys Pro Gln Asp Trp Ile Trp His Gly
1               5                   10                  15

Glu Asn Cys Tyr Leu Phe Ser Ser Gly Ser Phe Asn Trp Glu Lys
            20                  25                  30

<210> SEQ ID NO 91
<211> LENGTH: 27
<212> TYPE: PRT
<213> ORGANISM: artificial sequence
<220> FEATURE:
<223> OTHER INFORMATION: partial sequence 2

<400> SEQUENCE: 91

Ile Asn Ser Thr Ala Asp Leu Asp Phe Ile Gln Gln Ala Ile Ser Tyr
1               5                   10                  15

Ser Ser Phe Pro Phe Trp Met Gly Leu Ser Arg
            20                  25

<210> SEQ ID NO 92
<211> LENGTH: 20
<212> TYPE: PRT
<213> ORGANISM: artificial sequence
<220> FEATURE:
<223> OTHER INFORMATION: partial sequence 3

<400> SEQUENCE: 92

-continued

Asn Pro Ser Tyr Pro Trp Leu Trp Glu Asp Gly Ser Pro Leu Met Pro
1               5                   10                  15

His Leu Phe Arg
            20

<210> SEQ ID NO 93
<211> LENGTH: 22
<212> TYPE: PRT
<213> ORGANISM: artificial sequence
<220> FEATURE:
<223> OTHER INFORMATION: partial sequence 4

<400> SEQUENCE: 93

Val Leu Ala Ser Glu Gly Gln Thr Val Ala Ala Gly Glu Val Leu Leu
1               5                   10                  15

Ile Leu Glu Ala Met Lys
            20

<210> SEQ ID NO 94
<211> LENGTH: 14
<212> TYPE: PRT
<213> ORGANISM: artificial sequence
<220> FEATURE:
<223> OTHER INFORMATION: partial sequence 5

<400> SEQUENCE: 94

Ala Gly Ser Glu Phe Ala Leu Asn Leu Gln Glu Thr Leu Lys
1               5                   10

<210> SEQ ID NO 95
<211> LENGTH: 17
<212> TYPE: PRT
<213> ORGANISM: artificial sequence
<220> FEATURE:
<223> OTHER INFORMATION: partial sequence 6

<400> SEQUENCE: 95

Gly Ala Val Ser Gln Thr Tyr Pro Ser Gly Thr Cys Ala Tyr Ile Gln
1               5                   10                  15

Arg

<210> SEQ ID NO 96
<211> LENGTH: 930
<212> TYPE: DNA
<213> ORGANISM: Homo sapiens
<220> FEATURE:
<221> NAME/KEY: CDS
<222> LOCATION: (1)..(930)

<400> SEQUENCE: 96 gct caa aac atc aca gcc cgg att ggc gag cca ctg gtg ctg aag tgt      48
Ala Gln Asn Ile Thr Ala Arg Ile Gly Glu Pro Leu Val Leu Lys Cys
1               5                   10                  15 aag ggg gcc ccc aag aaa cca ccc cag cgg ctg gaa tgg aaa ctg aac      96
Lys Gly Ala Pro Lys Lys Pro Pro Gln Arg Leu Glu Trp Lys Leu Asn
                20                  25                  30 aca ggc cgg aca gaa gct tgg aag gtc ctg tct ccc cag gga gga ggc     144
Thr Gly Arg Thr Glu Ala Trp Lys Val Leu Ser Pro Gln Gly Gly Gly
            35                  40                  45 ccc tgg gac agt gtg gct cgt gtc ctt ccc aac ggc tcc ctc ttc ctt     192
Pro Trp Asp Ser Val Ala Arg Val Leu Pro Asn Gly Ser Leu Phe Leu
        50                  55                  60 ccg gct gtc ggg atc cag gat gag ggg att ttc cgg tgc cag gca atg     240

```
                                                                     -continued
Pro Ala Val Gly Ile Gln Asp Glu Gly Ile Phe Arg Cys Gln Ala Met
 65                  70                  75                  80 aac agg aat gga aag gag acc aag tcc aac tac cga gtc cgt gtc tac         288
Asn Arg Asn Gly Lys Glu Thr Lys Ser Asn Tyr Arg Val Arg Val Tyr
                 85                  90                  95 cag att cct ggg aag cca gaa att gta gat tct gcc tct gaa ctc acg         336
Gln Ile Pro Gly Lys Pro Glu Ile Val Asp Ser Ala Ser Glu Leu Thr
            100                 105                 110 gct ggt gtt ccc aat aag gtg ggg aca tgt gtg tca gag gga agc tac         384
Ala Gly Val Pro Asn Lys Val Gly Thr Cys Val Ser Glu Gly Ser Tyr
        115                 120                 125 cct gca ggg act ctt agc tgg cac ttg gat ggg aag ccc ctg gtg cct         432
Pro Ala Gly Thr Leu Ser Trp His Leu Asp Gly Lys Pro Leu Val Pro
    130                 135                 140 aat gag aag gga gta tct gtg aag gaa cag acc agg aga cac cct gag         480
Asn Glu Lys Gly Val Ser Val Lys Glu Gln Thr Arg Arg His Pro Glu
145                 150                 155                 160 aca ggg ctc ttc aca ctg cag tcg gag cta atg gtg acc cca gcc cgg         528
Thr Gly Leu Phe Thr Leu Gln Ser Glu Leu Met Val Thr Pro Ala Arg
                165                 170                 175 gga gga gat ccc cgt ccc acc ttc tcc tgt agc ttc agc cca ggc ctt         576
Gly Gly Asp Pro Arg Pro Thr Phe Ser Cys Ser Phe Ser Pro Gly Leu
            180                 185                 190 ccc cga cac cgg gcc ttg cgc aca gcc ccc atc cag ccc cgt gtc tgg         624
Pro Arg His Arg Ala Leu Arg Thr Ala Pro Ile Gln Pro Arg Val Trp
        195                 200                 205 gag cct gtg cct ctg gag gag gtc caa ttg gtg gtg gag cca gaa ggt         672
Glu Pro Val Pro Leu Glu Glu Val Gln Leu Val Val Glu Pro Glu Gly
    210                 215                 220 gga gca gta gct cct ggt gga acc gta acc ctg acc tgt gaa gtc cct         720
Gly Ala Val Ala Pro Gly Gly Thr Val Thr Leu Thr Cys Glu Val Pro
225                 230                 235                 240 gcc cag ccc tct cct caa atc cac tgg atg aag gat ggt gtg ccc ttg         768
Ala Gln Pro Ser Pro Gln Ile His Trp Met Lys Asp Gly Val Pro Leu
                245                 250                 255 ccc ctt ccc ccc agc cct gtg ctg atc ctc cct gag ata ggg cct cag         816
Pro Leu Pro Pro Ser Pro Val Leu Ile Leu Pro Glu Ile Gly Pro Gln
            260                 265                 270 gac cag gga acc tac agc tgt gtg gcc acc cat tcc agc cac ggg ccc         864
Asp Gln Gly Thr Tyr Ser Cys Val Ala Thr His Ser Ser His Gly Pro
        275                 280                 285 cag gaa agc cgt gct gtc agc atc agc atc atc gaa cca ggc gag gag         912
Gln Glu Ser Arg Ala Val Ser Ile Ser Ile Ile Glu Pro Gly Glu Glu
    290                 295                 300 ggg cca act gca ggc tct                                                 930
Gly Pro Thr Ala Gly Ser
305                 310

<210> SEQ ID NO 97
<211> LENGTH: 310
<212> TYPE: PRT
<213> ORGANISM: Homo sapiens

<400> SEQUENCE: 97

Ala Gln Asn Ile Thr Ala Arg Ile Gly Glu Pro Leu Val Leu Lys Cys
 1               5                  10                  15

Lys Gly Ala Pro Lys Lys Pro Pro Gln Arg Leu Glu Trp Lys Leu Asn
                20                  25                  30

Thr Gly Arg Thr Glu Ala Trp Lys Val Leu Ser Pro Gln Gly Gly Gly
        35                  40                  45
```

-continued

```
Pro Trp Asp Ser Val Ala Arg Val Leu Pro Asn Gly Ser Leu Phe Leu
    50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys Pro Glu Ile Val Asp Ser Ala Ser Glu Leu Thr
            100                 105                 110

Ala Gly Val Pro Asn Lys Val Gly Thr Cys Val Ser Glu Gly Ser Tyr
            115                 120                 125

Pro Ala Gly Thr Leu Ser Trp His Leu Asp Gly Lys Pro Leu Val Pro
        130                 135                 140

Asn Glu Lys Gly Val Ser Val Lys Glu Gln Thr Arg Arg His Pro Glu
145                 150                 155                 160

Thr Gly Leu Phe Thr Leu Gln Ser Glu Leu Met Val Thr Pro Ala Arg
                165                 170                 175

Gly Gly Asp Pro Arg Pro Thr Phe Ser Cys Ser Phe Ser Pro Gly Leu
            180                 185                 190

Pro Arg His Arg Ala Leu Arg Thr Ala Pro Ile Gln Pro Arg Val Trp
        195                 200                 205

Glu Pro Val Pro Leu Glu Glu Val Gln Leu Val Val Glu Pro Glu Gly
    210                 215                 220

Gly Ala Val Ala Pro Gly Gly Thr Val Thr Leu Thr Cys Glu Val Pro
225                 230                 235                 240

Ala Gln Pro Ser Pro Gln Ile His Trp Met Lys Asp Gly Val Pro Leu
                245                 250                 255

Pro Leu Pro Pro Ser Pro Val Leu Ile Leu Pro Glu Ile Gly Pro Gln
            260                 265                 270

Asp Gln Gly Thr Tyr Ser Cys Val Ala Thr His Ser Ser His Gly Pro
        275                 280                 285

Gln Glu Ser Arg Ala Val Ser Ile Ser Ile Ile Glu Pro Gly Glu Glu
    290                 295                 300

Gly Pro Thr Ala Gly Ser
305                 310

<210> SEQ ID NO 98
<211> LENGTH: 15
<212> TYPE: PRT
<213> ORGANISM: artificial sequence
<220> FEATURE:
<223> OTHER INFORMATION: biotinylated amino acid sequence

<400> SEQUENCE: 98

Gly Leu Asn Asp Ile Phe Glu Ala Gln Lys Ile Glu Trp His Glu
1               5                   10                  15

<210> SEQ ID NO 99
<211> LENGTH: 2339
<212> TYPE: DNA
<213> ORGANISM: artificial sequence
<220> FEATURE:
<223> OTHER INFORMATION: Biotin-RAGE
<220> FEATURE:
<221> NAME/KEY: CDS
<222> LOCATION: (1)..(42)
<220> FEATURE:
<221> NAME/KEY: CDS
<222> LOCATION: (1014)..(2336)
```

<400> SEQUENCE: 99

```
atg aga gtc aaa acc ttt gtg atc ttg tgc tgc gct ctg cag              42
Met Arg Val Lys Thr Phe Val Ile Leu Cys Cys Ala Leu Gln
1               5                   10 gtgagttaat tattttacta ttatttcaga aggtggccag acgatatcac gggccacctg   102
ataataagtg gtcgccaaaa cgcacagata tcgtaaattg tgccatttga tttgtcacgc   162
ccgggggggc tacggaataa actacattta tttatttaaa aaatgaacct tagattatgt   222
aacttgtgat ttatttgcgt caaaagtagg caagatgaat ctatgtaaat acctgggcag   282
acttgcaata tcctatttca ccggtaaatc agcattgcaa tatgcaatgc atattcaaca   342
atatgtaaaa caattcgtaa agcatcatta gaaaatagac gaaagaaatt gcataaaatt   402
ataaccgcat tattaattta ttatgatatc tattaacaat tgctattgcc ttttttcgc    462 aaattataat cattttcata acctcgaggt agcattctgt tacattttaa tacattggta   522
tgtgattata acacgagctg ctcactgagt ttctcgccag atcttctcag tgggtcgcgt   582
taccgatcac gtgatagatt ctatgaagca ctgctcttgt tagggctagt gttagcaaat   642
tctttcaggt tgagtctgag agctcaccta cccatcggag cgtagctgga ataggctacc   702
agctaatagg tagggaaaac aaagctcgaa acaagctcaa gtaataacaa cataatgtga   762
ccataaaatc tcgtggtgta tgagatacaa ttatgtactt tcccacaaat gtttacataa   822
ttagaatgtt gttcaacttg cctaacgccc cagctagaac attcaattat tactattacc   882
actactaagg cagtatgtcc taactcgttc cagatcagcg ctaacttcga ttgaatgtgc   942
gaaatttata gctcaatatt ttagcactta tcgtattgat ttaagaaaaa attgttaaca  1002
ttttgtttca g tat gtc gct tat aca aat gca ggc cat cat cat cat cat  1052
             Tyr Val Ala Tyr Thr Asn Ala Gly His His His His His
              15                  20                  25 cat cat cat cat cac agc agc ggc cat atc gac gac gac gac aag cat   1100
His His His His His Ser Ser Gly His Ile Asp Asp Asp Asp Lys His
             30                  35                  40 atg gct caa aac atc aca gcc cgg att ggc gag cca ctg gtg ctg aag   1148
Met Ala Gln Asn Ile Thr Ala Arg Ile Gly Glu Pro Leu Val Leu Lys
 45                  50                  55 tgt aag ggg gcc ccc aag aaa cca ccc cag cgg ctg gaa tgg aaa ctg   1196
Cys Lys Gly Ala Pro Lys Lys Pro Pro Gln Arg Leu Glu Trp Lys Leu
 60                  65                  70                  75 aac aca ggc cgg aca gaa gct tgg aag gtc ctg tct ccc cag gga gga   1244
Asn Thr Gly Arg Thr Glu Ala Trp Lys Val Leu Ser Pro Gln Gly Gly
                 80                  85                  90 ggc ccc tgg gac agt gtg gct cgt gtc ctt ccc aac ggc tcc ctc ttc   1292
Gly Pro Trp Asp Ser Val Ala Arg Val Leu Pro Asn Gly Ser Leu Phe
             95                  100                 105 ctt ccg gct gtc ggg atc cag gat gag ggg att ttc cgg tgc cag gca   1340
Leu Pro Ala Val Gly Ile Gln Asp Glu Gly Ile Phe Arg Cys Gln Ala
             110                 115                 120 atg aac agg aat gga aag gag acc aag tcc aac tac cga gtc cgt gtc   1388
Met Asn Arg Asn Gly Lys Glu Thr Lys Ser Asn Tyr Arg Val Arg Val
             125                 130                 135 tac cag att cct ggg aag cca gaa att gta gat tct gcc tct gaa ctc   1436
Tyr Gln Ile Pro Gly Lys Pro Glu Ile Val Asp Ser Ala Ser Glu Leu
140                 145                 150                 155 acg gct ggt gtt ccc aat aag gtg ggg aca tgt gtg tca gag gga agc   1484
Thr Ala Gly Val Pro Asn Lys Val Gly Thr Cys Val Ser Glu Gly Ser
                 160                 165                 170 tac cct gca ggg act ctt agc tgg cac ttg gat ggg aag ccc ctg gtg   1532
```

```
                Tyr Pro Ala Gly Thr Leu Ser Trp His Leu Asp Gly Lys Pro Leu Val
                            175                 180                 185 cct aat gag aag gga gta tct gtg aag gaa cag acc agg aga cac cct       1580
Pro Asn Glu Lys Gly Val Ser Val Lys Glu Gln Thr Arg Arg His Pro
        190                 195                 200 gag aca ggg ctc ttc aca ctg cag tcg gag cta atg gtg acc cca gcc       1628
Glu Thr Gly Leu Phe Thr Leu Gln Ser Glu Leu Met Val Thr Pro Ala
205                 210                 215 cgg gga gga gat ccc cgt ccc acc ttc tcc tgt agc ttc agc cca ggc       1676
Arg Gly Gly Asp Pro Arg Pro Thr Phe Ser Cys Ser Phe Ser Pro Gly
220                 225                 230                 235 ctt ccc cga cac cgg gcc ttg cgc aca gcc ccc atc cag ccc cgt gtc       1724
Leu Pro Arg His Arg Ala Leu Arg Thr Ala Pro Ile Gln Pro Arg Val
            240                 245                 250 tgg gag cct gtg cct ctg gag gag gtc caa ttg gtg gtg gag cca gaa       1772
Trp Glu Pro Val Pro Leu Glu Glu Val Gln Leu Val Val Glu Pro Glu
                255                 260                 265 ggt gga gca gta gct cct ggt gga acc gta acc ctg acc tgt gaa gtc       1820
Gly Gly Ala Val Ala Pro Gly Gly Thr Val Thr Leu Thr Cys Glu Val
            270                 275                 280 cct gcc cag ccc tct cct caa atc cac tgg atg aag gat ggt gtg ccc       1868
Pro Ala Gln Pro Ser Pro Gln Ile His Trp Met Lys Asp Gly Val Pro
285                 290                 295 ttg ccc ctt ccc ccc agc cct gtg ctg atc ctc cct gag ata ggg cct       1916
Leu Pro Leu Pro Pro Ser Pro Val Leu Ile Leu Pro Glu Ile Gly Pro
300                 305                 310                 315 cag gac cag gga acc tac agc tgt gtg gcc acc cat tcc agc cac ggg       1964
Gln Asp Gln Gly Thr Tyr Ser Cys Val Ala Thr His Ser Ser His Gly
                320                 325                 330 ccc cag gaa agc cgt gct gtc agc atc agc atc gaa cca ggc gag           2012
Pro Gln Glu Ser Arg Ala Val Ser Ile Ser Ile Glu Pro Gly Glu
            335                 340                 345 gag ggg cca act gca ggc tct aga tct ggc gcc ggc acc ccg gtg acc       2060
Glu Gly Pro Thr Ala Gly Ser Arg Ser Gly Ala Gly Thr Pro Val Thr
                350                 355                 360 gcc ccg ctg gcg ggc act atc tgg aag gtg ctg gcc agc gaa ggc cag       2108
Ala Pro Leu Ala Gly Thr Ile Trp Lys Val Leu Ala Ser Glu Gly Gln
365                 370                 375 acg gtg gcc gca ggc gag gtg ctg ctg att ctg gaa gcc atg aag atg       2156
Thr Val Ala Ala Gly Glu Val Leu Leu Ile Leu Glu Ala Met Lys Met
380                 385                 390                 395 gaa acc gaa atc cgc gcc gcg cag gcc ggg acc gtg cgc ggt atc gcg       2204
Glu Thr Glu Ile Arg Ala Ala Gln Ala Gly Thr Val Arg Gly Ile Ala
                400                 405                 410 gtg aaa gcc ggc gac gcg gtg gcg gtc ggc gac acc ctg atg acc ctg       2252
Val Lys Ala Gly Asp Ala Val Ala Val Gly Asp Thr Leu Met Thr Leu
            415                 420                 425 gcg ggt acc aag ctt ggg ccc gaa caa aaa ctc atc tca gaa gag gat       2300
Ala Gly Thr Lys Leu Gly Pro Glu Gln Lys Leu Ile Ser Glu Glu Asp
                430                 435                 440 ctg aat agc gcc gtc gac cat cat cat cat cat cat taa                   2339
Leu Asn Ser Ala Val Asp His His His His His His
        445                 450                 455

<210> SEQ ID NO 100
<211> LENGTH: 455
<212> TYPE: PRT
<213> ORGANISM: artificial sequence
<220> FEATURE:
<223> OTHER INFORMATION: Synthetic Construct
```

<400> SEQUENCE: 100

```
Met Arg Val Lys Thr Phe Val Ile Leu Cys Cys Ala Leu Gln Tyr Val
1               5                   10                  15
Ala Tyr Thr Asn Ala Gly His His His His His His His His
            20                  25                  30
Ser Ser Gly His Ile Asp Asp Asp Lys His Met Ala Gln Asn Ile
        35                  40                  45
Thr Ala Arg Ile Gly Glu Pro Leu Val Leu Lys Cys Lys Gly Ala Pro
    50                  55                  60
Lys Lys Pro Pro Gln Arg Leu Glu Trp Lys Leu Asn Thr Gly Arg Thr
65                  70                  75                  80
Glu Ala Trp Lys Val Leu Ser Pro Gln Gly Gly Pro Trp Asp Ser
                85                  90                  95
Val Ala Arg Val Leu Pro Asn Gly Ser Leu Phe Leu Pro Ala Val Gly
            100                 105                 110
Ile Gln Asp Glu Gly Ile Phe Arg Cys Gln Ala Met Asn Arg Asn Gly
        115                 120                 125
Lys Glu Thr Lys Ser Asn Tyr Arg Val Arg Val Tyr Gln Ile Pro Gly
130                 135                 140
Lys Pro Glu Ile Val Asp Ser Ala Ser Glu Leu Thr Ala Gly Val Pro
145                 150                 155                 160
Asn Lys Val Gly Thr Cys Val Ser Glu Gly Ser Tyr Pro Ala Gly Thr
                165                 170                 175
Leu Ser Trp His Leu Asp Gly Lys Pro Leu Val Pro Asn Glu Lys Gly
            180                 185                 190
Val Ser Val Lys Glu Gln Thr Arg Arg His Pro Glu Thr Gly Leu Phe
        195                 200                 205
Thr Leu Gln Ser Glu Leu Met Val Thr Pro Ala Arg Gly Gly Asp Pro
210                 215                 220
Arg Pro Thr Phe Ser Cys Ser Phe Ser Pro Gly Leu Pro Arg His Arg
225                 230                 235                 240
Ala Leu Arg Thr Ala Pro Ile Gln Pro Arg Val Trp Glu Pro Val Pro
                245                 250                 255
Leu Glu Glu Val Gln Leu Val Val Glu Pro Glu Gly Gly Ala Val Ala
            260                 265                 270
Pro Gly Gly Thr Val Thr Leu Thr Cys Glu Val Pro Ala Gln Pro Ser
        275                 280                 285
Pro Gln Ile His Trp Met Lys Asp Gly Val Pro Leu Pro Leu Pro Pro
290                 295                 300
Ser Pro Val Leu Ile Leu Pro Glu Ile Gly Pro Gln Asp Gln Gly Thr
305                 310                 315                 320
Tyr Ser Cys Val Ala Thr His Ser Ser His Gly Pro Gln Glu Ser Arg
                325                 330                 335
Ala Val Ser Ile Ser Ile Ile Glu Pro Gly Glu Glu Gly Pro Thr Ala
            340                 345                 350
Gly Ser Arg Ser Gly Ala Gly Thr Pro Val Thr Ala Pro Leu Ala Gly
        355                 360                 365
Thr Ile Trp Lys Val Leu Ala Ser Glu Gly Gln Thr Val Ala Ala Gly
370                 375                 380
Glu Val Leu Leu Ile Leu Glu Ala Met Lys Met Glu Thr Glu Ile Arg
385                 390                 395                 400
Ala Ala Gln Ala Gly Thr Val Arg Gly Ile Ala Val Lys Ala Gly Asp
                405                 410                 415
```

```
Ala Val Ala Val Gly Asp Thr Leu Met Thr Leu Ala Gly Thr Lys Leu
                420                 425                 430

Gly Pro Glu Gln Lys Leu Ile Ser Glu Glu Asp Leu Asn Ser Ala Val
            435                 440                 445

Asp His His His His His His
        450                 455

<210> SEQ ID NO 101
<211> LENGTH: 1212
<212> TYPE: DNA
<213> ORGANISM: Homo sapiens
<220> FEATURE:
<221> NAME/KEY: CDS
<222> LOCATION: (1)..(1212)
<220> FEATURE:
<221> NAME/KEY: misc_feature
<222> LOCATION: (114)..(114)
<223> OTHER INFORMATION: The 'Xaa' at location 114 stands for Arg, or
      Gln.
<220> FEATURE:
<221> NAME/KEY: misc_feature
<222> LOCATION: (117)..(117)
<223> OTHER INFORMATION: The 'Xaa' at location 117 stands for Val, or
      Xaa.
<220> FEATURE:
<221> NAME/KEY: misc_feature
<222> LOCATION: (228)..(228)
<223> OTHER INFORMATION: The 'Xaa' at location 228 stands for Ser, Asn,
      Arg, or His.
<220> FEATURE:
<221> NAME/KEY: misc_feature
<222> LOCATION: (272)..(272)
<223> OTHER INFORMATION: The 'Xaa' at location 272 stands for Met, or
      Ile.

<400> SEQUENCE: 101 atg gca gcc gga aca gca gtt gga gcc tgg gtg ctg gtc ctc agt ctg      48
Met Ala Ala Gly Thr Ala Val Gly Ala Trp Val Leu Val Leu Ser Leu
1               5                   10                  15 tgg ggg gca gta gta ggt gct caa aac atc aca gcc cgg att ggc gag      96
Trp Gly Ala Val Val Gly Ala Gln Asn Ile Thr Ala Arg Ile Gly Glu
            20                  25                  30 cca ctg gtg ctg aag tgt aag ggg gcc ccc aag aaa cca ccc cag cgg     144
Pro Leu Val Leu Lys Cys Lys Gly Ala Pro Lys Lys Pro Pro Gln Arg
        35                  40                  45 ctg gaa tgg aaa ctg aac aca ggc cgg aca gaa gct tgg aag gtc ctg     192
Leu Glu Trp Lys Leu Asn Thr Gly Arg Thr Glu Ala Trp Lys Val Leu
    50                  55                  60 tct ccc cag gga gga ggc ccc tgg gac agt gtg gct cgt gtc ctt ccc     240
Ser Pro Gln Gly Gly Gly Pro Trp Asp Ser Val Ala Arg Val Leu Pro
65                  70                  75                  80 aac ggc tcc ctc ttc ctt ccg gct gtc ggg atc cag gat gag ggg att     288
Asn Gly Ser Leu Phe Leu Pro Ala Val Gly Ile Gln Asp Glu Gly Ile
                85                  90                  95 ttc cgg tgc cag gca atg aac agg aat gga aag gag acc aag tcc aac     336
Phe Arg Cys Gln Ala Met Asn Arg Asn Gly Lys Glu Thr Lys Ser Asn
            100                 105                 110 tac cra gtc cgt gty tac cag att cct ggg aag cca gaa att gta gat     384
Tyr Xaa Val Arg Xaa Tyr Gln Ile Pro Gly Lys Pro Glu Ile Val Asp
        115                 120                 125 tct gcc tct gaa ctc acg gct ggt gtt ccc aat aag gtg ggg aca tgt     432
Ser Ala Ser Glu Leu Thr Ala Gly Val Pro Asn Lys Val Gly Thr Cys
    130                 135                 140 gtg tca gag gga agc tac cct gca ggg act ctt agc tgg cac ttg gat     480
Val Ser Glu Gly Ser Tyr Pro Ala Gly Thr Leu Ser Trp His Leu Asp
```

```
                    145                 150                 155                 160
ggg aag ccc ctg gtg cct aat gag aag gga gta tct gtg aag gaa cag          528
Gly Lys Pro Leu Val Pro Asn Glu Lys Gly Val Ser Val Lys Glu Gln
                165                 170                 175 acc agg aga cac cct gag aca ggg ctc ttc aca ctg cag tcg gag cta          576
Thr Arg Arg His Pro Glu Thr Gly Leu Phe Thr Leu Gln Ser Glu Leu
            180                 185                 190 atg gtg acc cca gcc cgg gga gga gat ccc cgt ccc acc ttc tcc tgt          624
Met Val Thr Pro Ala Arg Gly Gly Asp Pro Arg Pro Thr Phe Ser Cys
            195                 200                 205 agc ttc agc cca ggc ctt ccc cga cac cgg gcc ttg cgc aca gcc ccc          672
Ser Phe Ser Pro Gly Leu Pro Arg His Arg Ala Leu Arg Thr Ala Pro
        210                 215                 220 atc cag ccc mrt gtc tgg gag cct gtg cct ctg gag gag gtc caa ttg          720
Ile Gln Pro Xaa Val Trp Glu Pro Val Pro Leu Glu Glu Val Gln Leu
225                 230                 235                 240 gtg gtg gag cca gaa ggt gga gca gta gct cct ggt gga acc gta acc          768
Val Val Glu Pro Glu Gly Gly Ala Val Ala Pro Gly Gly Thr Val Thr
                245                 250                 255 ctg acc tgt gaa gtc cct gcc cag ccc tct cct caa atc cac tgg ats          816
Leu Thr Cys Glu Val Pro Ala Gln Pro Ser Pro Gln Ile His Trp Xaa
            260                 265                 270 aag gat ggt gtg ccc ttg ccc ctt ccc ccc agc cct gtg ctg atc ctc          864
Lys Asp Gly Val Pro Leu Pro Leu Pro Pro Ser Pro Val Leu Ile Leu
        275                 280                 285 cct gag ata ggg cct cag gac cag gga acc tac agc tgt gtg gcc acc          912
Pro Glu Ile Gly Pro Gln Asp Gln Gly Thr Tyr Ser Cys Val Ala Thr
    290                 295                 300 cat tcc agc cac ggg ccc cag gaa agc cgt gct gtc agc atc agc atc          960
His Ser Ser His Gly Pro Gln Glu Ser Arg Ala Val Ser Ile Ser Ile
305                 310                 315                 320 atc gaa cca ggc gag gag ggg cca act gca ggc tct gtg gga gga tca         1008
Ile Glu Pro Gly Glu Glu Gly Pro Thr Ala Gly Ser Val Gly Gly Ser
                325                 330                 335 ggg ctg gga act cta gcc ctg gcc ctg ggg atc ctg gga ggc ctg ggg         1056
Gly Leu Gly Thr Leu Ala Leu Ala Leu Gly Ile Leu Gly Gly Leu Gly
            340                 345                 350 aca gcc gcc ctg ctc att ggg gtc atc ttg tgg caa agg cgg caa cgc         1104
Thr Ala Ala Leu Leu Ile Gly Val Ile Leu Trp Gln Arg Arg Gln Arg
        355                 360                 365 cga gga gag gag agg aag gcc cca gaa aac cag gag gaa gag gag gag         1152
Arg Gly Glu Glu Arg Lys Ala Pro Glu Asn Gln Glu Glu Glu Glu Glu
    370                 375                 380 cgt gca gaa ctg aat cag tcg gag gaa cct gag gca ggc gag agt agt         1200
Arg Ala Glu Leu Asn Gln Ser Glu Glu Pro Glu Ala Gly Glu Ser Ser
385                 390                 395                 400 act gga ggg cct                                                         1212
Thr Gly Gly Pro <210> SEQ ID NO 102
<211> LENGTH: 404
<212> TYPE: PRT
<213> ORGANISM: Homo sapiens
<220> FEATURE:
<221> NAME/KEY: misc_feature
<222> LOCATION: (114)..(114)
<223> OTHER INFORMATION: The 'Xaa' at location 114 stands for Arg, or
      Gln.
<220> FEATURE:
<221> NAME/KEY: misc_feature
<222> LOCATION: (117)..(117)
<223> OTHER INFORMATION: The 'Xaa' at location 117 stands for Val, or
```

```
      Xaa.
<220> FEATURE:
<221> NAME/KEY: misc_feature
<222> LOCATION: (228)..(228)
<223> OTHER INFORMATION: The 'Xaa' at location 228 stands for Ser, Asn,
      Arg, or His.
<220> FEATURE:
<221> NAME/KEY: misc_feature
<222> LOCATION: (272)..(272)
<223> OTHER INFORMATION: The 'Xaa' at location 272 stands for Met, or
      Ile.

<400> SEQUENCE: 102

Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
        35                  40                  45

Leu Glu Trp Lys Leu Asn Thr Gly Arg Thr Glu Ala Trp Lys Val Leu
    50                  55                  60

Ser Pro Gln Gly Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Gln Ala Met Asn Arg Asn Gly Lys Glu Thr Lys Ser Asn
            100                 105                 110

Tyr Xaa Val Arg Xaa Tyr Gln Ile Pro Gly Lys Pro Glu Ile Val Asp
        115                 120                 125

Ser Ala Ser Glu Leu Thr Ala Gly Val Pro Asn Lys Val Gly Thr Cys
130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
                165                 170                 175

Thr Arg Arg His Pro Glu Thr Gly Leu Phe Thr Leu Gln Ser Glu Leu
            180                 185                 190

Met Val Thr Pro Ala Arg Gly Gly Asp Pro Arg Pro Thr Phe Ser Cys
        195                 200                 205

Ser Phe Ser Pro Gly Leu Pro Arg His Arg Ala Leu Arg Thr Ala Pro
    210                 215                 220

Ile Gln Pro Xaa Val Trp Glu Pro Val Pro Leu Glu Glu Val Gln Leu
225                 230                 235                 240

Val Val Glu Pro Glu Gly Gly Ala Val Ala Pro Gly Gly Thr Val Thr
                245                 250                 255

Leu Thr Cys Glu Val Pro Ala Gln Pro Ser Pro Gln Ile His Trp Xaa
            260                 265                 270

Lys Asp Gly Val Pro Leu Pro Leu Pro Pro Ser Pro Val Leu Ile Leu
        275                 280                 285

Pro Glu Ile Gly Pro Gln Asp Gln Gly Thr Tyr Ser Cys Val Ala Thr
    290                 295                 300

His Ser Ser His Gly Pro Gln Glu Ser Arg Ala Val Ser Ile Ser Ile
305                 310                 315                 320

Ile Glu Pro Gly Glu Glu Gly Pro Thr Ala Gly Ser Val Gly Gly Ser
                325                 330                 335

Gly Leu Gly Thr Leu Ala Leu Ala Leu Gly Ile Leu Gly Gly Leu Gly
            340                 345                 350
```

Thr Ala Ala Leu Leu Ile Gly Val Ile Leu Trp Gln Arg Arg Gln Arg
        355                 360                 365

Arg Gly Glu Glu Arg Lys Ala Pro Glu Asn Gln Glu Glu Glu Glu
    370                 375                 380

Arg Ala Glu Leu Asn Gln Ser Glu Glu Pro Ala Gly Glu Ser Ser
385                 390                 395                 400

Thr Gly Gly Pro

<210> SEQ ID NO 103
<211> LENGTH: 17
<212> TYPE: PRT
<213> ORGANISM: artificial sequence
<220> FEATURE:
<223> OTHER INFORMATION: tryptic fragments of bovine RAGE polypeptide

<400> SEQUENCE: 103

His Met Ala Gln Asn Ile Thr Ala Arg Ile Gly Glu Pro Leu Val Leu
1               5                   10                  15

Lys

<210> SEQ ID NO 104
<211> LENGTH: 38
<212> TYPE: PRT
<213> ORGANISM: artificial sequence
<220> FEATURE:
<223> OTHER INFORMATION: tryptic fragments of bovine RAGE polypeptide

<400> SEQUENCE: 104

Gly His His His His His His His His Ser Ser Gly His Ile
1               5                   10                  15

Asp Asp Asp Asp Lys His Met Ala Gln Asn Ile Thr Ala Arg Ile Gly
            20                  25                  30

Glu Pro Leu Val Leu Lys
        35

<210> SEQ ID NO 105
<211> LENGTH: 36
<212> TYPE: PRT
<213> ORGANISM: artificial sequence
<220> FEATURE:
<223> OTHER INFORMATION: tryptic fragments of bovine RAGE polypeptide

<400> SEQUENCE: 105

Val Leu Ser Pro Gln Gly Gly Gly Pro Trp Asp Ser Val Ala Arg Val
1               5                   10                  15

Leu Pro Asn Gly Ser Leu Phe Leu Pro Ala Val Gly Ile Gln Asp Glu
            20                  25                  30

Gly Ile Phe Arg
        35

<210> SEQ ID NO 106
<211> LENGTH: 966
<212> TYPE: DNA
<213> ORGANISM: artificial sequence
<220> FEATURE:
<223> OTHER INFORMATION: BirA

<400> SEQUENCE: 106
ttatttttct gcactacgca gggatatttc accgcccatc cagggtttta ttattccatc      60
ctgctcaagt aataaagccc cctgtttgtc tattccgcgt gaaatgccaa atatttcttt    120

```
atcaccaatg ataagtttca ctgggcgatt aataaaatta tccagctttt cccagcgcga    180
cagataaggt gccaatcctt cttgttcgaa gagttccaac gcagcacgta attcacgtat    240
tagcatggcc gccaacgtat tacgatcgag attgatcccc gcttcctgca gcgtgatcca    300
cccctgatta acgacactct cttcaacacg gcgcattgcc atgttgatcc cggctccaat    360
gactatttgc gccgcatcgc cagttttgcc agtcagctcc accagaatgc ctgccagctt    420
gcgatcctgc agatagaggt cattaggcca tttaacacga actttatctg cacccagctt    480
gcgtaatact tccgccatca cgataccgat aaccagactt aaaccaatcg ccgccgccgg    540
gccttgttcc agacgccaga acatcgacaa atataagttt gcgccaaaag gcgaaaacca    600
tttccgaccc cggcgaccac ggccagcctg ctggtattct gcaatgcaag catcgcccga    660
tttaagctct ccgatacgat caagaaggta ctgattcgtg agtcaatca ctggcagcac     720 ggctacacta ccgccatcca gctgacccaa tatctgttta gcattaagta actggatagg    780
ctcaggcagg ctgtatcctt tacccggaac ggtaaagaca tcaacgcccc agtcacgcag    840
tgtctgaatg tgtttattaa tagccgcccg gctcattccc agcgtttcac ccaactgctc    900
gccagagtga aattcaccgt tcgctaacag ggcaatcaat ttcagtggca cggtgttatc    960
cttcat                                                                966
```

<210> SEQ ID NO 107
<211> LENGTH: 321
<212> TYPE: PRT
<213> ORGANISM: artificial sequence
<220> FEATURE:
<223> OTHER INFORMATION: BirA

<400> SEQUENCE: 107

```
Met Lys Asp Asn Thr Val Pro Leu Lys Leu Ile Ala Leu Leu Ala Asn
1               5                   10                  15

Gly Glu Phe His Ser Gly Glu Gln Leu Gly Glu Thr Leu Gly Met Ser
            20                  25                  30

Arg Ala Ala Ile Asn Lys His Ile Gln Thr Leu Arg Asp Trp Gly Val
        35                  40                  45

Asp Val Phe Thr Val Pro Gly Lys Gly Tyr Ser Leu Pro Glu Pro Ile
    50                  55                  60

Gln Leu Leu Asn Ala Lys Gln Ile Leu Gly Gln Leu Asp Gly Gly Ser
65                  70                  75                  80

Val Ala Val Leu Pro Val Ile Asp Ser Thr Asn Gln Tyr Leu Leu Asp
                85                  90                  95

Arg Ile Gly Glu Leu Lys Ser Gly Asp Ala Cys Ile Ala Glu Tyr Gln
            100                 105                 110

Gln Ala Gly Arg Gly Arg Arg Gly Arg Lys Trp Phe Ser Pro Phe Gly
        115                 120                 125

Ala Asn Leu Tyr Leu Ser Met Phe Trp Arg Leu Glu Gln Gly Pro Ala
    130                 135                 140

Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
                165                 170                 175

Leu Tyr Leu Gln Asp Arg Lys Leu Ala Gly Ile Leu Val Glu Leu Thr
            180                 185                 190

Gly Lys Thr Gly Asp Ala Ala Gln Ile Val Ile Gly Ala Gly Ile Asn
        195                 200                 205
```

Met Ala Met Arg Arg Val Glu Glu Ser Val Val Asn Gln Gly Trp Ile
                210                 215                 220

Thr Leu Gln Glu Ala Gly Ile Asn Leu Asp Arg Asn Thr Leu Ala Ala
225                 230                 235                 240

Met Leu Ile Arg Glu Leu Arg Ala Ala Leu Glu Leu Phe Glu Gln Glu
                245                 250                 255

Gly Leu Ala Pro Tyr Leu Ser Arg Trp Glu Lys Leu Asp Asn Phe Ile
                260                 265                 270

Asn Arg Pro Val Lys Leu Ile Gly Asp Lys Glu Ile Phe Gly Ile
                275                 280                 285

Ser Arg Gly Ile Asp Lys Gln Gly Ala Leu Leu Glu Gln Asp Gly
                290                 295                 300

Ile Ile Lys Pro Trp Met Gly Gly Glu Ile Ser Leu Arg Ser Ala Glu
305                 310                 315                 320

Lys

<210> SEQ ID NO 108
<211> LENGTH: 287
<212> TYPE: PRT
<213> ORGANISM: artificial sequence
<220> FEATURE:
<223> OTHER INFORMATION: g+k5_with_Myc_Tag_N

<400> SEQUENCE: 108

Met Arg Val Lys Thr Phe Val Ile Leu Cys Cys Ala Leu Gln Tyr Val
1               5                   10                  15

Ala Tyr Thr Asn Ala Glu Gln Lys Leu Ile Ser Glu Glu Asp Leu Met
                20                  25                  30

Ala Gln Val Gln Leu Gln Gln Ser Gly Pro Gly Leu Val Lys Pro Ser
            35                  40                  45

Gln Thr Leu Ser Leu Thr Cys Ala Ile Ser Gly Asp Ser Val Ser Ser
    50                  55                  60

Arg Asp Ala Ala Trp Asn Trp Ile Arg Gln Ser Pro Ser Arg Gly Leu
65                  70                  75                  80

Glu Trp Leu Gly Arg Thr Tyr Tyr Arg Ser Glu Trp Tyr Thr Asp Tyr
                85                  90                  95

Ala Val Ser Leu Glu Ser Arg Leu Thr Val Asn Pro Asp Thr Ser Arg
            100                 105                 110

Asn Gln Phe Ser Leu Gln Leu Asn Ser Val Thr Pro Glu Asp Thr Ala
        115                 120                 125

Val Tyr Leu Cys Ala Arg Gly Ser Ser Trp Gly His Ala Pro Ala Phe
    130                 135                 140

Phe Asp Tyr Trp Gly Gln Gly Thr Leu Val Thr Val Ser Ser Gly Gly
145                 150                 155                 160

Gly Gly Ser Gly Gly Gly Ser Gly Gly Gly Ser Asp Ile Gln
                165                 170                 175

Met Thr Gln Ser Pro Ser Ser Leu Ser Ala Ser Val Glu Asp Arg Val
            180                 185                 190

Ala Ile Thr Cys Arg Ala Ser Gln Ser Val Ser Thr Tyr Val Ala Trp
        195                 200                 205

Tyr Gln Gln Lys Pro Gly Lys Ala Pro Lys Leu Leu Ile Ser Gln Ala
    210                 215                 220

Ser Ser Leu Glu Asn Gly Val Pro Ser Arg Phe Ser Gly Ser Gly Ser
225                 230                 235                 240

Gly Thr Asp Phe Thr Leu Thr Ile Ser Ser Leu Gln Pro Glu His Phe

```
                245                 250                 255
Ala Thr Tyr Tyr Cys Gln Gln Tyr Thr Thr Tyr Pro Tyr Thr Phe Gly
            260                 265                 270

Gln Gly Thr Lys Leu Glu Ile Lys Arg His His His His His His
        275                 280                 285

<210> SEQ ID NO 109
<211> LENGTH: 287
<212> TYPE: PRT
<213> ORGANISM: artificial sequence
<220> FEATURE:
<223> OTHER INFORMATION: g+k5_with_Myc_Tag_C

<400> SEQUENCE: 109

Met Arg Val Lys Thr Phe Val Ile Leu Cys Cys Ala Leu Gln Tyr Val
1               5                   10                  15

Ala Tyr Thr Asn Ala Met Ala Gln Val Gln Leu Gln Gln Ser Gly Pro
            20                  25                  30

Gly Leu Val Lys Pro Ser Gln Thr Leu Ser Leu Thr Cys Ala Ile Ser
        35                  40                  45

Gly Asp Ser Val Ser Ser Arg Asp Ala Ala Trp Asn Trp Ile Arg Gln
    50                  55                  60

Ser Pro Ser Arg Gly Leu Glu Trp Leu Gly Arg Thr Tyr Tyr Arg Ser
65                  70                  75                  80

Glu Trp Tyr Thr Asp Tyr Ala Val Ser Leu Glu Ser Arg Leu Thr Val
                85                  90                  95

Asn Pro Asp Thr Ser Arg Asn Gln Phe Ser Leu Gln Leu Asn Ser Val
            100                 105                 110

Thr Pro Glu Asp Thr Ala Val Tyr Leu Cys Ala Arg Gly Ser Ser Trp
        115                 120                 125

Gly His Ala Pro Ala Phe Phe Asp Tyr Trp Gly Gln Gly Thr Leu Val
    130                 135                 140

Thr Val Ser Ser Gly Gly Gly Gly Ser Gly Gly Gly Gly Ser Gly Gly
145                 150                 155                 160

Gly Gly Ser Asp Ile Gln Met Thr Gln Ser Pro Ser Ser Leu Ser Ala
                165                 170                 175

Ser Val Glu Asp Arg Val Ala Ile Thr Cys Arg Ala Ser Gln Ser Val
            180                 185                 190

Ser Thr Tyr Val Ala Trp Tyr Gln Gln Lys Pro Gly Lys Ala Pro Lys
        195                 200                 205

Leu Leu Ile Ser Gln Ala Ser Ser Leu Glu Asn Gly Val Pro Ser Arg
    210                 215                 220

Phe Ser Gly Ser Gly Ser Gly Thr Asp Phe Thr Leu Thr Ile Ser Ser
225                 230                 235                 240

Leu Gln Pro Glu His Phe Ala Thr Tyr Tyr Cys Gln Gln Tyr Thr Thr
                245                 250                 255

Tyr Pro Tyr Thr Phe Gly Gln Gly Thr Lys Leu Glu Ile Lys Arg Glu
            260                 265                 270

Gln Lys Leu Ile Ser Glu Glu Asp Leu His His His His His His
        275                 280                 285

<210> SEQ ID NO 110
<211> LENGTH: 251
<212> TYPE: PRT
<213> ORGANISM: Artificial Sequence
<220> FEATURE:
<223> OTHER INFORMATION: biotinylated amino acid sequence
```

```
<400> SEQUENCE: 110

Gly Ala Gly Thr Pro Val Thr Ala Pro Leu Ala Gly Thr Ile Trp Lys
1               5                   10                  15

Val Leu Ala Ser Glu Gly Gln Thr Val Ala Ala Gly Glu Val Leu Leu
                20                  25                  30

Ile Leu Glu Ala Met Lys Met Glu Thr Glu Ile Arg Ala Ala Gln Ala
            35                  40                  45

Gly Thr Val Arg Gly Ile Ala Val Lys Ala Gly Asp Ala Val Ala Val
    50                  55                  60

Gly Asp Thr Leu Met Thr Leu Ala Gly Ser Gly Ser Asp Leu Tyr Asp
65                  70                  75                  80

Asp Asp Lys Val His Gln Thr Ser Leu Tyr Lys Lys Ala Gly Ser
                85                  90                  95

Glu Phe Ala Leu Asn Leu Gln Glu Thr Leu Lys Arg Val Ala Asn Cys
                100                 105                 110

Ser Ala Pro Cys Pro Gln Asp Trp Ile Trp His Gly Glu Asn Cys Tyr
            115                 120                 125

Leu Phe Ser Ser Gly Ser Phe Asn Trp Glu Lys Ser Gln Glu Lys Cys
        130                 135                 140

Leu Ser Leu Asp Ala Lys Leu Leu Lys Ile Asn Ser Thr Ala Asp Leu
145                 150                 155                 160

Asp Phe Ile Gln Gln Ala Ile Ser Tyr Ser Ser Phe Pro Phe Trp Met
                165                 170                 175

Gly Leu Ser Arg Arg Asn Pro Ser Tyr Pro Trp Leu Trp Glu Asp Gly
            180                 185                 190

Ser Pro Leu Met Pro His Leu Phe Arg Val Arg Gly Ala Val Ser Gln
        195                 200                 205

Thr Tyr Pro Ser Gly Thr Cys Ala Tyr Ile Gln Arg Gly Ala Val Tyr
    210                 215                 220

Ala Glu Asn Cys Ile Leu Ala Ala Phe Ser Ile Cys Gln Lys Lys Ala
225                 230                 235                 240

Asn Leu Arg Ala Gln His His His His His His
                245                 250

<210> SEQ ID NO 111
<211> LENGTH: 72
<212> TYPE: PRT
<213> ORGANISM: Artificial Sequence
<220> FEATURE:
<223> OTHER INFORMATION: biotinylated amino acid sequence

<400> SEQUENCE: 111

Gly Ala Gly Thr Pro Val Thr Ala Pro Leu Ala Gly Thr Ile Trp Lys
1               5                   10                  15

Val Leu Ala Ser Glu Gly Gln Thr Val Ala Ala Gly Glu Val Leu Leu
                20                  25                  30

Ile Leu Glu Ala Met Lys Met Glu Thr Glu Ile Arg Ala Ala Gln Ala
            35                  40                  45

Gly Thr Val Arg Gly Ile Ala Val Lys Ala Gly Asp Ala Val Ala Val
    50                  55                  60

Gly Asp Thr Leu Met Thr Leu Ala
65                  70
```

BIOTINYLATED AND OXIDIZED LDL RECEPTOR AND ADVANCED GLYCATION END PRODUCT RECEPTOR PRODUCED USING GENETICALLY ENGINEERED SILKWORM

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690204_401USPC_SEQUENCE_LISTING.txt. The text file is 88.9 KB, was created on Nov. 5, 2019, and is being submitted electronically via EFS-Web.

TECHNICAL FIELD

The present invention relates to detection of an oxidized LDL-like molecule (modified LDL) associated with arteriosclerosis and evaluation of the effect of food intake on suppressing generation of oxidized LDL-like molecules. The present invention also relates to soluble Receptor for Advanced Glycation End products (sRAGE). More specifically, the present invention relates to detection of advanced glycation end products (AGEs) associated with the onset of diabetic vascular disorders and evaluation of the effect of food intake on suppressing generation and accumulation of AGEs.

BACKGROUND ART

Westernization of lifestyle in recent years has led to an increase in circulatory diseases and increase in the mortality rate due to such diseases. Among vascular disorders, arteriosclerosis poses the biggest risk. There is a very strong societal demand for establishment of pre-onset diagnosis, with increased interest in the health of citizens and an increase in medical expenditure in an aging society. There is a strong suggestion for the possibility of modified LDLs, such as oxidized LDL playing an important role in the onset of atherosclerosis in view of the detection of such LDLs being limited to lesions of humans and hyperlipidemia animal models (Non Patent Literature 1). Since it is reported that the blood concentration of modified LDLs, such as oxidized LDLs, is correlated with the onset of arteriosclerosis (Non Patent Literature 2), establishment of a system for measuring modified LDLs such as oxidized LDLs would have great societal significance.

It is apparent that modified LDLs such as oxidized LDLs play an import role in the early stages of arteriosclerosis. Thus, the amount of modified LDLs, such as oxidized LDLs, in the living body can be an indicator for the effect of improving lifestyle such as the dietary habit. Meanwhile, modified LDL such as oxidized LDL is a general term for molecules generated by oxidative modification of LDLs, which is a collection with heterogeneous structures (FIG. 1). For this reason, various monoclonal antibodies have been developed, but each monoclonal antibody only detect some of the molecules, such that it is difficult to accurately measure the amount of modified LDLs, such as oxidized LDLs, in a living body. Thus, there is a demand for the development of a technique capable of detecting a broad range of molecule types.

In this context, systems for detecting characteristic molecules (malondialdehyde (MDA), phosphatidylcholine (oxidized PC), and the like) that are generated when LDLs are oxidatively modified by using monoclonal antibodies have been developed (Non Patent Literatures 3 to 5).

A detection system using Apolipoprotein B (ApoB) that is present in all LDLs has also been developed. In particular, ApoB is highly homologous in mammals, such that it is difficult to create an excellent monoclonal antibody. Thus, monoclonal antibodies with a chicken as a host have been recently created and used in practical applications (Non Patent Literature 6). A detection technique combining such antibodies and oxidized LDL receptor has been developed.

While Patent Literatures 1 to 5 and Non Patent Literatures 7 to 20 have further disclosures of single chain antibodies and LDLs, none are descriptions related to the creation of a single chain antibody allowing detection of oxidized LDL-like molecules.

Although the inventors made a single chain antibody against modified LDLs, the inventors have not been able to make a single chain antibody to the level of performing analysis or evaluation. While numerous other techniques related to LDLs (Patent Literatures 6 to 15) have been published, the sensitivity thereof is insufficient.

Further, the inventors of the present invention have developed a simple method (Non Patent Literature 22) and a precise method (Non Patent Literature 23) of having a recognition region (CTLD14) of a receptor (LOX-1) that recognizes a wide range of oxidatively modified LDL molecule types expressed in a large quantity as an inclusion body with E. coli, and then refolds and utilizes the region as a molecule which recognizes oxidized LDLs.

Furthermore, an approach producing an extracellular region of LOX-1 as a secretion protein in an animal cell and utilizing the extracellular region as a molecule recognizing oxidized LDLs has been developed.

Meanwhile, diabetic vascular disorders (nephropathy, retinopathy, neuropathy, and the like) due to diabetes, which are typical lifestyle related diseases, are closely related to dietary habits. Advanced glycation end products (AGEs) produced in the living body are onset/progression factors thereof. However, AGEs in the living body are in various forms, such that measurement thereof is difficult. While many agricultural, forestry and fishery products are reported to have an effect of suppressing the generation of AGEs, a detection/evaluation technique of AGEs which is meaningful for living organisms has not been established. For this reason, it is difficult to provide objective information related to prevention of diabetic vascular disorders through food, such that there is a need for establishing an effective evaluation approach. Meanwhile, RAGE (receptor for AGEs) is known as a receptor that recognizes AGEs. RAGE recognizes AGEs with various structures. AGEs lead to pathogenesis upon recognition by RAGE. For this reason, AGEs recognized by RAGE are considered AGEs that are meaningful to living organisms (FIG. 42).

Under such a circumstance, an approach of making an antibody against the typical structure of (carboxymethyllysine or the like) AGEs to detect some of AGEs by an enzyme antibody reaction method or the like has been developed. An approach for detection/quantification of some of the AGE molecules with a known structure by HPLC, MS, or the like has been developed. An approach of detection by fluorescence has been developed for fluorescent AGEs (pentosidine or the like). Although a detection approach for making an antibody that widely recognizing AGEs and detecting AGEs with an enzyme antibody reaction or the like has been reported, such an approach has poor data reproducibility. An AGE detection approach that focuses on RAGE's recognition ability to reconstruct the function thereof has been established.

CITATION LIST

Patent Literature

[PTL 1] Japanese Laid-Open Publication No. 2014-511378
[PTL 2] Japanese Laid-Open Publication No. 2009-525048
[PTL 3] Japanese Laid-Open Publication No. 2006-517138
[PTL 4] Japanese Laid-Open Publication No. 2005-531500
[PTL 5] International Publication No. WO 01/095938 pamphlet
[PTL 6] Japanese Laid-Open Publication No. 2012-100585
[PTL 7] Japanese Laid-Open Publication No. 2008-008894
[PTL 8] Japanese Laid-Open Publication No. 2005-097203
[PTL 9] Japanese Laid-Open Publication No. 2004-175754
[PTL 10] Japanese Laid-Open Publication No. 2003-227837
[PTL 11] Japanese Laid-Open Publication No. 2002-017353
[PTL 12] Japanese Laid-Open Publication No. 2001-091517
[PTL 13] Japanese Laid-Open Publication No. 09-288106
[PTL 14] Japanese Laid-Open Publication No. 08-304396
[PTL 15] International Publication No. WO 2011/136332 pamphlet
[PTL 16] Japanese Laid-Open Publication No. 2009-108037
[PTL 17] Japanese Laid-Open Publication No. 2004-325444
[PTL 18] Japanese Laid-Open Publication No. 2003-535339
[PTL 19] Japanese Laid-Open Publication No. 2003-36499
[PTL 20] Japanese Laid-Open Publication No. 2003-238404
[PTL 21] Japanese Laid-Open Publication No. 2003-125786
[PTL 22] Japanese Laid-Open Publication No. 2002-320489
[PTL 23] Japanese Laid-Open Publication No. 2002-181820

Non Patent Literature

[NPL 1] Kita et al. Proc. Natl. Acad. Sci USA 84: 5928-5931(1987)
[NPL 2] Ehara et al., Circulation 103: 1955-1960(2001)
[NPL 3] Kotani K. et al., Biochim. Biophys. Acta 1215:121-125 (1994)
[NPL 4] Itabe H. et al., J. Biol. Chem. 271: 33208-17 (1996)
[NPL 5] Itabe H. et al., J. Lipid Res 4.37: 45-53 (1996)
[NPL 6] Sato Y et al., Atherosclerosis, 200: 303-309 (2008)
[NPL 7] Castro J M A et al., Toxicon, 87(1): 81-91 (2014)
[NPL 8] Ammayappan A et al., J. Virology 87(24): 13543-13555(2013)
[NPL 9] Kurasawa J H et al., J. Biol. Chem. 288 (30): 22033-22041 (2013)
[NPL 10] Extebarria A et al., Human Mutation, 33(1): 232-243(2012)
[NPL 11] Fang L. et al., J. Clinical Investigation 121(12): 4861-4869 (2011)
[NPL 12] Tsimikas S et al., J. American Coll. Cardiol. 58 (16): 1715-1727 (2011)
[NPL 13] Hermansson A et al., J. Experi. Med. 207 (5): 1081-1093 (2010)
[NPL 14] Tashiro J. et al., Eur. J. Clinical Invest. 28 (9): 712-719 (1998)
[NPL 15] Liao W et al., Biochem. Biophy. Res. Comm. 373 (2): 235-240 (2008)
[NPL 16] Schiopu A et al., Circulation 100(14): 2047-2052 (2004)
[NPL 17] Ritsch A. et al., Clinical Chem. Lab. Med. 42 (3): 247-255 (2004)
[NPL 18] Niskanen L et al., Metabolism-Clinical Experimental, 52(2): 213-217 (2003)
[NPL 19] Nagata N. et al., Alcohol Clinical Experimental Res. 23 (4 Suppl): 24S-28S (1999)
[NPL 20] Magrane J et al., J. Lipid Res. 39 (11):2172-2181 (1998)
[NPL 21] Takashi Fujimura et al., Annual Meeting of the Japan Society for Bioscience, Biotechnology, and Agrochemistry Summary 2A04p14 (2007)
[NPL 22] Xie et al., Protein Express. Purif. 32, 68-74 (2003)
[NPL 23] Kumano-Kuramochi et al., The Biochemical Journal, 442, 171-180 (2012)
[NPL 24] Ohki et al., Structure, 13: 905-917 (2005)
[NPL 25] ATHROSCLEROSIS 200, 303-309 (2008)
[NPL 26] Biochemistry, 46, 6973-6970 (2007)
[NPL 27] J. Biol. Chem., 282, 4218-4231 (2007)
[NPL 28] Clinical Biochem., 33(4), 243-253 (2000)
[NPL 29] Nat. Med., 4, 1025-1031 (1998)
[NPL 30] J. Lipid Res., 37, 45-53 (1996)
[NPL 31] J. Biol. Chem., 267, 5133-5138 (1992)

SUMMARY OF INVENTION

Solution to Problem

The inventors have created a silkworm that coexpresses a protein of interest (e.g., CTLD14, sRAGE) and a biotin ligase (BirA), and manufactured a protein biotinylated at a high efficiency by oral administration of biotin. Biotinylated CTLD14 obtained from such a silkworm had an excellent pH stable characteristic. It was further discovered that LDLs with various oxidatively modified structures can be detected in 20 minute or less by a lateral flow assay incorporating an anti-LDL chicken antibody, a single chain antibody, a non-biotinylated CTLD14, and a streptavidin by using metal colloid modified CTLD14. Further, E. coli form sRAGEs that are not glycosylated are fragmented and lost activity in about 1.5 months, but it was revealed that sRAGEs obtained from the above-described silkworm were glycosylated and stably maintained activity over nearly one year of storage. It was discovered that AGEs with various structures could be detected by maintaining directionality via biotin of the resulting silkworm form biotinylated sRAGE and by establishing a process.

While antibodies to a specific molecule had been able to detect only a specific molecule, diligent research by the inventors have made it possible to detect a broad range of oxidized LDL-like molecules. Anti-ApoB antibodies were difficult to distinguish from unmodified LDLs, and such antibodies were difficult to detect when ApoB was modified. Meanwhile, the present invention enables distinction thereof from unmodified LDLs, and detection thereof, even with a modification in ApoB.

The inventors, as a result of diligent research, have created a genetically modified silkworm producing a ligand recognition region (sRAGE) of a receptor (RAGE) for advanced glycation end products (AGEs) in the middle silk gland, and have established an efficient purification method to manufacture an improved sRAGE. Furthermore, it was discovered that the resulting improved sRAGE is glycosylated and is a very stable molecule such that a trace amount of AGE concentration, AGEs with various structures and the like can be detected, thus completing the present invention. For improved sRAGE (FIG. 34), the present invention has established an approach for creating a genetically modified silkworm producing sRAGE in the middle silk gland, and to efficiently purify a large quantity of sRAGE from silk gland extract (FIG. 36).

In another aspect, the present invention provides a technique for solving the problem, i.e., it was impossible to detect every molecular type with antibodies or instrument analysis due to the diversity of the structures of oxidized LDLs (general term for structures generated by oxidative modification), which are risk factors for arteriosclerosis. LOX-1 (lectin like oxidized LDL receptor-1; oxidized LDL receptor on the vascular endothelium that does not recognize LDLs, but recognizes a broad range of oxidized LDLs) recognizes oxidized LDLs to induce vascular endothelial dysfunction, which occurs at the earliest stage of arteriosclerosis. Thus, in this aspect of the present invention, an oxidized LDL detection system utilizing the recognition ability of LOX-1 was developed while bearing in mind that oxidized LDLs recognized by LOX-1 are truly important molecules as risk factors for arteriosclerosis (FIG. 1).

Thus in this aspect, the present invention provides a technique that enables detection of a broad range of molecule types so that the amount of oxidized LDLs in the living body can be accurately measured. This is because antibodies to a specific molecule can only detect a specific molecule and are unable to detect a broad range of oxidized LDL-like molecules, while an approach for preparing CTLD14 by refolding, which was developed as a solution thereof, has safety issues such as coagulation in several months, for a simple method, and had issues such as how the entire process takes 10 days or more and how the approach is complex, for the precise method. Furthermore, the approach of having LOX-1 secreted and produced in an animal cell has disadvantages such as the need for a special facility for aseptic culture of cells and the like, high cost of culture, and inferior productivity to an approach using E. coli. For anti-ApoB antibodies, it is difficult to distinguish from unmodified LDLs, and the measurement precision is unreliable. There are also other issues such as difficulty of detection when ApoB is modified. The present invention provides a technique for solving such problems.

In other words, the present invention provides: improved CTLD14 (silk worm form); method of manufacturing improved CTLD14 by creating a genetically modified silkworm expressing CTLD14 in the middle silk gland, having a large quantity of CTLD14 expressed as a soluble protein, and purifying the protein; and anti-LDL chicken polyclonal antibodies and combinations thereof.

More specifically, the present invention provides the following.

<Single Chain Antibody Related Inventions (Sequence and Antibody Characteristic)>

(1) A single chain antibody comprising: the amino acid sequence set forth by any one of SEQ ID NOs: 76 to 80 or a variant thereof; or a fragment thereof.

(2) A detection agent for detecting an LDL and a modified LDL (also called an LDL modified product), comprising the single chain antibody or a fragment thereof of item 1, wherein the LDL and modified LDL comprise at least one molecule selected from the group consisting of an acetylated LDL and a partially oxidized LDL.

(3) The detection agent of item 2, wherein the LDL and modified LDL comprise an acetylated LDL and a partially oxidized LDL.

(4) The detection agent of item 2 or 3, wherein the LDL and modified LDL comprise an LDL, a fully oxidized LDL, an aldehyde modified LDL (e.g., malondialdehyde modified LDL), an acetylated LDL, and a partially oxidized LDL.

(5) The detection agent of any one of items 2 to 4, wherein the LDL and modified LDL are detectable at a sensitivity of 100 ng/100 µl well or less.

(6) The detection agent of any one of items 2 to 5, wherein the LDL and modified LDL are detectable at a sensitivity of 20 ng/100 µl well or less.

(7) The detection agent of any one of items 2 to 6, wherein the LDL and modified LDL are an LDL, a partially an oxidized LDL and a fully oxidized LDL, and are detectable at a sensitivity of 10 ng/100 µl well or less.

(8) The detection agent of any one of items 2 to 7, wherein the LDL and modified LDL are an LDL and a fully oxidized LDL and are detectable at a sensitivity of 5 ng/100 µl well or less.

<Stable Supply System>

(A1) A method of producing the single chain antibody or a fragment thereof of item 1, wherein the method comprises:
A) introducing a nucleic acid encoding an amino acid sequence of the single chain antibody or a fragment thereof into a cell expressing the nucleic acid;
B) culturing the cell and taking out an inclusion body from the cell;
C) refolding the inclusion body;
D) contacting a solution obtained by refolding with a purification column to elute out an eluent; and
E) dialyzing the eluted single chain antibody or a fragment thereof with a dialysis solution.

(A2) The method of item A1, wherein the refolding is performed with an amount of inclusion body at 2 mg to 10 mg (e.g., 8.6 mg) per protein.

(A3) The method of item A1 or A2, wherein the agarose column is an Ni-NTA slurry.

(A4) The method of any one of items A1 to A3, wherein the eluent is a solution comprising imidazole.

(A5) The method of any one of items A1 to A4, wherein the eluent is phosphate buffered saline (PBS) comprising imidazole.

(A6) The method of any one of items A1 to A5, wherein the dialysis solution is PBS (−).

(A7) The method of any one of items A1 to A6, wherein the dialyzing is performed using a cellulose ester film tube.

(A8) The method of any one of items A1 to A7, wherein the dialyzing is preformed using a cellulose ester film tube and PBS (−) that is 400 times the sample volume as the dialysis solution.

(A9) A method of manufacturing the single chain antibody or a fragment thereof of item 1, comprising:
A) incorporating a nucleic acid molecule encoding the single chain antibody of a fragment thereof expressibly into a silkworm or an organism providing a sugar chain similar to that of a silkworm;
B) placing the silkworm or the organism adding a sugar chain similar to that of a silkworm under a condition where the nucleic acid molecule is expressed in order to express the single chain antibody or a fragment thereof; and
C) obtaining the single chain antibody or a fragment thereof.

<Complex/Indirect/Sandwich System with LOX-1>

(B1) A system for detecting or quantifying an oxidatively modified LDL using the single chain antibody or a fragment thereof of item 1 and a ligand recognition region of an oxidized LDL receptor (LOX-1).

(B2) The system of item B1, wherein the system uses an antigen-antibody reaction.

(B3) The system of item B1 or B2, wherein the system is for performing ELISA.

(B4) The system of any one of items B1 to B3, wherein the system is for performing sandwich ELISA.

(B5) The system of any one of items B1 to B4, wherein the system is for performing a lateral flow assay.

(B6) The system of item B5, wherein the system comprises a membrane for deployment of a specimen by a capillary phenomenon, the membrane comprising: a conjugation section comprising a ligand recognition region of an oxidized LDL receptor (LOX-1) labeled with a metal colloid, a silica particle or a latex particle and a sample, or the single chain antibody or a fragment thereof of item 1 labeled with a metal colloid, a silica particle, or a latex particle; a detection section comprising a ligand recognition region of an oxidized LDL receptor (LOX-1), or the single chain antibody or a fragment thereof of item 1; and a control section comprising a binding molecule to the ligand recognition region of the oxidized LDL receptor (LOX-1) or a binding molecule to a single chain antibody.

(B7) The system of item B5 or B6, wherein the system comprises a membrane for deployment of a specimen by a capillary phenomenon, the membrane comprising: a conjugation section comprising CTLD14 labeled with a metal colloid, a silica particle or a latex particle and a sample, or the single chain antibody or a fragment thereof of item 1 labeled with a metal colloid, a silica particle, or a latex particle; a detection section comprising CTLD14 or the single chain antibody or a fragment thereof of item 1; and a control section comprising a binding molecule to the CTLD14.

(B8) The system of item B7, wherein the CTLD14 is subjected to biotinylation, His tag addition, Myc tag addition, Flag tag addition, E tag addition, or Strep tag addition, and the binding molecule for the respective modification is streptavidin, an anti-His antibody, an anti-Myc antibody, an anti-Flag antibody, an anti-E tag antibody, or Strep-Tactin.

<System Using Chicken Anti-Oxidized LDL Antibody>

(C1) A system for detecting or quantifying an oxidatively modified LDL using an anti-modified LDL antibody, a modified product, or a fragment thereof, and a ligand recognition region of an oxidized LDL receptor (LOX-1) in a lateral flow assay format.

(C2) A system for examination of a modified LDL associated disease (e.g., lipid abnormality, arteriosclerosis, diabetes, ischemic heart disease, or cerebrovascular disorder) using an anti-modified LDL antibody, a modified product, or a fragment thereof and a ligand recognition region of an oxidized LDL receptor (LOX-1) in a lateral flow assay format.

(C3) The system of item C2, wherein the modified LDL associated disease is selected from the group consisting of lipid abnormality, arteriosclerosis, diabetes, ischemic heart disease, and cerebrovascular disorder.

(C4) A system for evaluating a prophylactic effect of food intake on a modified LDL associated disease (e.g., lipid abnormality, arteriosclerosis, diabetes, ischemic heart disease, or cerebrovascular disorder) using an anti-modified LDL antibody, a modified product, or a fragment thereof, and a ligand recognition region of an oxidized LDL receptor (LOX-1) in a lateral flow assay format.

(C5) The system of item C4, wherein the modified LDL associated disease is selected from the group consisting of lipid abnormality, arteriosclerosis, diabetes, ischemic heart disease, and cerebrovascular disorder.

<D. Improved CTLD14 (Silkworm Form)>

(D1) C-type lectin-like domain (CTLD) 14 having a silkworm form sugar chain, comprising the amino acid sequence set forth by SEQ ID NO: 86 or a variant thereof.

(D2) The CTLD14 of item D1, wherein the silkworm form sugar chain comprises one or more types of sugar chains from a trimannosyl core, a complex type sugar chain, an oligomannose type sugar chain, and a hybrid type sugar chain.

(D3) The CTLD14 of item D1 or D2, wherein the silkworm form sugar chain comprises a sugar chain to which 0 to 4 molecules of 2 molecules of GlcNAc and 2 molecule of Man are bound per two molecules, in addition to a trimannosyl core (GlcNAc-β1,4-GlcNAc-β1,4-Man(-α1,6-Man)-α1,3-Man viewed from an asparagine residue) structure.

(D4) The CTLD14 of any one of items D1 to D3, wherein the silkworm sugar chain comprises one or more of the following combinations view from an asparagine residue:
1) a combination of GlcNAc-β1,4-GlcNAc-β1,4-Man(-α1,3-Man-α1,6-Man(-α1,3-Man)-α1,6-Man and GlcNAc-β1,4-GlcNAc-β1,4-Man(-α1,6-Man-β1,2-GlcNAc)-α1,3-Man-β1,2-GlcNAc;
2) a combination of GlcNAc-β1,4-GlcNAc-β1,4-Man(-α1,3-Man)-α1,6-Man(-α1,3-Man)-α1,6-Man-α1,2-Man and GlcNAc-β1,4-GlcNAc-β1,4-Man(-α1,6-Man-β1,2-GlcNAc)-α1,3-Man; and
3) a combination of GlcNAc-β1,4-GlcNAc-β1,4-Man(-α1,3-Man)-α1,6-Man(-α1,3-Man)-α1,6-Man-α1,2-Man and GlcNAc-β1,4-GlcNAc-β1,4-Man(-α1,6-Man-β)-α1,3-Man-β1,2-GlcNAc.

(D5) The CTLD14 of any one of items D1 to D4, wherein the silkworm sugar chain binds to asparagine at position 111 and/or asparagine at position 155 of SEQ ID NO: 86.

(D6) The CTLD14 of any one of items D1 to D5, wherein the CTLD14 is biotinylated.

(D7) A composition for detecting a modified LDL, comprising the CTLD14 of any one of items D1 to D6.

(D8) The composition of item D7, wherein the composition is for distinguishing an unmodified LDL from a modified LDL to detect a modified LDL.

(D9) The composition of item D8, wherein the unmodified LDL and the modified LDL are LDLs and oxidized LDLs.

(D10) The composition of item D8 or D9, wherein the unmodified LDL and the modified LDL are LDLs and oxidized LDLs from multiple species of mammals.

(D11) The composition of item D10, wherein the mammals comprise mice and humans.

<E. Method of Manufacturing Improved CTLD14 by Creating a Genetically Modified Silkworm Expressing CTLD14 in the Middle Silk Gland, Having a Large Quantity of CTLD14 Expressed as a Soluble Protein and Purifying the Protein>

(E1) A method of manufacturing C-type lectin-like domain (CTLD) 14, comprising: A) incorporating a nucleic acid molecule encoding CTLD14 expressibly into a silkworm or an organism adding a sugar chain similar to that of a silkworm; B) placing the silkworm or the organism adding a sugar chain similar to that of a silkworm under a condition where the nucleic acid molecule is expressed in order to express the CTLD14; and C) obtaining the CTLD14. (E2) The method of item E1, wherein the expression is performed in the posterior silk gland, the middle silk gland, or the entire body of the silkworm or the organism adding a sugar chain similar to that of a silkworm. (E3) The method of item E1 or E2, wherein the expression is performed in a middle silk gland of the silkworm or the organism adding a sugar chain similar to that of a silkworm. (E4) The method of any one of items E1 to E3, wherein the CTLD14 is expressed in a biotinylated or biotinylatable state. (E5) The method of any one of items E1 to E4, wherein the organism comprises a nucleic acid sequence encoding a biotin ligase, and biotin is orally administered to the silkworm in the step C). (E6) The method of any one of items E1 to E5, wherein the CTLD14 is expressed in a biotinylated state. (E7) The method of any one of items E1 to E6, wherein the organism comprises a tag sequence to be biotinylated. (E8) The method of item E7, wherein the tag sequence to be biotinylated is one of BIOEASE™ Tag biotin ligase birA substrate peptide (Life Technologies, Carlsbad, Calif.) and AVITAG™ biotin ligase birA substrate peptide [SEQ ID NO:98] (Avidity LLC, Aurora, Colo.). (E9) The method of items E1 to E8, wherein step A) is accomplished by microinjection of an expression vector comprising the nucleic acid encoding CTLD14. (E10) The method of any one of items E1 to E9, wherein the nucleic acid molecule comprises the nucleic acid sequence set forth by SEQ ID NO: 85 or a variant thereof. (E10-1) The method of any one of items E1 to E10, wherein the CTLD14 has the feature of one or more of items D1 to D6. (E11) A silkworm or an organism adding a sugar chain similar to that of a silkworm expressibly incorporated with a nucleic acid molecule encoding CTLD14. (E12) The silkworm or the organism adding a sugar chain similar to that of a silkworm of item E11, wherein the nucleic acid molecule comprises the nucleic acid sequence set forth by SEQ ID NO: 85 or a variant thereof. (E13) The organism of item E11 or E12, wherein the organism comprises a sequence encoding a biotin ligase. (E14) The organism of item E13, wherein the biotin ligase is BirA (SEQ ID NO: 116). (E15) The organism of item E13 or E14, wherein the biotin ligase and the CTLD14 are coexpressed in a middle silk gland. (E16) The organism of any one of items E11 to E15, wherein the organism comprises a tag sequence to be biotinylated. (E17) The organism described in item E16, wherein the tag sequence to be biotinylated is one of BIOEASE™ Tag biotin ligase birA substrate peptide (Life Technologies, Carlsbad, Calif.) and AVITAG™ biotin ligase birA substrate peptide [SEQ ID NO:98] (Avidity LLC, Aurora. Colo.). <F. Anti-LDL Chicken Polyclonal Antibodies and Combination thereof> (F1) A composition for detecting a modified LDL, comprising an anti-LDL chicken antibody. (F2) The composition of item F1, wherein the anti-LDL chicken antibody is a polyclonal antibody. (F3) The composition of item F1 or F2, further comprising CTLD14. (F4) The composition of any one of items F1 to F3, wherein the CTLD14 is CTLD14 comprising a silkworm form sugar chain. (F5) The composition of item F4, wherein the CTLD14 comprising a silkworm form sugar chain is the CTLD14 of any one of items D1 to D6. (F6) The composition of any one of items F1 to F5, wherein the composition is for detecting LDLs and oxidized LDLs. (F7) The composition of item F6, wherein the LDLs and the oxidized LDLs are LDLs and oxidized LDLs of multiple species of mammals. (F8) The composition of item F7, wherein the mammals are mice and humans. (F9) A kit for detecting a modified LDL, comprising an anti-LDL chicken antibody and CTLD14. (F10) The kit for detecting a modified LDL of item F9, wherein the anti-LDL chicken antibody is a polyclonal antibody. (F11) The kit for detecting a modified LDL of item F8 or F9, wherein the anti-LDL chicken antibody is an anti-oxidized LDL chicken antibody or an anti-oxidized single chain antibody. (F12) The kit of any one of items F9 to F11, wherein the CTLD14 is the CTLD14 of item D1. (F13) The composition of any one of items F10 to F12, for detecting LDLs and oxidized LDLs. (F14) The kit of item F13, wherein the LDLs and the oxidized LDLs are LDLs and oxidized LDLs of multiple species of mammals. (F15) the kit of item F14, wherein the mammals comprise mice and humans. <Improved sRAGE (Silkworm Form)>(G1) A reconstructed receptor for advanced glycation end products (sRAGE) having a silkworm form sugar chain, comprising the amino acid sequence set forth by SEQ ID NO: 97 or a variant thereof. (G2) The sRAGE of item G1, wherein the silkworm form sugar chain comprises one or more types of sugar chains from a trimannosyl core, a complex type sugar chain, an oligomannose type sugar chain, and a hybrid type sugar chain. (G3-1) The sRAGE of item G1 or G2, wherein the silkworm form sugar chain comprises a sugar chain to which 0 to 4 molecules of 0 to 2 molecules of GlcNAc and 0 to 4 molecule of Man are bound per molecule, in addition to a trimannosyl core (GlcNAc-β1,4-GlcNAc-β1,4-Man (-α1,6-Man)-α1,3-Man viewed from an asparagine residue). (G3-2) The sRAGE of items G1 to G2 or G3-1, wherein the silkworm form sugar chain comprises a sugar chain to which 0 to 8 molecules of 0 to 4 molecules of GlcNAc and 0 to 8 molecule of Man are bound per 2 molecules, in addition to a trimannosyl core (GlcNAc-β1,4-GlcNAc-β1,4-Man (-α1,6-Man)-α1,3-Man viewed from an asparagine residue). (G4-1) The sRAGE of any one of items G1 to G2 and G3-1 to G3-2, wherein the composition ratio of the silkworm form sugar chain is oligomannose type: 87 to 97%, complex type: 2 to 8%, and hybrid type: 1 to 5%. (G4-2) The sRAGE of any one of items G1 to G2, G3-1 to G3-2, and G4-1, wherein the composition ratio of the silkworm form sugar chain is oligomannose type: 90 to 94%, complex type: 3 to 6%, and hybrid type: 2 to 4%. (G4-3) The sRAGE of any one of items G1 to G2, G3-1 to G3-2, and G4-1 to G4-2, wherein the composition ratio of the silkworm form sugar chain is oligomannose type: 92.5%, complex type: 4.6%, and hybrid type: 2.5%. (G5-1) The sRAGE of any one of items G2, G3-1 to G3-2 and G4-1 to G4-3, wherein the oligomannose type comprises $(Man)_5(GlcNAc)_2$, $(Man)_7(GlcNAc)_2$, $(Man)_6(GlcNAc)_2$ and $(Man)_3(GlcNAc)_2$. (G5-2) The sRAGE of any one of items G2, G3-1 to G3-2, G4-1 to G4-3, and G5-1, wherein the composition ratio of the oligomannose type to the entire sugar chain is $(Man)_5(GlcNAc)_2$: 45 to 56%, $(Man)_7(GlcNAc)_2$: 23 to 33%, $(Man)_6(GlcNAc)_2$: 7 to 15%, and $(Man)_3(GlcNAc)_2$: 1 to 5%. (G5-3) The sRAGE of any one of items G2, G3-1 to G3-2, G4-1 to G4-3, and G5-1 to G5-2, wherein the composition ratio of the oligomannose type to the entire sugar chain is $(Man)_5(GlcNAc)_2$: 48 to 54%, $(Man)_7(GlcNAc)_2$: 25 to 31%, $(Man)_6(GlcNAc)_2$: 9 to 13%, and $(Man)_3(GlcNAc)_2$: 2 to 4%. (G5-4) The sRAGE of any one of items G2, G3-1 to G3-2, G4-1 to G4-3, and G5-1 to G5-3, wherein the composition ratio of the oligomannose type to the entire sugar chain is $(Man)_5(GlcNAc)_2$: 51%, $(Man)_7(GlcNAc)_2$: 27.5%, $(Man)_6(GlcNAc)_2$: 10.8%, and $(Man)_3(GlcNAc)_2$: 2.8%. (G6-1) The sRAGE of any one of items G2, G3-1 to G3-2, G4-1 to G4-3, and G5-1 to G5-4, wherein the complex type comprises (Man).sub.3(GlcNAc).sub.3. (G6-2) The sRAGE of any one of items G2, G3-1 to G3-2, G4-1 to G4-3, G5-1 to G54, and G6-1, wherein the composition ratio of the complex type to the entire sugar chain is $(Man)_3(GlcNAc)_3$: 2 to 8%. (G6-3) The sRAGE of any one of items G2, G3-1 to G3-2, G4-1 to G4-3, G5-1 to G54, and G6-1 to G6-2, wherein the composition ratio of the complex type in the entire sugar chain is $(Man)_3(GlcNAc)_3$: 3 to 6%. (G6-4) The sRAGE of any one of items G2, G3-1 to G3-2, G4-1 to G4-3, G5-1 to G54, and G6-1 to G6-3, wherein the composition ratio of the complex type to the entire sugar chain is $(Man)_3(GlcNAc)_3$: 4.6%. (G7) The sRAGE of any one of items G2, G3-1 to G3-2, G4-1 to G4-3, G5-1 to G5-4, and G6-1 to G6-4, wherein the hybrid type is $(Man)_4(GlcNAc)_3$. (G8) The sRAGE of any one of items G1 to G2, G3-1 to G3-2, G4-1 to G4-3, G5-1 to G54, G6-1 to G6-4, and G7, wherein the silkworm form sugar chain binds to asparagine at position 3 and/or asparagine at position 59 of SEQ ID NO: 97. (G9) The sRAGE of any one of items G1 to G2, G3-1 to G3-2, G4-1 to G4-3, G5-1 to G54, G6-1 to G6-4, and G7 to G8, wherein the sRAGE is biotinylated. (G10) A reagent with the sRAGE of any one of items G1 to G2, G3-1 to G3-2, G4-1 to G4-3, G5-1 to G54, G6-1 to G64, and G7 to G9 immobilized, wherein the sRAGE is immobilized on a substrate via the biotin. (G11) A composition for detecting advanced glycation end products (AGEs), comprising the sRAGE of any one of items G1 to G2, G3-1 to G3-2, G4-1 to G4-3, G5-1 to G54, G6-1 to G64, and G7 to G9. (G12) A method of detecting AGEs, comprising contacting the sRAGE of any one of items G1 to G2, G3-1 to G3-2, G4-1 to G4-3, G5-1 to G54, G6-1 to G6-4, and G7 to G9 with a specimen to detect the AGEs. (G13) A method of manufacturing sRAGE, comprising A) incorporating a nucleic acid molecule encoding the sRAGE expressibly into a silkworm or an organism adding a sugar chain similar to that of a silkworm; B) placing the silkworm or the organism adding a sugar chain similar to that of silkworm under a condition where the gene is expressed in order to express the sRAGE; and C) obtaining the sRAGE. (G14) The method of item G13, wherein the expression is performed in a posterior silk gland, a middle silk gland, or the entire body of the silkworm or the organism adding a sugar chain similar to that of a silkworm. (G15) The method of item G13 or G14, wherein the expression is performed in the middle silk gland of the silkworm or the organism adding a sugar chain similar to that of a silkworm. (G16) The method of any one of items G13 to G15, wherein the sRAGE is expressed in a biotinylated or biotinylatable state. (G17) The method of any one of items G13 to G16, wherein the sRAGE is expressed in a biotinylated state. (G18) The method of any one of items G13 to G17, wherein the organism comprises a nucleic acid sequence encoding a biotin ligase and biotin is orally administered to the silkworm in the step C). (G19) The method of any one of items G13 to G18, wherein the organism comprises a tag sequence to be biotinylated. (G20) The method of item G19, wherein the tag sequence to be biotinylated is one of BIOEASE™ Tag biotin ligase birA substrate peptide (Life Technologies. Carlsbad, Calif.) and AVITAG™ biotin ligase birA substrate peptide [SEQ ID NO:98] (Avidity LLC, Aurora Colo.). (G21) The method of any one of items G13 to G20, wherein step A) is accomplished by microinjection of an expression vector comprising the nucleic acid encoding sRAGE. (G22) The method of any one of items G13 to G21, wherein the nucleic acid molecule comprises the nucleic acid sequence set forth by SEQ ID NO: 96 or a variant thereof. (G22-1) The method of any one of items G13 to G22, wherein the sRAGE has the feature of one or more of items G1 to G2, G3-1 to G3-2, G4-1 to G4-3, G5-1 to G54, G6-1 to G6-4, and G7 to G9. (G23) A silkworm or an organism adding a sugar chain similar to that of a silkworm expressibly incorporated with a nucleic acid encoding sRAGE. (G24) The silkworm or the organism adding a sugar chain similar to that of a silkworm of item G23, wherein the nucleic acid molecule comprises the nucleic acid sequence set forth by SEQ ID NO: 96 or a variant thereof. (G25) The organism of item G23 or G24, wherein the organism comprises a sequence encoding a biotin ligase. (G26) The organism of item G25, wherein the biotin ligase is BirA (SEQ ID NO: 106). (G27) The organism of item G25 or G26, wherein the biotin ligase and the sRAGE are coexpressed in a middle silk gland. (G28) The organism of any one of items G23 to G27, wherein the organism comprises a tag sequence to be biotinylated. (G29) The organism of item G28, wherein the tag sequence to be biotinylated is one of BIOEASE™ Tag biotin ligase birA substrate peptide (Life Technologies, Carlsbad, Calif.) and AVITAG™ biotin ligase birA substrate peptide [SEQ ID NO:98] (Avidity LLC, Aurora, Colo.).

<Modified Silkworm Organism>

(H1) A silkworm or an organism adding a sugar chain similar to that of a silkworm coexpressably incorporated with a nucleic acid molecule encoding a target and a biotin ligase. (H2) The organism of item H1, wherein the biotin ligase is BirA. (H3) The organisms of item H1 or H2, wherein the target is a C-type lectin-like domain (CTLD14) or a receptor for advanced glycation end products (sRAGE) or a variant thereof. (H4) The organism of item H3, wherein the CTLD14 is encoded by SEQ ID NO: 85, and the sRAGE is encoded by SEQ ID NO: 96. (H5) The organism of any one of items H1 to H4, wherein the organism comprises a tag sequence to be biotinylated. (H6) The organism of item H5, wherein the tag sequence to be biotinylated is one of BIOEASE™ Tag biotin ligase birA substrate peptide (Life Technologies, Carlsbad, Calif.) and AVITAG™ biotin ligase birA substrate peptide [SEQ ID NO:98] (Avidity LLC, Aurora, Colo.). (H7) A method of manufacturing a biotinylated protein, comprising: A) incorporating a nucleic acid molecule encoding a protein and a biotin ligase coexpressably into a silkworm or an organism adding a sugar chain similar to that of a silkworm; B) placing the silkworm or the organism adding a sugar chain similar to that of silkworm under a condition where the nucleic acid molecule is expressed in order to express the biotin ligase and the protein; and C) administering biotin to the organism to obtain a biotinylated protein. (H8) The method of item H7, wherein the expression is performed in a middle silk gland of the silkworm. (H9) The method of item H7 or H8, wherein the protein is expressed in a biotinylated state. (H10) The method of any one of items H7 to H9, wherein step A) is accomplished by microinjection of an expression vector comprising the nucleic acid encoding the protein. (H11) The method of any one of items H7 to H10, wherein the protein is a C-type lectin-like domain (CTLD14) or a receptor for advanced glycation end products (sRAGE), or a single chain antibody comprising the amino acid sequence set forth by any one of SEQ ID NOs: 76 to 80 or a variant thereof, or a fragment or variant thereof. (H12) The method of any one of items H7 to H11, wherein the organism comprises a tag sequence to be biotinylated. (H13) The method of item H12, wherein the tag sequence to be biotinylated is one of BIOEASE™ Tag biotin ligase birA substrate peptide (Life Technologies, Carlsbad, Calif.) and AVITAG™ biotin ligase birA substrate peptide [SEQ ID NO:98] (Avidity LLC, Aurora, Colo.).

In the present invention, one or more features described above are intended to be provided not only as the explicitly described combinations but as other combinations thereof. The additional embodiments and advantages of the present invention are recognized by those skilled in the art who have read the following disclosure in detail as needed.

Advantageous Effects of Invention

The present invention constructed a silkworm coexpressing a biotin ligase (BirA) and CTLD14 or sRAGE. Oral administration of biotin to such a silkworm has the excellent effect of biotinylating the expressed protein at a high efficiency. It was further revealed that the resulting protein has a silkworm form sugar chain added and has an excellent stability (e.g., stability with respect to pH or long-term stability of nearly one year).

Use of CTLD14 biotinylated at a high efficiency allows use of streptavidin, which can bind to biotin in a lateral flow assay detection system. Such a detection system can detect LDLs with various oxidatively modified structures in 20 minutes or less.

Further, AGEs with various structures and the like can be detected by immobilizing the silkworm form biotinylated sRAGE of the invention while maintaining the directionality via biotin.

In the present invention, a human single chain antibody library was constructed, and a single chain antibody capable of recognizing oxidized LDLs or the like was obtained from a single chain antibody library consisting of γ+κ chain by biopanning to reveal the genetic sequence thereof. Five clones were obtained in the present invention. The amino acid sequences of the five single chain antibodies selected in the present invention are all sequences that have not been reported in other groups, but were homologous (57 to 86%) to a light chain Fab fragment of an anti-oxidized LDL antibody in the VL region thereof. The VL region of γ+κ19 exhibited 86% homology to the amino acid sequence of a light chain Fab region of an oxidized LDL antibody registered by the group of Jang et al. (Accession No. AA049738). The light chain Fab fragment (Accession No.: AAX57559) of an antibody to malondialdehydized LDLs registered by the same group exhibited 83% homology to the VL region of γ+κ12. It was also found that the VL region of γ+κ5 is also homologous to an antibody to PCSCK9, which was recently reported (Schiele, 2014). PCSK9 is known as a molecule inducing LDLR degradation (Maxwell, 2004). The anti-PCSK9 antibody by Schiele et al. has the function of binding to the C-terminal region of PCSK9 to inhibit the interaction of PCSK9 with LDLR, thus ultimately lowering blood LDL levels (see Schiele, F., Park, J., Redemann, N., Luippold, G., and Nar, H. (2014) An antibody against the C-terminal domain of PCSK9 lowers LDL cholesterol levels in vivo. J. Mol. Biol. 426, 843-852; and Maxwell, K. N., and Breslow, J. L. (2004) Adenoviral-mediated expression of Pcsk9 in mice results in a low-density lipoprotein receptor knockout phenotype. Proc. Natl. Acad. Sci. U.S.A 101, 7100-7105).

The present invention revealed that expression of clones No. 5 and 19 (SEQ ID NOs: 76 and 78) is possible in the generated library of E. coli. It was also discovered that mass expression of clone No. 5 is possible. The present invention further established a stable supply system of the obtained single chain antibody (γ+κ5). Establishment of such a stable supply system of a single chain antibody was not previously possible. Thus, the present invention achieves a significant effect with respect to this point.

The present invention further evaluated the binding characteristic to discover that an ability to recognize a broad range of modified LDLs, such as partially oxidized LDLs and acetylated LDLs, in addition to fully oxidized LDLs and LDSs, is confirmed. The present invention has an excellent ability to recognize oxidized LDLs in a low concentration region, and is capable of quantifying and evaluating especially oxidatively modified LDLs by sandwich ELISA combined with an oxidized LDL receptor (LOX-1) or the like. The present invention is also capable of detecting an oxidized LDL-like molecule from a broad range of organism species such as humans and mice.

The antibody of the present invention is a single chain antibody with an apparent sequence. Thus, an efficient production system by various expression systems can be developed, and modifications such as glycosylation are possible. In addition, functional modification by introducing a mutation or the like is also possible.

Thus, the present invention provides a single chain antibody recognizing oxidized LDLs and the like, a stable supply system for a single chain antibody, a method of detecting a modified LDL using a single chain antibody, and a method of specifically detecting an oxidized LDL-like molecule in combination with an oxidized LDL receptor (LOX-1).

In another aspect, the present invention obtains a large quantity of purified CTLD14 in several days or less by using a simple approach with a genetically modified silkworm (FIG. 23). This is superior among approaches providing a recognition region of LOX-1 relative to conventional methods with respect to the cost, simplicity, and productivity.

The improved CTLD14, to which a silkworm sugar form chain of the invention is added, does not recognize unmodified LDLs, but it was revealed that such CTLD14 broadly recognizes modified LDLs and the dynamic range of detection is broader than conventional CTLD14 prepared from E. coli (FIGS. 27 and 28).

It was revealed that the anti-LDL chicken polyclonal antibody obtained in the present invention can recognize unmodified LDLs and modified LDLs with various modifications. Such an antibody is also capable of detecting types of modified LDLs that are not recognized by an anti-ApoB chicken monoclonal antibody (FIG. 26).

As demonstrated by the present invention, modified LDLs, which were difficult to detect with conventional methods, can be detected by combining an anti-LDL chicken polyclonal antibody and CTLD14 (FIG. 28).

Meanwhile, the present invention has a significant feature in terms of being a breakthrough compared to the current state, where AGEs that can be subjected to instrument analysis are less than 10% of all AGEs. A conventional detection method using reconstructed RAGE (sRAGE) can also detect a broad range of AGEs, but had practical problems such as sRAGE fragmenting to lose the recognition ability in about a month and a half (see FIG. 38). The present invention is significant in that this was also overcome. In particular, the improved sRAGE of the invention is glycosylated and a very stable molecule, maintaining the recognition activity over a long period of time in storage at 4° C. (confirmed up to about one year as of the filing) (FIGS. 38, 40, and 53). The improved sRAGE of the invention was also capable of detecting trace amounts of AGE concentration, AGEs with various structures, and the like (FIG. 40).

BRIEF DESCRIPTION OF DRAWINGS

FIG. 1 shows a schematic diagram of an LDL and an oxidized LDL. As shown, oxidized LDL (modified LDL) is a general term for various structures. Oxidized LDLs are considered to be related to the onset of lifestyle diseases from the early stages. Conventionally available monoclonal antibodies merely recognize one structure in a molecule. There is a problem with homology of antigens, such that it is difficult to make a useful mouse monoclonal antibody for antibodies to a common molecule (ApoB). Use of chicken monoclonal antibodies is considered.

FIG. 2 shows a schematic diagram of single chain antibodies and an exemplary summary of the production procedure. A single chain antibody was produced, as shown in the Examples, by developing a single chain gene antibody library (e.g., pCANTAB5E), presenting the antibody library to the phage, selecting a single chain antibody by biopanning, obtaining a promising clone from a library consisting of γ+κ, and determining the gene sequence. A promising clone could not be obtained from a library consisting of μ+λ. A single chain antibody is advantageous in that an antibody can be selected in a short period of time after library construction without immunization of animals, and modifications such as glycosylation using various expression systems are possible, and alterations by introducing a mutation or the like are also simple.

FIG. 3A shows evaluation, by ELISA, of a prepared phage presented single chain antibody in a library consisting of γ+κ. Each clone No. is shown from the left (5, 12, 14, 15, 19, 31, 40, 79, and 96). The rightmost column shows the result for PBS.

FIG. 3B shows evaluation, by ELISA, of a prepared soluble single chain antibody in a library consisting of γ+κ. Each clone No. is shown from the left (5, 12, 14, 15, 19, 31, 40, 79, and 96). The rightmost column shows the result for PBS.

FIG. 4A shows evaluation, by ELISA, of a prepared phage presented single chain antibody in a library consisting of μ+λ. Each clone No. is shown from the left (1, 2, 3, 4, 11, 13, 15, 93, and 94). The rightmost column shows the result for PBS.

FIG. 6 shows results of SDS-PAGE of culture supernatant and microbial cell for culture using TG1, HB2151, and BLR. The left most column shows the molecular weight marker. Four bands on the left shows results for TG1 (among them, two on the left show results for no induction (among the two, left shows results for microbial cell and right shows results for supernatant) and two on the right shows results with induction (among the two, left shows results for microbial cell and right shows results for supernatant)). The next four bands show results for HB2151 (among them, two on the left shows results for no induction (among the two, left shows results for microbial cell and right shows results for supernatant) and two on the right shows results with induction (among the two, left shows results for microbial cell and right shows results for supernatant)). The four bands on the right show results for BLR (among them, two on the left shows results for no induction (among the two, left shows results for microbial cell and right shows results for supernatant) and two on the right show results with induction (among the two, left shows results for microbial cell and right shows results for supernatant)).

FIG. 7 shows the results of Western blot using an anti-E antibody as a primary antibody. Each band indicates, from the left, molecular weight marker, γ+κ5 with no induction, and γ+κ5 with induction. Near 30.8 kDa is the band for γ+κ5 (with G3 signal+E tag).

FIG. 8 shows results of SDS-PAGE performed for evaluating purification using anti-E antibody immobilization sepharose. Each band indicates, from the left, molecular weight marker, γ+κ5 with no induction, and γ+κ5 with induction. Near 30.8 kDa is the band for γ+κ5 (with G3 signal+E tag).

FIG. 9A shows results of SDS-PAGE for insoluble and soluble fractions for culture using pET-22b (+) as an expression vector.

FIG. 9B shows results of Western blot using anti-His tag antibody of induction and no induction sections as a primary antibody for culture using pET-22b (+) as an expression vector.

FIG. 18 shows a schematic diagram of production by a genetically modified silkworm.

FIG. 19 shows amino acid information and sugar chain information of improved CTLD14 (silkworm form glycosylated biotinylated CTLD14), and a schematic diagram of dimerization on the right.

FIG. 20 shows examples of structures of a silkworm form sugar chain (N-linked sugar chain) of sRAGE or CTLD14 (typical N-linked sugar chain structure seen in glycoproteins expressed in silkworm middle silk gland (Iizuka et al., FEBSJ., 277, 5806-5820)). Assumed combinations of sugar chains in CTLD14 include, but are not limited to, a combination of 2 (one of oligomannose type) and complex type 4, and a combination of 3 (one of oligomannose type) and hybrid type (5 or 6). In the Figure, squares indicate N-acetylglucosamine (GlcNAc) and circles indicate mannose (Man).

FIG. 21 shows expression for each genetically modified silkworm line of CTLD14. 1→indicates the band for Biotin_CTLD14 (with a BIOEASE™ Tag biotin ligase birA substrate peptide (Life Technologies, Carlsbad, Calif.)), and 2→indicates CTLD14 with a myc tag. 'A' shows Coomassie blue (CBB) staining, and 'B' shows the results of Western blot (anti-His tag antibody). In each diagram from the left, negative control, lines 1-4 of Biotin-CTLD14, and lines 1-3 of Myc-CTLD14 are shown. The left end indicates the molecular weight (kDa).

FIG. 32 FIG. 32 is a table summarizing the difference in mass of peptides and ions observed at the mass spectrum near the 13.1 minute, which is expanded and shown in FIG. 31. FIG. 32 is a result of studying the sugar chain structure that is expected to be added in detail. While an ion indicating a difference in mass suggesting that a part of a sugar was lost with the preparation of a specimen was found, the presence of a sugar chain shown as [Chemical 1](1) (left column, 892.34), [Chemical 2] (2) (1298.5), [Chemical 3] (3) or [Chemical 4] (4) (1095.42) was confirmed. In view of the above, it is possible that a sugar chain is linked to NCS (111N) or NST (155N) in silkworm form CTLD14. Furthermore, the sugar chain mass number is expected to be about 2500. In view of the results of FIGS. 29 to 32, the following combination is assumed: (trimannosyl core 892)×2+ (GlcNAc203)×2+(Man162)×2 or (trimannosyl core 892)× 2+(GlcNAc203)×1+(Man162)×3.

FIG. 34 shows the amino acid sequence of RAGE expressed in a genetically modified silkworm.

FIG. 35 shows results of electrophoresis of a middle silk gland extract of a genetically modified silkworm. A sample was prepared by taking out a middle silk gland from genetically modified silkworm lines (1 to 4) and a negative control (only middle silk gland GALA4, no UAS: no expression of sRAGE) and subsequently adding 1 ml of PBS comprising 1% Triton X-100 to one middle silk gland and inverting and mixing for 2 hours at 4° C. The left side shows results of staining proteins with Coomassie brilliant blue after electrophoresis of a specimen with 4 to 12% gradient SDS-polyacrylamide gel. The amount of specimen added to each lane was 5 μl/lane on the left side and 10 μl/lane on the right side. M: molecular weight markers (benchmark: Invitrogen). 1 to 4 indicate the line numbers of created genetically modified silkworms, and Nega: indicates the negative control. The right side shows results of SD Western blot. A specimen, after deployment with 4 to 12% gradient SDS-PAGE, was transcribed onto a PVDF film. Anti-His rabbit antibody (1000-fold dilution)+anti-His mouse antibody (3000-fold dilution) were used as primary antibodies, and the specimen was subsequently reacted with the secondary antibody HRP-labeled anti-rabbit & mouse antibody (200, 000-fold dilution). The specimen was finally reacted with ECL Prime for detecting the generated luminescence to confirm sRAGE expression.

FIG. 39 shows confirmation of glycosylation of silkworm form RAGE. 20 µg of silkworm form sRAGE after purification was treated with PNGase F and subjected to 12% SDS-PAGE. (+) indicates a PNGase F treated specimen, and (−) indicates a specimen subjected to the same reaction in the absence of PNGase F. Left: shows results of CBBR staining, where the amount of specimen added was 6.7 µg/lane. A molecular weight shift due to deglycosylation by PNGase F treatment was confirmed. Middle: shows results of glycoprotein staining before and after PNGase F treatment by Glycoprotein Staining (Pierce 24562). The specimen was no longer detected as a glycoprotein due to deglycosylation from PNGase F treatment. Right: shows a diagram confirming no change in reactivity with an anti-RAGE antibody even after PNGase F treatment. Specimens after PNGase F treatment and without PNGase F treatment were transcribed onto a PVDF film after deployment with 12% SDS-PAGE, reacted with an anti-RAGE rabbit antibody as a primary antibody, and subsequently reacted with a secondary antibody HRP-modified anti-rabbit IgG antibody. sRAGE was finally detected with ECL. Detection was performed with RAGE antibodies in both cases.

FIG. 40 shows results of detecting various AGEs by a sandwich ELISA-like approach using silkworm form sRAGE and *E. coli* form sRAGE. ● (filled circles) indicate R-AGEs, which are AGEs prepared by ribose treatment of BSA. ▲ (filled triangles) indicate F-AGEs, which are AGEs prepared by fructose treatment. ■ (filled squares) indicate G-AGEs, which are AGEs prepared by glucose treatment. □ (open squares) indicate Ctl-AGEs, which are controls treated in the absence of sugar. The left side shows results of using *E. coli* form sRAGE stored at 4° C. for one week following purification. As shown in FIG. 6, *E. coli* form is fragmented in about 40 days. Thus, the ability to recognize AGEs is lost after 40 days such that it would be impossible to detect AGEs observed in this diagram. The right diagram shows results of AGE detection by silkworm form sRAGE 90 days after purification. It was confirmed that the recognition ability is maintained even after 90 days, and the same detection as an *E. coli* form on week one after purification is possible.

FIG. 41 shows results of mass spectrometry on silkworm form sRAGE. sRAGE created by using a silkworm contained in a gel fragment was acetamidated and then digested with trypsin and measured with MALDI-TOFMS and LC-ESIMS. Mass spectrums on sRAGE treated with and without PNGase F were compared. An ion comprising two amino acid sequences including sequences expected to have N-linked glycosylation (NIT, NGS) was not observed before PNGase F treatment but observed after treatment, such that N of both NIT and NGS were considered to be glycosylated.

FIG. 42 shows a schematic diagram of RAGE and AGEs. As shown, the molecular form of AGEs is diverse. Thus, detection with an antibody or chemical analysis has limitations. Multi-recognition ability of RAGE or the like is important in order to detect such AGEs with a diverse form.

FIG. 48 is a table summarizing the stability of *E. coli* form CTLD14 and silkworm form CTLD14. *E. coli* form can use a limited number of buffers, such that the application thereof was limited. Meanwhile, it was revealed that the silkworm form, in the absence of salt, is stable at a pH of 7 to 9.5, and stable in Tris based buffer, resulting in a wide selection for utilization in a detection/evaluation system.

FIG. 53 shows the results of SDS-PAGE on *E. coli* form and silkworm form sRAGE. FIG. 53 shows, from the left lane, *E. coli* form, day 1 of storage; *E. coli* form, day 40 of storage; silkworm form, day 1 of storage; silkworm form, 1.5 months of storage; and silkworm form, 11th month of storage.

FIG. 54 shows sugar chain structures of silkworm sRAGE. N1, N2, N3, and N4-1 are oligomannose form, N4-2 is a complex form, and N4-3 is a hybrid form sugar chain.

FIG. 55 shows a composition ratio, quantified value, and sugar composition of each sugar chain identified in Examples 22.

DESCRIPTION OF EMBODIMENTS

Figure 4B:
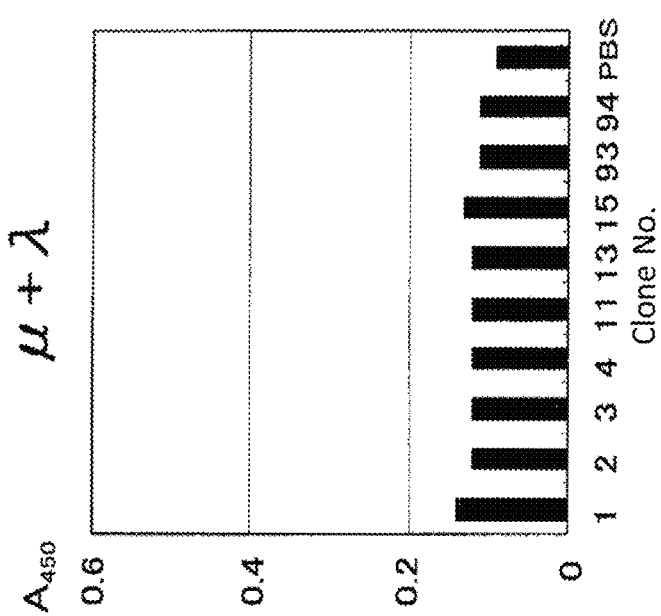
FIG. 4B shows evaluation, by ELISA, of a prepared soluble single chain antibody in a library consisting of μ+λ. Each clone No. is shown from the left (1, 2, 3, 4, 11, 13, 15, 93, and 94). The rightmost column shows the result for PBS.

The present invention is disclosed hereinafter. Throughout the entire specification, a singular expression should be understood as encompassing the concept thereof in the plural form, unless specifically noted otherwise. Thus, singular articles (e.g., "a", "an", "the" and the like in case of English) should also be understood as encompassing the concept thereof in the plural form unless specifically noted otherwise. Further, the terms used herein should be understood to be used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

Definitions of the Terms

The definitions of the terms especially used herein are provided below.

As used herein, an "antibody" includes, in a broad sense, polyclonal antibodies, monoclonal antibodies, multi-specific antibodies, chimeric antibodies, anti-idiotype antibodies, and functional fragments thereof (e.g., $F(ab')_2$ and Fab fragments), as well as other conjugates or functional equivalents produced by recombination (e.g., chimeric antibodies, humanized antibodies, multifunctional antibodies, bispecific or oligospecific antibodies, single chain antibodies, scFv, diabodies, $sc(Fv)_2$ (single chain $(Fv)_2$), and scFv-Fc). Furthermore, such an antibody may be fused, by a covalently bond or recombination, with an enzyme such as alkaline phosphatase, horseradish peroxidase, or a galactosidase. For instance, "anti-modified LDL antibody" as used herein refers to any antibody to a modified LDL. Narrowly defined, antibody refers to a full-length antibody (e.g., polyclonal antibody, monoclonal antibody, or the like), and may refer to a variant or fragment thereof. The antibody used in the present invention only needs to bind to a target thereof (LDL, oxidized LDL-like molecule or the like), regardless of the origin, type, shape or the like thereof. Specifically, an antibody can be manufactured based on a known antibody such as a non-human animal antibody (e.g., a mouse antibody, a rat antibody, or a camel antibody), a human antibody, a chimeric antibody, or a humanized antibody. In the present invention, a single chain antibody is used. It is preferable that an antibody binds distinctly or specifically to a target. Variants of an antibody may be formed by an antibody binding to various molecules, such as polyethylene glycol. A variant of an antibody can be obtained by applying a chemical modification to the antibody by using a known approach.

As used herein, "single chain antibody" is also referred to as "scFv (single chain FV)" and corresponds to the variable regions ($V_H$ and $V_L$) of a heavy chain and light chain of an antibody which are linked with a suitable peptide linker. Such a construct can be constructed at a gene level and introduced into *E. coli* using a protein expression vector to express a single chain antibody protein.

As used herein, "fragment" refers to a polypeptide or polynucleotide with a sequence length of 1 to n-1 with respect to the full length polypeptide or polynucleotide (with length n). The length of a fragment can be appropriately changed in accordance with the objective. Examples of the lower limit of such a length include 3, 4, 5, 6, 7, 8, 9, 10, 15, 20, 25, 30, 40, 50 and more amino acids for a polypeptide. Lengths represented by an integer that is not specifically listed herein (e.g., 11 and the like) also can be suitable as a lower limit. Further, examples of the lower limit length include 5, 6, 7, 8, 9, 10, 15, 20, 25, 30, 40, 50, 75, 100, and more nucleotides for a polynucleotide. Lengths represented by an integer that is not specifically listed herein (e.g., 11 and the like) also can be suitable as a lower limit. As used herein, the length of a polypeptide or a polynucleotide can be represented by the number of amino acids or nucleic acids as discussed above, respectively, but the aforementioned numbers are not absolute. The aforementioned numbers as the upper limit or the lower limit are intended to encompass several numbers above and below the number (or for example, 10% above or below) as long as there is the same function. To express such an intention, the number may be expressed herein by appending "about" in front of the number. However, it should be understood that the presence of absence of "about" herein does not affect the interpretation of the numerical value thereof. The length of a useful fragment herein may be determined by whether at least one of the functions of a full-length protein, which is a reference for the fragment, is retained.

As used herein, "homology" of genes refers to the level of identity of two or more genetic sequences with one another. Thus, two genes with high homology have higher identity or similarity of sequences. It is possible to investigate whether two types of genes are homologous by direct comparison of sequences or, for nucleic acids, by a hybridization method under a stringent condition. When two genetic sequences are directly compared, the genes are homologous when DNA sequences are representatively at least 50% identical, preferably at least 70% identical, and more preferably at least 80%, 90%, 95%, 96%, 97%, 98%, or 99% identical between the genetic sequences.

Similarity, identity, and homology of amino acid sequences and base sequences are calculated herein with default parameters using the sequence analysis tool BLAST. Identity can be searched by using, for example, BLAST 2.2.9 (published on May 12, 2004) of NCBI. The value of identity herein generally refers to a value aligned at the default condition by using the aforementioned BLAST. However, when a higher value is output by changing a parameter, the highest value is considered the value of identity. When identity is evaluated in multiple regions, the highest value thereamong is considered the value of identity.

As used herein, a "corresponding" amino acid refers to an amino acid which has, or is expected to have, in a certain protein molecule or a polypeptide molecule, a similar action to a predetermined amino acid in a benchmark protein or polypeptide for comparison, such as amino acids at positions 232 and 249 in LOX-1.

As used herein, a "corresponding" gene refers to a gene of a certain species which has or is expected to have a similar action to that of a predetermined gene in a benchmark species for comparison. When there is a plurality of genes having such action, the corresponding gene refers to a gene having the same evolutionary origin. Hence, a gene corresponding to a certain gene (e.g., LOX-1) may be an ortholog of such a gene. Thus, genes corresponding to human genes can be found in other animals (mouse, rat, pig, rabbit, guinea pig, cow, sheep, and the like). Such a corresponding gene can be identified by using a technique that is well known in the art. For example, a corresponding gene in a certain animal can be found by searching a database comprising sequences of the animal (e.g., mouse, rat, pig, rabbit, guinea pig, cow, sheep, and the like) by using the benchmark gene of the corresponding gene as a query sequence.

As used herein, "variant" refers to a substance, such as a polypeptide or a polynucleotide which is partially changed. Examples of such a variant include substituted variant, addition variant, deletion variant, truncated variant, allelic mutant and the like. Allele refers to genetic variants that belongs to the same gene locus but are distinguished from each other. Thus, "allelic mutant" refers to a variant in an allelic relationship to a certain gene. "Homolog" refers to having homology (homology of preferably 60% or greater, and more preferably 80% or greater, 85% or greater, 90% or greater, or 95% or greater) at an amino acid level or nucleotide level to a certain gene in a certain species. A method of obtaining such a homolog is apparent from the descriptions herein. "Ortholog" is also referred to as orthologous gene and refers to two genes derived from species differentiation from a common ancestor. For instance, using hemoglobin gene family with a multigenic structure as an example, human and mouse a hemoglobin genes are orthologs, but the human a hemoglobin gene and β hemoglobin genes are paralogs (genes produced by gene duplication). Since orthologs are useful in estimating a molecular phylogenetic tree, orthologs can also be useful in the present invention.

As used herein, "conservative (-ly altered) variant" applies to both amino acid sequences and nucleic acid sequences. A conservatively altered variant for a specific nucleic acid sequence refers to a nucleic acid encoding an identical or essentially identical amino acid sequence, and when a nucleic acid does not encode an amino acid sequence, this refers to an essentially identical sequence. Examples of such an alteration method of base sequences include cleavage by a restriction enzyme or the like, linking processing or the like by processing with DNA polymerase, Klenow fragment, DNA ligase or the like, partially specific base substitution using synthetic oligonucleotide or the like (specific site directed mutagenesis; Mark Zoller and Michael Smith, Methods in Enzymology, 100, 468-500 (1983)), but other methods commonly used in the field of molecular biology can also be used for alteration. Due to gene code degeneracy, many functionally identical nucleic acids encode any predetermined protein. For example, codons GCA, GCC, GCG, and GCU all encode the amino acid alanine. Thus, at all positions where alanine is specified by a codon, the codon can be changed to any described corresponding codon without changing the encoded polypeptide. Such a variation in a nucleic acid is a "silent alteration" (mutation), which is one type of conservatively altered mutation. All nucleic acid sequences encoding a polypeptide herein also describe all possible silent mutations of the nucleic acid. It is understood that each codon (excluding AUG, which is generally the only codon for methionine and TGG, which is generally the only codon for tryptophan) in a nucleic acid may be altered to produce a functionally identical molecule in the art. Thus, each silent mutation of a nucleic acid encoding a polypeptide is implicitly encompassed in each described sequence. Preferably, such an alteration can be made to avoid substitution of cysteine, which is an amino acid that has a significant effect on the higher order structure of polypeptides.

For example, a certain amino acid can be substituted with another amino acid in a protein structure such as a binding site of a ligand molecule without an apparent decrease or loss of interactive binding ability. It is the interactive ability and property of a certain protein that determines the biological function of the protein. Thus, a specific amino acid can be substituted in an amino acid sequence or at a DNA encoding sequence level. Even after the substitution, a protein maintaining the original property can be generated. Thus, various alterations can be made to the peptides disclosed herein, or corresponding DNA encoding the peptides, without apparent loss of biological usefulness.

Such a nucleic acid can also be obtained by a well-known PCR method and can be chemically synthesized. Such methods may be combined with a method such as site specific mutagenesis, hybridization, or the like.

The amino acid hydrophobicity index may be considered when designing such alterations. The importance of the hydrophobic amino acid index in imparting an interactive biological function in proteins is commonly recognized in the art (Kyte. J and Doolittle, R. F. J. Mol. Biol. 157 (1): 105-132, 1982). The hydrophobic property of an amino acid contributes to the secondary structure of a generated protein and defines the interaction of the protein with another molecule (e.g., enzyme, substrate, receptor, DNA, antibody, antigen, or the like). Each amino acid is assigned a hydrophobicity index based on the hydrophobicity and charge property thereof. They are isoleucine (+4.5); valine (+4.2); leucine (+3.8); phenylalanine (+2.8); cysteine/cystine (+2.5); methionine (+1.9); alanine (+1.8); glycine (-0.4); threonine (-0.7); serine (-0.8); tryptophan (-0.9); tyrosine (-1.3); proline (-1.6); histidine (-3.2); glutaminic acid (-3.5); glutamine (-3.5); aspartic acid (-3.5); asparagine (-3.5); lysin (-3.9); and arginine (-4.5)).

It is well known in the art that it is possible to produce a protein, which has a certain amino acid substituted with another amino acid having a similar hydrophobicity index and still has a similar biological function (e.g., protein with equivalent ligand binding ability). In such an amino acid substitution, the hydrophobicity index is preferably ±2 or less, more preferably ±1 or less, and still more preferably ±0.5 or less. It is understood in the art that such a substitution of an amino acid based on hydrophobicity is effective. As described in U.S. Pat. No. 4,554,101, the following hydrophilicity index is assigned to amino acid residues: arginine (+3.0); lysine (+3.0); aspartic acid (+3.0±1); glutaminic acid (+3.0±1); serine (+0.3); asparagine (+0.2); glutamine (+0.2); glycine (0); threonine (-0.4); proline (-0.5±1); alanine (-0.5); histidine (-0.5); cysteine (-1.0); methionine (-1.3); valine (-1.5); leucine (-1.8); isoleucine (-1.8); tyrosine (-2.3); phenylalanine (-2.5); and tryptophan (-3.4). It is understood that an amino acid can be substituted with another amino acid having a similar hydrophilicity index and can still give rise to a biological equivalent. In such an amino acid substitution, the hydrophilicity index is preferably ±2 or less, more preferably ±1 or less, and still more preferably ±0.5 or less.

As used herein, "conservative substitution" refers to a substitution in which the hydrophilicity index or/and hydrophobicity index of the original amino acid and substituting amino acid are similar in an amino acid substitution. Examples of conservative substitutions are well known to those skilled in the art, including, but not limited to, the following substitutions in each group: arginine and lysine; glutamic acid and aspartic acid; serine and threonine; glutamine and asparagine; valine, leucine and isoleucine; and the like.

To make a functionally equivalent polypeptide herein, an amino acid addition, deletion, or modification can also be made in addition to amino acid substitutions. Amino acid substitution refers to substitution of 1 or more, such as 1 to 10, preferably 1 to 5, and more preferably 1 to 3 amino acids in the original peptide. Amino acid addition refers to addition of 1 or more, such as 1 to 10, preferably 1 to 5, and more preferably 1 to 3 amino acids in the original peptide chain. Amino acid deletion refers to deletion of 1 or more, such as 1 to 10, preferably 1 to 5, and more preferably 1 to 3 amino acids from the original peptide. Examples of amino acid modifications include, but are not limited to, amidation, carboxylation, sulfation, halogenation, alkylation, phosphorylation, hydroxylation, acylation, (e.g., acetylation) and the like. An amino acid that is substituted or added may be a natural-occurring amino acid, a non-naturally-occurring amino acid, or an amino acid analog. Naturally-occurring amino acids are preferred.

As used herein, "substitution, addition, and/or deletion" of a polypeptide or polynucleotide refers to a substitution, addition, or removal of an amino acid or a substitution thereof, or a nucleotide or a substitution thereof in the original peptide or polynucleotide, respectively. A technique for such a substitution, addition, and/or deletion is well known in the art. Examples of such techniques include site specific mutagenesis techniques, and the like. These changes in the reference nucleic acid molecule or polypeptide can be made to the 5' terminus or the 3' terminus of the nucleic acid molecule, at the amino terminal region or carboxy terminal region of an amino acid sequence setting forth the polypeptide, or anywhere between such terminal regions, individually dispersed between residues in the reference sequence, as long as the function of interest (e.g., LOX-1 recognition ability or the like) is retained. A substitution, addition, or deletion may be any number as long as it is one or more. Such a number can be increased, as long as the function of interest (e.g., LOX-1 recognition ability or the like) is retained in a variant with the substitution, addition or deletion. Examples of such a number may be 1 or several, preferably 20% or less, 15% or less, 10% or less, or 5% or less of the full length, 150 or less, 100 or less, 50 or less, 25 or less, or the like.

As used herein, the term "tag sequence" refers to a substance for sorting out molecules by a specific recognition mechanism such as receptor-ligand, or more specifically a substance serving the role of a binding partner for binding a specific substance (e.g., having a relationship as in biotin-avidin or biotin-streptavidin). Accordingly, a specific substance to which a tag sequence binds to can be selected out, for example, by contacting the specific substance with a substrate to which a binding partner of the tag sequence is bound. Such a tag sequence is well known in the art. Representative tag sequences include, but are not limited to, myc tag, His tag, HA, Avi tag, and the like.

As used herein, "detection agent" broadly refers to any agent that can detect a substance or condition of interest (e.g., modified LDL, LOX-1, AGEs, cell, tissue, pathological condition or the like).

As used herein, "protein", "polypeptide", "oligopeptide" and "peptide" are used to have the same meaning and refer to an amino acid polymer of any length. Such a polymer may be a branched or straight chain or annular. An amino may be a naturally-occurring, a non-naturally-occurring, or an altered amino acid. The term may also encompass those assembled into a complex of a plurality of polypeptide chains. The term also encompasses natural or artificially altered amino acid polymers. Examples of such an alteration include disulfide bond formation, glycosylation, lipidation, acetylation, phosphorylation and any other manipulation or alteration (e.g., conjugation with a labeling component). The definition also encompasses, for example, polypeptides comprising one or more analogs of an amino acid (e.g., including a non-naturally-occurring amino acid, etc.), peptide-like compounds (e.g., peptoid), and other known alterations in the art.

As used herein, "amino acid" may be naturally-occurring or non-naturally-occurring as long as the objective of the present invention is met. As used herein "amino acid derivative" or "amino acid analog" refers to substances that are different from naturally-occurring amino acids, but have a similar function as the original amino acid. Such an amino acid derivative and amino acid analog are well known in the art. It is understood that an amino acid derivative and amino acid analog can be used herein as a substitute as long as the same biological function as an amino acid can be provided. As used herein, "naturally-occurring amino acid" refers to the L-isomer of a naturally-occurring amino acid. Naturally-occurring amino acids are glycine, alanine, valine, leucine, isoleucine, serine, methionine, threonine, phenylalanine, tyrosine, tryptophan, cysteine, proline, histidine, aspartic acid, asparagine, glutaminic acid, glutamine, γ-carboxy glutaminic acid, arginine, ornithine, and lysine. Unless specifically noted otherwise, all amino acids as used herein are L-forms, but embodiments using a D form amino acid are also within the scope of the present invention. As used herein, "non-naturally-occurring amino acid" refers to amino acids that are not generally found in nature in a protein. Examples of non-naturally-occurring amino acids include norleucine, para-nitro phenylalanine, homophenylalanine, para-fluorophenylalanine, 3-amino-2-benzyl propionic acid, D or L form of homoarginine, D-phenylalanine, and the like. As used herein "amino acid analog" refers to a molecule that is not an amino acid, but has a physical property and/or function similar to that of an amino acid. Examples of an amino acid analog include ethionine, canavanine, 2-methyl glutamine, and the like. Amino acid mimetics refers to compounds which have a structure that is different from a common chemical structure of amino acids, but function in a similar manner to naturally-occurring amino acids.

Amino acids can be mentioned herein by their commonly known three letter notation or single letter notation recommended by the IUPAC-IUB Biochemical Nomenclature Commission. Nucleotides can be similarly mentioned by their commonly recognized one letter notation.

As used herein, "polynucleotide", "oligonucleotide" and "nucleic acid" are used in the same meaning and refer to a nucleotide polymer of any length. The term also encompasses "oligonucleotide derivative" and "polynucleotide derivative" "Oligonucleotide derivative" or "polynucleotide derivative" refers to an oligonucleotide or a polynucleotide, which has a bond between nucleotides that is not normal or includes a nucleotide derivative. They are interchangeably used. Specific examples of such an oligonucleotide include 2'-O-methyl-ribonucleotide, oligonucleotide derivative with a phosphodiester bond in an oligonucleotide converted to a phosphorothioate bond, oligonucleotide derivative with a phosphodiester bond in an oligonucleotide converted to an N3'-P5' phosphoroamidate bond, oligonucleotide derivative with a ribose and phosphodiester bond in an oligonucleotide converted to a peptide nucleic acid bond, oligonucleotide derivative with uracil in an oligonucleotide substituted with C-5 propynyl uracil, oligonucleotide derivative with uracil in an oligonucleotide substituted with C-5 thiazole uracil, oligonucleotide derivative with cytosine in an oligonucleotide substituted with C-5 propynyl cytosine, oligonucleotide derivative with cytosine in an oligonucleotide substituted with phenoxazine-modified cytosine, oligonucleotide derivative with ribose in a DNA substituted with 2'-O-propylribose, oligonucleotide derivative with ribose in an oligonucleotide substituted with 2'-methoxyethoxyribose, and the like. Unless specifically noted otherwise, a specific nucleic acid sequence is further intended to encompass conservatively altered variants (e.g., degenerate codon substituted form) and complementary sequences thereof in addition to the explicitly shown sequences. Specifically, a degenerate codon substituted form can be obtained by creating a sequence in which the third position of one or more selected (or all) codons is substituted with a mixed base and/or deoxyinosine residue (Batzer et al., Nucleic Acid Res. 19: 5081 (1991); Ohtsuka et al., J. Biol. Chem. 260: 2605-2608 (1985); Rossolini et al., Mol. Cell. Probes 8: 91-98 (1994)).

As used herein, a "nucleotide" may be naturally-occurring or non-naturally occurring. "Nucleotide derivative" or "nucleotide analog" refers to substances that are different from naturally occurring nucleotides, but have a similar function as the original nucleotide. Such a nucleotide derivative and nucleotide analog are known in the art. Examples of such a nucleotide derivative and nucleotide analog include, but are not limited to, phosphorothioate, phosphoamidate, methyl phosphonate, chiral methyl phosphonate, 2'-O-methyl ribonucleotide, and peptide nucleic acid (PNA).

As used herein, "complex molecule" refers to molecules made by linking multiple types of molecules such as a polypeptide, polynucleotide, lipid, saccharide, or small molecule. Examples thereof include, but are not limited to, glycolipids, glycopeptides, and the like. For a polypeptide having an amino acid exemplified by SEQ ID NO: 97 or a variant or fragment thereof, nucleic acid molecules encoding a variant or fragment thereof or the like can also be used herein, as long as it has biological activity involved in diagnosis. A complex molecule comprising such a nucleic acid molecule can also be used.

As used herein, "nucleic acid" is also interchangeably used with gene, cDNA, mRNA, oligonucleotide and polynucleotide. A specific nucleic acid sequence also encompasses a "splice variant". Similarly, a specific protein encoded by a nucleic acid implicitly encompasses any protein encoded by the splice variant of the nucleic acid. As the name suggests, "splice variant" is a product of alternative splicing of a gene. After transcription, the first nucleic acid transcript may be spliced to encode a polypeptide with a different (another) nucleic acid splice product. While production mechanisms of spliced variants vary, they include alternative splicing of exons. Other polypeptides derived from the same nucleic acid by read-through transcription are also encompassed by this definition. Any product of a splicing reaction (including recombinant splice products) is encompassed by this definition.

As used herein, "gene" refers to an agent defining a genotype. A gene is generally arranged in a certain order in a chromosome. A gene defining the primary structure of a protein is referred to as a structural gene, and a gene affecting the expression thereof is referred to as a regulator gene. As used herein, "gene" may refer to a "polynucleotide", "oligonucleotide" and "nucleic acid" and/or "protein", "polypeptide", oligopeptide", and "peptide".

As used herein, "homology" of genes refers to the level of identity of two or more genetic sequences to one another. Thus, a higher level of homology of two genes results in a higher identity or similarity of sequences thereof. It is possible to examine whether two types of genes are homologous by direct comparison of sequences or by hybridization under stringent conditions for nucleic acids. When directly comparing two genetic sequences, the genes are homologous typically when DNA sequences between the genetic sequences are at least 50% identical, preferably at least 70% identical, and more preferably at least 80%, 90%, 95%, 96%, 97%, 98% or 99% identical.

Amino acids can be mentioned herein by their commonly known three letter notation or single letter notation recommended by the IUPAC-IUB Biochemical Nomenclature Commission. Nucleotides can be similarly mentioned by their commonly recognized one letter notation.

Similarity, identity, and homology of amino acid sequences and base sequences are calculated herein with default parameters using the sequence analysis tool BLAST. Identity can be searched for by using, for example, BLAST 2.2.9 (published on May 12, 2004) of NCBI. The value of identity herein generally refers to a value aligned at the default condition by using the aforementioned BLAST. However, when a higher value is output by changing a parameter, the highest value is considered the value of identity. When identify is evaluated in multiple regions, the highest value thereamong is considered the value of identity.

As used herein, "polynucleotide that hybridizes under stringent conditions" refers to a conventional, well-known condition in the art. Such a polynucleotide can be obtained by using colony hybridization, plaque hybridization, southern blot hybridization, or the like while using a polynucleotide selected from the polynucleotides of the invention as a probe. Specifically, such a polynucleotide refers to a polynucleotide which can be identified using a filter with immobilized DNA derived from a colony or a plaque for hybridization at 65° C. in the presence of 0.7 to 1.0 M NaCl, and then using a 0.1 to 2-fold concentration SSC (saline-sodium citrate) solution (composition of an SSC solution with 1-fold concentration is 150 mM sodium chloride and 15 mM sodium citrate) to wash the filter under 65° C. conditions. Hybridization can be performed in accordance with the method described in experimental publications such as Molecular Cloning 2nd ed., Current Protocols in Molecular Biology, Supplement 1 to 38, DNA Cloning 1: Core Techniques, A Practical Approach, Second Edition, Oxford University Press (1995). In this regard, a sequence comprising only an 'A' sequence or only a 'T' sequence is preferably excluded from a sequence that hybridizes under stringent conditions. Thus, the polypeptide used in the present invention (e.g., RAGE and the like) encompasses polypeptides encoded by a nucleic acid molecule that hybridizes under stringent conditions to a nucleic acid molecule encoding a polypeptide particularly described in the present invention.

As used herein, "hybridizable polynucleotide" refers to a polynucleotide that can hybridize to another polynucleotide under the above-described hybridization conditions. Specific examples of hybridizable polynucleotides include polynucleotides having at least 60% homology, preferably 80% or greater homology, and more preferably 95% or greater homology to a base sequence of DNA encoding a polypeptide having the amino acid sequence set forth by SEQ ID NO: 97 or the like.

Agents affecting the stability of double stranded DNA include the base composition, length, and degree of base pair mismatch. Hybridization conditions can be adjusted by those skilled in the art. These variables are applied to enable hybrid formation of DNAs related to different sequences. The melting temperature of fully matching DNA double strand can be estimated by the following formula Tm (° C.)=81.5+16.6 (log[$Na^+$])+0.41 (% G+C)−600/N−0.72 (% formamide).

Wherein N is the length of a formed double strand, [Na+] is the mole concentration of sodium ions in hybridization solution or washing solution, and % G+C is the percentage of (guanine+cytosine) base in a hybrid. For non-fully matching hybrids, the melting temperature decreases about 1° C. for each 1% of mismatch.

As used herein, "refolding" refers to unfolding an abnormal structure of a polypeptide which has lost its inherent function due to abnormal folding, and refolding into the original correct structure of the polypeptide using the inclusion ability of cycloamylose or by dilution dialysis under controlled oxidation reduction potential while preventing re-aggregation by a surfactant.

As used herein, "purification column" refers to a solid or semi-solid support that has affinity to or is capable of binding to a molecule such as a protein (e.g., antibody). Examples thereof include metal chelate agarose columns and the like. Each molecule can be separated by the difference in the affinity or binding ability of each molecule. Those skilled in the art select a suitable support depending on the characteristic of the molecule to be purified. For example, Ni-NTA agarose columns can efficiently purify a protein to which a His tag or the like is added.

As used herein, "Ni-NTA slurry" refers to a resin with nitrilotriacetic acid (NTA) immobilized on agarose chelated with nickel ions.

As used herein, "phosphate buffered saline (PBS)" is an aqueous solution with a pH of 7 to 8, comprising NaCl, KCl, $Na_2HPO_4$, and $KH_2PO_4$. The concentration and pH of each component can be suitably adjusted depending on the application. As used herein, "PBS (+)" means that a calcium ion and magnesium ion are contained, and "PBS (−)" means calcium ion and magnesium ion free. As used herein, unless explicitly noted otherwise, "PBS" refers to "PBS (−)". Typically, Dulbecco's PBS (−) can be used herein. The composition of Dulbecco's PBS (−) is 8 g of NaCl, 0.2 g of KCl, 1.15 g of $Na_2HPO_4$, and 0.2 g/L of $KH_2PO_4$ (pH 7.4).

As used herein, "cellulose ester film tube" refers to a dialysis tube manufactured by extrusion molding of a cellulose acetate polymer mixture.

As used herein, the term "receptor" is a biological structure comprising one or more binding domains that reversibly and specifically form a complex with one or more ligands, wherein formed complex has a biological structure. A receptor may be present completely outside of a cell (extracellular receptor), inside a cell membrane (receptor portion facing the extracellular environment and cytosol) or completely inside a cell (intracellular receptor). The receptors may also function independently of a cell. A receptor inside a cell membrane allows a cell to communicate (e.g., signaling) with the space outside of its boundary and function in transport of a molecule and ion to the inside and outside of the cell. As used herein, a receptor may be a full-length receptor or a fragment of a receptor.

As used herein, "oxidized LDL receptor" refers to any receptor receiving an oxidized LDL. Examples of oxidized LDL receptors include, but are not limited to, LOX-1 explained herein, as well as scavenger receptors such as SR-A, SR-B, and CD36 and the like. It is sometimes referred to as a "modified LDL receptor" in the art, but it is identical to an "oxidized LDL receptor".

As used herein, "modified LDL" is also called "LDL modified product" (used synonymously), which is any LDL modified product having various molecular modifications generated by an LDL contacting active oxygen, oxidative enzyme, $Fe^{3+}$ or the like in the body, or by cell dependent chemical change due to macrophage, vascular endothelial cells, or the like. Typical examples of LDL modified products that are present in the living body include, but are not limited to, oxidized LDLs (referred to as OxLDL herein, and examples thereof include fully oxidized LDLs (also referred to as fu OxLDL herein) and partially oxidized LDLs (also referred to as mo OxLDL herein)), aldehyde modified LDLs such as malondialdehydized LDLs (MDA-LDL) and crotonaldehyde (CRA) modified LDLs, acrolein modified LDLs, nonenal modified LDLs, 4-hydroxynonenal (HNE) modified LDLs, hexanoyl (HEL) modified LDLs, small particle LDLs (LDLs with a diameter of 255 nm or less), glycated LDLs, acetylated LDLs (AcLDL), and the like. When oxidized LDLs exhibit an abnormal value, diseases such as arteriosclerosis, ischemic heart disease (e.g., myocardial infarction, angina, and the like), cerebrovascular disorder (cerebral infarction, cerebral hemorrhage, subarachnoid hemorrhage, transient cerebral ischemic attack, and the like), aortic aneurysm, kidney infarction, hyperlipidemia, and the like are expected, but the diseases are not limited thereto (see "Kyo no Rinsho Kensa 2007-2008" [Modern clinical inspection 2007-2008], Publisher Nankodo Co., Ltd.) In a commonly used inspection method, MDA-LDL (normal range: 10 to 80 mL) and oxidized phosphatidyl choline (normal range: 8.4 U/mL to 17.6 U/mL) are used as reference substance.

As used herein, the term "lectin-like oxidized low density lipoprotein (LDL) receptor 1 (Lectin-like Oxidized LDL receptor)" is also referred to as LOX-1 and is one of the following: (1) a polypeptide consisting of the amino acid sequence set forth by SEQ ID NO: 82; (2) a polypeptide comprising the amino acid sequence set forth by SEQ ID NO: 82 described above comprising one or more amino acid substitutions, additions and/or deletions and exhibiting the activity of naturally-occurring LOX-1; (3) a polypeptide comprising an amino acid sequence with at least 90% sequence identity to the amino acid sequence set forth by SEQ ID NO: 82 described above and exhibiting the activity of naturally-occurring LOX-1; (4) a polypeptide comprising an amino acid sequence with at least 80% sequence homology to the amino acid sequence set forth by SEQ ID NO: 82 described above and exhibiting the activity of naturally-occurring LOX-1; (5) a polypeptide comprising an amino acid sequence encoded by the nucleic acid molecule set forth by SEQ ID NO: 81; (6) a polypeptide comprising an amino acid sequence encoded by a nucleic acid sequence that hybridizes under stringent conditions to a nucleic acid sequence complementary to the nucleic acid sequence set forth by SEQ ID NO: 81 described above and exhibiting the activity of naturally-occurring LOX-1; (7) a polypeptide comprising an amino acid sequence encoded by a nucleic acid molecule with one or several nucleotide substitutions, additions and/or deletions in the nucleic acid sequence set forth by SEQ ID NO: 81 described above and exhibiting the activity of naturally-occurring LOX-1; (8) a polypeptide comprising an amino acid sequence encoded by a nucleic acid molecule with at least 90% sequence identity to the nucleic acid sequence set forth by SEQ ID NO: 81 described above and exhibiting the activity of naturally-occurring LOX-1; and (9) a polypeptide comprising an amino acid sequence encoded by a nucleic acid molecule with at least 80% sequence homology to the nucleic acid sequence set forth by SEQ ID NO: 81 described above and exhibiting the activity of naturally-occurring LOX-1. The above-described identity or homology is calculated with the default parameters using the sequence analysis tool BLAST (BLAST 2.2.9 (published on May 12, 2004) of NCBI). Stringent conditions vary depending on the sequence. Determination of such a condition is within the technical scope of those skilled in the art. Further, Examples of LOX-1 include, but are not limited to, mammalian LOX-1 such as human LOX-1 (also referred to as hLOX-1), bovine LOX-1 (also referred to as b-LOX1), pig LOX-1, mouse LOX-1, and rabbit LOX-1. bLOX-1 is a glycoprotein with a molecular weight of about 50 kDa, consisting of 273 amino acid residues of the C-type lectin family, which is a cell membrane single-pass type II membrane protein with the N-terminus in a cytoplasm and the C-terminus outside the cell. hLOX-1 is also a glycoprotein with a molecular weight of about 50 kDa, consisting of 273 amino acid residues of the C-type lectin family, which is a cell membrane single-pass type II membrane protein with the N-terminus in a cytoplasm and the C-terminus outside the cell. LOX-1 consists of the following four domains: N-terminus side cytoplasmic domain, hydrophobic transmembrane domain, NECK domain, and C-type lectin-like domain.

Bovine LOX-1 (bLOX-1) is a glycoprotein with a molecular weight of about 50 kDa, consisting of 273 amino acid residues of the C-type lectin family, which is a cell membrane single-pass type II membrane protein with the N-terminus in a cytoplasm and the C-terminus outside the cell. Human LOX-1 (hLOX-1) is also a type II membrane protein of about 30 kDa (molecular weight of about 40 kDa by glycosylation at positions 139 and 183) consisting of 273 amino acid residues of the C-type lectin family. The receptor structurally consists of the following four domains: N-terminus side cytoplasmic domain, hydrophobic transmembrane domain, NECK domain, and C-type lectin-like domain (also referred to as CTLD herein). The CTLD is a functional domain for recognizing a ligand of LOX-1 and is highly conserved across species at especially six cysteine residue positions. The six cysteine residues in the CTLD are involved in intramolecular disulfide bonding of hLOX-1. In addition to the conserved CTLD, NECK domains in hLOX-1 and other known species have high sequence identity. According to Xie et al. (Protein Expression and Purification 32: 68-74 (2003)), it is the smallest domain sufficient for CTLD to bind to a modified LDL. It is revealed that even if CTLD is not glycosylated, a NECK domain can recognize and bind a modified LDL. It is known that: LOX-1 is expressed not only in vascular endothelial cells, but also in macrophage and activated vascular smooth muscle cells, and recognizes various structurally unrelated macromolecules (including modified LDLs, bacteria, senescent red blood cells, cells that have undergone apoptosis, and platelets) and play an important role in various biological phenomenon such as the biological defense mechanism and inflammatory cascade; and the expression thereof is regulated under various conditions by pathological conditions such as hyperlipidemia, diabetes, hyperglycosemia, high blood pressure, hypertensive nephrosclerosis, arteriosclerosis, ischemia reperfusion injury, or post-blood vessel balloon damage, and oxidized LDL, angiotensin II, endothelin, TNF-α, advanced glycation end products (AGEs), TGF-β, 8-iso-prostaglandin $F_2$., shear stress, and other stimulations (Folia Pharmacol. Jpn. 127, 103-107 (2006)).

As used herein, the term "C-type lectin-like domain" is also referred to as "CTLD" and has homology to the sugar chain recognition site of a member of the C-type lectin family. CTLD is well conserved among these members and species. The six cysteine residue positions are fully conserved. Further, CTLD is a functional domain for recognizing a ligand of LOX-1, and the six cysteine residues thereof are involved in the intramolecular disulfide bonds at three locations of hLOX-1. Thus, a mutant LOX-1-surfactant complex preferably retains cysteine at positions 144, 155, 172, 243, 256, and 264 in the amino acid sequence of SEQ ID NO: 82. Similarly, it is preferable that amino acids corresponding to cysteine at positions 144, 155, 172, 243, 256, and 264 in the amino acid sequence of SEQ ID NO: 82 are retained in the CTLD-surfactant complex of the invention. In addition to this conserved CTLD, NECK domain in hLOX-1 and other known species have high sequence identity. Further, cysteine at position 140 in hLOX-1 is involved in intramolecular disulfide bonding and forms a dimer of hLOX-1. However, the cysteine at position 140 is not required for recognition of a modified LDL. Thus, when expressed, it is not necessary that the cysteine at position 140 is retained, such that this can be mutated. Furthermore, a sugar chain is added to the N at position 183 and the N at position 139 in hLOX-1. The molecular weight of hLOX-1, to which a sugar chain is added, is 50 kDa. Generally, hLOX-1 is glycosylated, but even without glycosylation, hLOX-1 can recognize and bind a modified LDL as in normal glycosylated hLOX-1. The above-described CTLD is the smallest domain that is sufficient and required for binding a modified LDL. Four residues at the C-terminus of LOX-1 (LRAQ) are required for recognition and uptake of a ligand. Seven residues at the C-terminus (KANLRAQ) are required for folding and transport of hLOX-1. W150, R208, R229, R231, R248, and the like of hLOX-1 are amino acids required for ligand recognition and uptake. It is also reported that LOX-1 is cleaved from a cell membrane and released as a soluble form to be present in blood of healthy individuals.

As used herein, the term "CTLD-like polypeptide" encompasses all polypeptides encompassed by "CTLD", "PR (Protease-Resistant)-CTLD", "CTLD14" (CTLD14+ polypeptide having 14 amino acids on the C-terminal side of NECK domain) "PR-CTLD14", "CTLD+NECK" (CTLD+ polypeptide having a NECK domain), "PR-CTLD+NECK", and mutatnats thereof.

As used herein, it is understood that the term "CTLD molecule" encompasses CTLD-like polypeptides and any complex thereof. Thus, it is understood that CTLD molecules also encompass full length LOX-1, full length LOX-1 extracellular region (S61 to Q273), CTLD14 (129 to 143), CTLD (143 to 273) and the like. As used herein, the terms "CTLD14" and "PR-CTLD14" are represented by one of the following: (1) a polypeptide consisting of the amino acid sequence set forth by SEQ ID NO: 84; (2) a polypeptide comprising the amino acid sequence set forth by SEQ ID NO: 84 described above comprising one or several amino acid substitutions, additions and/or deletions; (3) a polypeptide comprising one or more amino acid substitutions, additions and/or deletions at an amino acid position other than positions 104 and 121 in the amino acid sequence set forth by SEQ ID NO: 84 and exhibiting the activity of naturally-occurring LOX-1; (4) a polypeptide comprising an amino acid sequence with at least 90% sequence identity to the amino acid sequence set forth by SEQ ID NO: 84 described above; (5) a polypeptide comprising an amino acid sequence with at least 80% sequence homology to the amino acid sequence set forth by SEQ ID NO: 84 described above; (6) a polypeptide comprising an amino acid sequence encoded by the nucleic acid molecule set forth by SEQ ID NO: 83; (7) a polypeptide comprising an amino acid sequence encoded by a nucleic acid sequence that hybridizes under stringent conditions to a nucleic acid sequence complementary to the nucleic acid sequence set forth by SEQ ID NO: 83 described above; (8) a polypeptide comprising an amino acid sequence encoded by a nucleic acid sequence that hybridizes under stringent conditions to a nucleic acid sequence complementary to the nucleic acid sequence set forth by SEQ ID NO: 83 described above, the amino acids at positions 104 and 121 in the encoded amino acid sequence retaining corresponding amino acids in SEQ ID NO: 84, and exhibiting the activity of naturally-occurring LOX-1; (9) a polypeptide comprising an amino acid sequence encoded by a nucleic acid sequence with one or several substitutions, additions and/or deletions in the nucleic acid sequence set forth by SEQ ID NO: 83 described above and exhibiting the activity of naturally-occurring LOX-1; (10) a polypeptide comprising an amino acid sequence encoded by a nucleic acid sequence with at least 90% sequence identity to the nucleic acid sequence set forth by SEQ ID NO: 83 described above; and (11) a polypeptide comprising an amino acid sequence encoded by a nucleic acid sequence with at least 80% sequence homology to the nucleic acid sequence set forth by SEQ ID NO: 83 described above. The above-described identity or homology is calculated with the default parameters using the sequence analysis tool BLAST (BLAST 2.2.9 (published on May 12, 2004) of NCBI). Stringent conditions vary depending on the sequence. Determination of such a condition is within the technical scope of those skilled in the art.

The above-described CTLD-like polypeptides including CTLD14 may include a non-naturally-occurring amino acid, or an amino acid analog, amino acid derivative or the like, as long as the activity of naturally-occurring LOX-1 is retained.

As used herein, the term "advanced glycation end products" is also referred to as AGEs. AGEs are involved in the onset/progression of diabetic vascular disorders known as vascular complication, which causes diminished quality of life in diabetes patients. Ocular, nervous, and renal disorders due to vascular complication are respectively called diabetic retinopathy, neurosis, nephropathy (collectively three major complications), which are characteristic pathological conditions of diabetes patients. Reducing sugars, including glucose, non-enzymatically react with an amino group of an amino acid or protein to form a glycation product such as Schiff base or a compound that has undergone Amadori rearrangement. The reaction up to this point is reversible and called the first half reaction. Subsequently, an advanced glycation end product is formed via complex and irreversible reactions such as fusion, cleavage, or crosslinking. Such a series of reaction is called glycation. AGEs is the general name for structures produced through such a process. Examples of AGE structures present in a living body include, but are not limited to, carboxymethyllysine (CML), carboxyethyllysine (CEL), pentosidine, pyraline, imidazoline, methylglyoxal, crossline, and the like. Products of albumin, immunoglobulin, ovalbumin or the like that are present in the plasma subjected to the above-described glycation also are AGEs and are commonly used in test systems as AGEs. In in vitro experimental systems, BSA (bovine serum albumin) subjected to glycation such as R-AGE (BSA glycated with ribose), F-AGE (BSA treated with fructose), G-AGE (BSA glycated with glucose), and the like are also commonly used. Hemoglobin A1c, used as an indicator of blood sugar control, is a compound that has undergone Amadori rearrangement, and is encompassed by AGEs. Further, any protein can be converted to AGEs. For instance, CML albumin and CEL albumin encompassed by AGEs are both AGEs of glycated albumin. Such an AGE generating reaction may occur in circulating blood in the living body, extracellular matrix or inside a cell. For example, AGEs that are present in the blood vessel of a diabetes patient are roughly separated into two groups, i.e., those with fluorescence and a crosslink structure (pentosidine, crossline, and the like) and those without fluorescence or crosslinks (carboxylmethyllysine, pyraline, methylglyoxal (MG)-imidazolone and the like). When AGEs exhibit an abnormal value, diseases such as microangiopathy (nephropathy, retinopathy, neuropathy, or the like) or macroangiopathy (ischemic heart disease, cerebrovascular disease, or obstructive arteriosclerosis) is expected. Commonly used inspection methods use pyraline (normal range: less than 23 pmol/mL in plasma), pentosidine (normal range: 0.00915 to 0.0431 µg/ml (when measured by ELISA)), and the like (see "Kyo no Rinsho Kensa 2007-2008" [Modern clinical inspection 2007-2008], Publisher Nankodo Co., Ltd.)

As used herein, "complex" refers to any structure comprising two or more parts. For example, when one part is a polypeptide, the other part may be a polypeptide or other substance (e.g., sugar, lipid, nucleic acid, other carbohydrate or the like). Two or more constituent parts of the complex herein may be covalently bonded or bonded by other bonds (e.g., hydrogen bond, ionic bond, hydrophobic interaction, van der Waals force or the like). When two or more parts are polypeptides, a complex may be called a chimeric polypeptide. Thus, the "complex" herein encompasses molecules made by linking multiple types of molecules such as polypeptides, polynucleotides, lipids, sugars, or small molecules.

As used herein, the term "ligand" is a binding partner for a specific receptor or a receptor family. A ligand may be an endogenous ligand to a receptor or, instead, a synthetic ligand to a receptor such as an agent, agent candidate, or a pharmacological means.

As used herein, "AGE(s) molecule" refers to any molecule encompassed by the above-described AGE. Examples of AGEs include, but are not limited to, Lys-AGE (glutaraldehyde modified lysine modified AGE), glucose modified AGE (G-AGE), ribose modified AGE (R-AGE), fructose modified AGE (F-AGE), and variants and complexes thereof.

As used herein, "molecule exhibiting AGE(s)-like activity" refers to a molecule with at least one of the aforementioned AGE activities (referred to as "AGE(s)-like activity" herein). Such an AGE(s)-like activity includes, but is not limited to, binding activity to RAGE (ligand activity).

As used herein, the term "Receptor for AGE" is also referred to as RAGE, which is one of the following: (1) a polypeptide consisting of the amino acid sequence set forth by SEQ ID NO: 8; (2) a polypeptide comprising the amino acid sequence set forth by SEQ ID NO: 102 described above comprising one or several amino acid substitutions, additions, and/or deletions, and exhibiting the activity of naturally-occurring RAGE; (3) a polypeptide comprising an amino acid sequence with at least 90% sequence identity to the amino acid sequence set forth by SEQ ID NO: 102 described above and exhibiting the activity of naturally-occurring RAGE; (4) a polypeptide comprising an amino acid sequence with at least 80% sequence homology to the amino acid sequence set forth by SEQ ID NO: 102 described above and exhibiting the activity of naturally-occurring RAGE; (5) a polypeptide comprising an amino acid sequence encoded by the nucleic acid molecule set forth by SEQ ID NO: 101; (6) a polypeptide comprising an amino acid sequence encoded by a nucleic acid molecule that hybridizes under stringent conditions to a nucleic acid sequence complementary to the nucleic acid sequence set forth by SEQ ID NO: 101 described above and exhibiting the activity of naturally-occurring RAGE; (7) a polypeptide comprising an amino acid sequence encoded by a nucleic acid molecule with one or several nucleotide substitutions, additions and/or deletions in the nucleic acid sequence set forth by SEQ ID NO: 101 described above and exhibiting the activity of naturally-occurring RAGE; (8) a polypeptide comprising an amino acid sequence encoded by a nucleic acid molecule with at least 90% sequence identity to the nucleic acid sequence set forth by SEQ ID NO: 101 described above and exhibiting the activity of naturally-occurring RAGE; and (9) a polypeptide comprising an amino acid sequence encoded by a nucleic acid molecule with at least 80% sequence homology to the nucleic acid sequence set forth by SEQ ID NO: 101 described above and exhibiting the activity of naturally-occurring RAGE. The above-described identity or homology is calculated with the default parameters using the sequence analysis tool BLAST (BLAST 2.2.9 (published on May 12, 2004) of NCBI). Stringent conditions vary depending on the sequence. Determination of such a condition is within the technical scope of those skilled in the art. RAGE is also a type I membrane protein with a molecular weight of about 35 kDa (complete RAGE with glycosylation has a molecular weight of 55 kDa), which was identified from a bovine lung in 1992, and belongs to the immunoglobulin superfamily that binds to AGEs. The extracellular domain of RAGEs has a structure where three domains with an immunoglobulin folding structure, one V immunoglobulin domain and two C immunoglobulin domains (C1 and C2 regions), are bound. RAGE also comprises a cell membrane single pass domain and 43 amino acid cytoplasmic domains. RAGE interacts with various classes of ligands (AGE, S100/calgranulin, amphoterin, and amyloid-β peptide). The V domain is a site required for ligand binding, and a cytoplasmic domain is required for RAGE-mediated intracellular signaling. RAGE also has a disulfide bond in each domain. Thus, it is preferred that the mutant RAGE-surfactant complex of the invention retains cysteine residues corresponding to positions 38, 99, 144, 208, 259, and 301 in the amino acid sequence of SEQ ID NO: 97. RAGE is express only at a low level in normal tissue and the vascular system. However, this receptor is upregulated where a ligand thereof is accumulated. RAGE expression increases in endothelial cells, smooth muscle cells, pericytes, renal mesangial cells, and infiltrating mononuclear phagocytes in a diabetic vascular system. Further, RAGE expression is increased at pathological sites such as arteriosclerotic foci where AGEs are accumulated. AGE-RAGE interaction changes an important cellular characteristic in vascular system homeostatis. For example, after RAGE binds to AGEs, a vascular endothelial cell increases VCAM-1, tissue factor, and IL-6 expression, and their permeability to a macromolecule. In a mononuclear phagocyte, RAGE activates cytokine and growth factor expression and induces cell migration according to soluble AGEs, while haptotaxis occurs with an immobilized ligand.

As used herein "RAGE ligand recognition region" or "sRAGE (soluble Receptor for Advanced Glycation End products") are interchangeably used and refer to a region that a RAGE ligand recognizes. More specifically, sRAGE, i.e., RAGE ligand recognition region, refers to all or part of an extracellular region of RAGE. sRAGE is typically comprised of, but not limited to, positions 22 to 332 of SEQ ID NO: 102 or SEQ ID NO: 97.

As used herein, the term "RAGE-like polypeptide" encompasses polypeptides called "RAGE 8", "mRAGE 8", "RAGE 1", "mRAGE 1", "RAGE 2", "mRAGE 2", "RAGE 3", "mRAGE 3", "RAGE 4", "mRAGE 4", "RAGE 7", "mRAGE 7", "RAGE 143", "mRAGE 143", "RAGE 223", "mRAGE 223", "RAGE 226", and "mRAGE 226" and mutants thereof. Explanations thereof are disclosed in Japanese Laid-Open Publication No. 2013-209330 and the like, the content of which is appropriately incorporated herein by reference.

As used herein, the term "RAGE molecule" is understood as encompassing RAGE-like polypeptides as well as any complex thereof. Thus, it is understood that RAGE molecule encompasses RAGE-like polypeptides, such as RAGE (full length), RAGE extracellular region (positions 22 to 332 of SEQ ID NO: 102), RAGE 143, RAGE 223, RAGE 226 and the like.

As used herein, molecules comprising a "RAGE ligand recognition region" include "RAGE molecule" that is not a full length RAGE (including "RAGE-like polypeptide") such as "RAGE 8", "mRAGE 8", "RAGE 1", "mRAGE 1", "RAGE 2", "mRAGE 2", "RAGE 3", "mRAGE 3", "RAGE 4", "mRAGE 4", "RAGE 7", "mRAGE 7", "RAGE 143", "mRAGE 143", "RAGE 223", "mRAGE 223", "RAGE 226", "mRAGE 226", and RAGE extracellular region (positions 22 to 332 of SEQ ID NO: 102).

The above-described RAGE-like polypeptide may comprise a non-naturally-occurring amino acid, or an amino acid analog, amino acid derivative, or the like, as long as the activity of naturally-occurring RAGE is retained.

It is also important to form an intramolecular disulfide bond in the above-described RAGE-like polypeptide. Thus, cysteine residues corresponding to positions 38, 99, 144, 208, 259, and 301 of the amino acid sequence of SEQ ID NO: 102 are preferably retained.

As used herein, "ligand" is a binding partner for a specific receptor or a receptor family. A ligand may be an endogenous ligand to a receptor or, instead, a synthetic ligand to a receptor such as an agent, agent candidate, or a pharmacological means.

As used herein, "antigen-antibody reaction" is used in the broadest meaning used in the art and refers especially to a reaction based on a specific bond between an antigen and an antibody. A reagent and method for quantification of an antigen (e.g., LDL) in a specimen by using the immunoblot (Western blot) format as the detection system are also provided.

As used herein, the term "bond" refers to physical interaction or chemical interaction between two proteins or compounds or related proteins or compounds, or a combination thereof. Examples of bonds include ionic bonds, nonionic bonds, hydrogen bonds, van der Waal bonds, hydrophobic interactions, and the like. Physical interaction (bond) can be direct or indirect. An indirect bond is mediated or caused by the effect of another protein or compound. A direct bond refers to interaction that is not mediate by or caused by an effect of another protein or compound, and involves no other substantial chemical intermediate.

As used herein, a first substance or agent "specifically interacting" with a second substance or agent refers to interaction at a higher affinity of the first substance or agent to the second substance or agent than to substances or agents other than the second substance or agent (especially other substances or agents that are present in a sample comprising the second substance or agent). Examples of specific interaction of a substance or agent include, but are not limited to, hybridization in a nucleic acid, antigen-antibody reaction in a protein, ligand-receptor reaction, enzyme-substrate reaction and the like, and when both a nucleic acid and protein are associated, reaction of a transcription factor and a binding site of the transcription factor and the like, protein-lipid interaction, nucleic acid-lipid interaction and the like. Thus, when substances or agents are both nucleic acids, first substance or agent "specifically interacting" to a second substance or agent encompasses the first substance or agent having at least partial complementarity to the second substance or agent. For example, when substances or agents are both proteins, examples of a first substance or agent "specifically interacting" with a second substance or agent include, but are not limited to, interaction due to an antigen-antibody reaction, interaction due to a receptor-ligand reaction, enzyme-substrate interaction, and the like. When two types of substances or agents include a protein and a nucleic acid, a first substance or agent "specifically interacting" with a second substance or agent encompasses interaction of a transcription factor and a binding region of a nucleic acid molecule targeted by the transcription factor. Thus, as used herein, "agent specifically interacting" with a biological agent such as a polynucleotide or a polypeptide encompasses agents that typically have the same or higher, preferably significantly (e.g., statistically significantly) higher affinity to the biological agent, such as the polynucleotide or polypeptide, than to other unrelated polynucleotides or polypeptides (especially those with identity of less than 30%). Such affinity can be measured, for example, by hybridization assay, binding assay, or the like.

As used herein, "contact(ed)" refers to physically bringing a compound, either directly or indirectly, closer to the polypeptide or polynucleotide of the invention. A polypeptide or polynucleotide may be present in many buffers, salts, solutions, or the like. Examples of contact include placing a compound in, for example, a beaker, microtiter plate, cell culture flask, microarray (e.g., gene chip), or the like comprising a polypeptide encoding a nucleic acid molecule or a fragment thereof.

When a mechanism such as enzyme-linked immunosorbent assay (ELISA) is used in the present invention, a microtiter plate is generally used as the solid phase (substrate). As used herein, the term "solid phase" is interchangeably used with "substrate" herein and refers to a constituent material of the device of the invention. A solid phase refers to a flat support where a molecule such as an antibody can be immobilized. Examples of materials of a substrate include any solid material which has a characteristic of binding to a biomolecule used in the present invention or is capable of being a derivative to have such a characteristic, either by a covalent or noncovalent bond. Examples of a suitable substrate include, but are not limited to, beads, gold particles, plates (e.g., microtiter plates), test tubes, chips, magnetic particles, membranes, fibers, slide glasses, metallic thin films, filters, tubes, balls, diamond-like carbon coated stainless steel, and the like.

Any material that can form a solid surface can be used as a material for use as a solid phase and a substrate. Examples thereof include, but are not limited to, glass, silica, silicone, ceramic, silicon dioxide, plastic, metals (including alloys), and natural and synthetic polymers (e.g., polystyrene, cellulose, amylose, chitosan, dextran, and nylon). A substrate may be formed from multiple layers of different materials. For example, inorganic insulating material such as glass, quartz glass, alumina, sapphire, forsterite, silicon carbide, silicon oxide, silicon nitride, or the like can be used. Further, it is possible to use an organic material such as polyethylene, ethylene, polypropylene, polyisobutylene, polyethylene terephthalate, unsaturated polyester, fluorine-containing resin, polyvinyl chloride, polyvinylidene chloride, polyvinyl acetate, polyvinyl alcohol, polyvinyl acetal, acrylic resin, polyacrylonitrile, polystyrene, acetal resin, polycarbonate, polyamide, phenol resin, urea resin, epoxy resin, melamine resin, styrene/acrylonitrile copolymer, acrylonitrile butadiene styrene copolymer, silicone resin, polyphenylene oxide, polysulfone, or the like. In the present invention, a film used in blotting such as a nylon film, nitrocellulose film, PVDF film, or the like can also be used. When a high density analyte is analyzed, it is preferable to use a material with hardness, such as glass, as the material. A preferred material to be used as a substrate varies depending on various parameters of measuring equipment or the like. Those skilled in the art can appropriately select a suitable material from the various aforementioned materials.

"Sandwich ELISA" refers to a specific format of ELISA, in which a molecule that can specifically bind to an antibody or antigen (e.g., LOX-1) is bound to a solid material and subjected to a specimen comprising an antigen, and then the solid material surface is washed to remove non-binding antigens, and then a labeled antibody (e.g., labeled antibody linked to an enzyme) is bound to an antigen in a bound state (when present) to form an antibody-antigen-antibody sandwich. Examples of enzymes that can to be linked to an antibody include alkaline phosphatase, horseradish peroxidase, luciferase, urease, and β-galactosidase. An antibody to which an enzyme is linked reacts to a substrate to generate a measurable color reaction product. Instead of a labeled antibody, an unlabeled antibody can also be used. In such a case, detection can be performed by having a labeled secondary antibody bind to an unlabeled antibody.

"Lateral flow assay" is one type of immunoassay, with non-competitive and competitive forms. Herein, this refers to a format where a specimen moves across a support by, for example, capillary phenomenon, and meets a movable labeled antibody, which binds to an analyte to form a conjugate, and the conjugate then crosses the support to meet an immobilized second antibody, which binds to an analyte such that the immobilized analyte is detected by detecting the labeled antibody. Competitive lateral flow assay is a format in which a labeled analyte moves across a support and competes with an unlabeled analyte to bind with an immobilized antibody. With a larger quantity of analyte in a specimen, there is less binding by a labeled analyte, such that the signal is weaker. For example, May et al., U.S. Pat. No. 5,622,871 and Rosenstein, U.S. Pat. No. 5,591,645 can be referred to.

As used herein, "LOX-1 ligand recognition region" refers to a region recognizing a ligand of an oxidized LDL receptor, C-type Lectin-like LDL receptor (LOX-1). More specifically, a LOX ligand recognition region is assumed to comprise a C-type Lectin-like Domain (CTLD), which is the smallest domain required for recognition. It is known that reconstitution as CTLD14 comprising not only the smallest domain required for recognition C-type Lectin-like domain (CTLD), but also Cys140 (required for intermolecular S—S bond of LOX-1) that is present in the NECK region results in 80% or more naturally forming a dimer in a solution to be present stably. It is known that CTLD14 is expressed as N-terminus biotinylated CTLD14 to confirm it is possible to accumulate at a high density on a substrate, and biotinylated CTLD14 is preferred when applied to a detection system immobilized on a substrate.

As used herein, "silkworm" refers to a commonly understood silkworm, which is one type of insect of the order Lepidoptera and genus Bombycidae. The official Japanese name is silkworm moth (scientific name: Bombix mori), and silkworm is the name of the larva thereof, but silkworm generally refers to all types. Silkworms feed on mulberries and produce silk to make a cocoon of a pupa. Silkworm is also called a domesticated silkworm, which is an insect that does not live in the wild. The ancestor of silkworms is considered to be the *Bombyx mandarina*, which inhabits East Asia. Silkworms and *Bombyx mandarina* are academically considered separate species, but crossbreeds thereof are reproductively capable. As used herein, silkworm encompasses *Bombyx mandarina*. As used herein, "organism adding a sugar chain similar to that of a silkworm" refers to an organism with the ability to add a sugar chain similar to that of a silkworm, and may include transgenic organisms and the like with a gene encoding an enzyme adding a sugar chain similar to that of a silkworm or the like.

As used herein, "silk gland" refers to a pair of left and right organs in the body of a mature silkworm for converting a large quantity of protein (amino acid), taken in from a leaf of a mulberry, into two types of silk proteins (fibroin and sericin). Silk gland is structured as a pair on the left and right and secretes liquid silk, which is the raw material for cocoon strands. A silk gland is divided into three parts, i.e., posterior silk gland, middle silk gland, and anterior silk gland. While silk can be synthesized using any silk gland in the present invention, the posterior silk gland or the middle silk gland is generally used, and preferably the middle silk gland is used considering the handling after synthesis, but it is not limited thereto. It is also possible to express silk in the entire body and collect the silk form the entire body.

The posterior silk gland is the elongated part at the rearmost portion and is about 20 cm when stretched. Fibroin proteins, which later become the main part of a cocoon strand, are synthesized therein.

The middle silk gland is a thick S-shaped part in the middle portion, and is about 6 cm when stretched. Fibroin proteins sent from the posterior silk gland are concentrated, accumulated, and arranged into a shape which can be readily formed into fiber. The other silk protein, sericin, is also secreted. This plays the role of an adhesive for consolidating fibroin proteins when spitting out a cocoon strand.

The anterior silk gland is a thin tapered tube connected to a fusula, with a length of about 4 cm. Liquid fibroin protein molecules are stretched, aligned in a certain direction, and assembled with each other to further remove moisture. An anterior silk gland merges with another pair of tubes at the tip of the tube, where the protein is spit out from a fusula to become a single cocoon strand.

A silkworm stops eating mulberry at the latter part of age 5 (mature silkworm). The body of a mature silkworm is full, with a pair of organs (silk gland) storing a starch syrup-like liquid (liquid silk), which is the raw material of a cocoon strand. The silk gland is connected to a fusula at the mouth of a silkworm through a thin spinneret. Liquid silk is stretched and solidified by passing through a thin spinneret to become a cocoon strand. Furthermore, a cocoon strand is sequentially pulled out from the silk gland by a series of motions, i.e., a larva applies a strand spit out from a spinneret to a nearby object and the head and chest are moved in a figure eight motion to pull the strand.

As used herein, "silkworm form sugar chain" refers to a unique sugar chain structure in a glycoprotein produced by a silkworm. Typical examples thereof include trimannosyl core (itself), oligomannose type sugar chain and complex type sugar chain, and hybrid types (see FIGS. 19 and 20). In the present invention, a silkworm form glycoprotein is produced using the middle silk gland. Thus, unless specifically noted otherwise, "silkworm form sugar chain" refers to the unique sugar chain form produced in the middle silk gland. An exemplary silkworm form sugar chain has a structure with a core in which two N-acetylglucosamine (GlcNAc) bound to asparagine (Asn) are bound, and then three molecules of mannose (Man) are bound (referred to as trimannosyl core represented by the following formula (1)), the structures have branches therefrom and various sugar chains bound thereto.

<Sugar Chain Structure>

Sugar chains are roughly classified into two types, i.e., sugar chains binding to asparagine (referred to as N-glycoside binding sugar chains) and sugar chains binding to serin, threonine or the like (referred to as O-glycoside binding sugar chains). While the aforementioned N-glycoside binding sugar chains have various structures [Seibutsu Kagaku Jikkenho 23-Totanpakushitsu Tosa Kenkyuho [Biochemical experimental methods 23-Glycoprotein sugar chain research method] (Scientific Society Press), Ed. by Reiko Takahashi (1989)], it is preferable in any case to have a common basic core structure as shown below. The same applies even in cases where the aforementioned glycoprotein is not an antibody.

The following applies to silkworm forms (Iizuka et al. FEBS Journal 276(2009)5806-5820). That is, in the aforementioned production method, the aforementioned silkworm form glycoprotein preferably comprises a glycoprotein having an N-glycoside binding sugar chain (trimannosyl core) comprising the sugar chain structure (also called trimannosyl core) set forth by the following chemical formula (1).

[Chemical 1]

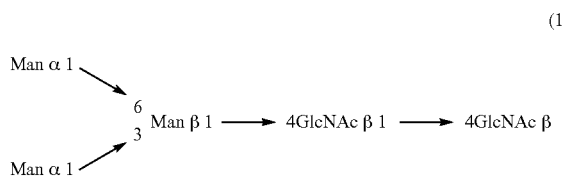

(1)

Although not wishing to be bound by any theory, the above-described sugar chain structure is a common feature of silkworm form sugar chains. This is because it is revealed, as shown in the Examples and the like, that the above-described sugar chain structure has excellent stability and is capable of broadly and sensitively detecting modified LDLs or AGEs such that the sugar chain is presumed to play a certain role. The sugar chain (1) is also denoted as N4-1 or sugar chain 000.1 herein.

In addition, the ends of a sugar chain binding to asparagine is referred to the reducing end and the opposite is referred to as the non-reducing end in the above-described structure. Examples of fucose binding to N-acetylglucosamine at the reducing end include an α1,3 bond, an α1,6 bond, and the like.

Examples of N-glycoside binding sugar chains include a high mannose type where only mannose is bound to the nonreducing end of a core structure (oligomannose type), a complex form having one or more branches of galactose-N-acetylglucosamine (hereinafter, referred to as Gal-GlcNAc) in parallel on the nonreducing end of a core structure and having a structure such as sialic acid, bisecting N-acetylglucosamine or the like on the nonreducing end side of Gal-GlcNAc, a hybrid type having branches of both the high mannose type (oligomannose type) and complex type on the nonreducing end side of a core structure, and the like.

In this embodiment, the aforementioned glycoprotein preferably includes glycoproteins having an N-glycoside binding sugar chain, comprising a sugar chain structure set forth by the following chemical formula (2), (3), or (4):

[Chemical 2]

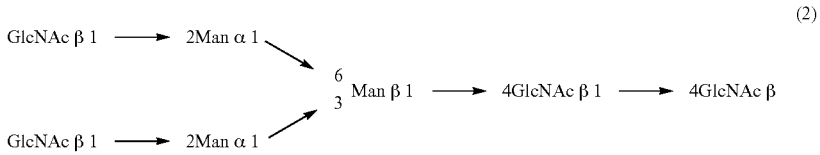

(2)

This type is also described as "GlcNAc-β1,4-GlcNAc-β1, 4-Man(-α1,6-Man-β1,2-GlcNAc)-α1,3-Man-β1,2-GlcNAc" viewed from the asparagine residue. Sugar chain (2) is also denoted as sugar chain 200.1 herein;

[Chemical 3]

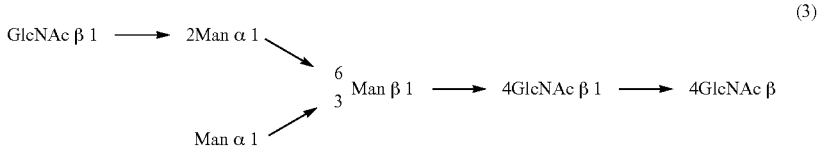

(3)

(This type is also described as "GlcNAc-β1,4-GlcNAc-β1, 4-Man(-α1,6-Man-β1,2-GlcNAc)-α1,3-Man" viewed from the asparagine residue and may be classified as a complex type.) Sugar chain (3) is also denoted as sugar chain 100.1 herein; and

[Chemical 4]

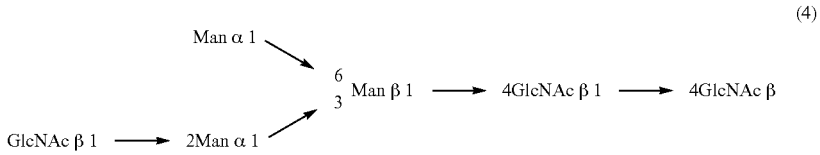

(4)

(This type is also described as "GlcNAc-β1,4-GlcNAc-β1,4-Man(-α1,6-Man)-α1,3-Man-β1,2-GlcNAc" viewed from the asparagine residue and may be classified as a complex type.) This is because it is known that silkworm form sugar chains include the aforementioned complex type sugar chain. Sugar chain (4) is also denoted as N4-2 or sugar chain 100.2 herein.

In the present invention, (2) is typically found. Among the aforementioned glycoproteins, glycoproteins having an N-glycoside binding sugar chain comprising a sugar chain structure set forth by chemical formula (3) or (4) may be included.

This is because when the proportion of glycoproteins having an N-glycoside binding sugar chain comprising a sugar chain structure set forth by chemical formula (2), (3), or (4) is 10 mol % or greater, 20 mol % or greater, or 30 mol % or greater, the N-glycoside binding sugar chain of glycoprotein has a more enhanced feature provided by a silkworm form sugar chain compared to an N-glycoside binding sugar chain of a glycoprotein produced by a common cell that does not produce a silkworm form.

(Oligomannose Type)

[Chemical 5]

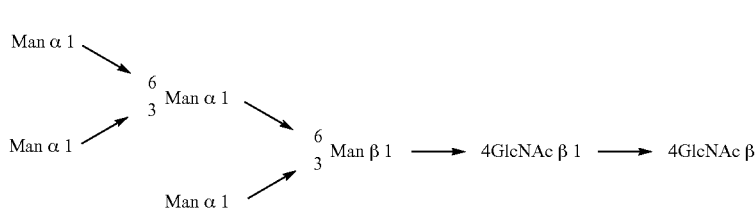

(5)

This structure is also described as "GlcNAc-@1,4-GlcNAc-β1,4-Man(-α1,3-Man)-α1,6-Man(-α1,3-Man)-α1,6-Man" viewed from the asparagine residue. Sugar chain (5) is also denoted as N3 or sugar chain M5.1 herein. In the present invention, (5) in addition to (2) are typically found.

[Chemical 6]

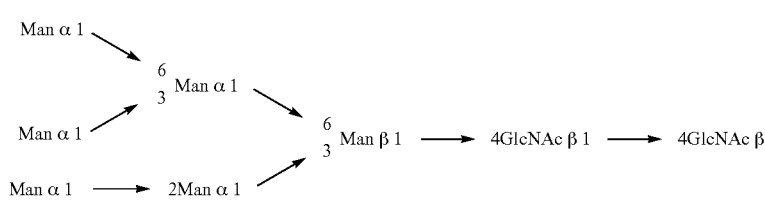

(6)

This structure is also described as "GlcNAc-β1,4-GlcNAc-β1,4-Man(-α1,3-Man-α1,2-Man)-α1,6-Man(-α1,3-Man)-α1,6-Man" viewed from the asparagine residue. Sugar chain (6) is also denoted as N2 or sugar chain M6.1 herein. In the present invention, (6) in addition to (2) are typically found.

In addition to these oligomannose types, it is understood that those with an additional sugar added can also be encompassed as the sugar chain of the invention.

(Specific Combination of Sugar Chains of CTLD14)

The silkworm form sugar chains comprised by the CTLD14 of the invention comprise one or more of the following combinations:

1) combination of GlcNAc-β1,4-GlcNAc-1,4-Man(-α1,3-Man)-α1,6-Man(-α1,3-Man)-α1,6-Man and GlcNAc-β1,4-GlcNAc-β1,4-Man(-α1,6-Man-β1,2-GlcNAc)-α1,3-Man-β1,2-GlcNAc (above-described formulas (5) and (2));

2) combination of GlcNAc-β1,4-GlcNAc-β1,4-Man(-α1,3-Man)-α1,6-Man(-α1,3-Man)-α1,6-Man-α1,2-Man and GlcNAc-β1,4-GlcNAc-β1,4-Man(-α1,6-Man-β1,2-GlcNAc)-α1,3-Man (above-described formulas (6) and (3));
and 3) combination of GlcNAc-β1,4-GlcNAc-β1,4-Man(-α1,3-Man)-α1,6-Man(-α1,3-Man)-α1,6-Man-α1,2-Man and GlcNAc-β1,4-GlcNAc-β1,4-Man(-α1,6-Man-β)-α1,3-Man-β1,2-GlcNAc (above-described formulas (6) and (4)).

(Sugar Chain of sRAGE)

Examples of sRAGE sugar chain types include the following in addition to the above-described (1)-(6) ([Chemical 1] to [Chemical 6]).

[Chemical 7]

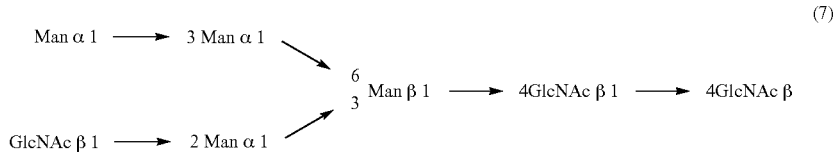

(7)

(This type is also described as "GlcNAc-β1,4-GlcNAc-β1,4-Man(-α1,6-Man-α1,3-Man)-α1,3-Man-β1,2-GlcNAc" viewed form the asparagine residue, and may be classified as a hybrid type.) Sugar chain (7) is also denoted as N4-3 or sugar chain H4.11.

[Chemical 8]

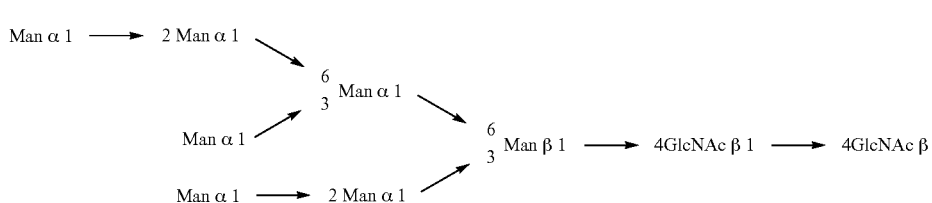

(8)

(This structure is also described as "GlcNAc-β1,4-GlcNAc-β1,4-Man(-α1,3-Man-α1,2-Man)-α1,6-Man(-α1,3-Man)-α1,6-Man-α1,2-Man" viewed from the asparagine residue and may be classified as an oligomannose type.) Sugar chain (8) is also denoted as N1 or sugar chain M7.2 herein.

sRAGE was revealed by sugar chain structure analysis to be about 90% or more oligomannose type sugar chains and comprise several % of complex and hybrid type sugar chains. Furthermore, it has an excellent effect of improving stability by glycosylation.

FIGS. 20 and 54 can be referred for sRAGE sugar chain types that can be comprised by the present invention.

In one embodiment, the silkworm form sugar chain of RAGE of the invention comprises a sugar chain to which 0 to 4 molecules of 0 to 2 molecules of GlcNAc and 0 to 4 molecule of Man are bound per molecule, in addition to a trimannosyl core (GlcNAc-β1,4-GlcNAc-β1,4-Man(-α1,6-Man)-α1,3-Man from the asparagine residue) structure. In another embodiment, the silkworm form sugar chain of RAGE of the invention comprises a sugar chain to which 0 to 8 molecules of 0 to 4 molecules of GlcNAc and 0 to 8 molecule of Man are bound per 2 molecules, in addition to a trimannosyl core (GlcNAc-β1,4-GlcNAc-β1,4-Man(-α1,6-Man)-α1,3-Man viewed from the asparagine residue) structure.

The sRAGE of the invention has two sites that can be glycosylated. A sugar chain may be added only to one of the two sites or to both. In a preferred embodiment, a sugar chain is added to both of the two sites that can be glycosylated. When both of the two sites are glycosylated, added sugar chains may be identical or different. Examples of added sugar chains include sugar chains with the above-described structure of (1) to (8) ([Chemical 1] to [Chemical 8]).

As discussed above, a silkworm form sugar chain is classified into oligomannose type, complex type, and hybrid type. For sRAGE sugar chain structures, 87% to 97% are oligomannose type, 2% to 8% are complex type, and 1% to 5% are hybrid type. Preferably, 90% to 94% are oligomannose type, 3% to 6% are complex type, and 2% to 4% are hybrid type. Most preferably, 92.5% are oligomannose type, 4.6% are complex type, and 2.5% are hybrid type.

In one embodiment, the sugar composition of silkworm form sRAGE has $(Man)_5(GlcNAc)2$ (N3 of FIG. 54) at 46% to 56%, $(Man)_7(GlcNAc)_2$ (N1 of FIG. 54) at 23% to 33%, $(Man)_6(GlcNAc)_2$ (N2 of FIG. 54) at 7% to 15%, $(Man)_3(GlcNAc)2$ (N4-1 of FIG. 54) at 1% to 5%, $(Man)_3(GlcNAc)3$ (N4-2 of FIG. 54) at 2% to 8%, and $(Man)_4(GlcNAc)_3$ (N4-3 of FIG. 54) at 1% to 5%. Preferably, the sugar composition has $(Man)_5(GlcNAc)_2$ at 48% to 54%, $(Man)_7(GlcNAc)_2$ at 25% to 31%, $(Man)_6(GlcNAc)_2$ at 9% to 13%, $(Man)_3(GlcNAc)_2$ at 2% to 4%, $(Man)_3(GlcNAc)_3$ at 3% to 6%, and $(Man)_4(GlcNAc)_3$ at 2% to 4%. Most preferably, the sugar composition has $(Man)_5(GlcNAc)_2$ at 51.4%, $(Man)_7(GlcNAc)_2$ at 27.5%, $(Man)_6(GlcNAc)_2$ at 10.8%, $(Man)_3(GlcNAc)_2$ at 2.8%, $(Man)_3(GlcNAc)_3$ at 4.6%, and $(Man)_4(GlcNAc)3$ at 2.5%.

There are not many types of sugars constituting a sugar chain binding to a glycoprotein, and there are about 7 to 8 types often observed, such as glucose, galactose, mannose, fucose, N-acetylglucosamine, N-acetylgalactosamine, N-acetylneuraminic acid, and xylose. The structural form is also limited to a certain degree. A minute structural difference thereamong is identified and precisely recognized to regulate various biological phenomenons.

As used herein, "fucose" refers to fucose in the common meaning, which is a type of deoxy sugar, 6-deoxy-galactose, with a chemical formula of $C_6H_{12}O_5$, molecular weight of 164.16, melting point of 163° C., and specific rotation of −76°, and classified as a hexose and monosaccharide. The L form is widely present in nature in animals and plants in the form of L-fucoside. In mammals and plants, fucose is found on an N-linked sugar chain on a cell surface.

As used herein, "N-acetylglucosamine" refers to the common N-acetylglucosamine (N-acetyl-D-glucosamine, GlcNAc, NAG), which is a monosaccharide derived from glucose and is an important substance for some biochemical mechanisms. Chemically, this substance is an amide between glucosamine and acetic acid. N-acetylglucosamine is a component of glycosaminoglycan (mucopolysaccharide) such as hyaluronic acid or glycoprotein in mammals. N-acetylglucosamine is the backbone of an N-linked glycoprotein with an oligosaccharide chain including mannose bound to asparagine (chitobiose structure), and it is the main constituent sugar of a sugar chain with a complex structure.

As used herein, "galactose" refers to the common galactose having the same molecular formula, $C_6H_{12}O_6$, and molecular weight, 180, as glucose. In the steric configuration, the —OH at position 2 (second from the top in a Fischer projection) and position 5 have the same direction, and those at positions 3 and 4 have the opposite directions; D-galactose has the same orientation as that of position 5 D-glyceraldehyde. It is the 4-epimer of glucose. In nature, most are D-galactose.

As used herein, "mannose" refers to the common mannose and is a type of monosaccharide classified as aldohexose, having the same molecular formula, $C_6H_{12}O_6$, and molecular weight, 180, as glucose. In the steric configuration, the —OH at position 2 (second from the top in a Fischer projection) and position 3 have the same direction, and those at positions 4 and 5 have the opposite direction; D-mannose has the same orientation as that of position 5 D-glyceraldehyde. It is the 2-epimer of glucose. In nature, most are D-mannose.

<Method of Analyzing Sugar Chain>

Neutral sugar/amino sugar composition analysis A sugar chain is typically comprised of a neutral sugar such as galactose, mannose, or fucose, an amino sugar such as N-acetylglycosamine, and an acidic sugar such as sialic acid. Composition analysis of a sugar chain can perform acid hydrolysis of the sugar chain with trifluoroacetic acid or the like and isolate a neutral sugar or amino sugar to analyze the composition ratio thereof. Examples of a specific method include a method using a sugar composition analyzer from Dionex (BioLC). BioLC is an apparatus for analyzing the sugar composition by HPAEC-PAD (high performance anion-exchange chromatography-pulsed amperometric detection) [J. Liq. Chromatogr., 6, 1577(1983)].

The composition ratio can also be analyzed by a fluorescent labeling method with 2-aminopyridine.

Specifically, the composition ratio can be calculated by fluorescent labeling from 2-amino pyridylation of a specimen subjected to acid hydrolysis according to a known method [Agric. Biol. Chem., 55(1), 283-284 (1991)] and subjecting the specimen to HPLC analysis.

Sugar Chain Structure Analysis

The sugar chain structure can be analyzed by two dimensional sugar chain mapping [Anal. Biochem., 171, 73 (1988), [Seibutsu Kagaku Jikkenho 23-Totanpakushitsu Tosa Kenkyuho [Biochemical experimental methods 23-Glycoprotein sugar chain research method] (Scientific Society Press), Ed. by Reiko Takahashi (1989)]. Two dimensional sugar chain mapping is a method of estimating a sugar chain structure, for example, by plotting the retention time or elution position of reversed phase chromatography in the X axis and retention time or elution position of a sugar chain by normal phase chromatography in the Y axis, and comparing with results thereof of a known sugar chain.

Specifically, a glycoprotein is subjected to hybriazine decomposition to isolate a sugar chain from the glycoprotein and the sugar chain is subsequently fluorescently labeled [J. Biochem., 95, 197 (1984)] by 2-aminopyridine (hereinafter, abbreviated as PA), and then the sugar chain is separated from excessive pyridylamination reagent by gel filtration to perform reversed phase chromatography. Subsequently, normal phase chromatography is performed with respect to each peak of fractionated sugar chain. The sugar chain structure can be estimated by plotting, based on these results, a two-dimensional sugar chain map, and comparing spots with a sugar chain standard (TaKaRa) or document [Anal. Biochem., 171, 73 (1988)]. Furthermore, mass spectrometry such as MALDI-TOF-MS or the like can be performed for each sugar chain to confirm the structure estimated by two dimensional sugar chain mapping.

<Method of Producing Glycoprotein>

In this embodiment, a glycoprotein is expressed in a silk gland cell in an insect classified in the order Lepidoptera such as silkworms.

The aforementioned insect is preferably a silkworm. This is because a silkworm has an established care providing method in the sericulture industry and has an excellent ability to spit out a cocoon from the silk gland such that a large quantity of the aforementioned glycoprotein can be efficiently obtained.

Silkworms typically make 0.3 to 0.5 g of cocoon per silkworm, but most are silk proteins such as fibroin synthesized at the posterior silk gland or sericin synthesized in the middle silk gland. In this manner, silkworm is an organism with an excellent ability to synthesize proteins. This is because a recombinant protein for analysis/evaluation or the like can be cheaply produced in large quantity by utilizing this ability.

Furthermore, it is preferable that the aforementioned silk gland cell is a middle silk gland cell. This is because sericin is synthesized in the middle silk gland, so if the aforementioned glycoprotein is expressed in sericin, a recombinant protein is localized in a sericin layer which is present around fibroin and dissolves relatively easily into water, such that a recombinant protein can be efficiently expressed in the middle silk gland and the recombinant protein contained in a cocoon can be readily extracted without modifying the steric structure.

That is, in the method of producing a glycoprotein in this embodiment, a step of expressing the glycoprotein preferably comprises a step of generating a cocoon comprising the glycoprotein of the invention in a silk gland of the aforementioned individual inspect (e.g., silkworm), which is genetically modified to express the glycoprotein of the invention. In this regard, generating a cocoon comprising the aforementioned glycoprotein in a silk gland of an individual insect typically would express the aforementioned glycoprotein in a silk gland cell of an insect.

In addition, a step of extracting a glycoprotein of interest preferably comprises a step of having a cocoon comprising the glycoprotein spit out from the aforementioned silk gland and a step of extracting the aforementioned glycoprotein from the aforementioned spit out cocoon. This is because fibroin or sericin is synthesized at a silk gland, so if the aforementioned glycoprotein is expressed in fibroin or sericin, a recombinant protein is localized in a fibroin layer or sericin layer, such that a recombinant protein can be efficiently expressed in the silk gland and the recombinant protein contained in a cocoon can be extracted.

In one embodiment, a step of expressing the aforementioned glycoprotein, in the above-described individual inspect, preferably comprises a step of using an individual insect with a gene encoding the aforementioned glycoprotein expressibly provided downstream of a sericin promoter in the genome of the aforementioned insect and a step of generating a cocoon comprising the aforementioned glycoprotein at a sericin portion as in the aforementioned cocoon.

In such a case, the step of extracting the aforementioned glycoprotein preferably comprises a step of immersing the aforementioned cocoon in an extract solution to extract the aforementioned glycoprotein in the aforementioned extract solution from the aforementioned sericin portion of the aforementioned cocoon. This is because a silk strand constituting a cocoon has a structure in which a sericin layer is present around a fibroin layer, which is present in the middle. Silk glands synthesizing a silk protein are functionally and morphologically distinguished into a posterior silk gland, a middle silk gland, and an anterior silk gland. Sericin constituting a sericin layer is synthesized in the middle silk gland, and fibroin constituting a fibroin layer is synthesized in the posterior silk gland. When a tissue expressing a glycoprotein is in the middle silk gland, the glycoprotein is secreted into a sericin layer of a silk strand. Meanwhile, when a tissue expressing a glycoprotein is in the posterior silk gland, the glycoprotein is secreted into a fibroin layer of a silk strand. In order to make a transgenic silkworm secreting a glycoprotein into a sericin layer, a promoter for inducing gene expression in a middle silk gland cell, for example, may be incorporated upstream of each structural gene in addition to the structural gene of a glycoprotein to express a glycoprotein in the middle silk gland, in a vector. Examples of a promoter inducing gene expression in a middle silk gland cell include promoters of the sericin 1 gene or the sericin 2 gene. The middle silk gland or the posterior silk gland is the synthetic pathway that is generally used, which can be similarly used in the present invention. Alternatively, a glycoprotein may be expressed systemically. When expressed in a silk gland, an extraction method of extracting the middle (and posterior) silk gland or a method of extraction from a cocoon can be used. When expressed systemically, a method of grinding the entire body or a method of squeezing out the body fluid can be used.

When such an expression vector is used, a transgenic silkworm secreting a glycoprotein in a sericin layer can be made with a single transfection operation. Meanwhile, a transgenic silkworm secreting a glycoprotein in a sericin layer can also be made by multiple transfection operations.

Indeed, the intent is not to exclude methods of making a transgenic silkworm secreting a glycoprotein in a fibroin layer. In order to express a glycoprotein in the posterior silk gland, a transgenic silkworm secreting an antibody into a fibroin layer may be made using a vector incorporating a promoter for inducing gene expression in a posterior silk gland cell upstream of each structural gene, in addition to a structural gene for a glycoprotein. Examples of promoters inducing gene expression in a posterior silk gland cell include promoters of a gene for a fibroin L chain, a fibroin H chain, fibrohexamarin, or the like.

As in the case of making a transgenic silkworm secreting a glycoprotein in a sericin layer, when making a transgenic silkworm secreting a glycoprotein into a fibroin layer, the aforementioned expression vector set may be used to make a transgenic silkworm by multiple transfection operations.

These expression vectors have a function of introducing a gene into a silkworm chromosome. For instance, if a partial sequence of an insect derived DNA transposon is incorporated, a gene can be introduced into a silkworm chromosome. Specific embodiments include plasmid vectors having a pair of oppositely faced repetitive sequences that are present at the end of DNA transposon and expression vectors incorporating a gene sequence inserted in a chromosome i.e., glycoprotein gene and a promoter, in a region sandwiched between the pair of oppositely faced repetitive sequences. Insect derived DNA transposon such as piggy- Bac and mariner (Insect Mol. Biol. 9, 145-155, 2000), Minos (Insect Mol. Biol. 9, 277-281, 2000) and the like are known, but a piggyBac derived sequence is most frequently utilized. In order to make a transgenic silkworm, a small amount of the plasmid is injected into a silkworm egg with a piggyBac transposase expression vector (helper plasmid). This helper plasmid is a recombinant plasmid vector substantially incorporating only a piggyBac transposase gene region, which lacks one or both of piggyBac oppositely faced repetitive sequences. In a helper plasmid, endogenous transposase promotor may be directly used or a silkworm/actin promotor, fruit fly HSP70 promotor or the like may be used as a promoter for transposase expression. To facilitate screening of next generation silkworms, a marker gene can be incorporated simultaneously in a vector incorporating a polypeptide to be inserted.

A promoter and a nucleic acid sequence can be bound herein to induce expression of a nucleic acid sequence of a structural gene that is present downstream of the promoter by binding a transcription regulating factor to the promoter. Examples of the combinations of the above-described transcription regulating factor and target sequence include GAL4 and UAS, TetR and TRE, and the like. GAL4 and UAS or TetR and TRE can be used to accurately regulate the expression site, timing, and quantity of a gene of interest to allow the gene to be readily expressed in many tissues. Further, a line can be created even if the gene to be expressed is a lethal gene.

In one embodiment, a glycoprotein manufactured by the method of the invention is not limited in any way, as long as the glycoprotein is manufactured by the method of the present invention. A glycoprotein may or may not have a signal sequence (e.g., fibroin H signal peptide), enterokinase recognition site (e.g., DDDDK (SEQ ID NO: 89)), biotinylated site (e.g., BIOEASE™ tag), or tag sequence (e.g., BIOEASE™ Tag biotin ligase birA substrate peptide Life Technologies, Carlsbad, Calif.), His tag, or the like). That is, glycoproteins manufactured by the method of manufacturing a glycoprotein of the invention encompass both glycoproteins with a signal sequence and glycoproteins without a signal sequence.

Examples of silkworm eggs with promotor of a nucleic acid sequence encoding a protein specifically expressed in a silk gland in the present invention and a nucleic acid sequence encoding a glycoprotein whose expression is directly regulated by said promoter include silkworm eggs having a nucleic acid sequence encoding a glycoprotein of interest, operably linked downstream to a promoter of a nucleic acid sequence encoding a protein specifically expressed in a silk gland. Such a silkworm egg can be manufactured by introducing into a silkworm egg a nucleic acid sequence encoding a glycoprotein of interest, the nucleic acid sequence operably linked downstream to a promoter of a nucleic acid sequence encoding a protein specifically expressed in a silk gland.

Further, examples of silkworm eggs with a promotor of a nucleic acid sequence encoding a protein specifically expressed in a silk gland in the present invention and a nucleic acid sequence encoding a recombinant glycoprotein whose expression is indirectly regulated by said promotor include silkworm eggs having (i) nucleic acid sequence encoding a transcription regulating factor functionally bound downstream of a promoter of a nucleic acid sequence encoding a protein specifically expressed in a silk gland and (ii) nucleic acid sequence encoding a recombinant antibody, operably linked downstream to a target promoter of the transcription regulating factor. In the present invention, a nucleic acid sequence encoding a recombinant antibody whose expression is directly or indirectly regulated by a promotor of a nucleic acid sequence encoding a protein specifically expressed in a silk gland, preferably has a signal sequence for promoting antibody secretion to increase yield. Specific embodiments of a signal sequence are explained elsewhere herein. Any known signal sequence can be used.

One exemplary manufacturing method raises a larva (F0 generation) hatched from a silkworm egg that is injected with a small amount of vector. All resulting F0 generation silkworms are crossbred with a wild silkworm or with another F0 silkworm. A transgenic silkworm is selected out from next generation (F1 generation) silkworms. A transgenic silkworm is selected out by using, for example, PCR or Southern blot. When a marker gene is incorporated, the phenotype can be utilized for selection. For example, when a fluorescent protein gene such as GFP is utilized as a marker gene, selection can be performed by irradiating an excitation light on a silkworm egg or larva of the F1 generation and detecting fluorescence emitted by a fluorescent protein. A transgenic silkworm can be created by such a method described above.

When a glycoprotein of interest is collected from a cocoon of a transgenic silkworm, the glycoprotein is collected from a sericin layer when the glycoprotein is localized in a sericin layer and from a fibroin layer when contained in a fibroin layer. A glycoprotein can be readily collected especially from a sericin layer. Since sericin constituting a sericin layer is hydrophilic, a recombinant protein localized in this layer can be extracted without using a solution that would denature the protein. An extraction solution for extracting a glycoprotein of interest from a sericin layer is not particularly limited, as long as the glycoprotein can be extracted. For example, such a solution may be a neutral saline, surfactant, or other solutions comprising a reagent for efficient extraction. To extract a glycoprotein from a cocoon using these extraction solution, a method of immersing and stirring a fragmented cocoon in an extraction solution or the like can be used. Further, a mechanical treatment may be used in combination, e.g., a cocoon may be processed into fine powder prior to extraction, or ultrasound treatment may be applied upon extraction. Further, the aforementioned silkworm silk gland cell may be appropriately transformed to express a transferase (e.g., β-galactose transferase, N-acetylglucosamine transferase, or the like) for further glycosylation.

A reporter gene may be incorporated to confirm expression in practicing the present invention. Such a reporter gene is not particularly limited, as long as the expression can be detected. Examples thereof include CAT gene, lacZ gene, luciferase gene, β-glucuronidase (GUS), GFP gene and the like that are commonly used by those skilled in the art. The expression level of a reporter gene can be measured by a method known to those skilled in the art, depending on the type of reporter gene. For example, when a reporter gene is a CAT gene, the expression level of the reporter gene can be measured by detecting acetylation of chloramphenicol by the gene product. When a reporter gene is an lacZ gene, the expression level of the reporter gene can be measured by detecting coloration of a dye compound by catalytic action of the gene expression product. Further, when the reporter gene is a luciferase gene, the same is accomplished by detecting fluorescence of a fluorescent compound by catalytic action of the gene expression product. Further, when the reporter gene is ß-glucuronidase (GUS), the same is accomplished by detecting coloration of 5-bromo-4-chloro-3-indolyl-β-glucuronide (X-Gluc) or light emission of Glucuron (ICN) by catalytic action of the gene expression product. Furthermore, when the reporter gene is a GFP gene, the same is accomplished by detecting fluorescence by a GFP protein.

The manufacturing method of a recombinant glycoprotein of the invention comprises a step of collecting a glycoprotein of interest synthesized in a silkworm body. The synthesized glycoprotein of interest is secreted into the middle silk gland or posterior silk gland in an active state without being insolubilized. Thus, a glycoprotein of interest can be collected from the middle silk gland or posterior silk gland. An exemplary method of collecting a glycoprotein of interest from the middle silk gland or posterior silk gland can dissect a silkworm reaching the spinning stage, extract the middle silk gland or posterior silk gland in 20 mM Tris-HCl with pH of 7.4, and opening the silk gland with tweezers or scalpel to collect the glycoprotein of interest in the silk gland.

The glycoprotein of interest of the invention can also be collected, for example, from a cocoon spun out by a transgenic silkworm. A method well known to those skilled in the art, such as a collection method of dissolving a cocoon in 60% LiSCN and dialyzing with 20 mM Tris and 5M urea (Inoue, S., Tsuda, H., Tanaka, H., Magoshi, Y and Mizuno (2001) Sericologia 4, 157-163.) can be used as a collection method. Examples of other possible protein collection methods include a method of using a surfactant, a method of dissolving in an aqueous solution and the like.

Further, the silkworm in the present invention is not particularly limited, but for mass production of glycoprotein of interest, it is preferable to use a silkworm with suppressed production of a protein constituting a silk strand by a mutation of a nucleic acid sequence region (including a coding region, promoter region, or untranslated region) encoding the protein constituting a silk strand such as a fibroin protein. Such a silkworm is a silkworm of a mutated line with production of a protein constituting a silk strand suppressed by a mutation in a nucleic acid sequence region encoding the protein constituting a silk strand, preferably a silkworm of exarate pupa line with suppressed production of a protein constituting a silk strand by the mutation, and more preferably Nd-s$^D$. It may be any silkworm with suppressed production of a protein constituting a silk strand, regardless of whether the cause of suppressed production of a protein constituting a silk strand is artificial or is dependent on a mutation that has occurred in a nature.

One embodiment of such a silkworm is a silkworm well known to those skilled in the art as a sericin silkworm. Use of a sericin silkworm enables mass production of a glycoprotein of interest in the middle silk gland and facilitates purification of a protein synthesized from a nucleic acid sequence encoding a recombinant antibody introduced into a chromosome. Further, use of a sericin silkworm is preferred also in terms of production quantity when a recombinant antibody is produced in the posterior silk gland.

As the silkworm in the present invention, a silkworm with a property of laying a nondormant egg or a silkworm having a property of laying a dormant egg (e.g., breeds used in practice such as Gunma, 200, Shunrei, Shogetsu, Kinshu, Showa or the like) can be used. In this regard, a dormant egg refers to an egg which temporarily suspends embryogenesis after the egg has been laid. A nondormant egg refers to an egg from which a larva hatches without suspension of embryogenesis after the egg has been laid. A silkworm with a property of laying a dormant egg, when used, is allowed to lay a nondormant egg and DNA is introduced into the nondormant egg. Examples of a method of having a nondormant egg laid with Gunma include a method of incubating a dormant egg at 15° C. to 21° C. to have an adult born from the dormant egg lay a nondormant egg, preferably a method of incubating a dormant egg at 16° C. to 20° C. to have an adult born from the dormant egg lay a nondormant egg, and more preferably a method of incubating a dormant egg at 18° C. to have an adult born from the dormant egg lay a nondormant egg, and most preferably a method of incubating a dormant egg at 18° C. and raising a larva born from the dormant egg under full light to have the grown adult lay a nondormant egg. Further, examples for 200 include a method of incubating a dormant egg at 15° C. to 21° C. to have an adult born from the dormant egg lay a nondormant egg, preferably a method of incubating a dormant egg at 16° C. to 20° C. to have an adult born from the dormant egg lay a nondormant egg, and more preferably a method of incubating a dormant egg at 18° C. to have an adult born from the dormant egg lay a nondormant egg or a method of raising a larva born from a dormant egg under full light and having the grown adult lay a nondormant egg, and most preferably a method of incubating a dormant egg at 25° C. and raising a larva born from the dormant egg under full light to have the grown adult lay a nondormant egg.

An egg can be incubated, for example, by placing the egg in an 18° C. to 25° C. incubator or a thermostatic chamber. A larva can be raised by using an artificial feed in a breeding room at 20° C. to 29° C.

The incubation of the above-described dormant egg of the present invention can be performed according to common silkworm egg incubation method by those skilled in the art. For example, incubation is carried out according to the method described in "Ministry of Education (1978), Sanshu Seizo (Production of silkworm species) p. 193, Jikkyo Shuppan, Tokyo". Further, the provision of care to a silkworm larva in the present invention can be performed by a method well known to those skilled in the art. For example, the provision of care can be performed according to the method described in "Ministry of Education (1978) Sanshu Seizo (Production of silkworm species) p. 193, Jikkyo Shuppan, Tokyo".

In the present invention, whether a laid egg is a nondormant egg can be determined by the color of the egg. It is commonly known that a dormant egg has a dark brown color and a nondormant egg has a yellowish white color. Accordingly, a laid egg is determined as a nondormant egg by not having a dark brown color, or more preferably by having a yellowish white color.

Hereinafter, a specific example of a method of introducing a nucleic acid molecule into a silkworm egg is disclosed. However, the method of introducing a nucleic acid molecule into a silkworm egg in the invention is not limited thereto. For example, a tube for nucleic acid molecule injection into a silkworm egg can be used to directly introduce a nucleic acid molecule into an egg, while a preferred embodiment physically or chemically opens a hole on the egg shell in advance to introduce a nucleic acid molecule from the hole. In doing so, the tube for nucleic acid molecule injection can be inserted into the egg from the hole such that the insertion angle is nearly perpendicular to the side surface on the ventral side of the egg.

Examples of a method of physically opening a hole on the egg shell in the present invention include a method of opening a hole using a needle, microlaser or the like. A hole can be suitably opened on the egg shell by a method using a needle. The needle is not particularly limited in terms of the material, strength or the like thereof, as long as a hole can be opened on the silkworm egg shell. The needle in the present invention refers to a stick-like needle with a pointed tip, but the overall shape is not particularly limited, as long as a hole can be opened on the egg shell. For example, the "needle" of the invention also encompasses pyramid shape substances with a pointed tip and trigonal pyramid shaped substances with a pointed tip. In the present invention, a tungsten needle can be suitably used. The needle of the present invention may have thickness (diameter) at a level that is capable of opening a hole through which a capillary discussed below can pass. The thickness is generally 2 to 20 µm and preferably 5 to 10 µm. Meanwhile, examples of a method of chemically opening a hole on the egg shell include a method of opening a hole using a chemical product (hypochlorous acid or the like) or the like.

In the present invention, the position where a hole is opened is not particularly limited, as long as it is a position where the insertion angle with respect to the side surface on the ventral side of an egg can be nearly perpendicular when a tube for nucleic acid injection is inserted from the hole. Preferably, the position is on the side surface of the ventral side or the opposite side thereof, more preferably on the side surface on the ventral side, and still more preferably on the center part slightly towards the back end on the side surface on the ventral side of an egg.

As used herein, "nearly perpendicular" refers to 70° to 120°, and preferably 80° to 100°. As used herein "position that becomes a reproductive cell in the future" is generally a position close to the surface on the ventral side of an egg (generally a position that is 0.01 mm to 0.05 mm from the egg surface), and preferably a position near the egg surface in the middle of the ventral side of an egg which is slightly towards the posterior pole.

While the tube for nucleic acid molecule injection of the invention is not particularly limited in terms of the material, strength, inner diameter or the like thereof, when a hole is physically or chemically opened on the egg shell prior to inserting the tube for nucleic acid molecule injection, the thickness (outer diameter) of the tube is preferably a size that can pass through the opened hole. Examples of the tube for nucleic acid molecule injection of the invention include glass capillaries and the like.

A preferred embodiment of the method of introducing a nucleic acid molecule of the invention performs a step of physically or chemically opening a hole on the above-described silkworm egg and inserting a tube for nucleic acid molecule injection into an egg from the hole such that the insertion angle of the tube for nucleic acid molecule injection is nearly perpendicular to the side surface on the ventral side of the egg to inject a nucleic acid molecule by using an integrated manipulator with a needle and a tube for nucleic acid molecule injection. In a preferred embodiment, the present invention is generally carried out by using an apparatus having such a manipulator as one of its constituent element.

Such an apparatus is comprised of a dissecting microscope, irradiation apparatus, movable stage, course adjustment manipulator secured to a microscope with a metal fitting, micromanipulator installed on said manipulator, and injector for adjusting air pressure for injection of a nucleic acid molecule. The pressure used in an injector is supplied by a nitrogen tank. The pressure switch can be turned on with a food switch. Injection is applied to an egg secured on a substrate such as a glass slide. The position of an egg is determined by a movable stage. Further, a glass capillary of the micromanipulator is operated by an operating unit connected with four tubes. The actual procedure involves determining the position of a tungsten needle with respect to an egg with a course adjustment manipulator and moving the egg in the horizontal direction with a level of a stage to open a hole. Subsequently, the operation unit lever of the micromanipulator is operated to guide the tip of the glass capillary to the position of the hole to insert the capillary into the egg again with the lever of the stage. In this case, it is necessary that the glass capillary is inserted perpendicularly with respect to the side surface on the ventral side of the egg. The foot switch is turned on to inject the nucleic acid molecule, and the lever is operated to withdraw the capillary from the egg. The opened hole is closed with an instant adhesive or the like, and the egg is protected with a thermostatic and humidistat incubator. Examples of optimal apparatus used in the present invention include the apparatus described in Japanese Patent No. 1654050 and said apparatus with an improvement.

In one embodiment of the present invention, a silkworm egg used in introduction of a nucleic acid molecule may be immobilized on a substrate. Examples of the substrate of the invention that can be used include, but are not particularly limited to, slide glass, plastic plate and the like. In the above-described embodiment of the present invention, it is desirable that eggs are aligned and immobilized in the same direction in order to accurately inject a nucleic acid molecule into a position that becomes a reproductive cell in the future in a silkworm egg. In the above-described embodiment, the number of silkworm eggs immobilized to a substrate is not particularly limited. When multiple silkworm eggs are used, the direction toward which the silkworm eggs are immobilized to a substrate is preferably a direction in which the ventral and dorsal orientation is consistent. In the present invention, the above-described silkworm egg is immobilized to a substrate, for example, by having eggs laid on a commercially available paper board (rose paperboard) preapplied with a water-soluble glue, detaching the eggs by adding water to the paperboard, then aligning the wet eggs on the substrate, and air-drying the eggs. Eggs are preferably immobilized on a slide glass with aligned direction. Further, double sided tape, adhesive or the like can be used to immobilize eggs to a substrate.

It is possible to confirm whether a nucleic acid molecule is introduced in a silkworm egg, for example, by a method of re-extracting the injected nucleic acid molecule from the egg for measurement (Nagaraju, J., Kanda, T., Yukuhiro, K., Chavancy, G., Tamura, T. and Couble, P. (1996) Attempt of transgenesis of the silkworm (*Bombyx mori* L) by egg-injection of foreign DNA. Appl. Entomol. Zool., 31, 589-598), a method of observing expression of the injected nucleic acid molecule in the egg (Tamura, T., Kanda, T., Takiya, S., Okano, K. and Maekawa, H. (1990). Transient expression of chimeric CAT genes injected into early embryos of the domesticated silkworm, *Bombyx mori*. Jpn. J. Genet., 65, 401-410) or the like.

As used herein, "purified" biological agent (e.g., nucleic acid, protein or the like) refers to a biological agent having at least some of the agents that are naturally accompanied therewith removed. Thus, purity of a biological agent in a purified biological agent is generally higher than that in a normal condition of the biological agent (i.e., concentrated).

As used herein, the term "purified" preferably refers to the presence of at least 75 wt. %, more preferably at least 85 wt. %, still more preferably at least 95 wt. %, and the most preferably at least 98 wt. % of biological agents of the same type.

As used herein, "corresponding" amino acid or nucleic acid refers to an amino acid or nucleotide which has, or is expected to have, action similar to a given amino acid or nucleotide in a polypeptide or polynucleotide that is a baseline of comparison in a certain polypeptide molecule or polynucleotide molecule; and particularly for an enzyme molecule refers to an amino acid that is at the same position in an active site and provides the same contribution to catalytic activity. For instance, for antisense molecules, this may be a similar portion in an ortholog corresponding to a specific portion of the antisense molecule. A corresponding amino acid may be a specific amino acid that has undergone cysteinylation, glutathionylation S—S bond formation, oxidation (e.g., oxidation of methionine side chain), formylation, acetylation, phosphorylation, glycosylation, myristylation or the like. Alternatively, a corresponding amino acid may be an amino acid responsible for dimerization. Such a "corresponding" amino acid or nucleic acid may be a region or domain over a certain range. Thus, such a region or domain is called a "corresponding" region or domain herein.

As used herein, "corresponding" gene (e.g., polypeptide molecule or polynucleotide molecule) refers to a gene (e.g., polypeptide molecule or polynucleotide molecule) which has, or is expected to have, action similar to a given gene in a species that is a baseline of comparison in a certain species. When there are multiple genes with such action, the gene with evolutionarily the same origin is referred. Thus, a corresponding gene for a certain gene may be an ortholog of the gene. Thus, for mouse or rat CTLD14 or LOX-1 or RAGE (or soluble form sRAGE), it is possible to find respective corresponding CTLD14 or LOX-1 or RAGE (sRAGE or soluble form sRAGE) in humans. Such a corresponding gene can be identified using a technique that is well known in the art. For example, for a corresponding gene in a certain animal (e.g., mouse), a baseline gene (e.g., CTLD14 or LOX-1 or RAGE (or soluble form sRAGE)) of a corresponding gene can be found by searching a sequence database of the animal (e.g., human or rat) using the sequence of the certain animal as a query sequence.

As used herein, "fragment" refers to a polypeptide or polynucleotide with a sequence length of 1 to n-1 with respect to the full length polypeptide or polynucleotide (with length n). The length of a fragment can be appropriately changed in accordance with the objective. Examples of the lower limit of such a length include 3, 4, 5, 6, 7, 8, 9, 10, 15, 20, 25, 30, 40, 50 and more amino acids for a polypeptide. Lengths represented by an integer that is not specifically listed herein (e.g., 11 and the like) also can be suitable as a lower limit. Further, examples of length include 5, 6, 7, 8, 9, 10, 15, 20, 25, 30, 40, 50, 75, 100, and more nucleotides for a polynucleotide. Lengths represented by an integer that is not specifically listed herein (e.g., 11 and the like) also can be suitable as a lower limit. As used herein, when a full length version functions as a marker, such a fragment is understood to be within the scope of the present invention as along as the fragment itself also functions as a marker.

As used herein, "heterogeneous" refers to nucleotide sequences or amino acid sequences that are different sequences or non-corresponding sequences, or sequences derived from different species. For example, a human nucleotide sequence or an amino acid sequence is heterologous to a mouse nucleotide sequence or an amino acid sequence. In addition, the nucleotide sequence or amino acid sequence of human LOX-1 or RAGE is heterologous to a nucleotide sequence or amino acid sequence of human albumin.

As used herein, "fragment" refers to a polypeptide or polynucleotide with a sequence length of 1 to n-1 with respect to the full length polypeptide or polynucleotide (with length n). The length of a fragment can be appropriately changed in accordance with the objective. Examples of the lower limit of such a length include 3, 4, 5, 6, 7, 8, 9, 10, 15, 20, 25, 30, 40, 50 and more amino acids for a polypeptide. Lengths represented by an integer that is not specifically listed herein (e.g., 11 and the like) also can be suitable as a lower limit. Further, examples of length include 5, 6, 7, 8, 9, 10, 15, 20, 25, 30, 40, 50, 75, 100, and more nucleotides for a polynucleotide. Lengths represented by an integer that is not specifically listed herein (e.g., 11 and the like) also can be suitable as a lower limit. As used herein, the length of a polypeptide or a polynucleotide can be represented by the number of amino acids or nucleic acids as discussed above, respectively, but the aforementioned numbers are not absolute. The aforementioned numbers as the upper limit or the lower limit are intended to encompass several numbers above and below the number (or for example 10% above or below) as long as there is the same function. To express such an intention, the number may be expressed herein by appending "about" in front of the number. However, it should be understood that the presence of absence of "about" herein does not affect the interpretation of the numerical value thereof. The length of a useful fragment herein may be determined by whether at least one of the functions of a full-length protein, which is a reference for the fragment, is retained.

As used herein, "biological function", when referring to a certain gene or a nucleic acid molecule or a polypeptide related thereto, refers to a specific function that the gene, the nucleic acid molecule or the polypeptide may have in a living body. Examples of such a function include, but are not limited to, production of a specific antibody, enzyme activity, impartation of resistance and the like. In the present invention, examples of this function include, but are not limited to, a function of an LOX-1 recognizing an oxidized LDL or the like, a function of RAGE recognizing a marker such as hemopexin and the like. As used herein, biological function can be exerted by "biological activity". As used herein, "biological activity" refers to the activity a certain agent (e.g., polynucleotide, protein or the like) may have in a living body. Biological activity encompasses an activity of exerting a variety of functions (e.g., transcription promoting activity), and also encompasses, for example, an activity of activating or inactivating another molecule by an interaction with a certain molecule. When two agents interact, biological activity thereof may be a bond between the two molecules and a biological change induced thereby. For example, two molecules are considered to be bound together if, when one molecule is precipitated using an antibody, the other molecule co-precipitates. Observation of such co-precipitation is thus one example of a determination approach. For example, when a certain agent is an enzyme, the biological activity thereof encompasses enzyme activity thereof. In another example, when a certain agent is a ligand, binding to a receptor corresponding to the ligand is encompassed. Such biological activity can be measured by a technique that is well known in the art.

Thus, "activity" refers to various measurable indicators, which indicate or reveal a bond (either direct or indirect) or affect a response (i.e., having a measurable effect in response to some exposures of stimuli). Examples thereof include affinity of a compound that directly binds to the polypeptide or polynucleotide of the invention, the amount of proteins upstream or downstream after some stimulations or events, or the level of other similar functions.

As used herein, "marker (substance)" refers to a substance that can be an indicator for tracking whether a subject is or at risk of suffering from a certain condition (e.g., disease associated with a modified LDL, or a disease associated with AGEs, such as diabetes or diabetic complications such as diabetic nephropathy, diabetic retinopathy or diabetic neurosis). Examples of such a marker include genes, gene products, metabolites, enzymes and the like. In the present invention, diagnosis, preliminary detection, prediction, or prediagnosis of a pathological condition such as lipid abnormality, arteriosclerosis, diabetes, ischemic heart disease (e.g., myocardial infarction, angina, and the like), cerebrovascular disorder (cerebral infarction, cerebral hemorrhage, subarachnoid hemorrhage, transient cerebral ischemic attack, and the like), aortic aneurysm, kidney infarction, other modified LDL associated diseases, hyperlipidemia and other lipid abnormalities, diabetes, hyperglycosemia, high blood pressure, hypertensive nephrosclerosis, arteriosclerosis, ischemia reperfusion injury, and post-blood vessel balloon damage can be materialized by using an agent or means specific to a marker associated with such a condition, or a composition, kit or system comprising the same or the like. In the present invention, diagnosis, preliminary detection, prediction, or prediagnosis of a certain condition (e.g., disease such as diabetes or diabetic complication such as diabetic nephropathy, diabetic retinopathy or diabetic neurosis) can be materialized by using an agent or means specific to a marker associated with such a condition, or a composition, kit or system comprising the same or the like.

As used herein, "gene product" refers to a protein or mRNA encoded by a gene. It was discovered herein that a gene product which is not directly associated with glycometabolism (i.e., protein that is not associated with glycometabolism such as insulin or the like) can be used as an indicator of diabetes.

As used herein, "subject" refers to a target subjected to diagnosis, detection or the like of the present invention (e.g., human).

As used herein, "sample" refers to any substance obtained from a subject or the like. For example, body fluid (blood, saliva, urine, lacrimal fluid, and the like) is encompassed. Preferably, blood, urine, or lacrimal fluid is used. Although there is a difference in specificity depending on the marker, those skilled in the art can appropriately select a preferred sample based on the descriptions herein.

As used herein, "agent" is used broadly and may be any substance or other elements (e.g., energy, radiation, heat, electricity and other forms of energy) as long as the intended objective can be achieved. Examples of such a substance include, but are not limited to, protein, polypeptide, oligopeptide, peptide, polynucleotide, oligonucleotide, nucleotide, nucleic acid (including for example DNAs such as cDNA and genomic DNA, RNAs such as mRNA), polysaccharide, oligosaccharide, lipid, organic small molecule (e.g., hormone, ligand, information transmitting substance, organic small molecule, molecule synthesized by combinatorial chemistry, small molecule that can be used as medicine (e.g., small molecule ligand and the like) and a composite molecule thereof. Typical examples of an agent specific to a polynucleotide include, but are not limited to, a polynucleotide having complementarity with a certain sequence homology (e.g., 70% or greater sequence identity) to a sequence of the polynucleotide, polypeptide such as a transcription factor that binds to a promoter region and the like. Typical examples of an agent specific to a polypeptide include, but are not limited to, an antibody directed specifically to the polypeptide or a derivative or analog thereof (e.g., single chain antibody), a specific ligand or receptor when the polypeptide is a receptor or ligand, a substrate when the polypeptide is an enzyme and the like.

As used herein, "interaction", for two substances, refers to a force (e.g., intermolecular force (Van der Waals force), hydrogen bond and hydrophobic interaction or the like) existing between one substance and the other substance. Generally, two substances that have interacted are in a conjugated or bound state.

Thus, as used herein, "agent specifically interacting" with a biological agent such as a polynucleotide or a polypeptide encompasses agents that typically have the same or higher, preferably significantly (e.g., statistically significantly) higher affinity to the biological agent such as polynucleotide or polypeptide than to other unrelated polynucleotide or polypeptide (especially those with identity of less than 30%). Such affinity can be measured, for example, by hybridization assay, binding assay or the like.

As used herein, a first substance or agent "specifically interacting" with a second substance or agent refers to interaction at a higher affinity of the first substance or agent to the second substance or agent than to substances or agents other than the second substance or agent (especially other substances or agents that are present in a sample comprising the second substance or agent). Examples of specific interaction of a substance or agent include, but are not limited to, ligand-receptor reaction, hybridization of nucleic acids, antigen-antibody reaction in a protein, enzyme-substrate reaction and the like, and when both nucleic acids and proteins are involved, reaction of a transcription agent and a binding site of the transcription agent and the like, protein-lipid interaction, nucleic acid-lipid interaction and the like. Thus, when substances or agents are both nucleic acids, first substance or agent "specifically interacting" to a second substance or agent encompasses the first substance or agent having at least partial complementarity to the second substance or agent. For example, when substances or agents are both proteins, examples of a first substance or agent "specifically interacting" with a second substance or agent include, but are not limited to, interaction due to antigen-antibody reaction, interaction due to a receptor-ligand reaction, enzyme-substrate interaction and the like. When two types of substances or agents include a protein and a nucleic acid, a first substance or agent "specifically interacting" with a second substance or agent encompasses interaction of a transcription factor and a binding region of a nucleic acid molecule targeted by the transcription factor.

As used herein, "means" refers to anything that can be a tool for accomplishing an objective. As used herein, "selective recognizing means" in particular refers to means capable of recognizing a certain subject different from others.

As used herein, the term "bond" refers to physical interaction or chemical interaction between two proteins or compounds or related proteins or compounds, or a combination thereof. Examples of bond include ionic bond, nonionic bond, hydrogen bond, van der Waal bond, hydrophobic interaction and the like. Physical interaction (bond) can be direct or indirect. An indirect bond is mediated or caused by an effect of another protein or compound. A direct bond refers to interaction that is not mediate by or caused by an effect of another protein or compound and involves no other substantial chemical intermediate.

As used herein, "contact(ed)" refers to physically bringing a compound, either directly or indirectly, closer to a polypeptide or polynucleotide that can function as a marker, ligand, or the like of the invention. A polypeptide or polynucleotide may be present in many kinds of buffers, salt, solution or the like. Examples of contact include placing a compound in, for example, a beaker, microtiter plate, cell culture flask, microarray (e.g., gene chip) or the like comprising a polypeptide, encoding a nucleic acid molecule or a fragment thereof.

As used herein, "label" refers to an entity (e.g., substance, energy, electromagnetic wave or the like) for distinguishing a molecule or substance of interest from others. Such a method of labeling includes RI (radioisotope) method, fluorescence method, biotin method, chemiluminescent method and the like. When a plurality of markers of the invention or agents or means for capturing the same are labeled by a fluorescence method, labeling is performed with fluorescent substances having different fluorescent emission maximum wavelengths. It is preferable that the difference in fluorescent emission maximum wavelengths is 10 nm or greater. When labeling a ligand, any label that does not affect the function can be used, but DiI, DiD, DiO or the like is desirable as a fluorescent substance for LDL labeling. DiI is a fat-soluble fluorescent dye which is capable of introducing a fluorescent label by being inserted into a lipid bilayer of an LDL or oxidized LDL without impairing the molecular feature. When labeling AGEs, Alexa Fluor is desirable as a fluorescent substance. Alexa Fluor is a water-soluble fluorescent dye obtained by modifying coumarin, rhodamine, fluorescein, cyanine or the like. This is a series compatible with a wide range of fluorescence wavelengths. Relative to other fluorescent dyes for the corresponding wavelength, Alexa Fluor is very stable, bright and has a low level of pH sensitivity. Combinations of fluorescent dyes with fluorescence maximum wavelength of 10 nm or greater include a combination of Alexa 555 and Alexa 633, combination of Alexa 488 and Alexa 555 and the like. When a nucleic acid is labeled, any substance that can bind to a base portion thereof can be used. However, it is preferable to use a cyanine dye (e.g., Cy3, Cy5 or the like of the CyDye™ series), rhodamine 6G reagent, N-acetoxy-N2-acetylaminofluorene (AAF), AAIF (iodine derivative of AAF) or the like. Examples of a fluorescent substance with a difference in fluorescent emission maximum wavelengths of 10 nm or greater include a combination of Cy5 and a rhodamine 6G reagent, a combination of Cy3 and fluorescein, a combination of a rhodamine 6G reagent and fluorescein and the like. The present invention can utilize such a label to alter a subject of interest to be detectable by the detecting means to be used. Such alteration is known in the art. Those skilled in the art can appropriately carry out such a method in accordance with the label and subject of interest.

As used herein, "diagnosis" refers to identifying various parameters associated with a disease, disorder, condition or the like in a subject to determine the current or future state of such a disease, disorder, or condition. The condition in the body can be investigated by using the method, apparatus, or system of the present invention. Such information can be used to select and determine various parameters of disease, disorder, or condition in a subject, formulation or method for the treatment or prevention to be administered, or the like. As used herein, "diagnosis" when narrowly defined refers to diagnosis of the current state, but when broadly defined includes "predictive diagnosis", "prediagnosis" and the like. Diagnosis in the early stages may be referred to as "early diagnosis".

As used herein, "predictive diagnosis" and "prediagnosis" in particular are interchangeably used. "Predictive diagnosis" and "prediagnosis" refer to use of a molecule capable of recognizing CTLD14 or modified LDL or the like to detect a stage prior to onset of a pathological condition such as lipid abnormality, arteriosclerosis, diabetes, ischemic heart disease (e.g., myocardial infarction, angina, or the like), cerebrovascular disorder (cerebral infarction, cerebral hemorrhage, subarachnoid hemorrhage, transient cerebral ischemic attack, or the like), aortic aneurysm, kidney infarction, other modified LDL associated diseases, lipid abnormality such as hyperlipidemia, diabetes, hyperglycosemia, high blood pressure, hypertensive nephrosclerosis, arteriosclerosis, ischemia reperfusion injury, or post-blood vessel balloon damage. "Predictive diagnosis" and "prediagnosis" include determination of future risk of onset of such diseases; diagnosis of a pathological condition such as lipid abnormality, arteriosclerosis, diabetes, ischemic heart disease (e.g., myocardial infarction, angina, or the like), cerebrovascular disorder (cerebral infarction, cerebral hemorrhage, subarachnoid hemorrhage, transient cerebral ischemic attack, or the like), aortic aneurysm, kidney infarction, other modified LDL associated diseases, lipid abnormality such as hyperlipidemia, diabetes, hyperglycosemia, high blood pressure, hypertensive nephrosclerosis, arteriosclerosis, ischemia reperfusion injury, or post-blood vessel balloon damage; and determination of the presence of a risk of suffering from diabetes intended for prevention thereof. Furthermore, "predictive diagnosis" and "prediagnosis", in the context of diabetes or diabetic complications such as diabetic nephropathy, diabetic retinopathy or diabetic neurosis, refer to using a molecule capable of recognizing sRAGE or AGE or the like to detect a stage prior to onset of diabetes or diabetic complications such as diabetic nephropathy, diabetic retinopathy or diabetic neurosis. "Predictive diagnosis" and "prediagnosis" include determination of future risk of onset of such disease, determination of the presence of a risk of suffering from diabetes to prevent diabetes or diabetic complication diabetic nephropathy, diabetic retinopathy or diabetic neurosis. The condition in the body can be examined in advance by using the method, kit, composition, detection agent, diagnostic agent, system or the like of the invention. Such information can be used to select and determine various parameters of disease, disorder, or condition in a subject, formulation or method for treatment or prevention to be administered, or the like. As used herein, "predictive diagnosis" and "prediagnosis" also encompass diagnosis at a stage where other conventional methods cannot diagnose, such that they are used to partially overlap with the concept of "early diagnosis".

Since the diagnostic method of the invention in principle can utilize what comes out from a body and can be conducted away from a medical practitioner such as a physician, the present invention is industrially useful. In order to clarify that the method can be conducted away from a medical practitioner such as a physician, the term as used herein may be particularly called "assisting" "predictive diagnosis, prediagnosis or diagnosis".

As used herein, the term "detection agent" broadly refers to all agents capable of detecting a substance of interest (e.g., modified LDL, AGE or the like).

As used herein, the term "diagnostic agent" broadly refers to all agents capable of diagnosing a condition of interest (e.g., disease or the like).

As used herein, "therapy" refers to the prevention of exacerbation, preferably maintaining of the current condition, more preferably alleviation, and still more preferably disappearance of a disease or disorder in case of such a condition.

As used herein, "prevention" refers to taking a measure against a disease or disorder from being in such a condition prior to being in such a condition. It is possible to use the predictive diagnosis or prediagnosis of the invention to prevent or take measures to prevent lipid abnormality, arteriosclerosis, diabetes, ischemic heart disease (e.g., myocardial infarction, angina, or the like), cerebrovascular disorder (cerebral infarction, cerebral hemorrhage, subarachnoid hemorrhage, transient cerebral ischemic attack, or the like), aortic aneurysm, kidney infarction, other modified LDL associated diseases, lipid abnormality such as hyperlipidemia, diabetes, hyperglycosemia, high blood pressure, hypertensive nephrosclerosis, arteriosclerosis, ischemia reperfusion injury, or post-blood vessel balloon damage. The predictive diagnosis or prediagnosis of the invention can be carried out to prevent or take measures against diabetic complications such as diabetic nephropathy, diabetic retinopathy or diabetic neurosis.

Disclosure of Preferred Embodiments

Preferred embodiments are described hereinafter. It is understood that the embodiments are exemplification of the present invention and the scope of the present invention should not be limited to such preferred embodiments. Thus, it is understood that those skilled in the art can readily make alterations, changes, etc. within the scope of the present invention while referring to the preferred embodiments herein. Those skilled in the art can appropriately combine any of the embodiments.

(Single Chain Antibody or Fragment Thereof)

In one aspect of the present invention, the present invention provides a single chain antibody comprising the amino acid sequence set forth by any one of SEQ ID NOs: 76 to 80 or a variant thereof, or a fragment or variant thereof. Preferably, the single chain antibody comprises the amino acid sequence set forth by SEQ ID NO: 76 or 78 or a variant thereof. More preferably, the single chain antibody comprises the amino acid sequence set forth by SEQ ID NO: 76, or a variant thereof. The single chain antibody or a fragment thereof of the invention can specifically bind to an LDL and/or a modified product thereof.

In one embodiment, examples of a variant of the amino acid sequence set forth by any one of SEQ ID NOs: 76 to 80 include variants comprising an amino acid mutation, insertion, or deletion. This variant is homologous or identical to at least 60%, at least 70%, at least 80%, at least 85%, at least 90%, at least 95%, at least 97%, at least 98%, or at least 99% of amino acids with the amino acid sequence set forth by any one of SEQ ID NOs: 1 to 5 over at least 50, at least 100, at least 150, at least 200, or at least 250 adjacent amino acid sequences.

(Detection Agent Comprising Single Chain Antibody or Fragment Thereof and Detection Method)

In another aspect, the present invention provides a detection agent for detecting an LDL and/or a modified product thereof (modified LDL), comprising a single chain antibody comprising the amino acid sequence set forth by any one of SEQ ID NOs: 76 to 80 or a variant thereof, or a fragment or variant thereof. This detection agent may further comprise a molecule capable of recognizing an oxidatively modified LDL in addition to the single chain antibody or a fragment thereof. Examples of a molecule capable of recognizing an oxidatively modified LDL include, but are not limited to, CTLD14, anti-LDL chicken antibody, combinations thereof and the like.

The detection agent of the invention can detect an LDL and/or a modified product thereof (modified LDL) at a high sensitivity. The detection agent of the invention is capable of detection at a sensitivity of at least 100 ng/100 µl well or less, at least 90 ng/100 µl well or less, at least 80 ng/100 µl well or less, at least 70 ng/100 µl well or less, at least 60 ng/100 µl well or less, at least 50 ng/100 µl well or less, at least 40 ng/100 µl well or less, at least 30 ng/100 µl well or less, at least 29 ng/100 µl well or less, at least 25 ng/100 µl well or less, at least 20 ng/100 µl well or less, at least 15 ng/100 µl well or less, at least 10 ng/100 µl well or less, or most preferably at least 5 ng/100 µl well or less.

In one embodiment, the present invention provides a method of detecting or quantifying an LDL and/or a modified product (modified LDL) thereof, comprising (A) contacting a sample subjected to detection or quantification with a single chain antibody comprising the amino acid sequence set forth by any one of SEQ ID NOs: 76 to 80 or a variant thereof, or a fragment or variant thereof, and (B) detecting a bond of the single chain antibody comprising the amino acid sequence set forth by any one of SEQ ID NOs: 76 to 80 or a variant thereof, or a fragment or variant thereof to a target, wherein the presence or level of the bond indicates the presence or level of the LDL and/or the modified product (modified LDL) thereof in the sample.

In the present invention, any approach known in the art can be used as the approach of contacting a sample with the above-described single chain antibody or a fragment or variant thereof of the invention. Examples of such an approach include, but are not limited to, mixing both in a solution and subsequently incubating them and the like.

In the present invention, any approach known in the art can be used as the approach of detecting a bond of the above-described single chain antibody or a fragment or variant thereof to an LDL and/or a modified product (modified LDL) thereof. For example, it is understood that when one of the molecules is labeled (e.g., fluorescent labeling), any approach for detecting the label can be utilized. In this regard, the presence or level of the above-described bond indicates the presence or level of the LDL and/or the modified product (modified LDL) thereof in the sample.

In the present invention, quantification of a bond of the above-described single chain antibody or a fragment or variant thereof to an LDL and/or a modified product (modified LDL) thereof can be materialized by any quantification approach in the above-described detection. Such quantification may be denoted in relative (level) or absolute value. Examples of such an approach include, but are not limited to, plotting the intensity of a label subjected to detection for a known amount of LDL and/or a modified product (modified LDL) thereof and creating calibration lines to extrapolate a value from detection data of a sample.

In one embodiment, as a solid phase used in the detection method of the invention, anything can be utilized as long as a molecule to be immobilized such as a CTLD molecule or modified LDL can be immobilized. In one embodiment, when a mechanism such as enzyme-linked immunosorbent assay (ELISA) is used, a microtiter plate is generally used as the solid phase (substrate). Examples of materials of a substrate include any solid material which has a characteristic of binding to a biomolecule used in the present invention or capable of being a derivative to have such a characteristic, either by a covalent bond or a noncovalent bond. Examples of such a material that can be used include organic materials such as polyethylene, ethylene, polypropylene, polyisobutylene, polyethylene terephthalate, unsaturated polyester, fluorine-containing resin, polyvinyl chloride, polyvinylidene chloride, polyvinyl acetate, polyvinyl alcohol, polyvinyl acetal, acrylic resin, polyacrylonitrile, polystyrene, acetal resin, polycarbonate, polyamide, phenol resin, urea resin, epoxy resin, melamine resin, styrene/acrylonitrile copolymer, acrylonitrile butadiene styrene copolymer, silicone resin, polyphenylene oxide, and polysulfone.

An immobilization method to a solid phase can be carried out by any method known in the art. For example, a bond by a silanol group (SiOH) on a solid phase surface, an ionic bond by a modification functional group and hydrophobic bond by a matrix of a material, a bond via an aromatic ring contained in a matrix can be preferably used. After immobilization to a solid phase, the solid phase may be dried or used in a moist state. Drying facilitates storage.

As used herein, the term "solid phase" is interchangeably used with "substrate" and refers to a material with which the device of the invention is constructed. A solid phase refers to a flat support where a molecule such as an antibody can be immobilized. For detection using the principle of surface plasmon resonance in the present invention, a solid phase is preferably a glass substrate with one surface as a meal thin film comprising gold, silver, or aluminum. When using a mechanism such as enzyme-linked immunosorbent assay (ELISA) in the present invention, a microtiter plate is generally used as a solid phase (substrate). In detection using the principle of crystal oscillator microbalance in the present invention, a frequency converting element (e.g., crystal oscillator or surface acoustic wave element) is used as a solid phase and directly bonded to a receptor. A crystal substrate with one surface covered with silicone and the other surface having a gold electrode is used as a solid phase. Examples of materials of a substrate include any solid material which has a characteristic of binding to a biomolecule used in the present invention or capable of being a derivative to have such a characteristic, either by a covalent bond or a noncovalent bond. Examples of a suitable substrate include, but are not limited to, beads, gold particles, semiconductor nanoparticles (e.g., CdTe nanoparticles, CdSe nanoparticles, GaN nanoparticles, ZnS nanoparticles, InP nanoparticles and the like), silica nanoparticles, polystyrene nanoparticles, acrylic nanoparticles, latex nanoparticles, carbon nanoparticles, plates (e.g., microtiter plates), test tubes, chips, magnetic particles, membranes, fibers, slide glasses, metallic thin films, filters, tubes, balls, diamond-like carbon coated stainless steel and the like.

Any material that can form a solid surface can be used as such a material for use as a solid phase and substrate. Examples thereof include, but are not limited to, glass, silica, silicone, ceramic, silicon dioxide, plastic, metals (including alloys), natural and synthetic polymers (e.g., polystyrene, cellulose, amylose, chitosan, dextran, and nylon). A substrate may be formed from multiple layers of different materials. For example, an inorganic insulating material such as glass, quartz glass, alumina, sapphire, forsterite, silicon carbide, silicon oxide, silicon nitride or the like can be used. Further, it is possible to use an organic material such as polyethylene, ethylene, polypropylene, polyisobutylene, polyethylene terephthalate, unsaturated polyester, fluorine-containing resin, polyvinyl chloride, polyvinylidene chloride, polyvinyl acetate, polyvinyl alcohol, polyvinyl acetal, acrylic resin, polyacrylonitrile, polystyrene, acetal resin, polycarbonate, polyamide, phenol resin, urea resin, epoxy resin, melamine resin, styrene/acrylonitrile copolymer, acrylonitrile butadiene styrene copolymer, silicone resin, polyphenylene oxide, polysulfone, or the like. In the present invention, a film used in blotting such as a nylon film, nitrocellulose film, PVDF film or the like can also be used. When a high density analyte is analyzed, it is preferably to use a material with hardness such as glass as the material. A preferred material as a substrate varies depending on the various parameters of measuring equipment or the like. Those skilled in the art can appropriately select a suitable material from the various aforementioned materials.

As used herein, "chip" refers to a micro-sized integrated circuit having diverse functions and constituting a part of a system. As used herein, a solid phase to which a receptor is immobilized is called a receptor chip and/or receptor microchip.

As used herein, "detection" or "quantification" of polynucleotide or polypeptide expression can be accomplished by using a suitable method including, for example, an immunological measuring method and measurement of mRNAs. Examples of a molecular biological measuring method include northern blot, dot blot, PCR and the like. Examples of an immunological measurement method include ELISA using a microtiter plate, RIA, fluorescent antibody method, western blot, immunohistochemical staining and the like. Further, examples of a quantification method include ELISA, RIA and the like. Quantification may also be performed by a gene analysis method using an array (e.g., DNA array, protein array). DNA arrays are outlined extensively in (Ed. by Shujunsha, Saibo Kogaku Bessatsu "DNA Maikuroarei to Saishin PCR ho" [Cellular engineering, Extra issue, "DNA Microarrays and Latest PCR Methods"]). Protein arrays are discussed in detail in Nat Genet. 2002 December; 32 Suppl: 526-32. Examples of a method of analyzing gene expression include, but are not limited to, RT-PCR, RACE, SSCP, immunoprecipitation, two-hybrid system, in vitro translation and the like, in addition to the methods discussed above. Such additional analysis methods are described in, for example, Genomu Kaiseki Jikkenho Nakamura Yusuke Labo Manyuaru [Genome analysis experimental method Yusuke Nakamura Lab Manual], Ed. by Yusuke Nakamura, Yodosha (2002) and the like. The entirety of the descriptions therein is incorporated herein by reference.

As used herein, "probe" refers to a substance that can be means for search, which is used in a biological experiment such as in vitro and/or in vivo screening. Examples thereof include, but are not limited to, a nucleic acid molecule comprising a specific base sequence, a peptide comprising a specific amino acid sequence, a specific antibody, a fragment thereof and the like. As used herein, a probe can be used as marker detecting means.

A nucleic acid molecule generally used as a probe includes those having a nucleic acid sequence with a length of at least 8 contiguous nucleotides, which is homologous or complementary to a nucleic acid sequence of a gene of interest. Such a nucleic acid sequence may be a nucleic acid sequence with a length of preferably at least 9 contiguous nucleotides, more preferably at least 10 contiguous nucleotides, still more preferably at least 11 contiguous nucleotides, at least 12 contiguous nucleotides, at least 13 contiguous nucleotides, at least 14 contiguous nucleotides, at least 15 contiguous nucleotides, at least 20 contiguous nucleotides, at least 25 contiguous nucleotides, at least 30 contiguous nucleotides, at least 40 contiguous nucleotides, or at least 50 contiguous nucleotides. A nucleic acid sequence used as a probe comprises a nucleic acid sequence that is at least 70% homologous, more preferably at least 80% homologous, still more preferably at least 90% homologous, or at least 95% homologous with the aforementioned sequence.

As used herein, "search" refers to utilizing a certain nucleic acid base sequence electronically, biologically, or by another method to find another nucleic acid base sequence having a specific function and/or property. Examples of electronic search include, but are not limited to, BLAST (Altschul et al., J. Mol. Biol. 215: 403-410 (1990)), FASTA (Pearson & Lipman, Proc. Natl. Acad. Sci., USA 85: 2444-2448 (1988)), Smith and Waterman method (Smith and Waterman, J. Mol. Biol. 147: 195-197 (1981)), Needleman and Wunsch method (Needleman and Wunsch, J. Mol. Biol. 48: 443-453 (1970)) and the like. Examples of biological search include, but are not limited to, stringent hybridization, a macroarray with a genomic DNA applied to a nylon membrane or the like or a microarray with a genomic DNA applied to a glass plate (microarray assay), PCR, in situ hybridization and the like. Herein, a gene used in the present invention is intended to include corresponding genes identified by such electronic search or biological search.

As used herein, "primer" refers to a substance required for initiating a reaction of a polymeric compound to be synthesized in a polymer synthesizing enzyme reaction. A synthetic reaction of a nucleic acid molecule can use a nucleic acid molecule (e.g., DNA, RNA or the like) complementary to a portion of a sequence of a polymeric compound to be synthesized. A primer can be used herein as a marker detecting means.

Examples of a nucleic acid molecule generally used as a primer include those having a nucleic acid sequence with a length of at least 8 contiguous nucleotides, which is complementary to a nucleic acid sequence of a gene of interest. Such a nucleic acid sequence may be a nucleic acid sequence with a length of preferably at least 9 contiguous nucleotides, more preferably at least 10 contiguous nucleotides, still more preferably at least 11 contiguous nucleotides, at least 12 contiguous nucleotides, at least 13 contiguous nucleotides, at least 14 contiguous nucleotides, at least 15 contiguous nucleotides, at least 16 contiguous nucleotides, at least 17 contiguous nucleotides, at least 18 contiguous nucleotides, at least 19 contiguous nucleotides, at least 20 contiguous nucleotides, at least 25 contiguous nucleotides, at least 30 contiguous nucleotides, at least 40 contiguous nucleotides, or at least 50 contiguous nucleotides. A nucleic acid sequence used as a probe comprises a nucleic acid sequence that is at least 70% homologous, more preferably at least 80% homologous, still more preferably at least 90% homologous, or at least 95% homologous to the aforementioned sequence. A sequence suitable as a primer may vary depending on the property of a sequence intended for synthesis (amplification). However, those skilled in the art are capable of designing an appropriate primer in accordance with an intended sequence. Design of such a primer is well known in the art, which may be performed manually or by using a computer program (e.g., LASERGENE, PrimerSelect, or DNAStar).

As used herein, "kit" refers to a unit generally providing portions to be provided (e.g., antibody, label, and the like) into two or more separate sections. This form of a kit is preferred when a composition that should not be provided in a mixed state and is preferably mixed immediately before use is intended to be provided. Such a kit advantageously comprises an instruction or manual describing how the provided portions should be used or how a reagent should be handled. When the kit is used herein as a reagent kit, the kit generally comprises an instruction describing how to use an antibody and the like.

As used herein, "instruction" is a document with an explanation of the method of use of the present invention for a physician or other users. The instruction describes detection method, method of use of a diagnostic agent, or description instructing administration of a medicament or the like of the present invention. Further, an instruction may have a description instructing administration to the skeletal muscle (e.g., by injection or the like) as a site of administration. The instruction is prepared in accordance with a format defined by a regulatory authority of the country in which the present invention is practiced (e.g., Health, Labor and Welfare Ministry in Japan or Food and Drug Administration (FDA) in the U.S. or the like), with an explicit description showing approval by the regulatory authority. The instruction is a so-called package insert and is typically provided in, but not limited to, paper media. The instructions may also be provided in a form such as electronic media (e.g., web sites provided on the Internet or emails).

As used herein, "in a living body" or "in vivo" refers to inside of a living body. Under specific context, "in a living body" refers to the position where a substance of interest should be disposed.

As used herein, "in vitro" refers to a state where a portion of a living body is extracted or isolated to "outside of a living body" (e.g., in a test tube) for various research purposes. This is a term that is an antonym of in vivo.

As used herein, when a procedure is performed outside of the body, but the subject of the procedure is intended to be subsequently returned into the body, the series of operations is referred to as "ex vivo".

The formulation procedure for an in vitro diagnostic agent or the like of the invention as a medicament or the like is known in the art. The procedure is described, for example, in Japanese Pharmacopoeia, the United States Pharmacopeia, pharmacopeia of other countries, or the like. Thus, those skilled in the art can determine the amount to be used without undue experimentation from the descriptions herein.

In one embodiment, a modified LDL used in the present invention may be an oxidized LDL (OxLDL), malondialdehydized LDL (MDA-LDL), acrolein modified LDL, nonenal modified LDL, crotonaldehyde (CRA) modified LDL, 4-hydroxynonenal (HNE) modified LDL, hexanoyl (HEL) modified LDL, small particle LDL, glycated LDL, acetylated LDL or a variant thereof.

(Stable Supply System of Single Chain Antibody or Fragment Thereof)

Another aspect of the present invention provides a method of producing the single chain antibody or a fragment thereof. The method comprises: (A) introducing a nucleic acid encoding an amino acid sequence of the single chain antibody or a fragment thereof into *E. coli* expressing the nucleic acid; (B) culturing the *E. coli* and taking out an inclusion body from the *E. coli*; (C) extracting the single chain antibody or fragment thereof from the inclusion body and refolding; (D) contacting a solution obtained by refolding with Ni-NTA slurry to elute out an eluent comprising imidazole; and (E) dialyzing the eluted single chain antibody or a fragment thereof with a dialysis solution.

The *E. coli* used in the present invention is preferably selected from the group consisting of DH5a strain, BL21 (DE3) strain, HB2151 strain, BLR strain, and TG1 strain. The *E. coli* is most preferably the BL21 (DE3) strain. Examples of expression vectors include, but are not limited to, T7 promotor based *E. coli* protein expression vector (pET-22b (+) and the like). The expression vector is most preferably pET-22b (+).

An inclusion body can be extracted by using a technique known in the art. For example, an inclusion body can be extracted by ultrasound treatment, French press, or homogenization followed by centrifugation. An inclusion body is mainly found in a pellet. A reducing agent such as DTT and a denaturant such as guanidine, guanidine derivative, urea or urea derivative can be mixed into an inclusion body suspension to solubilize an inclusion body to extract a single chain antibody or a fragment thereof. Herein, refolding condition is represented by a value of the amount of inclusion body subjected to a single purification (50 ml refolding) converted into the protein concentration measured by BCA method and expressing the resultant value as the amount "per protein". For example, "2 to 10 mg (e.g., 8.6 mg) per protein" means that a value of the amount of inclusion body subjected to a single purification (50 ml refolding) converted into protein concentration measured by BCA method is 2 to 10 mg (e.g., 8.6 mg). In the present invention, it is important to have "2 to 10 mg (e.g., 8.6 mg) per protein" to attain excellent yield.

In one embodiment of the present invention, refolding of a single chain antibody or a fragment thereof that can be used preferably uses cycloamylose (CA) method (Machida et al., FEBS Lett. 486 (2000): 131-135), but other methods known in the art can also be used. When refolding is performed by the CA method, it is performed in a solution comprising an ionic surfactant comprising cycloamylose and DL-cysteine. The lower limit of the degree of polymerization of cycloamylose is 17 or greater, preferably 25 or greater, and more preferably 40 or greater, and the upper limit of the degree of polymerization is 150 or less, preferably 100 or less, and more preferably 40 or less.

In one embodiment of the present invention, examples of ionic surfactant that can be used include, but are not limited to, acetyltrimethylammonium bromide, sodium dodecyl sulfate, sodium deoxycholate, 3-[(3-cholamidopropyl) dimethylammonio]-1-propanesulfonic acid, hexadecyltrimethylammonium bromide (hereinafter, also abbreviated as CTAB), myristyl sulfobetaine (hereinafter, also abbreviated as SB 3-14), and the like. It is preferably SB 3-14 and more preferably CTAB.

Dialysis is performed one or multiple times (e.g., 2 to 4 times) using a cellulose ester film tube (Spectra/Por® Biotech CE, molecular weight cut-off 8000, 10 mm width). The dialysis solution is for example phosphate buffered saline (PBS), and Dulbecco's PBS (−) can be typically used as PBS (The composition of Dulbecco's PBS (−) is 8 g of NaCl, 0.2 g of KCl, 1.15 g of $Na_2HPO_4$, and 0.2 g/L of $KH_2PO_4$ (pH 7.4).) A volume that is at least 20-fold, at least 50-fold, at least 100-fold, at least 200-fold, at least 300-fold, or preferably at least 400-fold the sample volume is used. When PBS is used as the dialysis solution, PBS (−) is preferable. PBS (−) is free of calcium and magnesium ions.

(Detection/Quantification System or Kit of LDL and Modified Product (Modified LDL) Thereof)

In another aspect, the present invention provides a system or kit for detecting or quantifying an LDL or a modified product (modified LDL) thereof using the single chain antibody or a fragment thereof of the invention. Any form explained in the aforementioned section of (Single chain antibody or fragment thereof), the section of (Detection agent comprising single chain antibody or fragment thereof), the section of (Stable supply system of single chain antibody or fragment thereof) or any other section can be used as the single chain antibody or a fragment or variant thereof, approach of detection or quantification and means used therein, kit, system, or the like used in this aspect.

In one representative embodiment, this kit or system may be a kit or system for materializing direct ELISA.

In another aspect, the present invention provides a system for detecting or quantifying a modified LDL such as an oxidatively modified LDL using the single chain antibody or a fragment thereof of the invention and a molecule capable for recognizing an oxidatively modified LDL such as a ligand recognition region of an oxidized LDL receptor (LOX-1). Any form explained in the aforementioned section of (Single chain antibody or fragment thereof), the section of (Detection agent comprising single chain antibody or fragment thereof), the section of (Stable supply system of single chain antibody or fragment thereof) or other sections can be used as the single chain antibody or a fragment thereof that can be used in this aspect.

In one representative embodiment, the present invention provides a kit or a system for detecting or quantifying a modified LDL such as an oxidatively modified LDL. The kit or system comprises (A) a labeled single chain antibody or a fragment or variant thereof of the invention and a solid phase having a molecule capable of recognizing an oxidatively modified LDL such as a ligand recognition region (e.g., CTLD14) of immobilized LOX-1, or a molecule capable of recognizing an oxidatively modified LDL such as a ligand recognition region (e.g., CTLD14) of LOX-1 which is labeled and a solid phase having an immobilized single chain antibody or a fragment or variant of the invention; and (B) means for detecting the label. The presence or level of the label in this context indicates the presence or level of an oxidatively modified LDL. It is understood that any embodiment explained in (Detection agent comprising single chain antibody or fragment thereof and detection method) can be used for a modified LDL, CTLD molecule, solid phase, label, contact or bond detection technique or means, bond level calculation and the like that can be used in the kit of the invention. The format thereof typically uses the format of indirect ELISA (sandwich ELISA), but is not limited thereto.

Typical examples of molecules that can recognize an oxidatively modified LDL which can be used include oxidized LDL receptors (LOX-1), CTLD14, anti-LDL chicken antibodies, single chain antibody of the invention (SEQ ID NO: 76, 77, 78, 79, or 80) or a variant thereof and the like. More specifically, such a molecule typically may be a molecule comprising CTLD among the four domains of LOX-1: N-terminal cytoplasmic domain, hydrophobic transmembrane domain, NECK domain and C-type lectin-like domain (also referred to as CTLD herein); or CTLD14; full-length LOX-1; full-length LOX-1 extracellular region or a variant thereof, and preferably CTLD14 is used. This is due to high stability in long-term storage, but such a molecule is not limited thereto.

In another embodiment of the present invention, the system is for use in an antigen-antibody reaction, such as ELISA, sandwich ELISA, or lateral flow assay.

A preferred embodiment of the present invention provides a system for performing a lateral flow assay, comprising a membrane for the deployment of a specimen by a capillary phenomenon, the membrane comprising: a conjugation section comprising a ligand recognition region of an oxidized LDL receptor (LOX-1) labeled with a metal colloid, a silica particle or a latex particle and a sample, or the single chain antibody or a fragment thereof labeled with a metal colloid, a silica particle, or a latex particle; a detection section comprising a ligand recognition region of an oxidized LDL receptor (LOX-1), or the aforementioned single chain antibody or a fragment thereof; and a control section comprising a binding molecule to the ligand recognition region of the oxidized LDL receptor (LOX-1) or a binding molecule to a single chain antibody.

A preferred embodiment of the present invention provides a system for performing a lateral flow assay, comprising a membrane for the deployment of a specimen by a capillary phenomenon, the membrane comprising: a conjugation section comprising CTLD14 labeled with a metal colloid, a silica particle, or a latex particle and a sample, or the single chain antibody or a fragment thereof labeled with a metal colloid, a silica particle, or a latex particle; and a control section comprising a binding molecule to the CTLD14.

Examples of a metal colloid include, but are not limited to, gold colloid, platinum colloid, palladium colloid, silver colloid and the like.

Examples of latex particles include, but are not limited to, polyester-based polymers, carboxy modified systems, fluorescent latex particles, magnetic latex particles and the like. Further, examples of silica-based particles include, but are not limited to, silica particles and fluorescent silica particles.

Since an His tag or an E tag is added to the C-terminus of a single chain antibody, an anti-His antibody or an anti-E tag antibody is used as a bonding molecule. Furthermore, CTLD14 is biotinylated or added with an His tag, Myc tag, Flag tag, E tag, or Strep tag. In the respective cases, streptavidin, anti-His antibody, anti-Myc antibody, anti-Flag antibody, anti-E tag antibody, or Strep-Tactin is used as a binding molecule, which is not limited thereto.

In another embodiment, the present invention also provides a system for detecting or quantifying a modified LDL such as an oxidatively modified LDL using an anti-modified LDL antibody or a variant or fragment thereof and a molecule capable of recognizing an oxidatively modified LDL such as a ligand recognition region of LOX-1 (CTLD14) in a lateral flow assay format. Such a system in a lateral flow assay format was not provided conventionally for modified LDL detection and is advantageous because such a system can detect cases that a conventional assay system could not detect. Although not wishing to be bound by any theory, the advantages of the present invention include the following: (1) reaction time is short, typically 30 minutes or less; (2) detection is possible by visual inspection without the use of a special equipment; (3) a detection reagent does not need to be added such that a reaction is completed by only adding a specimen subjected to measurement and the like.

The present invention also provides a system for evaluating a modified LDL associated disease such as lipid abnormality, arteriosclerosis, diabetes, ischemic heart disease, or cerebrovascular disorder using an anti-modified LDL antibody or a variant or fragment thereof and a molecule capable of recognizing an oxidatively modified LDL such as a ligand recognition region of LOX-1 (e.g., CTLD14) in a lateral flow assay format. It is known that the expression of an oxidatively modified LDL is regulated under various conditions by a pathological condition such as lipid abnormality such as hyperlipidemia, diabetes, hyperglycosemia, high blood pressure, hypertensive nephrosclerosis, arteriosclerosis, ischemia reperfusion injury, or post blood vessel balloon damage, and oxidized LDL, angiotensin II, endothelin, TNF-α, advanced glycation end products (AGEs), TGF-β, 8-iso-prostaglandin $F_{2\alpha}$, shear stress and other stimulations (Folia Pharmacol. Jpn. 127, 103-107 (2006), Japanese Laid-Open Publication No. 2009-082076). Thus, such information can be used in evaluation by the present invention. Examples of modified LDL present in a living body include, but are not limited to, oxidized LDLs, malondialdehydized LDLs (MDA-LDL), acrolein modified LDLs, nonenal modified LDLs, small particle LDLs (LDLs with a diameter of 255 nm or less), glycated LDLs, and the like. When oxidized LDLs exhibit an abnormal value, diseases such as arteriosclerosis, ischemic heart disease (e.g., myocardial infarction, angina, and the like), cerebrovascular disorder (cerebral infarction, cerebral hemorrhage, subarachnoid hemorrhage, transient cerebral ischemic attack, and the like), aortic aneurysm, kidney infarction, hyperlipidemia, and the like are expected, but the diseases are not limited thereto (see "Kyo no Rinsho Kensa 2007-2008" [Modern clinical inspection 2007-2008], Publisher Nankodo Co., Ltd.) MDA-LDL (normal range: 10 to 80 U/L) and oxidized phosphatidyl choline (normal range: 8.4 U/mL to 17.6 U/mL) are used as a reference substance.

The method of assisting the diagnosis of a disease induced by a modified LDL of the invention detects a modified LDL in both a sample of a subject (e.g., healthy individual) who is not suffering from the above-described diseases and a sample of a subject (patient) who is suspected of suffer from the above-described diseases and compares the amounts of complex of a modified LDL and polypeptide of the invention between these samples to calculate a relative value of modified LDLs in a subject suspected of the above-described diseases with respect to a control subject. MDA-LDL (normal range: 10 to 80 U/L) and oxidized phosphatidyl choline (normal range: 8.4 U/mL to 17.6 U/mL) are used as a reference substance. These normal ranges can be referenced. When this relative value is an abnormal value, a patient is diagnosed as suffering from the above-described diseases. Typical examples of diseases induced by a modified LDL include, but are not limited to, arteriosclerosis, ischemic artery disease, arteritis, coronary vasospastic angina based on arteriosclerosis, dilated cardiomyopathy, ischemic heart disease (e.g., myocardial infarction, angina, and the like), cerebrovascular disorder (cerebral infarction, cerebral hemorrhage, subarachnoid hemorrhage, transient cerebral ischemic attack, and the like), aortic aneurysm, kidney infarction, hyperlipidemia, and the like.

The present invention also provides a system for evaluating a prophylactic effect of food intake on a modified LDL associated disease such as lipid abnormality, arteriosclerosis, diabetes, ischemic heart disease, or cerebrovascular disorder using an anti-modified LDL antibody, a variant or a fragment thereof and a molecule capable of recognizing an oxidatively modified LDL such as a ligand recognition region (e.g., CTLD14) of LOX-1 in a lateral flow assay format.

The anti-modified LDL antibody refers to any antibody against a modified LDL. Examples thereof include, but are not limited to, anti-LDL chicken antibodies in addition to the single chain antibody comprising the amino acid sequence set forth by any one of SEQ ID NOs: 76 to 80 or a variant thereof described herein, or a fragment or variant thereof. For example, chicken anti-LDL antibodies that can be used herein can be collected by inoculating the chicken skin 6 times with 0.3 mg of antigen (LDL) (adjuvant FCA) every two weeks, checking the increase in titer at and after the fifth inoculation, and exsanguinating after the sixth booster. In such a case, antibody activity can be measured by using 1 µg/ml of antigen (LDL) in a solid phase at 100 µl/well in accordance with common ELISA (HRP labeled anti-chicken IgY is used as a labeled secondary antibody).

When using immunoassay in the detection method of an antigen in this embodiment, it is preferable to use a carrier with an immobilized antibody. In this manner, an immunoassay system using an antibody immobilized on a carrier as a primary antibody can be readily constructed. For example, a sandwich EIA system can be constructed by preparing two types of antigen-specific antibodies with a different epitope, immobilizing one to a carrier as a primary antibody, and enzymatically labeling the other as a secondary antibody. In addition, an immunoassay system based on a binding inhibition method or competitive method can also be constructed. Furthermore, when a substrate is used as a carrier, immunoassay using an antibody chip is possible. With an antibody chip, multiple marker concentrations can be simultaneously measured, enabling quick measurements.

<Improved CTLD14 (Silkworm Form) and Manufacturing Method Thereof>

In one aspect, the present invention provides C-type lectin-like domain (CTLD) 14 having a silkworm from sugar chain, comprising the amino acid sequence set forth by SEQ ID NO: 86 or a variant thereof.

In a preferred embodiment, the silkworm form sugar chain in the present invention comprises one or more types of sugar chains from trimannosyl core, complex type sugar chain, oligomannose type sugar chain and hybrid type sugar chain.

In one embodiment, the silkworm form sugar chain comprises a sugar chain to which 0 to 4 molecules of 2 molecules of GlcNAc and 2 molecule of Man are bound per two molecules, in addition to a trimannosyl core (GlcNAc-β1, 4-GlcNAc-β1,4-Man(-α1,6-Man)-α1,3-Man viewed from the asparagine residue) structure.

In a specific embodiment, the silkworm form sugar chain comprises one or more of the following combinations viewed from an asparagine residue:
1) a combination of GlcNAc-β1,4-GlcNAc-β1,4-Man(-α1,3-Man)-α1,6-Man(-α1,3-Man)-α1,6-Man and GlcNAc-β1,4-GlcNAc-β1,4-Man(-α1,6-Man-β1,2-GlcNAc)-α1,3-Man-β1,2-GlcNAc;
2) a combination of GlcNAc-β1,4-GlcNAc-β1,4-Man(-α1,3-Man)-α1,6-Man(-α1,3-Man)-α1,6-Man-α1,2-Man and GlcNAc-β1,4-GlcNAc-β1,4-Man(-β1,6-Man-β1,2-GlcNAc)-α1,3-Man; and
3) a combination of GlcNAc-β1,4-GlcNAc-β1,4-Man(-α1,3-Man)-α1,6-Man(-α1,3-Man)-α1,6-Man-α1,2-Man and GlcNAc-β1,4-GlcNAc-β1,4-Man(-α1,6-Man-β)-α1,3-Man-β1,2-GlcNAc (see FIG. 20).

In one embodiment, the silkworm form sugar chain binds to asparagine at position 111 and/or asparagine at position 155 of SEQ ID NO: 86.

In another embodiment, CTLD14 of the invention is biotinylated. Biotinylation allows a measurement result to be obtained at a high sensitivity, and accumulation at a high density in a certain direction on a bead or membrane via streptavidin.

In one embodiment, CTLD14 of the invention can be used as a composition for detecting a modified LDL. Thus, the present invention provides a composition for detecting a modified LDL, comprising the CTLD14 comprising the silkworm form sugar chain of the invention.

The composition for detecting a modified LDL of the invention is for distinguishing an unmodified LDL from a modified LDL to detect a modified LDL. Although not wishing to be bound by any theory, the improved CTLD14 comprising a silkworm form sugar chain of the invention is characterized by widely recognizing modified LDLs and having high specificity with respect to unmodified LDLs, whereby the determination of a modified LDL used in the diagnosis of diabetes, arteriosclerosis or the like is possible at a high sensitivity. The universality, sensitivity, and measurement precision thereof far surpass the conventional techniques. The improved CTLD14 is especially excellent in terms of being capable of broad detection of molecules with a structure causing the onset in a living body. Further, such improved CTLD14 also achieves advantages in terms of the simplicity of manufacture and relative possibility of mass production.

Thus, the present invention provides a method of manufacturing C-type lectin-like domain (CTLD) 14, comprising: A) incorporating a nucleic acid molecule encoding CTLD14 expressibly into a silkworm or an organism adding a sugar chain similar to that of a silkworm; B) placing the silkworm or the organism adding a sugar chain similar to that of silkworm under a condition where the gene is expressed in order to express the CTLD14; and C) obtaining the CTLD14.

While the present invention is manufactured with a silkworm, any organism may be used as long as a silkworm form sugar chain can be added. It is understood that any organism adding a sugar chain similar to that of a silkworm can be used.

In one embodiment, the expression is performed in a middle silk gland of the silkworm or the organism adding a sugar chain similar to that of a silkworm.

In another embodiment, the CTLD14 is expressed in a biotinylated or biotinylatable state. Such biotinylation can be accomplished by incorporating a sequence that can bind biotin. For example, this can be accomplished by adding lysine (K) by recombination.

In a preferred embodiment of the present invention, step A) is accomplished by microinjection of an expression vector comprising a nucleic acid encoding the CTLD14. It is understood that an expression vector can be introduced by the approaches explained herein other than microinjection or any other known approaches.

In one embodiment, the nucleic acid molecule comprises the nucleic acid sequence set forth by SEQ ID NO: 85 or a variant thereof.

<Improved sRAGE (Silkworm Form) and Manufacturing Method Thereof>

In one aspect, the present invention provides a reconstructed receptor for advanced glycation end products (sRAGE) having a silkworm form sugar chain, comprising the amino acid sequence set forth by SEQ ID NO: 97 or a variant thereof.

In a preferred embodiment, the silkworm form sugar chain in the present invention comprises a trimannosyl core, complex type sugar chain, oligomannose type sugar chain or hybrid type sugar chain.

In one embodiment, the silkworm form sugar chain comprises a sugar chain to which 0 to 4 molecules of 0 to 2 molecules of GlcNAc and 0 to 4 molecules of Man are bound per molecule, in addition to a trimannosyl core (GlcNAc-β1,4-GlcNAc-β1,4-Man(-α1,6-Man)-α1,3-Man from the asparagine residue) structure. In another embodiment, the silkworm form sugar chain of RAGE of the invention comprises a sugar chain to which 0 to 8 molecules of 0 to 4 molecules of GlcNAc and 0 to 8 molecules of Man are bound per 2 molecules, in addition to a trimannosyl core (GlcNAc-β1,4-GlcNAc-β1,4-Man(-α1,6-Man)-α1,3-Man viewed from the asparagine residue) structure. In another embodiment, examples of the silkworm form sugar chains of sRAGE include, but are not limited to, sugar chains having the above-described structure of (1) to (8) ([Chemical 1] to [Chemical 8]).

In one embodiment, the composition ratio of the silkworm form sRAGE sugar chain has oligomannose type accounting for 90% or more, and complex type and hybrid type at less than 5%. The sugar composition of silkworm form sRAGE has $(Man)_5(GlcNAc)_2$ (N3 of FIG. 54) at 46% to 56%, $(Man)_7(GlcNAc)_2$ (Ni of FIG. 54) at 23% to 33%, $(Man)_6(GlcNAc)_2$ (N2 of FIG. 54) at 7% to 15%, $(Man)_3(GlcNAc)_2$ (N4-1 of FIG. 54) at 1% to 5%, $(Man)_3(GlcNAc)_3$ (N4-2 of FIG. 54) at 2% to 8%, and $(Man)_4(GlcNAc)_3$ (N4-3 of FIG. 54) at 1% to 5%. In a preferred embodiment, the sugar composition has $(Man)_5(GlcNAc)_2$ at 48% to 54%, $(Man)_7(GlcNAc)_2$ at 25% to 31%, $(Man)_6(GlcNAc)_2$ at 9% to 13%, $(Man)_3(GlcNAc)_2$ at 2% to 4%, $(Man)_3(GlcNAc)_3$ at 3% to 6%, and $(Man)_4(GlcNAc)_3$ at 2% to 4%. In a more preferred embodiment, the sugar composition has $(Man)_5(GlcNAc)_2$ at 51.4%, $(Man)_7(GlcNAc)_2$ at 27.5%, $(Man)_6(GlcNAc)_2$ at 10.8%, $(Man)_3(GlcNAc)_2$ at 2.8%, $(Man)_3(GlcNAc)_3$ at 4.6%, and $(Man)_4(GlcNAc)_3$ at 2.5%.

sRAGE to which the above-described sugar chain or the above-described sugar chain to which an additional sugar is added has excellent stability and has an ability to recognize AGEs with diverse structures.

In one embodiment, the silkworm form sugar chain binds to asparagine at position 3 and/or asparagine at position 59 of SEQ ID NO: 97.

In another embodiment, the sRAGE of the invention is biotinylated. Biotinylation allows a measurement result to be obtained at a high sensitivity in a bioassay, and accumulation at a high density in a certain direction on beads or membrane via streptavidin.

In one embodiment, the sRAGE of the invention can be used as a composition for detecting advanced glycation end products (AGEs). Thus, the present invention provides a composition for detecting AGEs comprising sRAGE comprising sRAGE comprising the silkworm form sugar chain of the invention.

Although not wishing to be bound by any theory, use of the sRAGE of the invention achieves a significant effect in terms of being able to raise the level of AGES subjected to analysis approximately from the conventional 10% to a level corresponding to nearly all AGEs and able to perform more accurate diagnosis. Further, conventional detection methods using reconstructed RAGE (sRAGE) can also detect a wide range of AGEs, but had practical problems in that sRAGE is fragmented in about a month and a half and loses recognition ability and the like. Meanwhile, use of the sRAGE of the invention is also significant in that this could also be overcome. The improved sRAGE of the invention was glycosylated and was a very stable molecule and maintained recognition activity for about a year over a long-period in storage at 4° C. Further, the improved sRAGE of the invention was able to detect a trace amount of AGE concentration, AGEs with diverse structures and the like.

Thus, in another aspect, the present invention also provides a method of manufacturing sRAGE, comprising A) incorporating a nucleic acid molecule encoding the sRAGE expressibly into a silkworm or an organism adding a sugar chain similar to that of a silkworm; B) placing the silkworm or the organism adding a sugar chain similar to that of silkworm under a condition where the gene is expressed in order to express the sRAGE; and C) obtaining the sRAGE.

While the present invention is manufactured with a silkworm, any organism may be used as long as a silkworm form sugar chain can be added. It is understood that any organism adding a sugar chain similar to that of a silkworm can be used.

In one embodiment, the expression is performed in a middle silk gland of a silkworm or an organism adding a sugar chain similar to that of a silkworm.

In a preferred embodiment of the present invention, step A) is accomplished by microinjection of an expression vector comprising the nucleic acid encoding the sRAGE. It is understood that an expression vector can be introduced by the approaches explained herein other than microinjection or any other known approaches.

In one embodiment, the nucleic acid molecule comprises the nucleic acid sequence set forth by SEQ ID NO: 96 or a variant thereof.

In one embodiment, the manufacturing method of a protein of the invention may be accomplished by (a) manufacturing a transgenic silkworm having a promoter of a nucleic acid sequence encoding a protein specifically expressed in a middle silk gland and a nucleic acid sequence encoding any protein whose expression is directly or indirectly regulated by the promotor or an organism adding a sugar chain similar to that of a silkworm, wherein the any protein is expressed in a silk gland or secreted into a cocoon strand; and (b) collecting the any protein from the manufactured transgenic silkworm or the organism adding a sugar chain similar to that of a silkworm.

In one exemplary embodiment, the step of producing a silkworm or an organism adding a sugar chain similar to that of a silkworm of the invention first produces a silkworm egg having a promoter of a nucleic acid sequence encoding a protein specifically expressed in the middle silk gland and a nucleic acid sequence encoding any protein whose expression is directly or indirectly regulated by the promotor. Next, the step can be materialized by selecting a transgenic silkworm expressing the protein or an organism adding a sugar chain similar to that of a silkworm among silkworms born from the manufactured silkworm eggs and the organisms adding a sugar chain similar to that of a silkworm.

In one exemplary embodiment, a transgenic silkworm or an organism adding a sugar chain similar to that of a silkworm can be selected, for example, by using a selection marker. As the selection marker in the present invention, those skilled in the art can use a commonly used marker, e.g., fluorescent protein such as CFP, GFP, YFP, or DsRed. A transgenic silkworm can only be detected from observing with a stereo microscope by using these markers. Since the fluorescent colors are different, multiple markers can be simultaneously used.

In yet another embodiment, examples of a method of collecting any protein from a manufactured transgenic silkworm or an organism adding a sugar chain similar to that of a silkworm include a method of collecting any protein from a cocoon spit out by the transgenic silkworm organism adding a sugar chain similar to that of a silkworm. As the collection method, a method well known to those skilled in the art, such as a method of collection by dissolving a cocoon with 60% LiSCN and dialyzing with 20 mM Tris and 5M urea (Inoue, S., Tsuda, H., Tanaka, H., Magoshi, Y and Mizuno(2001) Sericologia 4, 157-163.) can be used. For example, a method of using a surfactant, a method of dissolving with an aqueous solution or the like can be used as other protein collection methods.

Further, examples of a silkworm egg or an egg of an organism adding a sugar chain similar to that of a silkworm having a promoter of a nucleic acid sequence encoding a protein specifically expressed in a middle silk gland and a nucleic acid sequence encoding any protein whose expression is indirectly regulated by the promotor include silkworm eggs or eggs of an organism adding a sugar chain similar to that of a silkworm having (i) nucleic acid sequence encoding a transcription regulating factor functionally bound downstream of a promotor of a nucleic acid sequence encoding a protein specifically expressed in a silk gland and (ii) nucleic acid sequence encoding any protein, operably linked downstream to a target promoter of the transcription regulating factor.

Examples of a silkworm egg or an egg of an organism adding a sugar chain similar to that of a silkworm having a promoter of a nucleic acid sequence encoding a protein specifically expressed in the middle silk gland and a nucleic acid sequence encoding any protein whose expression is directly or indirectly regulated by the promotor include silkworm eggs or eggs of an organism adding a sugar chain similar to that of a silkworm having a nucleic acid sequence encoding any protein, operably linked downstream to a promotor of a nucleic acid sequence encoding a protein specifically expressed in the middle silk gland. Such a silkworm egg can be manufactured by introducing a nucleic acid sequence encoding any protein, operably linked downstream to a promoter of a nucleic acid sequence encoding a protein specifically expressed in the middle silk gland into an egg.

As used herein, "operably linked" refers to being linked such that expression of a protein of interest is materialized, and typically refers to a promotor and a nucleic acid sequence binding to induce expression of the nucleic acid sequence that is present downstream of the promotor by a transcription regulating factor binding to the promotor. Examples of a combination of a transcription regulating factor and a target sequence include GAL4 and UAS, TetR and TRE and the like. GAL4 and UAS or TetR and TRE can be used to accurately regulate the expression site, timing, and quantity of a gene or interest to allow the gene to be readily expressed in many tissues. Further, a line can be created even if the gene to be expressed is a lethal gene. The nucleic acid sequence used in the present invention can be prepared by a method such as hybridization technique, polymerase chain reaction (PCR) technique, site-directed mutagenesis, DNA synthesis or the like. It is possible for those skilled in the art to examine whether a prepared nucleic acid sequence has promotor activity by a well-known reporter assay or the like using a reporter gene. A reporter gene that can be used is explained elsewhere herein. Any known reporter gene can be used.

As the glycoprotein of the invention, a protein that does not irreversibly denature in a silk strand is preferred. Examples of such a protein include a protein without a secretion signal from a silk gland cell to a silk gland lumen.

DNA can be introduced into a silkworm egg or an egg of an organism adding a sugar chain similar to that of a silkworm, for example, according to a method of injecting a transposon as a vector into an egg at an early developmental stage (Tamura, T., Thibert, C., Royer, C., Kanda, T., Abraham, E., Kamba, M., Komoto, N., Thomas, J.-L., Mauchamp, B., Chavancy, G., Shirk, P., Fraser, M., Prudhomme, J.-C. and Couble, P., 2000, Nature Biotechnology 18, 81-84).

For example, it is also possible to introduce a vector having a nucleic acid sequence encoding a transposon transferase (helper vector) with a vector with the above-described DNA inserted between oppositely faced repetitive sequences of transposon (Handler A M, McCombs S D, Fraser M J, Saul S H. (1998) Proc. Natl. Acad. Sci. U.S.A. 95(13): 7520-5) into a silkworm egg or an egg of an organism adding a sugar chain similar to that of a silkworm. Examples of helper vector include, but are not limited to, pHA3PIG (Tamura, T., Thibert, C., Royer, C., Kanda, T., Abraham, E., Kamba, M., Komoto, N., Thomas, J.-L., Mauchamp, B., Chavancy, G., Shirk, P., Fraser, M., Prudhomme, J.-C. and Couble, P., 2000, Nature Biotechnology 18, 81-84).

As the transposon in the present invention, piggyBac is preferred, but the transposon is not limited thereto. Mariner, minos and the like can also be used (Shimizu, K., Kamba, M., Sonobe, H., Kanda, T., Klinakis, A. G., Savakis, C. and Tamura, T. (2000) Insect Mol. Biol., 9, 277-281; Wang W, Swevers L, Iatrou K. (2000) Insect Mol Biol 9(2): 145-55).

In the present invention, it is also possible to create a transgenic silkworm or an organism adding a sugar chain similar to that of a silkworm by using a baculovirus vector (Yamao, M., N. Katayama, H. Nakazawa, M. Yamakawa, Y. Hayashi et al., 1999, Genes Dev 13: 511-516).

Further, the silkworm or an organism adding a sugar chain similar to that of a silkworm of the invention is not particularly limited, but it is preferable, for mass production of a glycoprotein of interest, to use a silkworm or an organism adding a sugar chain similar to that of a silkworm with production of a protein constituting a silk strand suppressed by a mutation of a gene region (including a coding region, promotor region, and untranslated region) encoding a protein constituting the silk strand such as a fibroin protein. Such a silkworm or an organism adding a sugar chain similar to that of a silkworm is a mutated strain of a silkworm or an organism adding a sugar chain similar to that of a silkworm with production of a protein constituting a silk strand suppressed by a mutation of a gene region encoding the protein constituting a silk strand, preferably a silkworm of exarate pupa line or an organism adding a sugar chain similar to that of a silkworm with production of a protein constituting a silk strand suppressed by the mutation, and more preferably Nd-s$^D$. It may be a silkworm or an organism adding a sugar chain similar to that of a silkworm with suppressed production of a protein constituting a silk strand, regardless of whether the cause of suppressed production of a protein constituting a silk strand is artificial or is dependent on a mutation that has occurred in nature. Such a silkworm or an organism adding a sugar chain similar to that of a silkworm is a silkworm well known to those skilled in the art as sericin silkworm. Use of a sericin silkworm further facilitates purification of a protein synthesized from any gene introduced into a chromosome.

Further, as the silkworm or the organism adding a sugar chain similar to that of a silkworm in the present invention, not only a silkworm with a property of laying a nondormant egg, but also a silkworm having a property of laying a dormant egg (e.g., breeds used in practice such as Gunma, 200, Shunrei, Shogetsu, Kinshu, Showa or the like) can be used. In this regard, a dormant egg refers to an egg which temporarily suspends embryogenesis after the egg has been laid. A nondormant egg refers to an egg from which a larva hatches without suspension of embryogenesis after the egg has been laid.

A silkworm with a property of laying a dormant egg, when used, is allowed to lay a non-dormant egg and DNA is introduced into the non-dormant egg. Examples of a method of having a non-dormant egg laid with Gunma include a method of incubating a dormant egg at 15° C. to 21° C. to have an adult born from the dormant egg lay a non-dormant egg, preferably a method of incubating a dormant egg at 16° C. to 20-C to have an adult born from the dormant egg lay a non-dormant egg, and more preferably a method of incubating a dormant egg at 18° C. to have an adult born from the dormant egg lay a non-dormant egg, and most preferably a method of incubating a dormant egg at 18° C. and raising a larva born from the dormant egg under full light to have the grown adult lay a non-dormant egg. Further, examples for 200 include a method of incubating a dormant egg at 15° C. to 21° C. to have an adult born from the dormant egg lay a non-dormant egg, preferably a method of incubating a dormant egg at 16° C. to 20° C. to have an adult born from the dormant egg lay a non-dormant egg, and more preferably a method of incubating a dormant egg at 18° C. to have an adult born from the dormant egg lay a non-dormant egg or a method of raising a larva born from a dormant egg under full light and having the grown adult lay a non-dormant egg, and most preferably a method of incubating a dormant egg at 25° C. and raising a larva born from the dormant egg under full light to have the grown adult lay a non-dormant egg. An egg can be incubated, for example, by placing the egg in an 18° C. to 25° C. incubator or a thermostatic chamber. A larva can be raised by using an artificial feed in a breeding room at 20° C. to 29° C.

In the present invention, a photoperiodic condition refers to a daily light-dark cycle in egg incubation or larva rearing. Such a condition includes light and dark conditions. In particular, a full light condition refers to a 24-hour light condition without darkness. A photoperiodic condition can be varied depending on the breed. The incubation of the above-described dormant egg of the invention can be performed according to a common silkworm egg incubation method by those skilled in the art. For example, incubation is carried out according to the method described in "Ministry of Education (1978), Sanshu Seizo (Production of silkworm species) p. 193, Jikkyo Shuppan, Tokyo". Further, care for silkworm larva in the present invention can be provided by a method well known to those skilled in the art. For example, care can be provided according to the method described in "Ministry of Education (1978) Sanshu Seizo (Production of silkworm species) p. 193, Jikkyo Shuppan, Tokyo".

In the present invention, whether a laid egg is a non-dormant egg can be determined by the color of the egg. It is commonly known that a dormant egg has a dark brown color and a non-dormant egg has a yellowish white color. Accordingly, a laid egg is determined as a non-dormant egg by not having a dark brown color, or more preferably by having a yellowish white color in the present invention.

In another aspect, the present invention provides a silkworm or an organism adding a sugar chain similar to that of a silkworm coexpressably incorporated with a nucleic acid molecule encoding CTLD14 or sRAGE.

In this aspect of the embodiment, the nucleic acid molecule used in the present invention comprises the nucleic acid sequence set forth by SEQ ID NO: 85 or 96 or a variant thereof.

In one embodiment, the silkworm of the invention or an organism adding a sugar chain similar to that of a silkworm is a transgenic silkworm or an organism adding a sugar chain similar to that of a silkworm having a promoter of a nucleic acid sequence encoding CTLD14 or sRAGE specifically expressed in the middle silk gland and a nucleic acid sequence encoding any protein whose expression is directly or indirectly regulated by the promotor, the transgenic silkworm or the organism adding a sugar chain similar to that of a silkworm expressing the CTLD14 or sRAGE in the silk gland or secreting the CTLD14 or sRAGE in a cocoon strand. The state of the transgenic silkworm of the invention or an organism adding a sugar chain similar to that of a silkworm is not particularly limited. For example, it may be in a state of an egg. CTLD14 or sRAGE can be mass produced by using the transgenic silkworm of the invention or an organism adding a sugar chain similar to that of a silkworm.

The transgenic silkworms of the invention or organisms adding a sugar chain similar to that of a silkworm are preferably those having (i) a nucleic acid sequence encoding a transcription regulating factor, operably linked downstream of a promotor of a nucleic acid sequence encoding CTLD14 or sRAGE specifically expressed in a middle silk gland, and (ii) a nucleic acid sequence encoding CTLD14 or sRAGE, operably linked downstream of a promotor of a target promoter of the transcription regulating factor, or those having a nucleic acid sequence, operably linked to a nucleic acid sequence encoding CTLD14 or sRAGE downstream of a promotor of a nucleic acid sequence encoding CTLD14 or sRAGE specifically expressed in a middle silk gland.

In another embodiment, the present invention provides a silk gland or a cocoon of the transgenic silkworm of the invention or an organism (producing a silk gland or a cocoon) adding a sugar chain similar to that of a silkworm. Such a silk gland or a cocoon is useful as a silk gland or a cocoon containing a large quantity of CTLD14 or sRAGE.

Further, the present invention provides a nucleic acid sequence or a nucleic acid molecule (e.g., DNA) for use in the method of the invention. Examples of such a nucleic acid sequence or a nucleic acid molecule include (a) nucleic acid sequence encoding a transcription regulating factor, operably linked downstream to a promoter of a nucleic acid sequence encoding sericin, (b) nucleic acid sequence encoding any protein, operably linked downstream to a target promotor of the transcription regulating factor, (c) nucleic acid sequence encoding CTLD14 or sRAGE, operably linked downstream to a promoter of a nucleic acid sequence encoding sericin, and the like. They may be provided as a kit consisting of a combination thereof. The present invention also provides a vector with a nucleic acid sequence of (a) to (c) inserted between oppositely faced repetitive sequences of transposon. Furthermore, a kit comprising said vector and a vector (helper vector) having a nucleic acid sequence encoding a transposon transferase is provided.

<Detection, Prediction, Preliminary Detection, or Diagnosis of AGE Associated Disease, Disorder Etc.>

In one aspect, the present invention provides a method, kit, and composition for detection, prediction, preliminary detection or diagnosis of an AGE associated disease, disorder or the like by detecting advanced glycation end products (AGEs). The above section of <Improved sRAGE (silkworm form) and manufacturing method thereof> herein can be referred for the marker of the invention. It is understood that any embodiment described in this section can be used. Examples of such diseases include, but are not limited to, diabetes, diabetic complications such as diabetic nephropathy, diabetic retinopathy, and diabetic neurosis, neurodegenerative diseases such as Alzheimer's disease, rheumatoid arthritis, posterior longitudinal ligament ossification, osteoporosis, nonalcoholic steatohepatitis, periodontal disease, muscle atrophy, age-related macular degeneration, skin disease, skin aging, arteriosclerosis and the like. Although not wishing to be bound by any theory, while diabetic nephropathy is a disorder of the microvasculature, it is known to lead to not only microangiopathy, but also the onset of macroangiopathy such as arteriosclerosis. One of the causes is considered to be induction of vascular endothelial dysfunction via RAGE which is also expressed in the aortic vascular endothelium. Accordingly, suppression of native functions of RAGE can lead to adjustment of induction of vascular endothelial dysfunction (=vascular disorder) or the like. In this regard, a sample may be obtained by any means. When an attendant other than a physician is responsible for a measurement, a sample generally may be obtained by a physician in some form. The step of determining from the measurement result whether a sample has diabetes or a possibility thereof can be carried out by determining whether the result is abnormal relative to a normal value by comparing each marker. Although not wishing to be bound by any theory, according to an explanation based on one exemplary Example, diagnosis of these diseases or the like can be carried out by a comparative experiment of a diabetic model and a control.

In another embodiment, an approach of contacting a RAGE immobilized bead with a specimen and then reacting the specimen with a fluorescently labeled antibody corresponding to a molecule sought to be detected to measure fluorescence intensity can also be used.

Other reagents may be included in the kit for diagnosis of AGE associated disease or disorder of the invention. For example, a kit for EIA may comprise a carrier such as beads, blocking solution, buffer such as PBS, chromogenic substrate or the like. This method or kit can detect or diagnose diabetic complications such as diabetic nephropathy, diabetic retinopathy or diabetic neurosis at an early stage, which could not be detected or diagnosed with a conventional marker. Thus, in this context, such diagnosis can be considered early diagnosis. Of course, diagnosis can be similarly carried out at a period where diagnosis can be carried out with conventional sRAGE. Thus, detection and diagnosis are possible in the same meaning as with conventional sRAGE. The above section of <Improved sRAGE (silkworm form) and manufacturing method thereof> herein can be referred for the sRAGE of the invention. It is understood that any embodiment described in this section can be used.

A normal value used in the method of diagnosing a disease of the invention can be determined, for example, by collecting AGE concentration data in body fluid in a healthy individual with a definitive diagnosis as not suffering from diabetes based on the concentration value thereof. A normal value can also be determined based on a concentration value in the healthy individual when determining a future onset risk of diabetes. It is also possible to determine multiple normal values in steps to quantitatively determine the presence or future onset risk of diabetes.

As a body fluid sample used in the diagnostic method of a disease of the invention, urine or blood is preferably used. In particular, it is preferable to use serum or plasma (body fluid component) prepared from urine or blood collected from a subject as the measurement sample. Serum or plasma can be prepared from blood by a known method such as centrifugation.

In a specific embodiment, the RAGE ligand recognition region is selected from the group consisting of RAGE extracellular region (positions 22 to 332 of SEQ ID NO: 102), RAGE 8, mRAGE 8, RAGE 1, mRAGE 1, RAGE 2, mRAGE 2, RAGE 3, mRAGE 3, RAGE 4, mRAGE 4, RAGE 7, mRAGE 7, RAGE 143, mRAGE 143, RAGE 223, mRAGE 223, RAGE 226, and mRAGE 226, molecules comprising at least one of them, and a variant or complex thereof.

In still another embodiment, it is possible to mix a sample of serum, plasma, urine or the like with sRAGE immobilized beads and then collect the beads, and measure fluorescence after reacting the beads with multiple fluorescently labeled antibodies (fluorescent wavelengths of fluorescent labels are varied for each antibody) to quickly detect multiple markers simultaneously. The protocol is disclosed below more specifically.

1. sRAGE bead production: sRAGE is immobilized on agarose, silica, magnetic beads or the like. Simple and strong immobilization is possible through immobilization to avidin on the beads via a biotin tag of sRAGE.

2. Reaction with sRAGE beads: an sRAGE ligand in a sample is bound by adding the sRAGE beads to the sample and inverting and mixing for 30 minutes at a low temperature. sRAGE beads are collected by centrifugation (a magnet is used for magnetic beads) and washed with TBS.

3. An antibody against a molecule subjected to detection, labeled with a fluorescent dye, is added to the reactant in 2. Two or more types of molecules can be simultaneously detected by a combination of fluorescent dyes with different absorbance wavelengths (e.g., Alexa based combination of Alexa 488, 555, and 633, combination of Cy3 and Cy5 or the like). After one hour of reaction, the beads are collected and washed.

4. Detection: the fluorescence of the collected beads is measured with a fluorescence detector. Multiple molecules can be simultaneously detected by selecting an excitation wavelength and absorbance wavelength Highly sensitivity immunochromatography allows development into a simple and quick analysis. For example, Furukawa Electric Review 121, 17-22 (2008) can be referred for such techniques. Presumed examples include, but are not limited to, immunochromatographic system for performing a lateral flow assay, comprising a membrane for deployment of a specimen by a capillary phenomenon, the membrane comprising: a conjugation section comprising a ligand recognition region of RAGE labeled with a metal colloid, a silica particle or a latex particle and a sample, or a fragment thereof, and a detection section comprising a ligand recognition region of RAGE or a fragment thereof.

With a lab-on-a-chip, detection is possible to at a stage before expression at a protein level by detection of AGE expression in blood cells. For detection, a sensing chip from Panasonic or the like can be used (exemplary reference document includes PANASONIC Technical Journal 57, 21-26(2011)).

Expression at a gene level in blood cells can be carried out by referring to a document related to diagnosis of type II diabetes using, as an indicator, gene expression levels in a white blood cell by DNA microarray. As described in PANASONIC Technical Journal 57, 21-26 (2011), it is expected that a gene of interest can be detected from blood in one step by utilizing a sensing chip. Thus, gene detection can be performed in one step. Basically, detection can be carried out by designing the SNP sensor portion to be specialized for detection of the gene in the procedure of PANASONIC sensor chips.

In one embodiment, the sample is lacrimal fluid. If measurement can be readily made only with lacrimal fluid in this embodiment, it would be conceivable in the present invention, for example, to have lacrimal fluid mailed to perform a simple examination and subsequently perform ophthalmoscopy or the like.

The method of diagnosing an AGE associated disease or disorder such as diabetes or diabetic complications such as diabetic nephropathy, diabetic retinopathy or diabetic neurosis of the invention measures the presence or concentration of AGE in a sample (blood, urine or the like). In addition, the measurement value is compared to a normal value to diagnose a disease or disorder such as diabetes or diabetic complications such as diabetic nephropathy, diabetic retinopathy or diabetic neurosis or the like.

The method of diagnosing a disease of the invention can compare the concentration of at least one of the above-described markers in a sample (e.g., blood fluid such as blood or urine) of a subject to a normal value to determine the presence of onset or future onset risk of a disease or disorder. "Predictive diagnosis" and "prediagnosis" of a certain disease or disorder and "determination of future onset risk" of a disease or disorder are interchangeably used, and refer to determining the presence or the level of possibility (risk) of suffering from a disease or disorder in the future at a time with no onset of the disease or disorder.

In one aspect, the present invention can construct a system for materializing the method of the invention.

As used herein, "system" refers to any system for detection, predictive diagnosis, prediagnosis, diagnosis or the like. "System" generally refers to a system satisfying the following three conditions: consists of one or more constituent elements; with multiple constituent elements, the elements act and are associated with one another; and exhibits harmonious overall behavior/function. A system may be in any form, such as an apparatus, composition, or diagnostic agent. Thus, it is understood that examples of system include a large scale system comprising a measuring apparatus, system comprising chromatography, kit utilizing an immune reaction, composition comprising an antibody (e.g., diagnostic agent, in vitro drugs, comprising a monoclonal antibody of a marker) and the like.

In one embodiment, the present invention provides a system or composition for prediagnosis or diagnosis of whether a subject has an AGE associated disease (e.g., diabetes, diabetic complication such as diabetic nephropathy, diabetic retinopathy or diabetic neurosis, or the like), comprising sRAGE for detecting AGE in a sample derived from the subject. It is understood that the compositions or systems can use any agent or means as long as the above-described AGE can be identified. Thus, it is understood that not only the agent or means specifically described herein, but any equivalent agent or means known in the art can be used.

In one embodiment, the agent used in the present invention is selected from a group consisting of a nucleic acid molecule, polypeptide, lipid, sugar chain, organic small molecule and complex molecule thereof. The agent is preferably a protein or a complex molecule (e.g., glycoprotein, lipid protein or the like). Preferably, the agent is an antibody (e.g., polyclonal antibody or a monoclonal antibody). It is preferable that such an agent is labeled or labelable. This is because diagnosis is facilitated.

In a preferred embodiment of the present invention, the used means is selected from the group consisting of mass spectrometer, nuclear magnetic resonance measurement apparatus, X-ray analysis apparatus, SPR, chromatography (for example, HPLC, thin layer chromatography, and gas chromatography), immunological means (e.g., western blotting, ELISA, and RIA), biochemical means (for example, pI electrophoresis, Southern blotting, two dimensional electrophoresis), electrophoresis equipment, chemical analytical instruments, fluorescent two dimensional differential electrophoresis (2DE-DIGE), isotope labeling method (ICAT), tandem affinity purification (TAP method), physical means, laser microdissection and combination thereof.

In a preferred embodiment of the present invention, the system of the invention further comprises a standard for AGEs. Such a standard is preferably used to confirm whether AGE detection means is functioning normally.

In a preferred embodiment, the present invention can further comprise means for purifying a target sample. Examples of such purification means include chromatography and the like. Since diagnostic precision is improved by purification, purification means can be used in a preferred embodiment, but it is not essential.

In the present invention, a subject includes mammals. In one embodiment, a subject is a rodent. Such a rodent (e.g., rat, mouse or the like) is preferably has a model animal made, especially a diabetes or diabetic nephropathy model animal (e.g., streptozocin (Stz) mouse or the like). In another preferred embodiment, a subject includes humans.

In one embodiment, the agent or means used in the present invention has an ability to quantify the AGE of the invention. For such quantification, means or agent is preferably capable of accurately drawing calibration curves when drawing standard curves. Preferred examples thereof include antibody, mass spectrometry, chromatography analysis and the like. Thus, in a certain embodiment, the system of the invention further comprises quantification means for quantifying AGEs.

In one embodiment, quantification means comprises determination means for determining whether the AGEs are within a range of normal values by comparing standard curves and measurement results. Such determination means can be materialized by using a computer. In detection or diagnosis of the present invention, a method of measuring the concentration of AGEs can directly use a method commonly used in quantifying proteins if the method can specifically measure the concentration of the AGEs. For example, various immunoassays, mass spectrometry (MS), chromatography, electrophoresis or the like can be used.

One preferred embodiment in the detection or diagnosis of the invention is capturing AGEs on a carrier to measure the concentration of the captured AGEs. That is, a substance with affinity to AGEs is immobilized on a carrier to capture the AGEs on the carrier via the substance with affinity thereto. According to this embodiment, the effect of an impurity contained in a sample can be reduced such that the concentration of AGEs can be measured at a higher sensitivity and higher precision. Examples of detection method include known techniques, such as EIA (enzyme immunoassay), RIA (radioimmunoassay), ELISA (enzyme-linked immunosorbent assay), and the like.

When immunoassay is used as the measurement method of AGEs in this embodiment, it is preferable to use a carrier with an antibody immobilized thereon. In this manner, an immunoassay system using an antibody immobilized on a carrier as a primary antibody can be readily constructed. For example, a sandwich EIA system can be constructed by preparing two types of AGE or sRAGE specific antibodies with different epitopes, immobilizing one of the antibodies to a carrier as a primary antibody, and labeling the other with an enzyme as a secondary antibody. In addition, an immunoassay system based on a binding inhibition method or a competitive method can also be constructed. Furthermore, when a substrate is used as a carrier, immunoassay using an antibody chip is possible. With an antibody chip, multiple marker concentrations can be simultaneously measured, enabling quick measurements. Thus, the present invention can provide a reagent with sRAGE immobilized on a substrate. Such a reagent can be used to provide a composition for detecting AGEs.

When mass spectrometry is used as the measurement method of AGEs in this embodiment, AGEs can be captured on a carrier by an ionic bond or hydrophobic interaction in addition to antibodies. Ionic bonds and hydrophobic interaction do not have as much specificity as bioaffinity of an antigen and an antibody or the like. Substances other than AGEs are also captured. However, quantification with mass spectrometry is performed by a mass spectrometer spectrum reflecting the molecular weight, such that there is no issue. In particular, AGE concentration can be accurately measured by using a protein chip using a substrate as a carrier and carrying out surface-enhanced laser desorption/ionization-time-of-flight mass spectrometry (hereinafter, referred to as "SELDI-TOF-MS"). The type of substrates that can be used include a cation exchange substrate, an anion exchange substrate, a normal phase substrate, a reverse phase substrate, a metal ion substrate, an antibody substrate and the like, but a cationic exchange substrate, especially weak cationic exchange substrate, and metal ion substrate are preferably used.

<Chicken Antibodies and Combination Thereof>

In one aspect, the present invention provides a composition for detecting a modified LDL, comprising an anti-LDL chicken antibody. It is understood that the ability to distinguish an oxidized LDL (modified LDL) from an unmodified LDL is improved significantly compared to an antibody produced with another animal species (e.g., mouse or the like).

In a preferred embodiment, the anti-LDL chicken antibody of the invention is a polyclonal antibody. It was demonstrated that all of fully oxidized LDLs (fuOxLDL), MDA-LDL, AcLDL, and unmodified LDL are recognizable to the same extent by using a polyclonal antibody as the anti-LDL chicken antibody.

In one embodiment, the composition of the invention can further comprises CTLD14.

In another aspect, the present invention provides a composition for detecting a modified LDL, comprising an anti-LDL chicken antibody and CTLD14. Since all such modified LDLs can be comprehensively and stably detected, true risk factors for arteriosclerosis or the like can be detected.

CTLD14 used in the composition of the invention may be CTLD14 comprising a silkworm form sugar chain.

Any type of CTLD14 may be used as such CTLD14 comprising a silkworm form sugar chain, as long as a silkworm form sugar chain is comprised. In addition, heterogeneous CTLD14 may also be used. Meanwhile, CTLD14 having a silkworm form sugar chain, comprising the amino acid sequence set forth by SEQ ID NO: 86 or a variant thereof can also be used.

In a preferred embodiment, the composition of the invention is for detecting LDLs and oxidized LDLs. Although not wishing to be bound by any theory, conventional antibodies can only detect limited structures when such antibodies are used, and had issues such as nonspecificity or low reactivity even when LDLs to modified LDLs were broadly recognized, such that conventional antibodies were not practical. Antibodies that can be commonly used from experimental animals to humans were also not available. In this regard, the antibody of the invention can broadly recognize LDLs and oxidized LDLs of mammals from mice to humans. Thus, the antibody of the invention can broadly recognize LDLs to modified LDLs and has high reactivity and high specificity compared to unmodified LDLs, such that the antibody of the invention can be utilized in analysis/evaluation. This was not previously known and provided by the present invention for the first time.

The composition for detecting a modified LDL of the invention is for distinguishing an unmodified LDL from a modified LDL to detect a modified LDL. In one embodiment, an unmodified LDL and a modified LDL are an LDL and oxidized LDL, respectively. In one preferred embodiment, an LDL and an oxidized LDL that can be distinguished by using the present invention are an LDL and oxidized LDL from multiple species of mammals. Although not wishing to be bound by any theory, at most about one type of mammal could be distinguished in the past, but the antibody of the invention can broadly recognize LDLs and oxidized LDLs of mammals from mice to humans. It is noteworthy that LDLs and oxidized LDLs of multiple species of mammals can be distinguished. Thus, the multiple species of mammals include mice and humans.

In another aspect, the present invention provides a kit for detecting a modified LDL, comprising an anti-LDL chicken antibody and CTLD14.

In a preferred embodiment, an anti-LDL chicken antibody is a polyclonal antibody.

In a preferred embodiment, the CTLD14 may be CTLD14 provided by the present invention and comprising a silkworm form sugar chain.

In a preferred embodiment, an anti-LDL chicken antibody comprised in the kit of the invention is a polyclonal antibody, and CTLD14 is CTLD14 provided by the present invention and comprises a silkworm form sugar chain.

In one embodiment, the present invention is for detecting LDLs and oxidized LDLs. In a preferred embodiment, the LDLs and the oxidized LDLs are LDLs and oxidized LDLs of multiple species of mammals, which preferably include mice and humans. It is understood that providing such a kit provides an evaluation system with a significantly improved ability to distinguish an oxidized LDL (modified LDL) from an unmodified LDL compared to an antibody produced by another animal species (e.g., mouse or the like). Further, it was demonstrated that all of fully oxidized LDLs (fuOxLDL), MDA-LDLs, AcLDLs, glycated LDLs, and unmodified LDLs are recognizable to the same extent by using a polyclonal antibody as the anti-LDL chicken antibody.

In this manner, the present invention achieves an effect of detecting a wide range of modified LDLs with a significantly high sensitivity and stability by using CTLD14 having a silkworm form sugar chain of the invention and an anti-LDL chicken polyclonal antibody.

<Manufacture of Biotinylated Protein>

(Silkworm Co-Expressing Biotin Ligase)

One aspect of the present invention provides a silkworm or an organism adding a sugar chain similar to that of a silkworm coexpressably incorporated with a nucleic acid molecule encoding a target protein and a biotin ligase.

Since a target protein such as CTLD14 or a nucleic acid sequence encoding sRAGE comprises a biotinylated tag sequence, the target protein is biotinylated by coexpression of biotin ligase. In one embodiment, a biotin ligase is BirA (SEQ ID NO: 106). Examples of a tag sequence that is biotinylated include, but are not limited to, BIOEASE™ Tag biotin ligase birA substrate peptide (Life Technologies, Carlsbad, Calif.), AVITAG™ biotin ligase birA substrate peptide [SEQ ID NO:98] (Avidity LLC, Aurora, Colo.), and any sequence that can be biotinylated. These silkworms can efficiently manufacture biotinylated CTLD14 or biotinylated sRAGE by oral administration of biotin. The resulting biotinylated CTLD14 has excellent pH stability. LDLs with various oxidatively modified structures can be detected in 20 minutes or less by metal colloid modification and a lateral flow assay incorporating an anti-LDL chicken antibody, a single chain antibody, and streptavidin. Further, sugar chain structural analysis of the resulting sRAGE revealed that oligomannose type sugar chains consisting mainly of (Man)$_5$ (GlcNAc)$_2$ accounts for 90% or more and several % of complex type and hybrid type sugar chains are comprised. Furthermore, stability is improved by glycosylation (stable for nearly one year), and AGEs with various structures and the like can be detected by immobilization maintaining directionality via biotin.

(Manufacture of Biotinylated Protein by Silkworm Co-Expressing Biotin Ligase)

Another aspect of the present invention provides a method of manufacturing a biotinylated protein, comprising: A) incorporating a nucleic acid molecule encoding a protein and a biotin ligase coexpressably into a silkworm or an organism adding a sugar chain similar to that of a silkworm; B) placing the silkworm or the organism adding a sugar chain similar to that of silkworm under a condition where the nucleic acid molecule is expressed in order to express the biotin ligase and the protein; and C) administering biotin to the organism to obtain a biotinylated protein. The method of manufacturing a silkworm form biotinylated protein of the invention has an excellent effect of being able to express a large quantity of a protein of interest (e.g., CTLD14, sRAGE or the like) in several days or less in a biotinylated state at high biotinylation efficiency as a soluble protein. Furthermore, the glycosylation protein expressed by using a silkworm or an organism adding a sugar chain similar to that of a silkworm has better pH stability and lower rate of aggregation by desalination treatment than a protein using an E. coli expression system without glycosylation, and various buffer solutions can be utilized. Thus, the scope of utilization thereof is broad. The resulting biotinylated CTLD14 has excellent pH stability. LDLs with various oxidatively modified structures can be detected in 20 minutes of less by metal colloid modification and a lateral flow assay incorporating an anti-LDL chicken antibody, a single chain antibody, and streptavidin. Further, sugar chain structural analysis of the resulting sRAGE revealed that oligomannose type sugar chains consisting mainly of (Man)$_5$(GlcNAc)$_2$ account for 90% or more and several % of complex type and hybrid type sugar chains are comprised. Furthermore, stability is improved by glycosylation (stable for nearly one year), and AGEs with various structures and the like can be detected by immobilization maintaining directionality via biotin.

For biotin administration to a silkworm, oral administration of feed supplemented with biotin is preferred, but administration by a method such as injection is also possible.

In the preferred embodiment of the present invention, step A) is accomplished by microinjection of an expression vector comprising the nucleic acid molecule encoding the protein and a biotin ligase. Of course, it is understood that an expression vector can be introduced by an approach explained herein other than microinjection or any other known approach.

(Silk Form Biotinylated CTLD14)

In one aspect, the present invention provides CTLD14 biotinylated at a high efficiency. Due to the high efficiency of biotinylation, LDLs with various oxidatively modified structures can be detected in a short period of time of 20 minute or less by lateral flow assay incorporating streptavidin. In one embodiment, the biotinylation efficiency of CTLD14 of the invention is about 10% or greater, about 20% or greater, about 30% or greater about 40% or greater, or about 50% or greater. In a preferred embodiment, the biotinylation efficiency of CTLD14 of the invention is about 30% to about 40%. The resulting biotinylated CTLD14 has excellent pH stability. LDLs with various oxidatively modified structures can be detected in 20 minute or less by metal colloid modification and a lateral flow assay incorporating an anti-LDL chicken antibody, single chain antibody, and streptavidin.

In one embodiment, the CTLD14 of the invention has a silkworm form glycosylation. In addition to the above-described sugar chain structures of (1) to (6) ([Chemical 1] to [Chemical 6]), the sugar chain structure of CTLD14 of the invention comprises the above-described sugar chain of ((1) to (6) ([Chemical 1] to [Chemical 6]) to which an addition sugar is added. In a specific embodiment of the present invention, the CTLD14 of the invention has the amino acid sequence of SEQ ID NO: 86 with two sites that can be glycosylated. The sugar chains added to these glycosylation sites may be identical or different. When sugar chains are different, the added sugar chains may be any combination of the above-described sugar chains of the (1) to (6) ([Chemical 1] to [Chemical 6]).

(Silkworm Form Biotinylated sRAGE)

In another aspect, the preset invention provides sRAGE biotinylated at a high efficiency. Due to the high efficiency of biotinylation, immobilization to a substrate or the like while maintaining directionality via biotin is possible such that AGEs with various structures can be detected. In one embodiment, the biotinylation efficiency of sRAGE of the invention is about 10% or greater, about 20% or greater, about 30% or greater about 40% or greater, about 50% or greater, or about 60% or greater. In a preferred embodiment, the biotinylation efficiency of sRAGE of the invention is about 60% or greater. The sugar chain structural analysis of the resulting sRAGE revealed that oligomannose type sugar chains consisting mainly of $(Man)_5(GlcNAc)_2$ account for 90% or more and several % of complex type and hybrid type sugar chains are comprised. Furthermore, stability is improved by glycosylation (stable for nearly one year), and AGEs with various structures and the like can be detected by immobilization maintaining directionality via biotin.

In one embodiment, the sRAGE of the invention has a silkworm form glycosylation. In addition to the above-described sugar chain structures of (1) to (8) ([Chemical 1] to [Chemical 8]), the sugar chain structure of CTLD14 of the invention comprises the above-described sugar chain of ((1) to (8) ([Chemical 1] to [Chemical 8]) to which an addition sugar is added. In a specific embodiment of the present invention, the sRAGE of the invention has the amino acid sequence of SEQ ID NO: 100 with two sites that can be glycosylated. The sugar chains added to these glycosylation sites may be identical or different. When sugar chains are different, the added sugar chains may be any combination of the above-described sugar chains of (1) to (8) ([Chemical 1] to [Chemical 8]).

<Production of Single Chain Antibody by Silkworm>

In another aspect, the present invention is a method of manufacturing a single chain antibody or a fragment thereof, comprising (A) incorporating a nucleic acid molecule encoding the single chain antibody or a fragment thereof expressibly into a silkworm or an organism adding a sugar chain similar to that of a silkworm; (B) placing the silkworm or an organism adding a sugar chain similar to that of silkworm under a condition where the nucleic acid molecule is expressed in order to express the single chain antibody or fragment thereof; and (C) obtaining the single chain antibody or a fragment thereof. Production of a single chain antibody by E. coli required a process of an expressed protein forming an inclusion body and refolding, but the production with a silkworm of the invention does not require the process of refolding since it is expressed as a soluble protein.

In one embodiment, the protein manufactured by the present invention can have silkworm form glycosylation. Examples of added sugar chains include the above-described trimannosyl core, complex type oligomannose type, and hybrid type, and preferably has any one of the above-described structures of (1)-(8) ([Chemical 1] to [Chemical 8]).

In one embodiment, the single chain antibody or a fragment thereof comprises the amino acid sequence set forth by any one of SEQ ID NOs: 76-80 or a variant thereof.

(General Techniques)

The molecular biological approach, biochemical approach, and microbiological approach used herein are well known and conventional approaches in the art that are described in, for example, Sambrook J. et al. (1989). Molecular Cloning: A Laboratory Manual, Cold Spring Harbor and its 3rd Ed. (2001); Ausubel, F. M. (1987). Current Protocols in Molecular Biology, Greene Pub. Associates and Wiley-Interscience; Ausubel, F. M. (1989). Short Protocols in Molecular Biology: A Compendium of Methods from Current Protocols in Molecular Biology, Greene Pub. Associates and Wiley-Interscience; Innis, M. A. (1990). PCR Protocols: A Guide to Methods and Applications, Academic Press; Ausubel, F. M. (1992). Short Protocols in Molecular Biology: A Compendium of Methods from Current Protocols in Molecular Biology, Greene Pub. Associates; Ausubel, F. M. (1995). Short Protocols in Molecular Biology: A Compendium of Methods from Current Protocols in Molecular Biology, Greene Pub. Associates; Innis, M. A. et al. (1995). PCR Strategies, Academic Press; Ausubel, F. M. (1999). Short Protocols in Molecular Biology: A Compendium of Methods from Current Protocols in Molecular Biology, Wiley, and annual updates; Sninsky, J. J. et al. (1999). PCR Applications: Protocols for Functional Genomics, Academic Press, Bessatsu Jikken Igaku [Experimental Medicine, Supplemental Volume], Idenshi Donyu Oyobi Hatsugen Kaiseki Jikken Ho [Experimental Methods for Transgenesis & Expression Analysis], Yodosha, 1997 and the like, the relevant portions (which can be the entire document) of which are incorporated herein by reference.

DNA synthesis techniques and nucleic acid chemistry for making an artificially synthesized gene are described in, for example, Gait, M. J. (1985). Oligonucleotide Synthesis: A Practical Approach, IRLPress; Gait, M. J. (1990). Oligonucleotide Synthesis: A Practical Approach, IRL Press; Eckstein, F. (1991). Oligonucleotides and Analogues: A Practical Approach, IRL Press; Adams, R. L. et al. (1992). The Biochemistry of the Nucleic Acids, Chapman&Hall; Shabarova, Z. et al. (1994). Advanced Organic Chemistry of Nucleic Acids, Weinheim; Blackburn, G. M. et al. (1996). Nucleic Acids in Chemistry and Biology, Oxford University Press; Hermanson, G. T. (1996). Bioconjugate Techniques, Academic Press, and the like, the relevant portions of which are incorporated herein by reference.

Reference literatures such as scientific literatures, patents, and patent applications cited herein are incorporated herein by reference to the same extent that the entirety of each document is specifically described.

As described above, the present invention has been described while showing preferred embodiments to facilitate understanding. The present invention is described hereinafter based on Examples. The aforementioned description and the following Examples are not provided to limit the present invention, but for the sole purpose of exemplification. Thus, the scope of the present invention is not limited to the embodiments and Examples specifically described herein and is limited only by the scope of claims.

EXAMPLES

Biological materials used in the following Examples were handled in accordance with the standards stipulated by the Food Research Institute. The following manufacturing examples are disclosed, but it is understood that Japanese Laid-Open Publication No. 2012-122994 can be further referenced for CTLD and the like. For reagents, the specific products described in the Examples were used. However, the reagents can be substituted with an equivalent product from another manufacturer (Sigma, Wako Pure Chemical, Nacalai Tesque, Abcam, Santa Cruz Biotechnology, R & D Systems, Abnova, AssayPro, Origene, Biobyt, Biorad, Cell Signaling Technology, GE Healthcare, IBL, or the like).

Example 1: Production of Single Chain Antibody Gene Library

The methods of Marks et al. and Hawkins et al. were altered to create a single chain antibody gene library (Marks et al., J. Mol. Biol. 222:581-597(1991); Hawkins et al., Blood 83: 3279-3288(1994)). Bigdye® terminator v1.1 cycle sequencing kit (Applied Biosystems) was used and the protocol was followed for sequencing reactions. Further, the primers in Table 1 were used depending on the type of plasmid DNA. As used herein, the normal direction of a primer is called forward (FORWARD or FOR) and the opposite direction is called reverse (REVERSE or REV) or back (BACK). Reverse (REVERSE or REV) and back (BACK) indicate the same herein with respect to primers.

TABLE 1

Table 1. Sequencing primer

| Plasmid DNA | Primer name | DNA sequence |
|---|---|---|
| pCR2.1-TOPO | M13forward | 5'-GTAAAACGACGGCCAG-3' (SEQ ID NO: 1) |
| | M13reverse | 5'-CAGGAAACAGCTATGAC-3' (SEQ ID NO: 2) |
| pCANTAB-5E | pCANTAB5-S1 | 5'-CAACGTGAAAAAATTATTATTCGC-3' (SEQ ID NO: 3) |
| | pCANTAB5-S8 | 5'-GTAAATGAATTTTCTGTATGAGG-3' (SEQ ID NO: 4) |
| pET-22b (+) | T7promoter | 5'-TAATACGACTCACTATAGG-3' (SEQ ID NO: 5) |
| | T7terminator | 5'-GCTAGTTATTGCTCAGCGG-3' (SEQ ID NO: 6) |

(1. cDNA Synthesis)

First-strand cDNA was synthesized from human spleen poly A+ RNA (BD Biosciences) by using First-strand cDNA synthesis Kit (GE Healthcare). The primers in Table 2 were used in accordance with the type of antibody gene (γ chain, μ chain, κ chain, or λ chain).

TABLE 2

Table 2. First-strand cDNA synthesis primer

| HigG(gamma) | 51-GTCCACCTTGGTGTTGCTGGGCTT-3' (SEQ ID NO: 7) |
| HigM(mu) | 5'-TGGAAGAGGCACGTTCTTTTCTTT-3' (SEQ ID NO: 8) |
| Hkappa | 5'-AGACTCTCCCCTGTTGAAGCTCTT-3' (SEQ ID NO: 9) |
| Hlambda | 5'-TGAAGATTCTGTAGGGGCCACTGTCTT-3' (SEQ ID NO: 10) |

(2. Amplification of heavy chain variable region genes (γ chain, μ chain) and light chain variable region (κ chain, λ chain))

γ chain and μ chain were amplified by PCR using Human VH reverse primers (Table 3) and Human JH forward primers (Table 3) as a mixed primer.

TABLE 3

Human VH Reverse primers

| HVH1 REV | 5'-CAGGTGCAGCTGGTGCAGTCTGG-3' (SEQ ID NO: 11) |
| HVH2 REV | 5P-CAGGTCAACTTA AGGGAGTCTGG-3' (SEQ ID NO: 12) |
| HVH3 REV | 5'-GAGGTGCAGCTGGTGGAGTCTGG-3' (SEQ ID NO: 13) |
| HVH4 REV | 5'-CAGGTGCAGCTGCAGGAGTCGGG-3' (SEQ ID NO: 14) |
| HVH5 REV | 5'-GAGGTGCAGCTGTTGCAGTCTGC-3' (SEQ ID NO: 15) |
| HVH6 REV | 5'-CAGGTACAGCTGCAGCAGTCAGG-3' (SEQ ID NO: 16) |

Human JH Forward primers

| HJH12FOR | 5'-TGAGGAGACGGTGACCAGGGTGCC-3' (SEQ ID NO: 17) |
| HJH3 | 5'-TGA AGAGAGGTGACCATTGTCCC-3' (SEQ ID NO: 18) |
| HJH45FOR | 5'-TGAGGAGACGGTGACCAGGGTTCC-3' (SEQ ID NO: 19) |
| HJH6 FOR | 5'-TGAGGAGACGGTGACCGTGGTCCC-3' (SEQ ID NO: 20) |

κ chain was amplified by PCR using the Human V reverse primers (Table 4) and Human Jκ forward primers (Table 4) as a mixed primer.

TABLE 4-1

Table 4. Human $V_K$ reverse primers

| $HV_K1$ REV | 5'-GACATCCAGATGACCCAGTCTCC-3' (SEQ ID NO: 21) |
| $HV_K2$ REV | 5'-GATGTTGTGATGACTGAGTCTCC-3' (SEQ ID NO: 22) |
| $HV_K3$ REV | 5'-GAAATTGTGTTGACGCAGTCTCC-3' (SEQ ID NO: 23) |
| $HV_K4$REV | 5'-GACATCGTGATGACCCAGTCTCC-3' (SEQ ID NO: 24) |

TABLE 4-2

| $HV_K5$ REV | 5'-GAAACGACACTCACGCAGTCTCC-3' (SEQ ID NO: 25) |
| $HV_K6$ REV | 5'-GAAATTGTGCTGACTGAGTCTCC-3' (SEQ ID NO: 26) |

Human $J_K$ forward primers

| $HJ_K1$FOR | 5'-AGGTTTGATTTCCACCTTGGTCCC-3' (SEQ ID NO: 27) |

TABLE 4-2-continued

| | |
|---|---|
| HJ$_K$2FOR | 5'-ACGTTTGATCTCCAGCTTGGTCCC-3' (SEQ ID NO: 28) |
| HJ$_K$3FOR | 5'-ACGTTTGATATCCACTTTGGTCCC-3' (SEQ ID NO: 29) |
| HJ$_K$4FOR | 5'-ACGTTTGATCTCCACCTTGGTCCC-3' (SEQ ID NO: 30) |
| HJ$_K$5FOR | 5'-ACGTTTAATCTCCAGTCGTGTCCC-3' (SEQ ID NO: 31) |

λ chain was amplified by PCR using the Human V$_λ$ reverse primers (Table 5) and Human J$_λ$ forward primers (Table 5) as a mixed primer.

TABLE 5

Table 5.

Human V$_λ$ reverse primers

| | |
|---|---|
| HV$_λ$1 REV | 5'CAGTCTGTGTTGACGCAGCCGCC-3' (SEQ ID NO: 32) |
| HV$_λ$2 REV | 5'CAGTCTGCCCTGACTCAGCCTGC-3' (SEQ ID NO: 33) |
| HV$_λ$3a REV | 5'-TCCTATGTGCTGACTCAGCCACC-3' (SEQ ID NO: 34) |
| HV$_λ$3b REV | 5'-TCTTCTGAGCTGACTCAGGACCC-3' (SEQ ID NO: 35) |
| HV$_λ$4 REV | 5'-CACGTTATACTGACTCAACCGCC-3' (SEQ ID NO: 36) |
| HV$_λ$5 REV | 5'-CAGGCTGTGCTCACTCAGCCGTC-3' (SEQ ID NO: 37) |
| Hv$_λ$6 REV | 5'-AATTTTATGCTGACTCAGCCCCA-3' (SEQ ID NO: 38) |

Human J$_λ$ forward primers

| | |
|---|---|
| HJ$_λ$1FOR | 5'-ACCTAGGACGGTGACCTTGGTCCC-3' (SEQ ID NO: 39) |
| HJ$_λ$2-3FOR | 5'-ACCTAGGACGGTCAGCTTGGTCCC-3' (SEQ ID NO: 40) |
| HJ$_λ$4-5FOR | 5'-ACCTAAAACGGTGAGCTGGGTCCC-3' (SEQ ID NO: 41) |

PCR was performed in 25 cycles of a cycle of 3 minutes at 94° C. and then 1 minute at 94° C., 1 minute at 60° C., and 1 minute at 72° C., and then 10 minutes at 72° C.

TABLE 5A

| Reaction solution | |
|---|---|
| Template (First-strand cDNA) | 5 µl |
| reverse primer (20 pmol/µl each) | (number of primers mixed) µl |
| forward primer (20 pmol/µl each) | (number of primers mixed) µl |
| dNTPs (2.5 mM each) | 4 µl |
| 10xEx Taq buffer | 5 µl |
| Takara Ex Taq™ HS (5 U/µl) | 0.25 µl |
| Sterilized water | up to 50 µl |
| Total | 50 µl |

(3. Addition of Linker Sequence Between Heavy Chain Variable Region Gene and Light Chain Variable Region Gene)

To add a linker sequence to γ and µ chains, they were amplified by PCR using the Human VH reverse primers (Table 3) and Human JH forward linker primers (Table 6) as a mixed primer. To add a linker to a κ chain, the κ chain was amplified by PCR using the Human V$_κ$ back linker primers (Table 6) and Human J$_κ$ forward primers (Table 4) as a mixed primer. To add a linker sequence to a λ chain, λ chain was amplified by PCR using the Human V$_λ$ reverse linker primers (Table 6) and Human J$_λ$ forward primers (Table 5) as a mixed primer. PCR was performed in 25 cycles of a cycle of 3 minutes at 94° C. and then 1 minute at 94° C., 1 minute at 60° C., and 1 minute at 72° C., and then 10 minutes at 72° C.

TABLE 6-1

Table 6.

Human JH Forward linker primers

| | |
|---|---|
| HJH12FORLK | 5'-AGAGCCACCTCCGCCTGAACCGCCTCCACCTGAGGAGACGGTGACCAGGG-3' (SEQ ID NO: 42) |
| HJH3 FORLK | 5'-AGAGCCACCTCCGCCTGAACCGCCTCCACCTGAAGAGACGGTGACCATTG-3' (SEQ ID NO: 43) |
| HJH45FORLK | 5'-AGAGCCACCTCCGCCTGAACCGCCTCCACCTGAGGAGACGGTGACCAGGG-3' (SEQ ID NO: 44) |
| HJH6 FORLK | 5'-AGAGCCACCTCCGCCTGAACCGCCTCCACCTGAGGAGACGGTGACCGTGG-3' (SEQ ID NO: 45) |

Human V$_K$ Reverse linker primers

| | |
|---|---|
| HV$_K$1REVLK | 5'-GGCGGAGGTGGCTCTGGCGGTGGCGGATCGGACATCCAGATGACCCAG-3' (SEQ ID NO: 46) |

TABLE 6-2

| | |
|---|---|
| HV$_K$2REVLK | 5'-GGCGGAGGTGGCTCTGGCGGTGGCGGATCGGATGTTGTGATGACTCAGT-3' (SEQ ID NO: 47) |
| HV$_K$3 RELK | 5'-GGCGGAGGTGGCTCTGGCGGTGGCGGATCGGAAATTGTGTTGACGCAGT-3' (SEQ ID NO: 48) |
| HV$_K$4 REVLK | 5'-GGCGGAGGTGGCTCTGGCGGTGGCGGATCGGACATCGTGATGACCCAG-3' (SEQ ID NO: 49) |
| HV$_K$5 REVLK | 5'-GGCGGAGGTGGCTCTGGCGGTGGCGGATCGGAAACGACACTCACGCAGT-3' (SEQ ID NO: 50) |
| HV$_K$6 REVLK | 5'-GGCGGAGGTGGCTCTGGCGGTGGCGGATCGGAAATTGTGCTGACTCAGT-3' (SEQ ID NO: 51) |

Human V$_λ$ reverse linker primers

| | |
|---|---|
| HV$_λ$1 REVLK | 5.-GGCGGAGGTGGCTCTGGCGGTGGCGGATCGCAGTCTGTGTTGACGCAG-3 (SEQ ID NO: 52) |
| HV$_λ$2 REVLK | 5'-GGCGGAGGTGGCTCTGGCGGTGGCGGATCGCAGTCTGCCCTGACTCAG-3' (SEQ ID NO: 53) |
| HV$_λ$3a REVLK | 5'-GGCGGAGGTGGCTCTGGCGGTGGCGGATCGTCCTATGTGCTGACTCAG-3' (SEQ ID NO: 54) |
| HV$_λ$3b REVLK | 5'-GGCGGAGGTGGCTCTGGCGGTGGCGGATCGTCTTCTGAGCTGACTCAG-3' (SEQ ID NO: 55) |
| HV$_λ$4 REVLK | 5'-GGCGGAGGTGGCTCTGGCGGTGGCGGATCGCACGTTATACTGACTCAAC-3' (SEQ ID NO: 56) |
| HV$_λ$5 REVLK | 5'-GGCGGAGGTGGCTCTGGCGGTGGCGGATCGCAGGCTGTGCTCACTCAG-3' (SEQ ID NO: 57) |
| HV$_λ$6 REVLK | 5'-GGCGGAGGTGGCTCTGGCGGTGGCGGATCGAATTTTATGCTGACTCAG-3' (SEQ ID NO: 58) |

(4. Bond Between Heavy Chain Variable Region Gene and Light Chain Variable Region Gene)

Assembly PCR consisting of two stages, primary PCR and secondary PCR, was performed. A reaction solution of primary PCR is shown in Table 7A. The reaction condition was 7 cycles of a cycle of 5 minutes at 94° C. and then 1 minute at 94° C., 1 minute at 60° C., and 1 minute at 72° C.

TABLE 7A

| Primary PCR reaction solution | |
| --- | --- |
| VH gene (after addition of linker sequence) | 50 ng |
| VL gene (after addition of linker sequence) | 50 ng |
| dNTPs (2.5 mM each) | 4 µl |
| 10xEx Taq buffer | 5 µl |
| Takara Ex Taq ™ HS (5 U/µl) | 0.25 µl |
| Sterilized water | up to 50 µl |
| Total | 50 µl |

Subsequently, a Human VH reverse primer (Table 3) and Human $J_\kappa$ forward primer (Table 4) or Human $J_\lambda$ forward primer (Table 5) were added in the primary PCR reaction solution and reacted in 25 cycles of a cycle of 1 minutes at 94° C. and then 1 minute at 60° C., and 1 minute at 72° C., and then 10 minutes at 72° C. (Table 7B).

TABLE 7B

| Secondary PCR reaction solution | |
| --- | --- |
| reverse primer (20 pmol/µl each) | (number of primers mixed) µl |
| forward primer (20 pmol/µl each) | (number of primers mixed) µl |
| 10xEx Taq buffer | (dependent on amount of primer) µl |
| Total | 50 µl |

Added to primary PCR reaction solution (5. Addition of Restriction Enzyme Site to Single Chain Antibody Gene)

To add a restriction enzyme site (SfiI, NotI) to single chain antibody genes (γ+κ, µ+λ), they were separately amplified by PCR using the Human reverse SfiI primers (Table 7) and Human $J_\kappa$ forward NotI primers (Table 7) or Human JA forward Not primers (Table 7) as a mixed primer. The reaction condition was 25 cycles of a cycle of 3 minutes at 94° C. and then 1 minute at 94° C., and 2 minutes at 72° C., and then 10 minutes at 72° C.

TABLE 7-1

Table 7.

Human VH reverse Sfi I primers

HVH1 REV SfiI 5′-TCGCGGCCCAGCCGGCCATGGCCCAGGTGCAGCT
            GGTGCAG-3′ (SEQ ID NO: 59)

HVH2 REV SfiI 5.-TCGCGGCCCAGCCGGCCATGGCCCAGGTCAACTT
            AAGGGAG-3′ (SEQ ID NO: 60)

HVH3 REV SfiI 5′-TCGCGGCCCAGCCGGCCATGGCCGAGGTGCAGCT
            GGTGGAG-3′ (SEQ ID NO: 61)

HVH4 REV SfiI 5′-TCGCGGCCCAGCCGGCCATGGCCCAGGTGCAGCT
            GCAGGAG-3′ (SEQ ID NO: 62)

HVH5 REV SfiI 5′-TCGCGGCCCAGCCGGCCATGGCCGAGGTGCAGCT
            GTTGCAG-3′ (SEQ ID NO: 63)

HVH6 REV SfiI 5′-TCGCGGCCCAGCCGGCCATGGCCCAGGTACAGCT
            GCAGCAG-3′ (SEQ ID NO: 64)

TABLE 7-1-continued

Table 7.

Human $J_K$ forward Not I primers

HJ$_K$1FORNotI  5′-GATATGAGATACTGCGGCCGCACGTTTGATTTCC
                ACCTTGG-3′ (SEQ ID NO: 65)

HJ$_K$2FORNotI  5-GATATGAGATACTGCGGCCGCACGTTTGATCTCCA
                GCTTGG-3′ (SEQ ID NO: 66)

HJ$_K$3FORNotI  5′-GATATGAGATACTGCGGCCGCACGTTTGATATCC
                ACTTTGG-3 (SEQ ID NO: 67)

HJ$_K$4FORNotI  5′-GATATGAGATACTGCGGCCGCACGTTTGATCTCC
                ACCTTGG-3′ (SEQ ID NO: 68)

HJ$_K$5FORNotI  5′-GATATGAGATACTGCGGCCGCACGTTTAATCTC
                CAGTCGTG-3′(SEQ ID NO: 69)

TABLE 7-2

Human $J_\lambda$ Not I forward primers

HJ$_\lambda$1FORNotI    5′-GATATGAGATACTGCGGCCGCACCTAGGACGGTG
                        ACCTTGG-3′ (SEQ ID NO: 70)

HJ$_\lambda$2-3FORNotI  5′-GATATGAGATACTGCGGCCGCACCTAGGACGGTC
                        AGCTTGG-3′ (SEQ ID NO: 71)

HJ$_\lambda$4-5FORNotI  5′-GATATGAGATACTGCGGCCGCACCTAAAACGGTG
                        AGCTGGG-3′ (SEQ ID NO: 72)

(6. Bond to pCANTAB5E and restriction enzyme treatment (SfiI, NotI))

The protocol of Recombinant Phage Antibody System (GE Healthcare) was altered to perform restriction enzyme treatment consisting of two stages.

First, the sample was reacted for 2 hours at 50° C. in an SfiI reaction solution and cleaved with SfiI. After returning to room temperature, the sample was supplemented with a NotI additive solution, reacted for 1 hour at 37° C. and cleaved with NotI. Next, 100 µl of phenol:chloroform=1:1 was added and vortexed for one minute and then centrifuged (15000 rpm for 2 minutes) to collect the supernatant. The collected product was subjected to electrophoresis with agarose gel, and then purified and desalinated with Wizard® SV Gel and PCR Clean-Up System (Promega).

Next, the purified product was ligated to phagemid DNA pCANTAB5E. The product was reacted for 12 hours at 16° C., supplemented with equal amounts of phenol:chloroform=1:1 and vortexed for 1 minute, and centrifuged (15000 rpm for 2 minutes) to collect the supernatant. After ethanol precipitation with the obtained phagemid DNA as a single chain antibody gene library, it was dissolved with a suitable amount of sterilized water and used in electroporation.

Example 2: Screening of Single Chain Antibody Binding to LDL (1. Preparation of LDL)

Prepared LDLs were fully oxidized according to a common method (Steinbrecher, 1984) in order to prepare oxidized LDLs to be used as an antigen. That is, $CuSO_4$ was added to 1 mg/ml of LDL (dialyzed with PBS) so that the final concentration was 5 µM, and was reacted for 20 hours under aseptic conditions at 37° C., and then EDTA was added so that the final concertation was 1 mM. Next, the mixture was dialyzed with PBS, filtered, and sterilized the mixture was then supplemented with $NaN_3$ to have a concentration of 0.02% and was stored at 4° C.

(2. Biopanning)

Prepared oxidized LDLs were used to perform a screening called biopanning. 5 ml of 1 µg/ml oxidized LDL (diluted with PBS) was added to a slanted neck culture cell flask (25 ml, BD Falcon) and was reacted for 2 hours at room temperature, then washed with PBS (30 ml). Next, blocking buffer (PBS comprising 0.25% BSA) was added and reacted for 1 hour at room temperature, then washed three times with PBS (30 ml). 4.5 ml of prepared single chain antibody presenting phage was supplemented with 4 ml of 0.01% azidated sodium containing blocking buffer and was reacted for 15 minutes at room temperature, then added to the slanted neck culture cell flask. After reacting the mixture for 2 hours at 37° C., the mixture was washed 40 times and added to 2 ml of the *E. coli* TG1 strain with $A_{600}$=0.3 and was shaken and cultured for 1 hour at 37° C. 100 µl of bacterial solution was applied to a SOBAG agar medium and was cultured for 14 hours at 30° C. Bacterial cells were collected by adding 1 ml of 2×YT to the plate and scraping off the bacterial cells with a spreader.

(3. Selection of LDL Binding Clone)

95 colonies were obtained for each library. A colony with a single chain antibody binding to oxidized LDLs was selected using ELISA.

In the evaluation by ELISA, all phase presenting single chain antibodies prepared from 94 colonies exhibited a higher value than PBS, which was used as a negative control, in the library consisting of γ+κ(FIG. 3A). In this regard, as positive controls, clones 5, 12, 15, 19, 31, 40, and 96 exhibiting a value above or greater than the reference value of $A_{450}$=0.6 exhibited by the commercially available oxidized LDL monoclonal antibodies (LD1A-2) that were used were selected, and subjected to the next evaluation. Soluble single chain antibodies were prepared to perform ELISA in order to confirm whether the clones have a binding ability with only a protein moiety not presented by phage. Clones 5, 12, 19, 40, and 96 with the same or greater $A_{450}$ value than the negative controls, i.e., clones 19 and 79, were subjected to further evaluation as oxidized LDLs recognizing a single chain (FIG. 3B). In the library consisting of µ+λ, all phage presenting single chain antibodies prepared from 92 colonies exhibited a higher value than PBS (FIG. 4A). Since the PBS derived value was high, $A_{450}$=1 was used as a reference value. 52 clones exhibiting the same or greater value were selected to prepare a soluble single chain antibody to evaluate the binding ability. However, a clone exhibiting a positive was not obtained (FIG. 4B).

Figure 5:
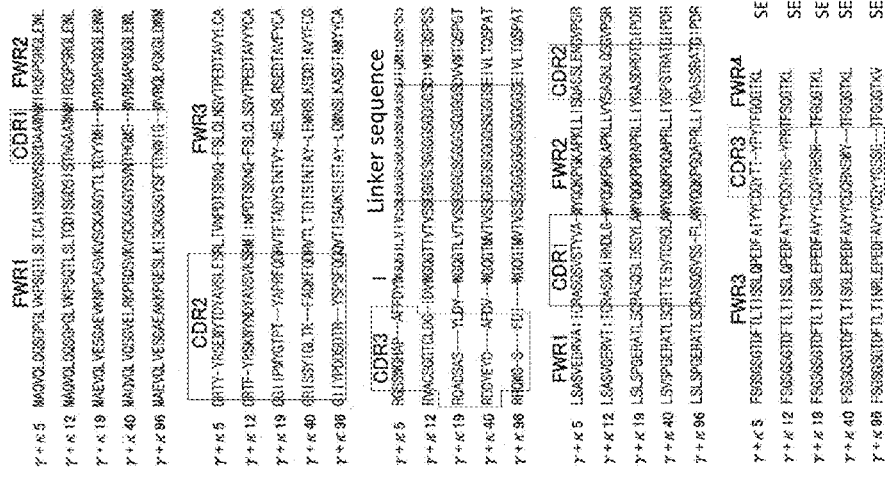
FIG. 5 shows the amino acid sequences of, from the top row, γ+κ5, γ+κ12, γ+κ19, γ+κ40, and γ+κ96 (amino acid sequence according to single letter notation). FWR1 indicates framework region 1, FWR2 indicates framework region 2, FWR3 indicates framework region 3, FWR4 indicates framework region 4, CDR1 indicates complementarity determining region 1, CDR2 indicates complementarity determining region 2, and CDR3 indicates complementarity determining region 3. Linker sequence indicates a sequence bound as a linker.

The clones of the 5 single chain antibodies obtained by the library consisting of γ+κ were named γ+κ5, γ+κ12, γ+κ19, γ+κ40, and γ+κ96, respectively. Each amino acid sequence is shown in FIG. 5.

Example 3: Expression of Single Chain Antibody (1. Used Bacterial Strain, Plasmid DNA and Phagemid DNA)

TABLE 8A

| Bacterial strain | |
|---|---|
| TG1 | K12D (lac-pro), supE, thi, hsdD5/F' [traD36, proAB, lacI', lacZDM15] |
| HB2151 | K12D (lac-pro), ara, nalthi/F' [proAB, lacI', lacZDM15] |
| BLR | F⁻, ompT, hsd$S_B$($r_B^-$ $m_B^-$), gal, dcm Δ (srl-recA)306::Tn10 (Tet$^R$) |
| BL21 (DE3) | F⁻, ompT, hsd$S_B$($r_B^-$ $m_B^-$), gal, dcm, (DE3) |

TABLE 8A-continued

| Phagemid DNA | |
|---|---|
| pCANTAB5E | Amp' |
| Plasmid DNA | |
| pET-22b(+) | Amp' |

(2. Culture of *E. coli*)

A 2×YT medium, LB medium, and SOBAG medium were used for culture, and an agar medium supplemented with 1.5% agar was used as a solid medium. When an agent was added, the final concentration was ampicillin 100 µg/ml, kanamycin 15 µg/ml, tetracycline 12.5 µg/ml, nalidixic acid 100 µg/ml, and X-gal 30 µg/ml. Glucose, when added for catabolite repression, was added such that the final concertation was 5%.

TABLE 8B

| 2×YT | (/L) |
|---|---|
| Bacto-trypton | 17 g |
| Bacto-yeast | 10 g |
| NaCl | 5 g |

TABLE 8C

| LB | (/L) |
|---|---|
| trypton | 10 g |
| Yeast extract | 5 g |
| NaCl | 10 g |
| Agar | 15 g |

Adjusted to pH7 with NaOH

| SOBAG | (/900 ml) |
|---|---|
| Bacto-trypton | 20 g |
| Bacto-yeast | 5 g |
| NaCl | 0.5 g |
| After dissolution, autoclaved and cooled to 50-60° C., then the following solutions were added. | |
| 1M MgCl$_2$ | 10 ml |
| 2M glucose | 55.6 ml |
| 20 mg/ml Ampicillin | 5 ml |

(3. Preparation of Phagemid DNA and Plasmid DNA from *E. coli*)

When a small quantity was prepared, a single colony was transplanted to a 2 ml LB medium, and plasmid DNA and phagemid DNA were prepared using a FlexiPrep kit (GE Healthcare).

When a large quantity was prepared, a single colony was transplanted to a 2 ml LB medium and was pre-cultured for 8 hours. 1% of culture liquid was transplanted to 25 ml LB medium and shaken and cultured for 14 hours. Phagemid DNA was then prepared using QIAGEN midi (QIAGEN).

(4. Agarose Gel Electrophoresis)

To confirm DNA bands, Mupid®-3 (Cosmo Bio) was used as the electrophoresis tank and 1×TAE was used as the buffer. UV was confirmed after electrophoresis at room temperature at 100 V for 30 minutes and staining with ethidium bromide. DNA Mass Ladder (TOYOBO) was used as the size marker.

When DNA was collected from agarose, the distances of electrophoresis and heat generation, which affect separation, were taken into consideration to further facilitate separation.

Mupid®-EXu (ADVANCE) was used as the electrophoresis tank and TBE, which has a stronger buffering action than TAE, was used as the buffer. After the sample was subjected to electrophoresis for 4 hours or longer at an electrophoresis temperature of 4° C. and voltage of 50 V and stained with ethidium bromide, a fragment comprising the DNA of interest was cut out.

(5. Transformation of E. coli)

When DH5a (Invitrogen), BL21 (DE3) (Novagen), HB2151 (GE Healthcare), and BLR (Novagen) were transformed, suitable amount of plasmid DNA was mixed with 50 µl of competent cells and was left standing in ice for 30 minutes, then given a heat shock for 45 seconds at 42° C. Further, the mixture was left standing for 2 minutes in ice, supplemented with 450 µl of SOC, and cultured for 1 hour at 37° C. The mixture was then applied to an agar medium comprising a suitable agent to obtain a transformant.

When TG1 (Stratagene) was transformed, 25 ng of desalinated DNA was added to 40 µl of competent cells and was left standing for 1 minute on ice. The mixture was then transferred to a 2 mm cuvette to perform electroporation at a setting of 2.5 kV, 200Ω, and 25 µF. The mixture was immediately supplemented with 960 µl of SOC and cultured for 1 hour at 37° C., then applied to a SOBAG agar medium to obtain a transformant.

(6. SDS-PAGE)

SDS-PAGE was performed by using a miniprotein II-D cell (BIORAD). Protein molecular marker "Daiichi" III (Daiichi Pharmaceutical) was used.

(7. Western Blot)

After separating proteins by SDS-PAGE, a Mini Trans-Blot Cell (BIORAD) was used for transcription onto a nitrocellulose film (BioTrace® NT). Precision plus Protein™ standards (BIORAD) were used as the molecular marker.

Detection was performed using ECL plus Western Blotting Detection Reagents (GE Healthcare). Anti-E antibodies or anti-His antibodies were used as the primary antibody, and HRP-labeled anti-mouse IgG (Fc specific) was used as the secondary antibody.

(8. Quantification of Protein)

Soluble proteins were quantified with a BCA Protein Assay Reagent Kit while using BSA (Albumin standard, PIERCE) as the standard protein. Insoluble proteins were quantified using a modified Lowry procedure (Peterson et al., Anal. Biochem. 83:6654-6659 (1977)).

Example 4: Purification of Single Chain Antibody Using Anti-E Antibody Immobilized Sepharose An anti-E antibody was immobilized on sepharose while referring to the protocol of NHS-activated sepharose 4 Fast Flow (GE Healthcare). 7.5 ml of ice-cooled 1 mM HCl was added to 500 µl of NHS-activated sepharose. After the mixture was mixed, centrifuged (3000 rpm, 5 minutes, 4° C.), and left standing for 5 minutes in ice, the supernatant was removed and washed to prepare a 50% slurry. An anti-E antibody solution was subjected to ultrafiltration (15000 rpm, 24 minutes, and 4° C.) by Microcon® YM-30 (MILLIPORE). 240 µl of 0.2 M NaHCO$_3$ and 0.5 M of NaCl (pH of 8.3) were added to exchange the buffer. Purified anti-E antibodies were mixed with the washed NHS-activated sepharose. The mixture was applied to a rotator and stirred for 3 hours at room temperature. The mixture was then centrifuged (3000 rpm, 5 minutes, and 4° C.) and left standing in ice for 5 minutes to remove the supernatant. Furthermore, 750 µl of 0.1 M Tris-HCl (pH 8.5) was added. The mixture was applied to a rotator and stirred for 2 hours at room temperature, then centrifuged (3000 rpm, 5 minutes, 4° C.) and left standing in ice for 5 minutes to remove the supernatant. 0.5 M acetate buffer (pH 4.5) comprising 1.5 ml of 0.5 M NaCl was added, mixed, then centrifuged (3000 rpm, 5 minutes, 4° C.) and left standing in ice for 5 minutes to remove the supernatant. Furthermore, 1.5 ml of 0.1 M Tris-HCl (pH 8.5) was added, then the mixture was centrifuged (3000 rpm, 5 minutes, 4° C.) and left standing in ice for 5 minutes to remove the supernatant. After repeating washing with two buffers three times, TBS was added to adjust to 0.5 ml.

When a single chain antibody is expressed using pCANTAB5E, an E tag is added to the C-terminus and transported to a periplasm fraction. Thus, a periplasm fraction was prepared by the following method. Bacterial cells collected from 25 ml of culture liquid were resuspended in 0.5 ml of ice cold 1×TES and 0.75 ml of ice cold 1/5× TES was added. The mixture was vortexed. The mixture was left standing in ice for 30 minutes and centrifuged (15000 rpm, 10 minutes) to collect the supernatant as the periplasm fraction.

Furthermore, 20 µl of anti-E antibody immobilized sepharose was added to the prepared periplasm fraction and applied to a rotator to stir for 12 hours at 4° C. A swing rotor was used for centrifugation (3000 rpm, 5 minutes, 4° C.) to separate a sepharose adsorption fraction and a flow-through fraction. 1 ml of TBS was added to the collected sepharose for three repeated washing (3000 rpm, 5 minutes, 4° C.). Sepharose, to which a soluble single chain antibody was bound, was collected.

Expression and purification of the five types of obtained single chain antibodies were attempted. In accordance with the protocol of the Recombinant Phage Antibody System (GE Healthcare), M13 phage was eluted out from each E. coli TG1 retaining pCANTAB5E-γ+κ5, 12, 19, 40, and 96. Furthermore, E. coli HB2151 was transformed, which is capable of expressing a single chain antibody more efficiently by TG1 by an infection of the phage.

A single colony of each E. coli HB2151 retaining pCANTAB5E-γ+κ5, 12, 19, 40, and 96 was transplanted from a 2 ml 2×YT (Amp, Nal, Glucose) agar medium to 2×YT (Amp, Glucose), and was pre-cultured for 12 hours at 37° C. 200 µl was transplanted to 2 ml 2×YT (Amp, Glucose) and cultured for 1 hour at 30° C. The medium was then separated into 2 groups of 1 ml, and was centrifuged (3900 rpm, 10 minutes) to collect bacterial cells. One of the groups was resuspended into 1 ml 2×YT (Amp, Glucose, non-induction section) and the other was resuspended in 2×YT (Amp, 1 mM, IPTG, induction section). After the two groups were cultured for 3 hours at 30° C., the bacterial cells were collected (3900 rpm, 10 minutes), separated from the supernatant, and subjected to SDS-PAGE.

Results:

A protein was detected in the supernatant fraction of the induction section for each clone. As a result, it was revealed that bacteriolysis occurred regardless of the type of single chain antibody.

The possibility of reducing the burden on E. coli was considered by culturing for a long period of time in the presence of a low concentration of IPTG. In this regard, examinations were performed in the same manner with the IPTG concentration and culture time of 0.02 mM and 9 hours, 0.05 mM and 9 hours, and 0.2 mM and 3 hours, in each case. It was revealed that bacteriolysis occurred in all cases.

To establish expression conditions of a single chain antibody protein, experiments were conducted hereinafter while focusing on γ+κ5. HB2151 retains protease such that a single chain antibody that is an exogenous protein may be decomposed. Thus, it was decided that *E. coli* BLR with loss of two types of protease was transformed to secure protein mass. BLR was transformed by using pCANTAB5E-γ+κ5, applied to a 2×YT (Amp, Tet, Glucose) agar medium and cultured for 12 hours at 37° C. A single colony was transplanted from the agar medium to 2.5 ml 2×YT (Amp, Glucose) and pre-cultured for 12 hours at 37° C. 1 ml was transplanted to 10 ml 2× YT (Amp, glucose) and was cultured for 1 hour at 30° C., and was separated into 2 groups of 5 ml each to collect bacterial cells. As was the case with HB2151, non-induction section and induction section were provided (each culture scale was 5 ml). Bacterial cells were cultured for 3 hours at 30° C. and separated from the culture supernatant. Each was analyzed by SDS-PAGE. It was revealed that a band cannot be found at a position corresponding to the molecular weight of a single chain antibody with Coomassie staining, and a protein is also present in the culture supernatant (FIG. 6, BLR induction section bacterial cells and supernatant). These results revealed that all three types of bacterial strains (TG1, HB2151, and BLR) expressing γ+κ5 with pCANTAB5E as the expression vector had bacteriolysis, and significant induced expression of γ+κ5 was not found (FIG. 6).

When using pCANTAB5E as the expression vector, an E-tag is added to the C-terminus of the expressed single chain antibody. Since affinity purification using an anti-E antibody is specific and has a high binding ability, it was conjectured that the protein of interest from bacterial cells which have undergone bacteriolysis can be concentrated. In this regard, production of the protein of interest in BLR was first examined by Western blot using an anti-E antibody as the primary antibody. The results demonstrate that a signal is detected at a position of the expected molecular weight, and the protein of interest is present without being decomposed (FIG. 7). Purification was then attempted using an anti-E antibody immobilized sepharose, but a band could not be confirmed with Coomassie staining. It was determined that an evaluable quantity of protein cannot be collected (FIG. 8).

Example 5: Expression of Single Chain Antibody Using pET-22b (+)

(Construction of pET-22b (+) γ+κ)

To obtain a sufficient quantity of a single chain antibody protein, a pET system was used as the host/vector system. For γ+κ5, SalI and NdeI were added to the 5' side and XhoI restriction enzyme site was added to the 3' side by PCT using a g+k reverse primer (Table 8) and g+k aFOR primer (Table 8). The reaction conditions were 25 cycles of a cycle of 3 minutes at 94° C., then 30 seconds at 94° C., 30 seconds at 55° C., and 30 seconds of 72° C. After electrophoresis with 1.5% agarose gel, the sample was purified and digested using NdeI and XhoI. pET-22b (+) was similarly digested and ligated to construct pET-22b (+)-γ+κ5 and pET-22b (+)-γ+κ19. The obtained plasmid DNA was used to transform *E. coli* DH5α, which was applied to a 2×YT (Amp) agar medium and cultured for 16 hours at 37° C. It was examined whether a gene of interest is contained by colony PCR, and plasmid DNA was prepared from a positive colony. Furthermore, the DNA base sequence of an inserted fragment was examined.

TABLE 8

Table 8. pET-22b(+) construction primers

| | |
|---|---|
| g+k a REV | 5'-GTCGACCATATGCCATGGCAGGTACAGCTGCAGCAGT CAGG-3' (SEQ ID NO: 73) |
| g+k b REV | 5'-GTCGACCATATGCCATGGGAGGTGCAGCTGGTGGAGT CTGG-3' (SEQ ID NO: 74) |
| g+k aFOR | 5'-CTCGAGACGTTTGATCTCCAG-3' (SEQ ID NO: 75) | pET-22b (+)-γ+κ5 and pET-22b (+)-γ+κ19 were used to transform the expression host BL21 (DE3). BL21 (DE3) retaining pET-22b (+)-γ+κ5 was transplanted from an agar medium to 2 ml LB (Amp) and was pre-cultured for 12 hours at 37° C. 1 ml of culture liquid was transplanted to 100 ml LB (Amp) and cultured such that $A_{600}$ was about 0.6 at 37° C. IPTG was then added so that the final concentration was 1 mM and the mixture was cultured for 4 hours at 37° C. The bacteria were collected (8000 rpm, 5 minutes) and washed three times with 10 ml of PBS. PBS, in an amount 3 times of the wet weight, was added for pulverization with ultrasound. The solution was centrifuged (15000 rpm, 15 minutes) and the collected supernatant was subjected to SDS-PAGE as a soluble fraction and precipitation was subjected thereto as an insoluble fraction. The same operation was also performed for γ+κ19.

Expression was confirmed at an expected molecular weight position by Coomassie staining for both γ+κ5 and γ+κ19 (FIG. 9A, after induction). When pET-22b (+) is cloned using an XhoI restriction enzyme site, a His tag is added to the C-terminus side. It was verified that a protein with a confirmed induction by Western blot using an anti-His tag antibody as the primary antibody is a single chain antibody of interest (FIG. 9B).

(Purification of Refolded Single Chain Antibody Using Nickel Agarose)

CA method (Machida, 2000) was used to refold a single chain antibody expressed as an inclusion body. 288 µl of inclusion body suspension (protein concentration of 25 mg/ml) was mixed with 900 µl of 8M guanidine hydrochloride and 12 µl of 4M DTT and was reacted for 1 hour at room temperature. 570 µl of the reaction product was separated into two groups and mixed with 0.1% CTAB/PBS or 0.1% SB3-14/PBS comprising DL-cysteine with a final concentration of 2 mM of 70-fold volume, and was reacted for 1 hour at room temperature. 10 ml of 3% cycloamylose was added to each group and was reacted overnight at room temperature. The reaction products were centrifuged (12000 rpm, 5 minutes). The supernatant was collected as a refolding solution.

Next, 1/25 volume of nickel agarose 50% slurry was added to the refolding solution. The mixture was applied to a rotator and stirred at 4° c. for 30 minutes. A swing rotor was used for centrifugation (3000 rpm, 5 minutes, 4° C.) and the washing operation was repeated three times. Nickel agarose with a single chain antibody bound thereto was then collected. 500 µl of PBS comprising 1M imidazole was added to the collected nickel agarose. The mixture was applied to a rotator and stirred at 4° C. for 30 minutes. A swing rotor was used for centrifugation (3000 rpm, 5 minutes, 4° C.). The imidazole elution fraction was collected to obtain a purified single chain antibody. However, aggregation after elution resulted in a significant decrease in yield.

(1. Culture)

pET-22b (+)-γ+κ5 was used to transform BL21 (DE3). The resulting transformant was cultured overnight at 37° C. in an LB liquid medium (50 μg/ml Ampicillin) and was transplanted in a new medium such that it was at 1%. After culture at 37° C. and addition of IPTG so that the final concentration was 1 mM when $A_{600}$ was 0.5 to 0.6, the solution was cultured for 4 hours. The culture liquid was centrifuged at 6000×g for 10 minutes and the resulting bacterial cells were washed three times with phosphate buffered saline (PBS). The bacterial cells were resuspended in PBS and, after pulverization with ultrasound waves, they were centrifuged at 10000×g for 10 minutes to obtain a precipitation as an inclusion body of γ+κ5.

(2. Refolding of Single Chain Antibody)

50 mg wet weight of γ+κ5 inclusion body was suspended in 150 μl of PBS. 450 μl of 8M guanidine hydrochloride solution and 6 μl of 4M dithiothreitol solution were added, mixed, and left standing for 1 hour or longer at room temperature. 40 ml of 0.1% CTAB/PBS solution comprising 2 mM of DL-cysteine (final concentration) was then added, mixed, and left standing for 1 hour at room temperature. Subsequently, 10 ml of 3% cycloamylose was added, mixed, and left standing overnight at room temperature. The reaction solution was centrifuged for 5 minutes at 12000 rpm. The supernatant was collected as the refolding solution.

(3. Purification of Single Chain Antibody)

Figure 10:
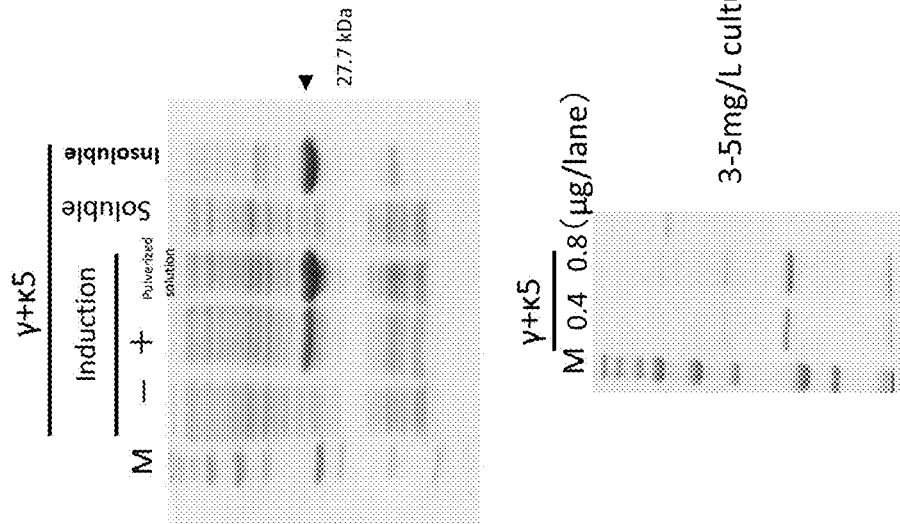
FIG. 10 shows results of SDS-PAGE for γ+κ5. For data on the right side, the top panel shows γ+κ5, and from the left, marker, before induction, after induction, pulverized bacterial cell solution entire fraction, soluble fraction, and insoluble fraction. The bottom panel shows results for γ+κ5 after purification, and marker and purified specimens (from the left, amount of electrophoresis of 0.4 μg/lane and 0.8 μg/lane).

To prevent reaggregation after elution, conditions for dialysis rate and efficiency were optimized. 50% nickel agarose slurry of 1/25 volume of the refolding solution was added and gently stirred with a rotator at 4° C. for 30 minutes. The mixture was then centrifuged for 5 minutes at 1000× g to collect nickel agarose. The nickel agarose was washed 2 to 3 times with an equivalent amount of PBS. 500 μl of PBS comprising 2M imidazole was added for elution. Elution was performed several more times with PBS comprising 1M imidazole. The eluted fraction was dialyzed with PBS with 400-times the sample volume using a cellulose ester film tube to obtain a purified single chain antibody. The purity and concentration of the resulting single chain antibody were evaluated by SDS-PAGE (FIG. 10). The yield was 3 to 5 mg per 1 L of culture liquid.

Example 6: Detection of Single Chain Antibody (1. Direct ELISA)

Antigen recognition activity of a purified single chain antibody was evaluated by direct ELISA. LDLs, acetylated LDLs, partially oxidized LDLs, and fully oxidized LDLs were used as antigens. 0.05 to 10 μg/ml of antigen solution was added to a polystyrene 96-well microwell plate at 100 μl/well and allowed to adsorb overnight at 4° C. The plate was washed three times with PBS (200 μl/well). Blocking buffer (0.25% BSA/PBS) was added at 200 μl/well. The mixture was left standing for 2 hours at room temperature. After the plate was washed three times with PBS (200 μl/well), 2.5 μg/ml/PBS single chain antibody was added at 100 μl/well and reacted for 1 hour at room temperature. The plate was washed five times with PBS (200 μl/well) and anti-His-HRP antibody diluted 1000-fold with blocking buffer was added at 100 μl/well and reacted for 1 hour at room temperature. After washing the plate five times with PBS (200 μl/well), 3,3',5,5'-tetramethyl-benzidine (TMB) was added at 50 μl/well. The luminescence was examined and 150 p/well of 1N HCl was added to suspend the reaction. Subsequently, the absorbance at 450 nm for each well of the plate was measured (FIG. 11).

Figure 11:
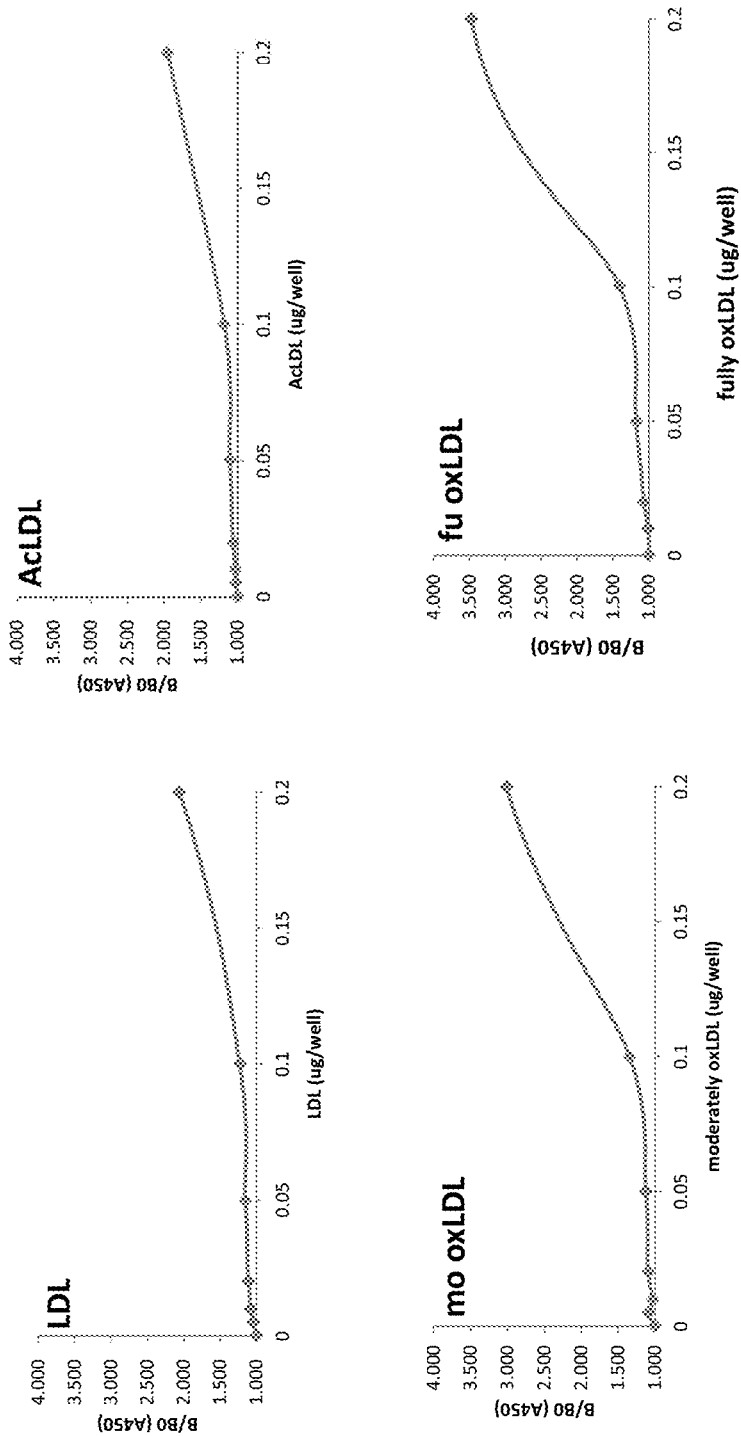
FIG. 11 shows results of evaluating antigen recognition activity of a single chain antibody (γ+κ5) by direct ELISA. LDL (top left panel), acetylated LDL (top right panel), partially oxidized LDL (bottom left panel), and fully oxidized LDL (bottom right panel) were used as antigens. For each panel, the vertical axis indicates B/B0 (relative ratio) of absorbance at 450 nm (A450). The horizontal axis indicates the amount of each specimen (μg/well).
Figure 12:
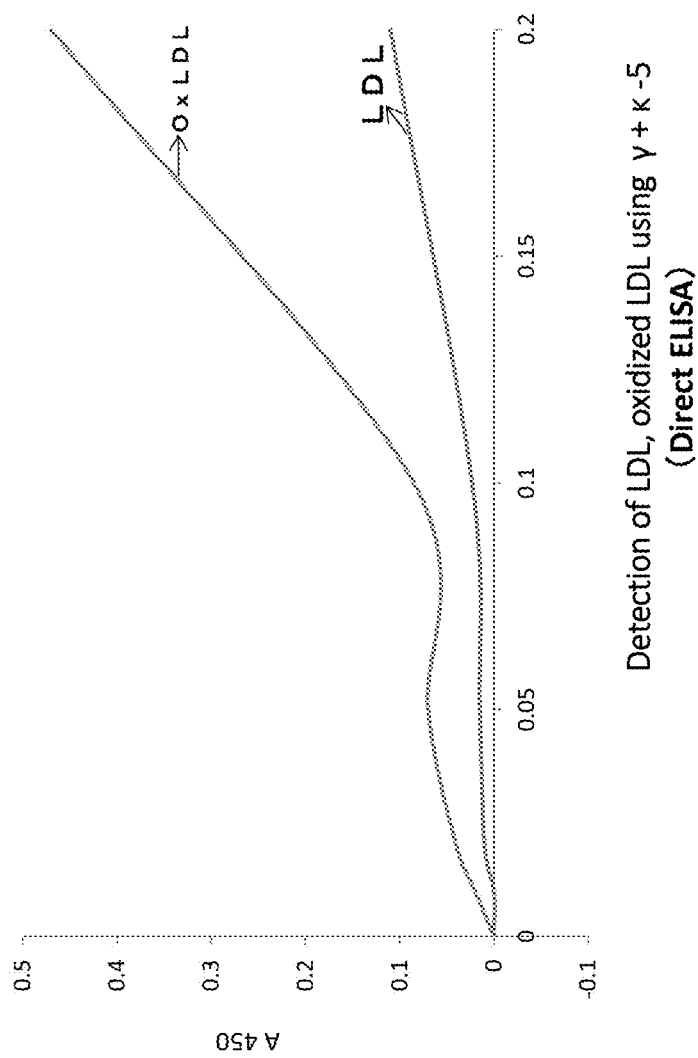
FIG. 12 shows the detection of LDLs and oxidized LDLs by direct ELISA using a single chain antibody (γ+κ5). The vertical axis indicates absorbance at 450 nm (A450). The horizontal axis indicates the amount of each specimen (μg/well).

Results:

As shown in FIG. 11, it was revealed that the single chain antibody γ+κ5 recognizes all of LDLs, acetylated LDLs, partially oxidized LDLs, and fully oxidized LDLs used as antigens, but the specificity to each antigen is different (FIG. 12). γ+κ5 is considered to have a feature of recognizing oxidized LDLs more strongly than LDLs at a low concentration. Further, the detection limit for each antigen was 5 ng/100 μl well for LDLs, 10 ng/100 μl well for acetylated LDLs, 10 ng/100 μl well for partially oxidized LDLs, and 20 ng/100 μl well for fully oxidized LDLs (FIG. 11). The detection limit was calculated as the detection limit at the lowest concentration at which detection was possible in measured specimens at different dilution levels.

(2. Sandwich ELISA)

Figure 13:
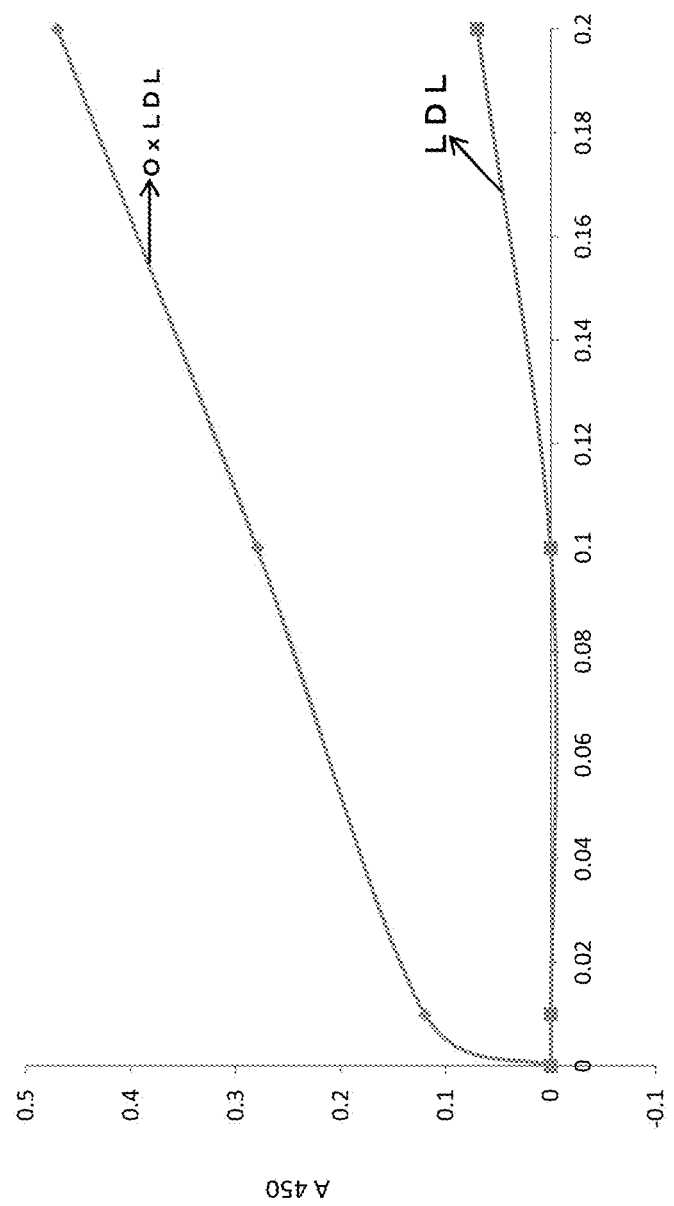
FIG. 13 shows results of evaluating antigen recognition activity of a single chain antibody (γ+κ5) by sandwich ELISA. LDLs and oxidized LDLs were used as antigens. The vertical axis indicates absorbance at 450 nm (A450). The horizontal axis indicates the amount of each specimen (μg/well).

Further, the ligand recognition region (CTLD14) of an oxidized LDL receptor LOX-1 was used to evaluate the ability to recognize oxidized LDLs by sandwich ELISA. In addition, recognition of acetylated LDLs, partially oxidized LDLs, and fully oxidized LDLs was evaluated by indirect ELISA (sandwich ELISA with CTLD14 (with His tag removed) and single chain antibody). 20 μg/ml/PBS of CTLD14 was added to a polystyrene 96-well microwell plate at 50 μl/well and allowed to adsorb overnight. The plate was washed three times with PBS (200 μl/well). Blocking buffer (0.25% BSA/PBS) was added at 250 μl/well. The mixture was left standing for 2 hours at room temperature. After the plate was washed three times with PBS (200 μl/well), 0.05 to 10 μg/ml of antigen solution (LSL or oxidized LDL) was added at 100 μl/well and was reacted for 2 hour at room temperature. The plate was washed five times with PBS (200 μl/well) and 2.5 μg/ml/PBS of single chain antibody was added at 100 μl/well and reacted for 1 hour at room temperature. The plate was then washed with PBS (200 μl/well) as in the direction method. After an anti-His-HRP antibody reaction, a TMB reaction was carried out to suspend the reaction. Subsequently, the absorbance at 450 nm was measured (FIG. 13).

Results: Sandwich ELISA using LOX-1 exhibited a weak detection signal for LDLs, while exhibiting a concentration dependent signal for fully oxidized LDLs (FIG. 13). This shows that when LDLs and oxidatively modified LDLs coexist, it is possible to recognize only oxidatively modified LDLs by a combination with LOX-1. It was also shown that acetylated LDLs and partially oxidized LDLs can also be detected.

Example 7: Detection System of Malondialdehyde Modified LDL

Next, a similar experiment is conducted by using another type of modified LDL to confirm whether another modified LDL can be detected.

(Method)

A similar experiment is conducted based on Example 6 by using malondialdehyde modified LDLs instead of oxidized LDLs and the like as a subject.

(Results)

It is expected that the presence of about 20 ng/well of malondialdehyde modified LDLs (MDA-LDL) can be detected.

Example 8: Detection System Based on Principle of Lateral Flow Assay

Figure 14:
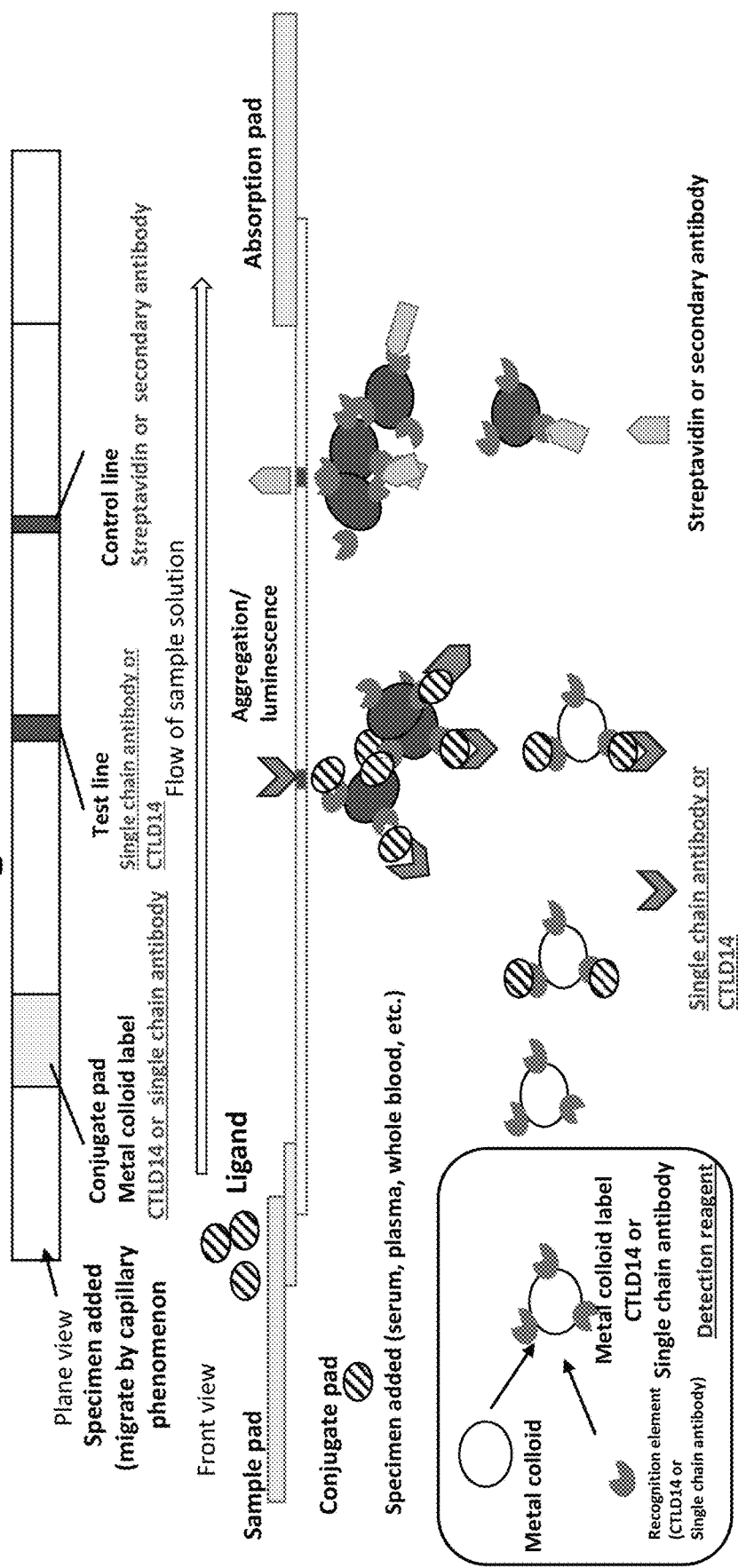
FIG. 14 shows a summary of a detection system based on the principle of lateral flow assay.
Figure 15:
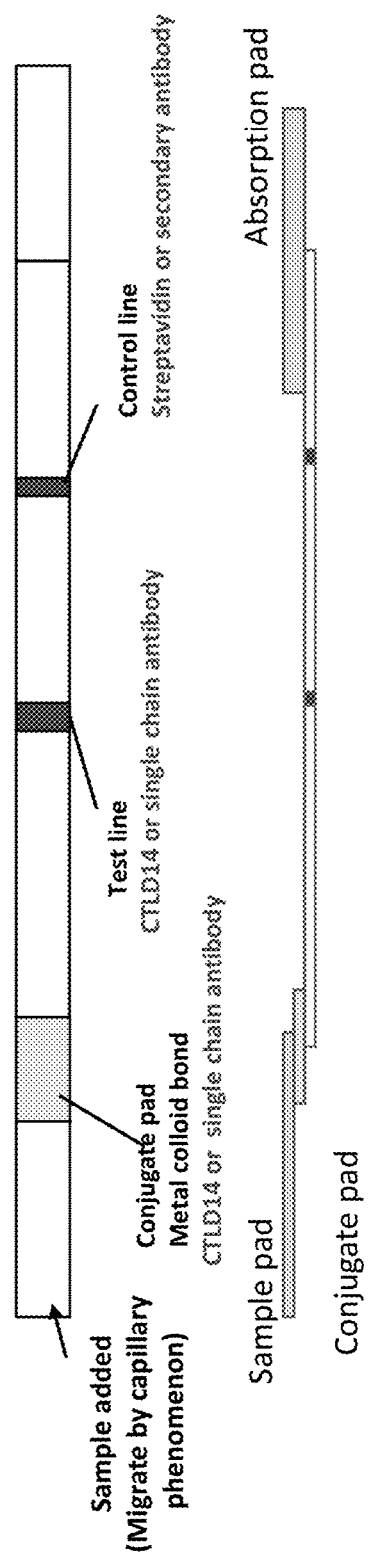
FIG. 15 shows a summary of a detection system based on the principle of lateral flow assay. In this example, a sample pad, conjugate pad, a pad comprising a test line, and an absorption pad are used. At the sample pad and conjugate pad, each sample is added for a conjugate generation reaction. A sample added to the sample pad migrates via the capillary phenomenon to the conjugate pad, which comprises, for example, metal colloid bound CTLD14 or the single chain antibody of the invention, such that a conjugate is generated. In addition, the conjugate pad and the pad comprising a test line include a test line and a control line, where the test line comprises CTLD14 or a single chain antibody. When a target is in the sample, a bond is made and detected. Detection is performed at the control line with streptavidin or the secondary antibody. Quantification is also possible.
Figure 16:
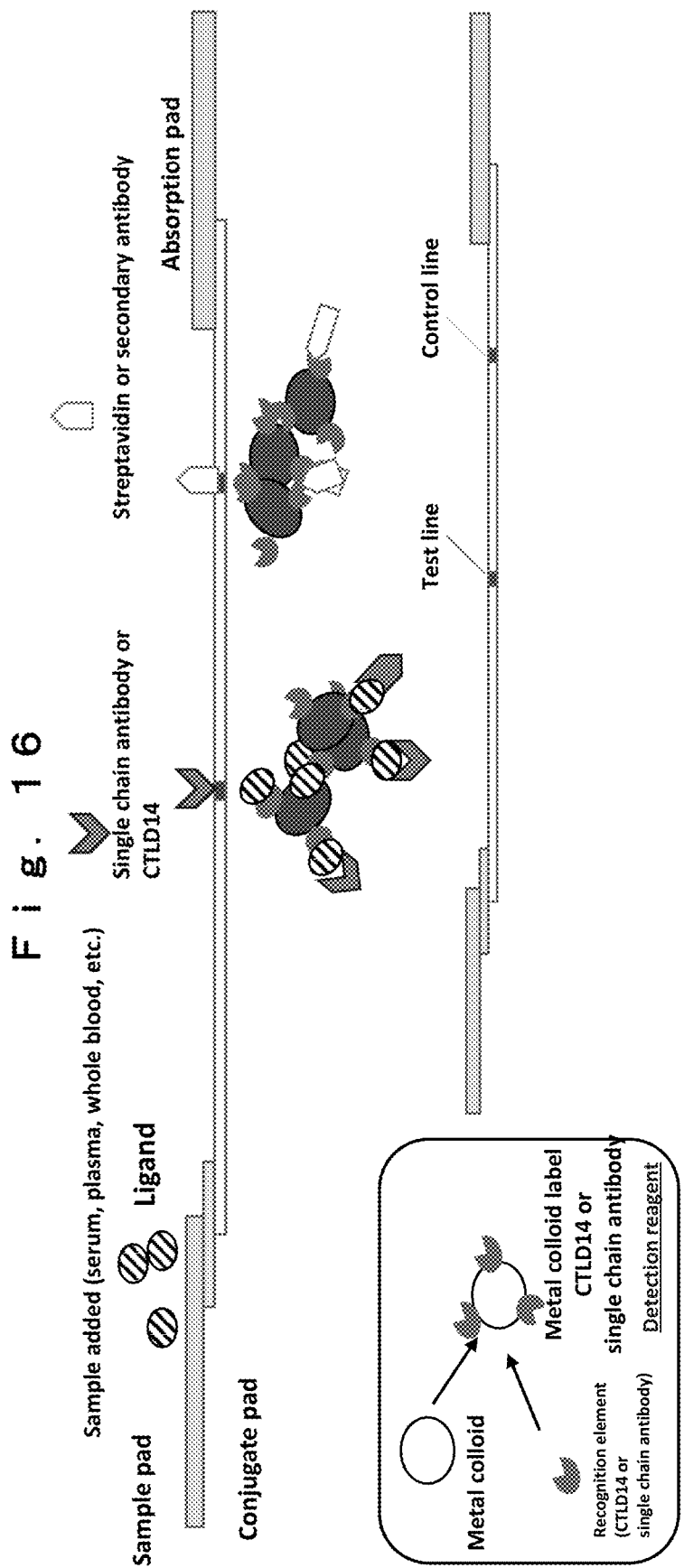
FIG. 16 shows an exemplary summary of a detection system based on the principle of lateral flow assay. In this example, when CTLD14 is labeled with a metal colloid (or a latex particle), a single chain antibody is applied to the test line, and a molecule matching the tag of CTLD14 (streptavidin for biotinylated CTLD14, anti-His antibody for His-Tag, or the like) or a secondary antibody is applied to the control line. Meanwhile, when a single chain antibody is labeled with a metal colloid (latex particle), CTLD14 can be applied to the test line and anti-His antibody or a secondary antibody can be applied to the control line.

In this Example, a detection system using the principle of lateral flow assay is constructed to detect LDLs more readily (FIGS. 14 to 16)

(Materials and Methods)

A single chain antibody or CTLD14 labeled with a metal colloid was used as a detection reagent. A membrane for lateral flow with CTLD14 or single chain antibody applied to a detection section, and streptavidin (when CTLD14 is biotinylated) or anti-His antibody (when CTLD14 comprises a His tag) applied to a control section, is used. Specimens such as serum, plasma, or whole blood are added to a sample pad. Modified LDL activity in a specimen is evaluated by the luminescence in a test run or by the ratio of luminescence of test run/control.

(Results)

Typically, the presence of a modified LDL can be detected by visual inspection in 30 minutes or less.

Example 9: Oxidatively Modified LDL Detection and Quantification System Using Chicken Anti-LDL Antibody and LOX-1 in Lateral Flow Format Next, this Example develops an oxidatively modified LDL detection and quantification system using an anti-LDL chicken antibody and LOX-1 in a lateral flow format.

(Materials and Method)

Anti-LDL chicken antibodies were ordered from and manufactured by Japan Lamb. The following is the details thereof. Anti-LDL chicken antibodies were collected by inoculating the chicken skin 6 times with 0.3 mg of antigen (LDL) (adjuvant FCA) every two weeks, checking the increase in titer at and after the fifth inoculation, and exsanguinating after the sixth booster. The antibody activity was measured using 1 μg/ml of antigen (LDL) in a solid phase at 100 μl/well in accordance with common ELISA. In this Example, HRP labeled anti-chicken IgY (e.g., available from Promega or the like) was used as a labeled secondary antibody.

CTLD14 or single chain antibody labeled with a metal colloid was used as a detection reagent. A membrane for lateral flow with CTLD14 or single chain antibody applied to a detection section and anti-LDL chicken antibody applied to a control section was used. Specimens such as serum, plasma, or whole blood were added to a sample pad. Modified LDL activity in a specimen was evaluated by the luminescence in a test run or by the ratio of luminescence of test run/control.

(Results)

This Example demonstrates that the presence of a modified LDL can be detected by visual inspection in 30 minutes or less.

Example 10: System for Examination of Lipid Abnormality, Arteriosclerosis, or Diabetes Using Anti-LDL Chicken Antibody and LOX-1 in Lateral Flow Assay Format Next, this Example develops a system for examination of a modified LDL associated disease such as lipid abnormality, arteriosclerosis, diabetes, ischemica heart disease, or cerebrovascular disorder using an anti-LDL chicken antibody and LOX-1 in lateral flow assay format.

(Materials and Method)

The materials and methods according to Example 9 can be used.

(Results)

This Example demonstrates that the presence of a modified LDL can be detected by visual inspection in 30 minutes or less, based upon which examination for a modified LDL associated disease such as lipid abnormality, arteriosclerosis, diabetes, ischemic heart disease, or cerebrovascular disorder can be conducted in a short period of time.

Example 11: System for Evaluating Prophylactic Effect of Food Intake by Using Anti-LDL Chicken Antibody and LOX-1 in Lateral Flow Assay Format This Example develops a System for evaluating an effect of food intake on preventing a modified LDL associated disease such as lipid abnormality, arteriosclerosis, diabetes, ischemic heart disease, or cerebrovascular disorder by using an anti-LDL chicken antibody and LOX-1 in a lateral flow assay format.

(Materials and Methods)

The materials and methods according to Example 9 can be used.

(Results)

This Example demonstrates that the presence of a modified LDL can be detected by visual inspection in 30 minutes or less, and based upon which an effect of food intake on preventing a modified LDL associated disease such as lipid abnormality, arteriosclerosis, diabetes, ischemic heart disease, or cerebrovascular disorder can be evaluated in a short period of time.

Comparative Example 1: Preparation of CTLD14 by Conventional Method

CTLD14 was synthesized by using a conventional method, $E.\ coli$ expression system, under a condition of modifying an inclusion body under reducing conditions as a comparison to the present invention. The protocol thereof is shown below.

Refolding was conducted by precision method: diluted dialysis method.

(Stepwise Dilution for Refolding)

(Preparation of dialysis buffer (1 to 5)*[a]) (*[a]: dialysis buffer 1 to 5 refers to the following buffer 1 to 5, and premix indicates a state where all reagents other than glutathione of each ingredient of buffer 1 to 5 are mixed.)

All reagents other than glutathione (reduced, oxidized) were mixed.

pH was suitably adjusted for each buffer.

buffer was stored at 4° C.

(Sample Preparation)

The protein concentration was adjusted to 1 mg/ml (dilution buffer: buffer solution C: buffer solution C: 6M guanidine HCl, 50 mM Tris, pH 8.0)

A tube (dialysis tube, Spectra/Por 7, RC, MWCO 8000) was used. Each dialysis buffer (1 to 5) (see below for 1 to 5) was prepared prior to use.

A required volume of glutathione (reduced oxidized) solution was thawed.

A dialysis buffer premix and a glutathione solution were mixed.

The volume was suitably adjusted and the mixture was thoroughly mixed.

(Dialysis)

The protein concentration was adjusted to 1 mg/ml (dialysis buffer: buffer C)

Dialysis was conducted for 12 hours at 4° C. with Buffer 1 (50 mM Tris-Cl, pH of 8.5, 4M guanidine HCl, 0.4 M L-arginine, 0.4 M NaCl, 10% glycerol, 0.5 mM oxidized glutathione, 5 mM reduced glutathione).

Dialysis was conducted for 12 hours at 4° C. with Buffer 2 (50 mM Tris-C1, pH of 8.5, 3M guanidine HCl, 0.4 M L-arginine, 0.4 M NaCl, 10% glycerol, 0.5 mM oxidized glutathione, 5 mM reduced glutathione).

Dialysis was conducted for 12 hours at 4° C. with Buffer 3 (50 mM Tris-C1, pH of 8.0, 2M guanidine HCl, 0.4 M L-arginine, 0.4 M NaCl, 10% glycerol, 0.5 mM oxidized glutathione, 5 mM reduced glutathione).

Dialysis was conducted for 12 hours at 4° C. with Buffer 4 (50 mM Tris-C1, pH of 8.0, 1M guanidine HCl, 0.4 M L-arginine, 0.4 M NaCl, 10% glycerol, 0.5 mM oxidized glutathione, 5 mM reduced glutathione) (started to aggregate at this point).

Dialysis was conducted for 12 hours at 4° C. with Buffer 5 (50 mM Tris-C1, pH of 8.0, 0.4 M L-arginine, 0.4 M NaCl, 10% glycerol, 0.5 mM oxidized glutathione, 5 mM reduced glutathione).

Dialysis was conducted for 48 to 96 hours at 4° C. with TBS (pH 7.6) (20 mM Tris-C1, pH 7.6, 150 mM NaCl) (buffer exchanged three times; each buffer exchange was spaced apart by 12 hours or more).

The protein solution in the tube was collected.

The solution was subjected to ultracentrifugation (100000× g, 60 minutes, 4° C.) to collect refolded proteins.

(Results)

Figure 17:
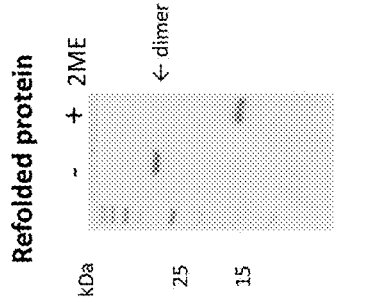
FIG. 17 shows results of treating E. coli form CTLD14, which was expressed with E. coli, purified, and then refolded by the precision method, with SDS-PAGE sample buffer (+) comprising β-mercaptoethanol (2ME) or with 2ME-free SDS-PAGE sample buffer (−), and subjecting the CTLD14 to SDS-PAGE and then Coomassie staining. When treated in the absence of 2ME, CTLD14 is detected at the dimer molecular weight position, whereas CTLD14 is detected at a monomer molecular weight position when treated in the presence of 2ME. This demonstrates that *E. coli* form CTLD14 refolded by the precision method correctly forms a dimer, which is a quaternary structure of a basic unit on a cell membrane. The yield of CTLD14 correctly forming a dimer was 12 mg per 1 L of culture.

FIG. 17 shows results of purification by the purification method.

Example 12: Production with Genetically Modified Silkworm

This Example attempted production with a genetically modified silkworm.

CTLD14 vector was injected into a silkworm egg by microinjection to obtain a CTLD14 expressing silkworm. Furthermore, the silkworm was crossbred with a line capable of expression in the middle silk gland to create a genetically modified silkworm expressing CTLD14 in the middle silk gland (extraction is simple and high purity).

FIG. 18 shows a schematic diagram thereof. The detailed protocol is shown below.

(Materials and Method)
(Line Production, Expression, Etc.)

The plasmid of CTLD14 to which a biotinylated tag (BIOEASE™ Tag biotin ligase birA substrate peptide (Life Technologies, Carlsbad, Calif.)) was added was basically constructed in accordance with the manufacturer's manual by using the pcDNA™6 BIOEASE™ Gateway® Biotinylation System by Life Technologies.

PCR primers (CTLD14-F: 5'-AATCTC-CAAGAAACACTGAAG-3' (SEQ ID NO: 87), CTLD14s-R: 5'-TCACTGTGCTCTTAGGTTTGC-3' (SEQ ID NO: 88)) were used for PCR amplification of a CTLD14 region by a plasmid comprising a LOX-1 gene (hLOX-1/pBS). The amplified CTLD14 region was inserted into the pCR8/GW/TOPO plasmid by using pCR™ 8/GW® TA Cloning® kit (ThermoFisher Scientific, Carlsbad, Calif.) for transformation into E. coli DH5α. Next, the CTLD14 sequence of pCR8 was introduced into pcDNA™ 6 BIOEASE™-DEST by an LR reaction for transformation into E. coli DH5α. The introduced CTLD14 sequence was confirmed by the DNA sequence, and a plasmid with CTLD14 to which a biotinylated tag (BIOEASE™ Tag biotin ligase birA substrate peptide (Life Technologies, Carlsbad. Calif.)) was added was constructed.

A UAS vector was constructed by inserting a fragment encoding CTLD14 and a fragment encoding a signal peptide of fibroin H chain amplified by PCR to downstream of the UAS (Upstream Activation Sequence) sequence of pBac [Ser-UAS/3×P3EGFP] (Ken-ichiro Tatematsu, Isao Kobayashi, Keiro Uchino, Hideki Sezutsu, Tetsuya Iizuka, Naoyuki Yonemura, Toshiki Tamura, Transgenic Research, 19, 473 (2010)). The expression vector was used to create a genetically modified silkworm. The w1-pnd line of white eye/white egg/nondormant line maintained at the National Institute of Agrobiological Sciences was used as the host line. The resulting genetically modified silkworm was crossbred with UAS (Upstream Activation Sequence) of a line expressing GAL4 in the middle silk gland (Ken-ichiro Tatematsu, Isao Kobayashi, Keiro Uchino, Hideki Sezutsu, Tetsuya Iizuka, Naoyuki Yonemura, Toshiki Tamura, Transgenic Research, 19, 473 (2010)). Among the resulting next-generation silkworms, individuals with both a GAL4 construct and UAS construct were selected out by a selection marker. Larvae of $6^{th}$ day in the $5^{th}$ instar were dissected to extract the middle silk gland. Proteins were extracted by shaking for 2 hours at 4° C. with 1 mL of extraction solution of PBS+1% Triton X-100 per gland.

(Purification)

CTLD14 was eluted out by having a solution of middle silk gland extract from which sericin was removed by freeze thaw treatment bind to Ni-Agarose balanced with PBS and raising the imidazole concentration in PBS step wise. 250 mM to 1 M imidazole elution fraction was collected and dialyzed with PBS. When the level of purification needs to be further increased, the fraction was subjected to purification with TALON (metal chelate affinity using Co instead of Ni). 200 to 500 mM imidazole elution fraction was collected and dialyzed with PBS (-) as purified CTLD14 (see FIG. 23).

(Glycopeptide Analysis)

Specimens with and without PNGase F treatment was subjected to electrophoresis with 15% SDS-PAGE and then Coomassie staining, and a protein band was cut out. Silkworm form CTLD14 contained in the cut out gel fragment was acetamidated and digested with trypsin and measured by MALDI-TOFMSLC-ESMS. The mass spectra of the PNGase F treatment section and treatment free section were compared. The amino acid sequence comprising a region expected to have N-linked glycosylation was observed.

(Dimer Formation)

Purified CTLD14 was treated with SDS-PAGE sample buffer (+) comprising @-mercaptoethanol (2ME) or SDS-PAGE sample buffer (-) free of 2ME, and subjected to SDS-PAGE and Coomassie staining to examine dimer formation.

(Results)

Figure 22:
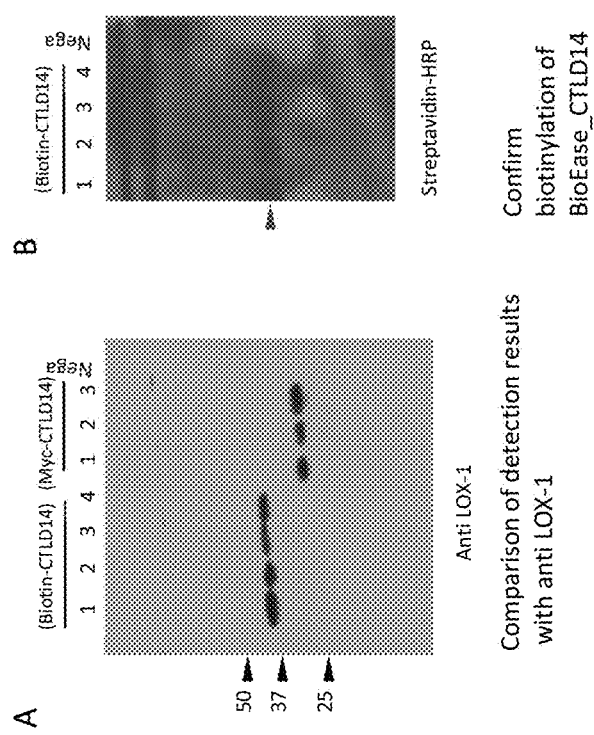
FIG. 22 shows a diagram examining whether Biotin-CTLD14 is biotinylated in the silkworm body. After Western blot, chemiluminescence from binding to horseradish peroxidase (HRP)-labeled streptavidin and then reacting with a substrate of HRP was detected by ECL. 'A' shows a comparison of detection results with anti-LOX-1. From the left, lines 1-4 of Biotin-CTLD14 and lines 1-3 of Myc-CTLD14 are shown. The right edge shows a negative control. 'B' examines biotinylation of BIOEASE™ Tag biotin ligase birA substrate peptide (Life Technologies, Carlsbad, Calif.) CTLD14. 'B' shows results of detecting chemiluminescence from binding to streptavidin-HRP and then reacting with a substrate of HRP by ECL. The right edge shows a negative control.

FIGS. 21 and 22 show results of analysis of expression. As shown in FIG. 21, multiple lines expressing CTLD14 with a different tag (biotin tag, myc tag; His tag as common tag for purification) were established. Expression of each line was examined. As shown in FIG. 21, detection was carried out with left: Coomassie staining and Right: His tags in Western blot. As indicated by "←1" in the Figure, clear expression of Biotin_CTLD14 (with BIOEASE™ Tag biotin ligase birA substrate peptide (Life Technologies, Carlsbad, Calif.)) was observed. Further, the molecular weight matched the estimated molecular weight (29 kDa only for the protein part and 29 kDa or greater with glycosylation).

As shown in FIG. 22, it was examined whether Biotin-CTLD14 was biotinylated in a silkworm body. After Western blot, it was bound to HRP-labeled streptavidin. After a reaction with the HRP substrate, chemiluminescence was detected with ECL. It was confirmed that CTLD14 derived from each line was biotinylated.

(Purification)

Figure 23:
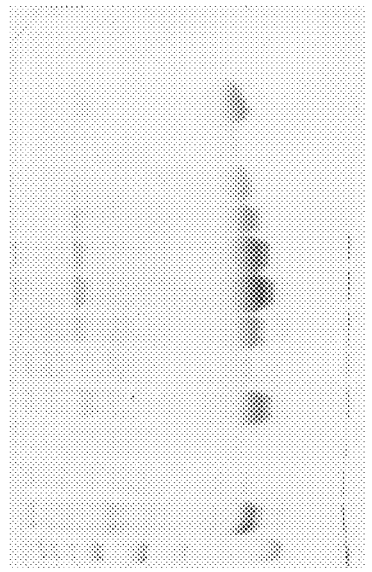
FIG. 23 shows the purification process of CTLD14 produced with a genetically modified silkworm. Sericin was removed from the middle silk gland extract by freeze-thawing, and then it was allowed to adsorb to Ni-agarose and eluted with imidazole. Subsequently, to increase the purity level, it was allowed to bind to TALON (carrier for metal chelate chromatography using Co instead of Ni). Purified silkworm form CTLD14 is shown, which was dialyzed with PBS (−) after collecting Lane 1: Ni-agarose elution fraction, 2: TALON non-adsorption fraction, 3: elution fraction upon washing with 5 mM imidazole, 4: TALON adsorption fraction, 5: 50 mM imidazole elution fraction, 6: 100 mM, 7: 200 mM, 8, 9: 500 mM, 10: 1M imidazole elusion fraction, 11: imidazole non-elution fraction, 12: 200 mM to 500 mM imidazole elution fraction.

After extracting middle silk glands with 1 ml of PBS+1% Triton X-100 per gland (2 ml/silkworm), the gland could be readily purified by treatment with two types of columns of Ni-NTA and TALON (possible in about 4 days or less). Quantitatively, it was possible to supply 0.3 mg/silkworm (FIG. 23).

(Sequence)

FIG. 19 shows information related to modification of the sugar chain and amino acid sequence of improved CTLD14 (silkworm form glycosylated biotinylated CTLD14) manufactured in this Example.

The structure of an N-linked sugar chain of a silkworm middle silk gland expressed protein is described below. CTLD14 is specifically expressed in the silkworm middle silk gland. Sugar chains of a glycoprotein expressed in the middle silk gland is rarely a paucimannose type (with fucose) sugar chain or high mannose type sugar chain, which are found in sites other than the middle silk gland, and are complex type sugar chain with a GlcNAc terminal or oligomannose type sugar chain. As a result of glycopeptide analysis, glycosylation sites are aspartic acids at two locations, NCS and NST. The total mass number of the two sugar chains was determined to be about 2500. Thus, it is estimated that a similar sugar chain is included. FIG. 20 shows the structure of an N-linked sugar chain of a silkworm middle silk gland expressed protein.

(Sugar Chain Analysis)

Figure 24:
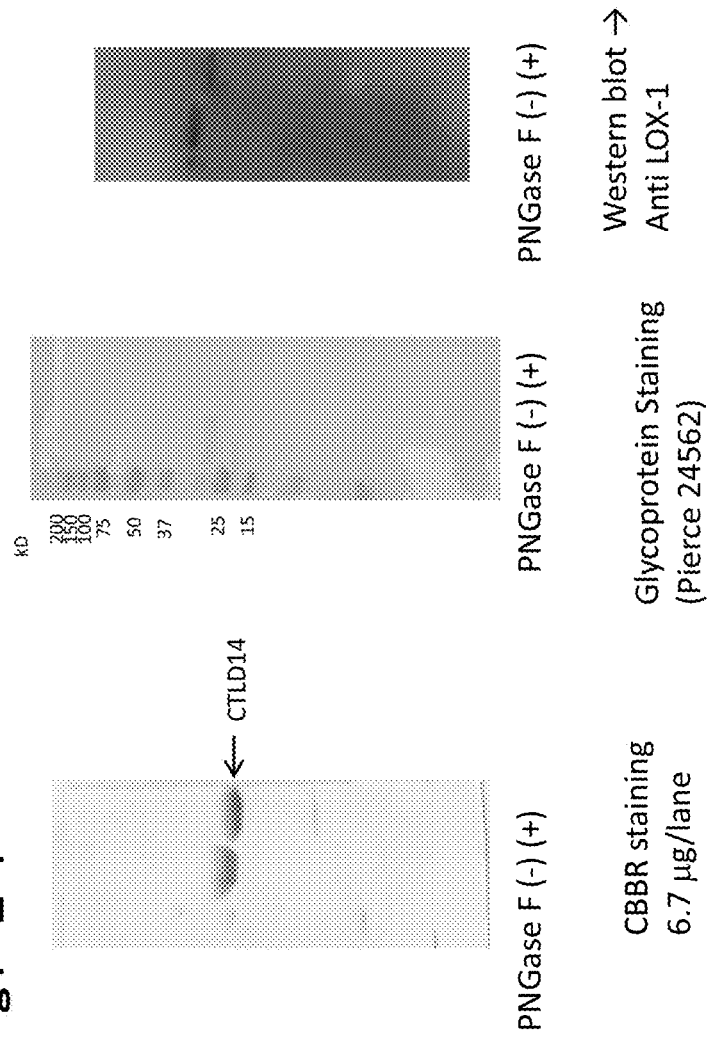
FIG. 24 shows results of examining glycosylation of silkworm derived CTLD14. 20 μg of post-purification silkworm form CTLD14 was treated with PNGase F and subjected to 15% SDS-PAGE. (+) refers to PNGase F treated specimen, and (−) refers to a specimen subjected to the exact same reaction in the absence of PNGase F. Left: results of CBBR staining, where the amount of specimen added is 6.7 μg/lane. A shift in molecular weight due to the removal of a sugar chain by PNGase F treated was confirmed. Middle: shows results of glycoprotein staining before and after PNGase F treatment by Glycoprotein Staining (Pierce 24562). A sugar chain was removed by PNGase F treatment such that the specimen was no longer detected as a glycoprotein. Right: diagram confirming that there is no change in reactivity with an anti-LOX-1 antibody after PNGase F treatment. Specimens after PNGase F treatment and without PNGase F treatment were transcribed onto a PVDF film after deployment with 15% SDS-PAGE, reacted with an anti-LOX-1 rabbit antibody as a primary antibody, and subsequently reacted with a secondary antibody HRP-modified anti-rabbit IgG antibody, and LOX-1 was finally detected with ECL. Detection was performed with LOX-1 antibodies both before and after PNGase F treatment.

Sugar chains were subjected to the above-described analysis. Glycosylation of silkworm-derived CTLD14 was examined to obtain the results shown in FIG. 24. As shown in FIG. 24, a shift in molecular weight by removal of a sugar chain by PNGase F treatment was confirmed (FIG. 24 left). When results of glycoprotein staining before and after PNGase F treatment were studied, it was no longer detected as a glycoprotein due to PNGase F treatment (FIG. 24 middle). In addition, when specimens before and after PNGase F treatment were subjected to detection with an anti-LOX-1 antibody after Western blot, the specimens were all detected with an anti-LOX-1 antibody (FIG. 24 right).

(Estimation of Sugar Chain Binding Position)

A specimen created using silkworm form CTLD14 contained in an electrophoresis gel fragment was subjected to reductive alkylation and trypsin digestion. The resulting peptide was measured by a matrix assisted laser desorption ionization-time of flight (MALDI-TOF) mass spectrometer and a liquid chromatography (LC) electrospray ionization Kingdon trap (ESI) mass spectrometer. For MALDI-TOFMS, AB SCIEX 4800 plus TOF/TOF Analyzer used α-cyano-4-hydroxy cinnamic acid as the matrix and irradiated 337 nm nitrogen gas laser onto the specimen for ionization to collect MS/MS spectrum from ions in the order of higher intensity. LC-ESIMS used Thermo Fischer Scientific's Orbitrap Veros Pro. Peptides separated (gradient program which raises the concentration of acetonitrile comprising 0.1% formic acid from 0% to 100% in 30 minutes and maintains the concentration for 10 minutes, 300 nL/min) using an EASY Spray column (PepMapCl8, 3 μm, 75 μm×15 cm, Thermo Fisher Scientific) with Thermo Fischer Scientific's nano LC (EASY nLC) were ionized to obtain each of their MS/MS spectrum. In each approach, ions were detected using the positive ion mode.

The mass spectra and MS/MS spectra were compared for samples with (PNGase-plus) and without (PNGase-minus) PNGase treatment.

CTLD: ions corresponding to two amino acid sequences 109-139 and 154-180 comprising a region expected to have N-linked glycosylation were not observed in specimens of PNGase-plus or PNGase-minus. However, ionization was observed in m/z which is 1 larger than the mass of ions corresponding to amino acid sequences 109-139 and 154-180 for only PNGase-plus. This is because an enzyme cleaves an N-linked sugar chain such that asparagine changes to aspartic acid (http://www.ncbi.nlm.nih.gov/books/NBK56012/). This is considered evidence for a sugar chain binding to asparagine.

Figure 29:
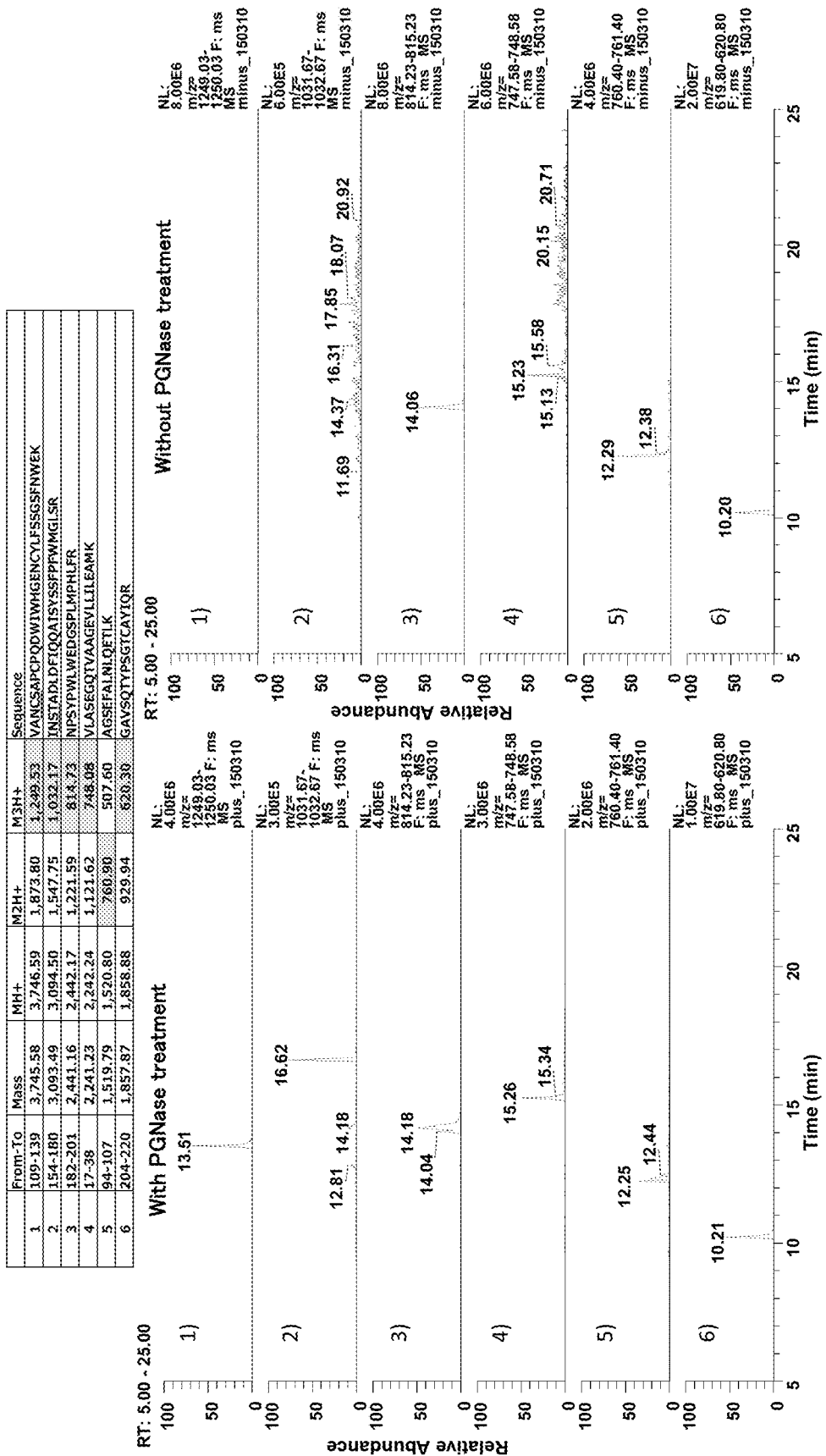
FIG. 29 shows results of LC-ESIMS of silkworm form CTLD14 trypsin digested substance with or without PNGase F treatment of silkworm form CTLD14. The focus was on peptide fragments (1, 2, 3) comprising N-X-S/T expected to be glycosylated and peptide fragments (4, 5, 6) with similar chain lengths to compare spectra by the presence and absence of PNGase F treatment. Peptides were not observed without PNGase F treatment in peptides 1 and 2 comprising NCS or NST, while a signal was observed after PNGase F treatment, thus demonstrating glycosylation. Meanwhile, a signal was observed at the same position for peptide 3 regardless of the presence/absence of PNGase F treatment, demonstrating the lack of glycosylation. Furthermore, a signal was observed at the same elution position for peptides 4-6 which have a similar chain length but do not maintain the glycosylation site, regardless of the presence/absence of PNGase F treatment. Thus, it was verified that observation by the present approach and determination of the presence or absence of glycosylation are effective.
Figure 30:
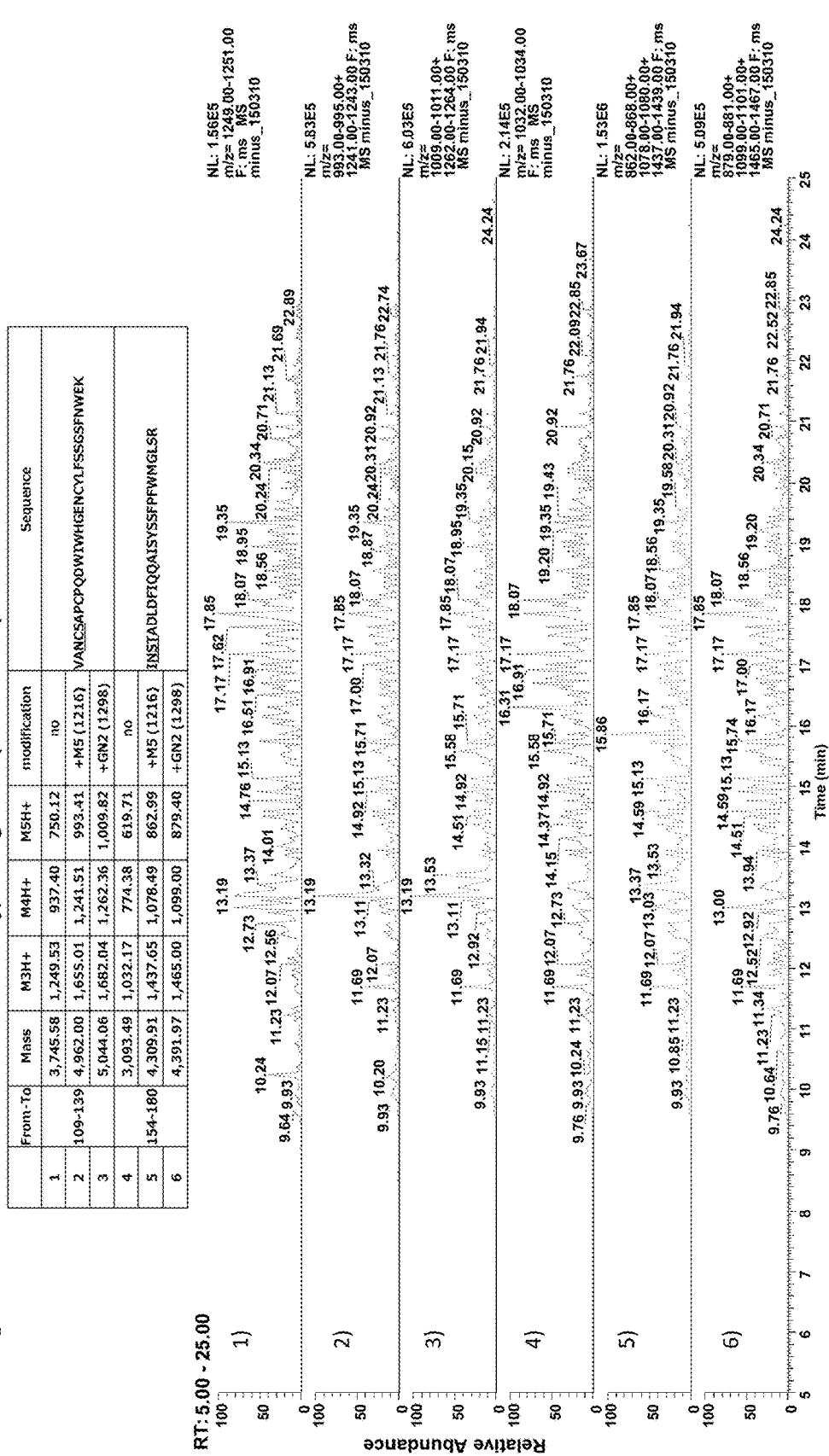
FIG. 30 shows results of LC-ESIMS of trypsin digested substance of a specimen without PNGase F treatment of CTLD14. It was examined whether an ion is detected when an expected silkworm form sugar chain is added to a peptide comprising NST and NCS. Ion (2) where a sugar chain corresponding to [Chemical 2] (2) was added and ion (3) where a sugar chain corresponding to [Chemical 5] (5) was added to a peptide comprising NCS were observed, such that [Chemical 2] (2) and [Chemical 5] (5) were revealed as sugar chain structures.
Figure 31:
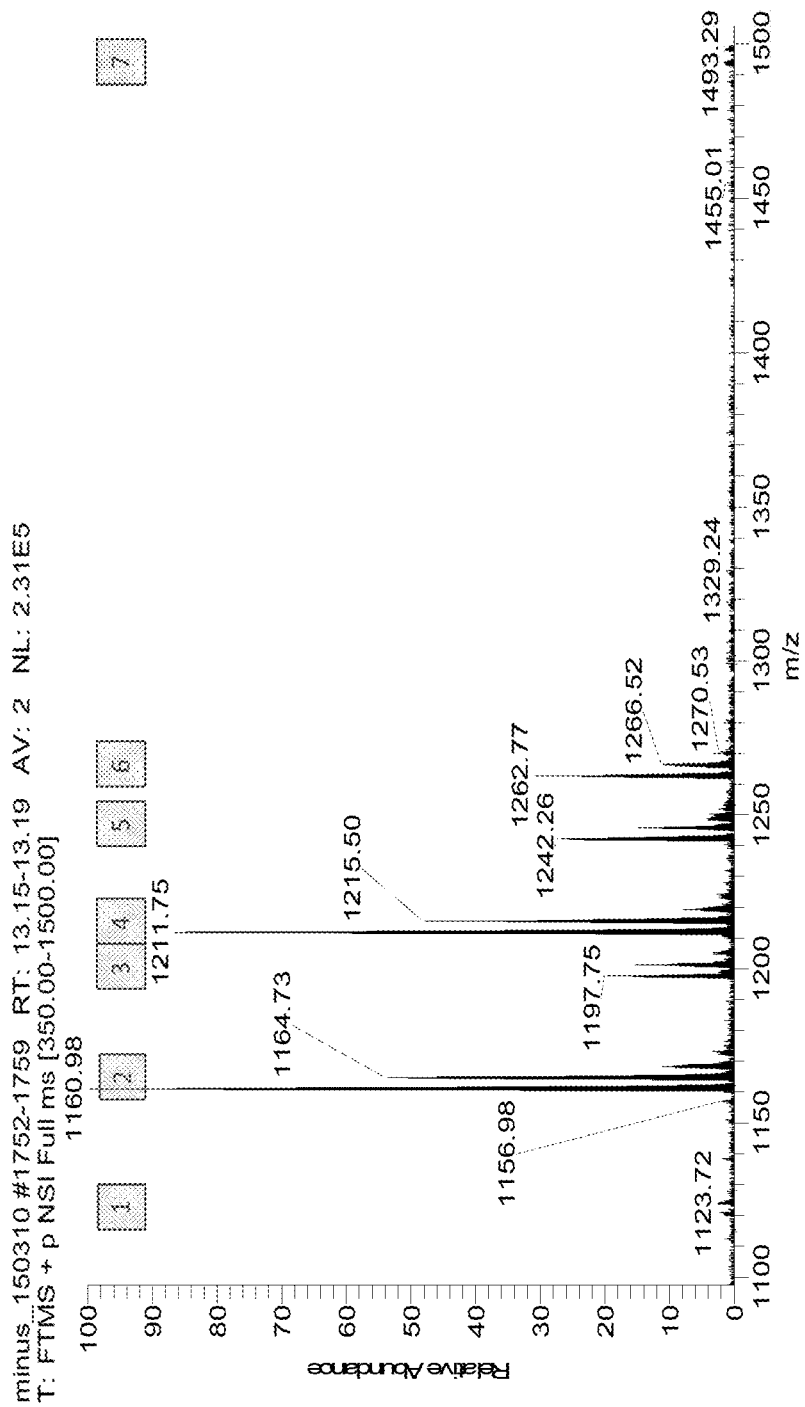
FIG. 31 is an expanded diagram of the mass spectrum near elution position 13.1 minute in FIG. 30 for observing the sugar chain structure expected to be added in more detail.

The above results suggested the possibility of a sugar chain binding to $^{111}N$ or $^{155}N$ in silkworm form CTLD. Results are shown in FIGS. 29 to 32. FIGS. 29 to 32 are summaries of results of mass spectrometry on silkworm form CTLD14. FIG. 29 shows results of LC-ESIMS on trypsin digestion product of silkworm form CTLD14 with and without PNGase F treatment. The focus was on peptide fragments (1, 2, and 3) comprising N-X-S/T expected to have glycosylation and peptide fragments (4, 5, and 6) with approximately the same chain length to compare spectra by the presence of absence of PNGase F treatment. Peptides were not observed without PNGase F treatment for peptides 1 and 2 comprising NCS or NST, while a signal was observed after PNGase F treatment. Thus, such peptides were demonstrated to be glycosylated. Meanwhile, a signal was observed at the same position regardless of the presence or absence of PNGase F treatment for peptide 3, which was demonstrated to be without glycosylation. Furthermore, for peptide 4 to 6, which have about the same chain length but do not maintain a glycosylation site, a signal was observed at the same elution position regardless of the presence or absence of PNGase F treatment. Thus, observation by this approach and determination of the presence of glycosylation were confirmed to be effective. FIG. 30 shows results of LC-ESIMS of trypsin digested product of a specimen without PNGase F treatment of CTLD14. It was examined whether an ion is detected when an expected silkworm form sugar chain is added to a peptide comprising NST and NCS. Ion (2) where a sugar chain corresponding to [Chemical 2] (2) is added and ion (3) where a sugar chain corresponding to [Chemical 5](5) is added to a peptide comprising NCS were observed, such that [Chemical 2] (2) and [Chemical 5] (5) were revealed as a sugar chain structure. FIG. 31 is an expanded diagram of a mass spectrum near elution position 13.1 minute in FIG. 30 for observing the sugar chain structure expected to be added in more detail. FIG. 32 is a table summarizing the difference in mass of peptides and ions observed at the mass spectrum near 13.1 minute which is expanded and shown in FIG. 31, and results of examining the sugar chain structures expected to be added in detail. While an ion indicating a difference in mass suggesting a part of a sugar has come off with the preparation of a specimen was found, the presence was confirmed of a sugar chain shown as [Chemical 1] (1) (left column, 892.34), [Chemical 2] (2) (1298.5), [Chemical 3] (3) or [Chemical 4] (4) (1095.42). In view of the above, it is possible that a sugar chain is linked to NCS (111N) or NST (155N) in silkworm CTLD14. Furthermore, the sugar chain mass number is expected to be about 2500. In view of the results of FIGS. 29-32, the following combination is estimated: (trimannosyl core 892)×2+(GlcNAc203)×2+(Man162)×2 or (trimannosyl core 892)×2+(GlcNAc203)×1+(Man162)×3.

(Dimer Formation)

Figure 25:
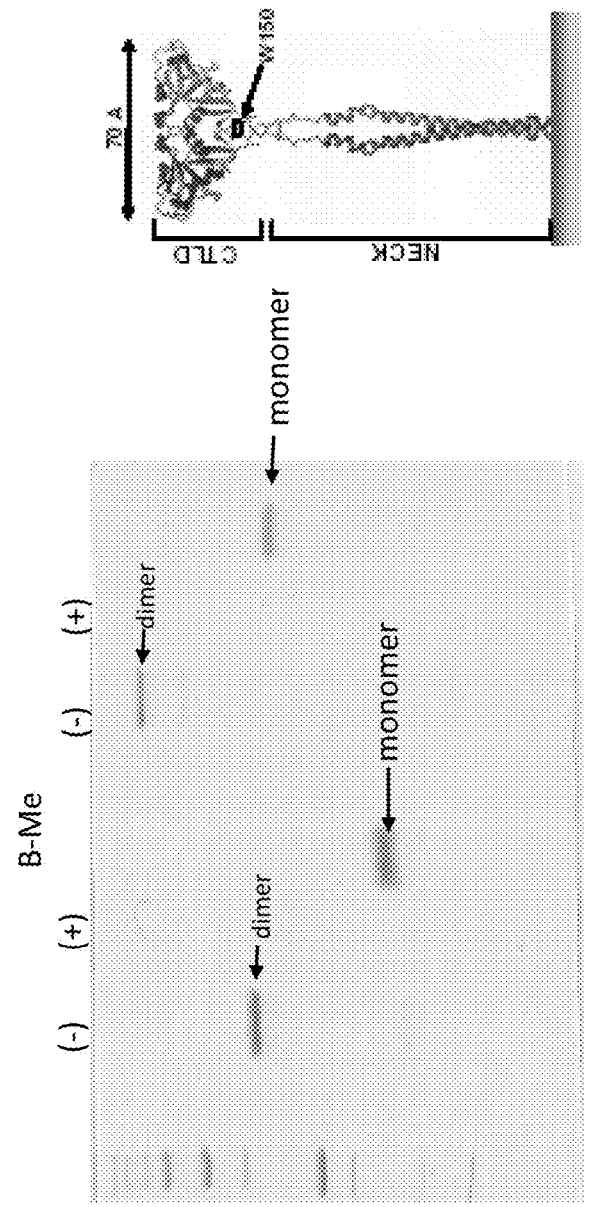
FIG. 25 confirms that a protein band at a dimer position shifts to a monomer position with 2-mercaptoethanol (β-Me) treatment. The left side shows *E. coli* form CTLD14, and the right side shows silkworm form CTLD14. CTLD14 was confirmed as forming a dimer which is the correct quaternary structure in the silkworm body.

CTLD14, for which a protein band at a dimer position is confirmed to shift to a monomer position by 2-mercaptoethanol (1-ME) treatment, was confirmed to form a dimer in the silkworm body (FIG. 25).

Example 13: Examination of Antibody for Evaluation Using Silkworm Form CTLD14

This Example developed an evaluation system using silkworm form CTLD14. In this case, an antibody to be combined with CTLD14 is required.

Conventional antibodies include anti-MDA-LDL, anti-oxidized PC and the like, which are merely antibodies that recognize a specific structure. The problems thereof include a disadvantage of having limited detectable structures.

Meanwhile, some antibodies broadly recognize LDLs to modified LDLs, but have problems such as nonspecificity or low reactivity. Such antibodies include anti-oxidized LDLs, anti-ApoB (large constituent protein of LDL), mouse monoclonal antibodies, rabbit polyclonal antibodies and the like. Examples of a disadvantage of an antibody obtained by immunizing mammals are that a good antibody cannot be obtained due to high homology of LDL (ApoB) among mammals. Thus, there was no antibody that can be commonly used from experimental animals to humans.

In this regard, current development proceeded with the focus on the chicken antibodies manufactured in Example 9. While a chicken monoclonal antibody itself already exists, a polyclonal antibody still has not been developed. As shown in the Examples, a monoclonal antibody had different recognition strength depending on the degree of LDL modification. Thus, the development thereof had a limitation. Therefore, it was decided that these Examples would use chicken polyclonal antibodies. With the above, manufacture of an antibody that broadly recognizes LDLs and oxidized LDLs of mammals from mice to humans was considered.

(Materials and Method)
(Anti-LDL Chicken Polyclonal Antibody)

The method of producing an anti-LDL chicken polyclonal antibody used in this Example was the same as that in Example 9.

(Anti-ApoB Chicken Monoclonal Antibody)

Commercially available antibodies (Pharma Foods, HUC20) were purchased and used.

(Anti-ApoB Mouse Monoclonal Antibody)

Commercially available antibodies (Acris BM2149) were purchased and used.

(LDL Detection Protocol)

LDLs, acetylated (Ac) LDLs, malondialdehydized (MDA) LDLs, partially oxidized (moOx) LDLs, and fully oxidized (fuOx) LDLs were used as subjects of detection. Commercially available LDLs (Biomedical Technologies, BT-903) and AcLDLs (Biomedical Technologies, BT-906) were used. MDA-LDLs were prepared by reacting commercially available LDLs with malondialdehyde. Oxidized LDLs were prepared by reacting commercially available LDLs with copper oxide. Oxidized LDLs reacted for 4 hours at 37° C. were considered partially oxidized, and those reacted for 20 hours at 37° C. were considered fully oxidized. Commercially available anti-ApoB chicken monoclonal antibodies (Pharma Foods, HUC20) were used. An anti-chicken IgY-HRP conjugate (Promega, G1351) was used as a secondary antibody. Commercially available anti-ApoB mouse monoclonal antibodies (*Acris* BM2149) were used. HPR-labeled anti-mouse IgG (Millipore, AP192P) was used as a secondary antibody.

(Direct Direction Method Using Chicken Anti-LDL Antibody)

LDLs subjected to detection (LDLs, acetylated LDLs, partially oxidized LDLs and fully oxidized LDLs) were added to a polystyrene 96-well microwell plate at 100 µl/well at concentrations of 0.2 and 1.5 µg/ml and allowed to adsorb overnight at 4° C. The plate was washed three times with PBS (200 µl/well). Blocking buffer (0.25% BSA/PBS) was added at 250 µl/well. The mixture was left standing for 2 hours at room temperature. After the plate was washed three times with PBS (200 µl/well), anti-ApoB chicken polyclonal antibodies diluted 3000-fold with blocking buffer or anti-ApoB chicken monoclonal antibodies diluted 8000-fold with blocking buffer were added at 100 µl/well and reacted for 1 hour at room temperature. The plate was washed five times with PBS (200 µl/well) and HRP-labeled anti-chicken IgY (Promega, G1351) diluted 2000-fold with blocking buffer was added at 100 µl/well and reacted for 1 hour at room temperature. After washing the plate five times with PBS (200 µl/well), 3,3',5,5'-tetramethyl-benzidine (TMB) was added at 50 µl/well. The luminescence was examined and 150 p/well of 1N HCl was added to suspend the reaction. Subsequently, the absorbance at 450 nm of each well of the plate was measured.

(Results)

Figure 26:
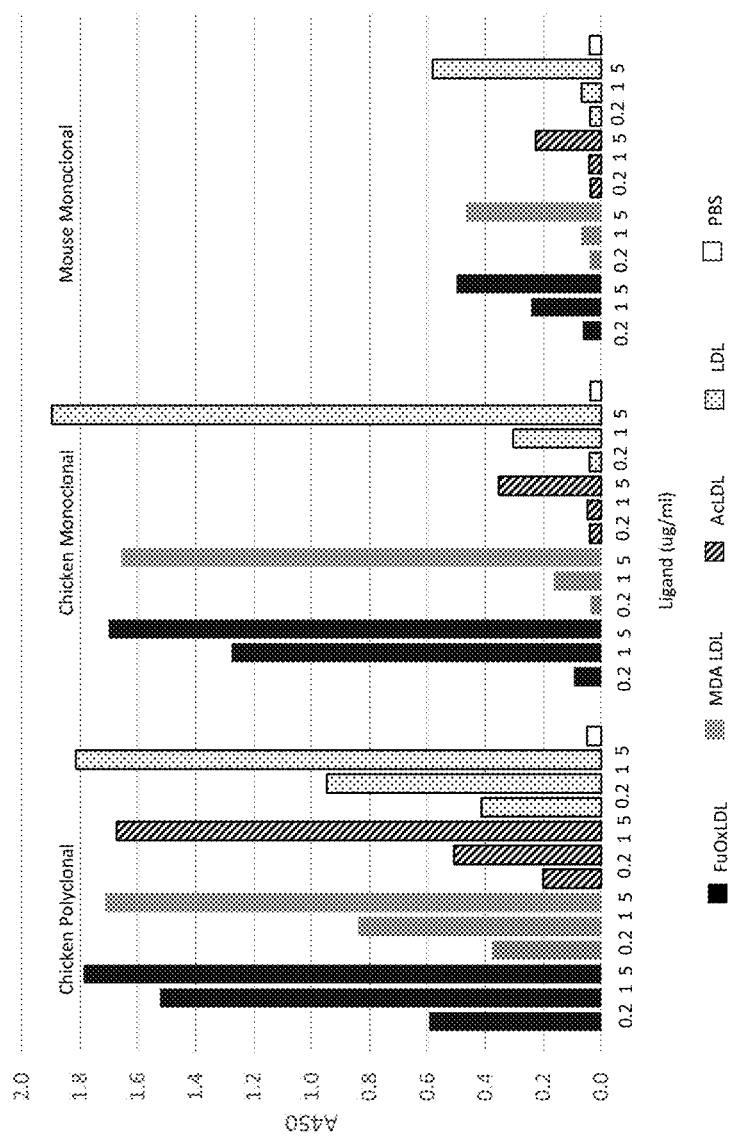
FIG. 26 is analysis of a feature of an anti-LDL chicken polyclonal antibody. LDLs, acetylated (Ac) LDLs, malondialdehydized (MDA) LDLs, and fully oxidized (fuOx) LDLs were used as subjects of detection. Commercially available LDLs (Biomedical Technologies, BT-903) and Ac LDLs (Biomedical Technologies, BT-906) were used. MDA-LDLs were prepared by reacting commercially available LDLs with malondialdehyde. Oxidized LDLs were prepared by reacting commercially available LDLs with copper oxide. Oxidized LDLs reacted for 4 hours at 37° C. were considered partially oxidized, and those reacted for 20 hours at 37° C. were considered fully oxidized. Commercially available anti-ApoB chicken monoclonal antibodies (Pharma Foods, HUC20) were used. HRP-labeled anti-chicken IgY (Promega, G1351) was used as a secondary antibody. Commercially available anti-ApoB mouse monoclonal antibodies (Acris BM2149) were used. HPR-labeled anti-mouse IgG (Millipore, AP192P) was used as a secondary antibody. Left: shows detection of LDLs by anti-LDL chicken polyclonal antibodies. Columns indicate, from the left, fully oxidized LDLs (fuOxLDL), MDA-LDL, AcLDL, unmodified LDL, and PBS, and the numbers indicate the concentration of the detection subjects. This shows that all of fully oxidized LDL (fuOxLDL), MDA-LDL, AcLDL, and unmodified LDL can be recognized. Middle: shows detection of anti-ApoB chicken monoclonal antibody LDLs. Columns indicate, from the left, fully oxidized LDLs (fuOxLDL), MDA-LDL, AcLDL, unmodified LDL, and PBS, and the numbers indicate the concentration of the detection subjects. The ability to recognize fully oxidized LDLs (FoxLDL) is high, but recognition strength is inconsistent depending on the type of modification. Right: shows detection by an anti-ApoB mouse monoclonal antibody. Columns indicate, from the left, fully oxidized LDLs (fuOxLDL), MDA-LDL, AcLDL, unmodified LDL, and PBS, and the numbers indicate the concentration of the detection subjects. It can be seen that the recognition ability was low overall, and there is no major difference in the ability to recognize oxidized LDLs and unmodified LDLs. In view of the above results, it can be understood that a true risk factor detection system for the onset of arteriosclerosis can be developed by a combination of an anti-LDL chicken polyclonal antibody and CTLD14.

Results are shown in FIG. 26. The left side shows detection of LDLs by an anti-LDL chicken polyclonal antibody. It can be seen that all of fully oxidized LDLs (fuOxLDL), MDA-LDL, AcLDL, and unmodified LDLs can be recognized. In FIG. 26, LDL detection by an anti-ApoB chicken monoclonal antibody is shown. It can be understood that the ability of recognizing a fully oxidized LDL (FoxLDL) is high, but the recognition strength is not consistent depending on the type of modification. The right side of FIG. 26 shows LDL detection by an anti-ApoB mouse monoclonal antibody. It can be understood that the recognition ability is low overall and there is no significant different in the ability to recognize oxidized LDLs and unmodified LDLs.

This Example proves that a detection system for a true risk factor for arteriosclerosis or the like can be developed with a combination of an anti-LDL chicken polyclonal antibody and CTLD14.

LDLs are highly homologous among mammals such that an excellent antibody is difficult to obtain when immunizing a mouse, but a chicken polyclonal antibody obtained by immunizing an avian, chicken, can be utilized broadly in detection of mammalian specimens. It is considered possible to be utilized broadly from detection in animal experiments (mouse, rat, rabbit or the like) to detection in humans by a combination thereof with CTLD14.

Example 14: Development of Assay Using CTLD14 Comprising Silkworm Form Sugar Chain Next, based on the results of Example 13, an attempt was made to develop a detection system of a true risk factor for the onset of arteriosclerosis by a combination of an anti-LDL chicken polyclonal antibody and CTLD14.

This Example carried out an oxidized LDL detection approach with silkworm form CTLD14 and an anti-LDL chicken antibody. A combination of *E. coli* form CTLD14 and the anti-LDL chicken antibody of the invention was used as a comparative example.

(Materials and Method)

*E. coli* form CTLD14 was manufactured as disclosed in Comparative Example 1.

Silkworm form CTLD14 was manufactured as disclosed in Example 12.

An anti-LDL chicken polyclonal antibody was manufactured as in Example 9.

Commercially available anti-ApoB chicken monoclonal antibodies (Pharma Foods, HUC20) were used.

(Sandwich Method)
(Materials)

CTLD14 expressed and purified with a silkworm and *E. coli* was used based on a direct direction method as well as the methods disclosed in Comparative Example 1 and Example 12 as discussed above.

(Method)
(Sandwich Method with CTLD14 and Chicken Antibody)

20 µg/ml/PBS of CTLD14 (silkworm expressed, *E. coli* expressed) were added to a polystyrene 96-well microwell plate at 50 µl/well and allowed to adsorb overnight. The plate was washed three times with PBS (200 µl/well). Blocking buffer (0.25% BSA/PBS) was added at 250 µl/well. The mixture was left standing for 2 hours at room temperature. After the plate was washed three times with PBS (200 µl/well), 0.05 to 8 µg/ml of LDLs (LDLs, acetylated LDLs, partially oxidized LDLs, and fully oxidized LDLs) were added at 100 µl/well and reacted for 2 hour at room temperature. The plate was washed five times with PBS (200 µl/well) and anti-LDL chicken polyclonal antibodies diluted 6000-fold with blocking buffer or anti-ApoB chicken monoclonal antibodies diluted 8000-fold with blocking buffer were added at 100 µl/well and reacted for 1 hour at room temperature. The plate was washed five times with PBS (200 µl/well) and HRP-labeled anti-chicken IgY (Promega, G1351) diluted 2000-fold with blocking buffer was added at 100 µl/well and reacted for 1 hour at room temperature. After washing the plate five times with PBS (200 µl/well), TMB was added at 50 µl/well. The luminescence was examined and 50 µl/well of 1N HCl was added to suspend the reaction. Subsequently, the absorbance at 450 nm of each well of the plate was measured.

(Results)

Figure 27:
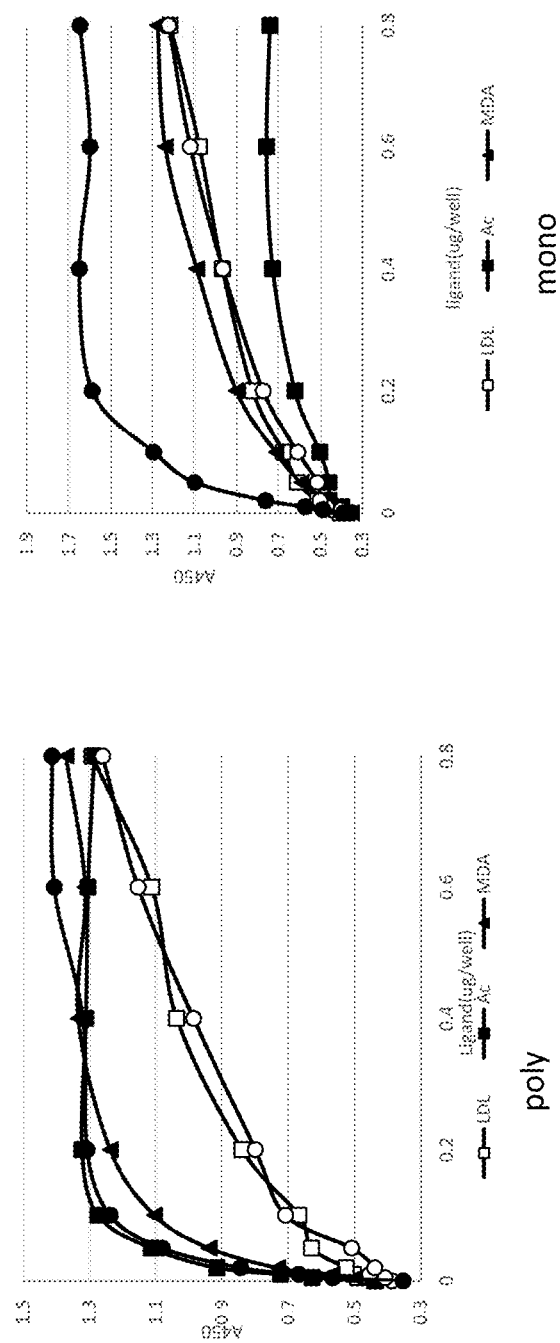
FIG. 27 shows results with a combination of *E. coli* form CTLD14 and the anti-LDL chicken antibody of the present application. Open squares indicate unmodified LDLs, filled squares indicate AcLDLs, filled triangles indicate MDA LDLs, open circles indicate mo (partially oxidized LDLs), and filled circles indicate fu (fully oxidized LDLs). Left: shows the results of detection of LDLs and modified LDLs by the sandwich method using *E. coli* derived CTLD14 and anti-LDL chicken polyclonal antibodies. At the low concentration region (10 ng/well, 0.1 μg/ml or less as solution concentration), oxidatively modified LDLs can be specifically detected (no significant difference from LDLs for moLDLs: partially oxidized LDLs). Right shows detection of LDLs and modified LDLs by the sandwich method using *E. coli* derived CTLD14 and anti-ApoB chicken monoclonal antibodies. The detection of fuLDL: fully oxidized LDLs is excellent, but MDA-LDLs, AcLDLs and moLDLs are poorly recognized. It was found that it is difficult to detect the typical LDL, MDA-LDL.

FIG. 27 shows results of a combination of *E. coli* form CTLD14 and the anti-LDL chicken antibody of the present application. The left side of FIG. 27 shows results of detection by the sandwich method using *E. coli* form CTLD14 and anti-LDL chicken polyclonal antibodies. At a low concentration region (0.1 µg/well, 1 µg/ml or less as solution concentration), it can be understood that oxidatively modified LDLs can be specifically detected (no significant difference from LDLs for moLDLs: partially oxidized LDLs). Right side of FIG. 27 shows detection by the sandwich method using *E. coli* form CTLD14 and anti-ApoB chicken monoclonal antibodies. The detection of fuOxLDL: fully oxidized LDLs are excellent, but the MDA-LDLs, AcLDLs and moOxLDLs are poorly recognized. It was found that it is difficult to detect the typical LDL, MDA-LDL.

Figure 28:
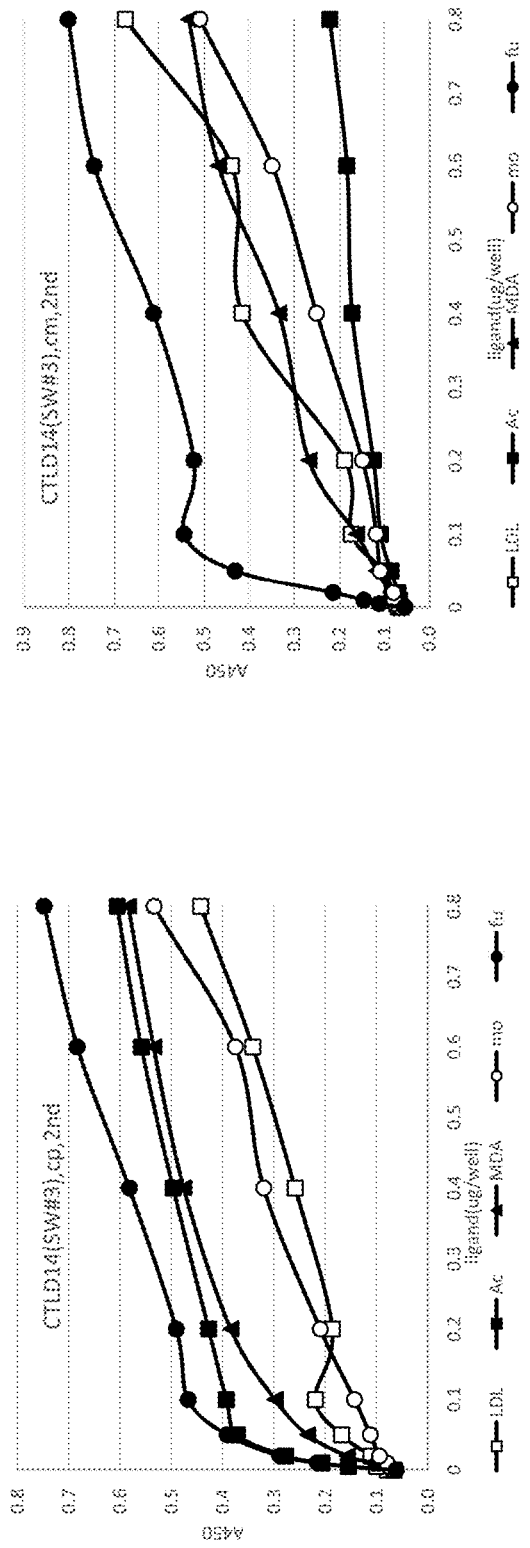
FIG. 28 shows results with a combination of silkworm form CTLD14 and the anti-LDL chicken antibody of the invention. Open squares indicate unmodified LDLs, filled squares indicate AcLDLs, filled triangles indicate MDA LDLs, open circles indicate mo (partially oxidized LDLs), and filled circles indicate fu (fully oxidized LDLs). Left: shows detection of LDLs and modified LDLs by the sandwich method using genetically modified silkworm form CTLD14 and anti-LDL chicken polyclonal antibodies. All modified LDLs can be detected (moLDL: partially oxidized LDLs are poorly recognized). Compared to a combination with *E. coli* form CTLD14, the concentration range for detection of a modified LDL without reacting with an LDL is very wide. Right: shows detection of LDLs and modified LDLs by the sandwich method using genetically modified silkworm form CTLD14 and anti-ApoB chicken monoclonal antibodies. Detection of fuOxLDL: fully oxidized LDLs is excellent, but there is difficulty in the detection of MDA-LDLs and AcLDLs.

FIG. 28 shows results of a combination of silkworm form CTLD14 and the anti-LDL chicken antibody of the invention. Left side of FIG. 28 shows detection by the sandwich method using silkworm form CTLD14 and anti-LDL chicken polyclonal antibodies. All modified LDLs can be detected (moOxLDL: partially oxidized LDLs are poorly recognized). Compared to a combination with *E. coli* form CTLD14, the concentration range where there is no reaction with an LDL while detecting a modified LDL is very wide. Right side of FIG. 28 shows detection by the sandwich method using genetically modified silkworm form CTLD14 and anti-ApoB chicken monoclonal antibodies. It is demonstrated that detection of fuOxLDL: fully oxidized LDLs are excellent, but there is difficulty in the detection of MDA-LDLs and AcLDLs.

Although data is not shown, it is expected that glycated LDLs can also be detected.

Example 15: Development of Additional Evaluation System Using CTLD14 Comprising Silkworm Form Sugar Chain An experiment is conducted using the same approach as Example 14 by using glycated LDLs as the subject.

As a result, it is expected that glycated LDLs are shown to be detectable by sandwich method using silkworm form CTLD14 and anti-LDL chicken polyclonal antibodies as in Example 14.

Comparative Example 2: Expression of sRAGE with *E. coli*

As a subject of comparison, sRAGE was expressed in an *E. coli* expression system, which is a conventional technique. The details are shown below.

(Methods and Materials)

Origami B (DE3) was used as a host bacterial cell. NdeI was used on the 5' side and XhoI (BamHI, SmaI, or HindIII can also be used) was used on the 3' side as the RAGE gene cloning site of interest. As a result, a biotinylated amino acid sequence that is recognized by a biotin ligase is added to the C-terminus side of the protein of interest. For RAGE, the N-terminus side is an extracellular domain which is essential for recognizing AGE. Thus, a biotinylated amino acid sequence was added to the C-terminal side such that immobilization is possible at the C-terminal side upon chipping or the like. By using this procedure, a nucleic acid sequence encoding the biotinylated amino acid sequence "GLN-DIFEAQKIEWHE" (SEQ ID NO: 98) is linked to the C-terminal side of the amino acid sequence of SEQ ID No: 97 to make a plasmid disposed under the control of a T7 promotor. This plasmid and a plasmid expressing a biotin ligase gene (plasmid in which a biotin ligase gene is inserted into a p15A line plasmid, pAC vector, which can stably coexist in the same cell due to a different incompatibility group with a ColEl line pET vector) were both used to transform a host bacterial cell. The medium used to culture the transformed host cell was an altered LB medium (0.5% NaCl, 0.5% yeast extract, and 1% trypsin) supplemented with 50 µg/ml ampicillin, 34 µg/ml chloramphenicol, 15 µg/ml kanamycin, and 12.5 µg/ml tetracycline. The pre-cultured solution cultured over night at 25° C. was added to the medium so that the final concentration would be 5% and stirred and cultured at 25° C. It is also possible to shorten the culture period up to the start of induction by increasing the added amount to the culture to 5% or greater. When pre-culture was conducted at 37° C., the proportion obtained as soluble decreased when the added amount exceeded 5%. When the absorbance in terms of $A_{600}$ reached 0.5 to 0.7 after culture, 1 m MIPTG and 50 µM d-biotin (D form [(+)-cis-hexahydro-2-oxo-1H-thieno-(3,4)-imidazole-4-valeric acid)]) (all final concentrations) were added to start biotinylation and induction of a protein of interest, and the mixture was further stirred and cultured for 18 hours, whereby the protein of interest was able to be expressed as a soluble biotinylated protein. At a culture temperature of 37° C., nearly 100% of the protein of interest would be insoluble. About 80% of expressed proteins of interest could be expressed as a soluble protein by decreasing the culture temperature to 25° C.

(Preparation of RAGE from Culture Liquid)

After collection of bacterial cells, the cells were suspended in a lysis buffer (protease inhibitor supplemented 20 mM Tris, 150 mM NaCl, 10 mM imidazole, pH of 7.6) and pulverized with ultrasound waves. The centrifuged supernatant was used as raw solution (soluble fraction). A His tag present at the N-terminus was utilized to bind to an Ni agarose column, and elution was performed by an imidazole concentration gradient with a FPLC system. After a fraction comprising soluble biotinylated RAGE was collected and dialyzed with a lysis buffer, AviTag (C-terminal) ("GLN-DIFEAQKIEWHE" (SEQ ID NO: 98)) was used for binding to a streptavidin mutein matrix (Roche) column. Purified soluble biotinylated RAGE was obtained by elution with 3 mM d-biotin. Ultimately, 5 mg of purified soluble biotinylated RAGE could be obtained per 1 L of culture.

(Results)

Figure 38:
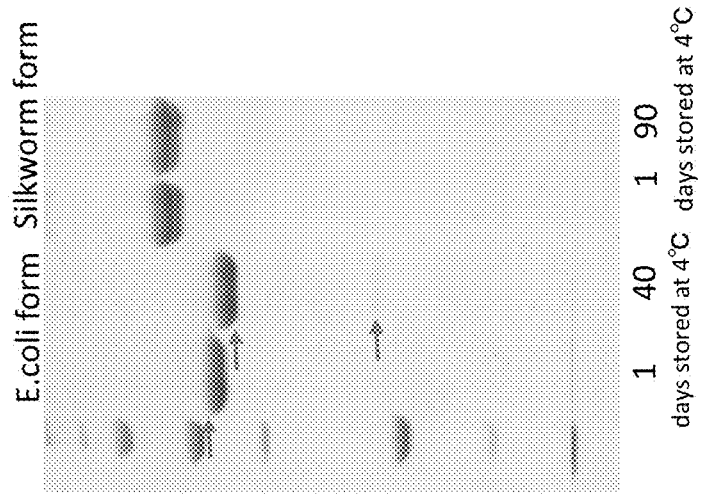
FIG. 38 shows stability of silkworm form sRAGE. The left side shows *E. coli* form sRAGE and the right side shows the silkworm form sRAGE of the invention. Results are shown for specimens immediately after purification (1 day), after 40 days of storage at 4° C., and immediately after purification (1 day) and after 90 days of storage were subjected to 12% SDS-PAGE and Coomassie staining. The arrows show fragmented sRAGE. Even after 90 days, fragmentation was not observed in silkworm forms, such that significant improvement in stability was confirmed.

While sRAGE expression in an *E. coli* expression system is possible, it is very unstable. In addition, nearly 100% is fragmented in about 1.5 months and lose the recognition ability. MiniRAGE which was stabilized only at sites required for recognition and amino acid mutation of a fragmented site was also created, but the expression is low and the recognition ability is inferior compared to a full length extracellular matrix (sRAGE) (FIG. 38).

Example 16: Improvement in Stability by Glycosylation

Figure 33:
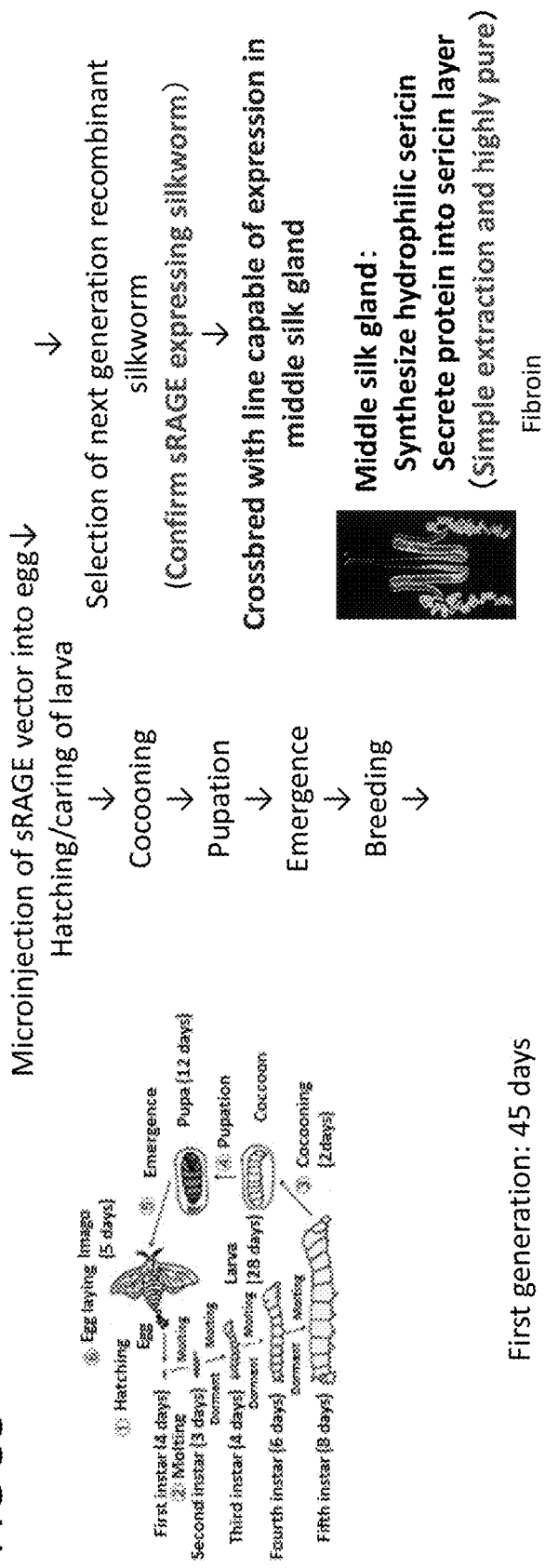
FIG. 33 is a schematic diagram of production by the silkworm used in the present invention.

In this regard, this Example attempted to produce sRAGE by a genetically modified silkworm, which is the focus in the present invention. Briefly, an sRAGE vector was injected into a silkworm egg by microinjection to obtain a RAGE expressing silkworm. Furthermore, the silkworm was crossbred with a line capable of expression in the middle silk gland to create a genetically modified silkworm expressing RAGE in the middle silk gland (extraction is simple and high purity). FIG. 33 shows a schematic diagram. The detailed protocol is shown below.

(Materials and Methods)

(Line Production, Expression, Etc.)

A UAS vector was constructed by inserting a fragment encoding sRAGE and a fragment encoding a signal peptide of fibroin H chain amplified by PCR to the downstream of the UAS (Upstream Activation Sequence) sequence of pBac [Ser-UAS/3×P3EGFP] (Ken-ichiro Tatematsu, Isao Kobayashi, Keiro Uchino, Hideki Sezutsu, Tetsuya Iizuka, Naoyuki Yonemura, Toshiki Tamura, Transgenic Research, 19, 473 (2010)). The expression vector was used to create a genetically modified silkworm. The wl-pnd line of white eye/white egg/nondormant line maintained at the National Institute of Agrobiological Sciences was used as the host line. The resulting genetically modified silkworm was crossbred with UAS (Upstream Activation Sequence) of a line expressing GAL4 in the middle silk gland (Ken-ichiro Tatematsu, Isao Kobayashi, Keiro Uchino, Hideki Sezutsu, Tetsuya Iizuka, Naoyuki Yonemura, Toshiki Tamura, Transgenic Research, 19, 473 (2010)). Among the resulting next-generation silkworms, individuals with both a GAL4 construct and UAS construct were selected out by a selection marker. Larvae of $6^{th}$ day in the $5^{th}$ instar were dissected to extract the middle silk gland. Proteins were extracted by shaking for 2 hours at 4° C. with 1 mL of extraction solution of PBS+1% Triton X-100 per gland.

(Purification)

sRAGE was eluted out by having a solution of middle silk gland extract from which sericin was removed by freeze thaw treatment bind to Ni-Agarose balanced with PBS and raising the imidazole concentration in PBS stepwise. 250 mM to 1 M imidazole elution fraction was collected and dialyzed with PBS. When the level of purification needs to be further increased, the fraction was subjected to purification with TALON (metal chelate affinity using Co instead of Ni). 100 mM to 1M imidazole elution fraction was collected and dialyzed with PBS (−) as purified sRAGE (see FIG. 36).

(Glycopeptide Analysis)

Specimen with and without PNGase F treatment were subjected to electrophoresis with 15% SDS-PAGE and then Coomassie staining, and a protein band was cut out. The silkworm form sRAGE contained in the cut out gel fragment was acetamidated and digested with trypsin and measured by MALDI-TOFMS LC-ESMS. The mass spectra of the PNGase F treatment section and treatment free section were compared. The amino acid sequence comprising a region expected to have N-linked glycosylation was measured.

(Results)

FIG. 35 shows results of analysis of expression. A middle silk gland was extracted from four lines of genetically modified silkworms (1 to 4) and a negative control (only middle silk gland GALA4, no UAS: sRAGE is not expressed). Subsequently, 1 ml of PBS comprising 1% Triton X-100 was added to one middle silk gland. The mixture was prepared by inverting and mixing for 2 hours at 4° C. The left side shows results of staining proteins with Coomassie brilliant blue after electrophoresis of a specimen with 4 to 12% gradient SDS-polyacrylamide gel. The amount of specimen added to each lane was 5 µl/lane on the left side and 10 µl/lane on the right side. M: molecular weight markers (benchmark: Invitrogen) 1 to 4 indicate the line numbers of created genetically modified silkworms, and Nega: indicates negative control. The right side shows results of Western blot. A specimen, after deployment with 4 to 12% gradient SDS-PAGE, was transcribed onto a PVDF film. Anti-His rabbit antibody (1000-fold dilution)+anti-His mouse antibody (3000-fold dilution) was used as the primary antibody, and subsequently reacted with the secondary antibody, HRP-labeled anti-rabbit IgG & anti-mouse IgG antibody (200,000-fold dilution). The specimen was finally reacted with ECL Prime for detecting the generated luminescence to confirm sRAGE expression. The molecular weight was consistent with the estimated molecular weight (44 kDa only for the protein part and 44 kDa or greater with glycosylation).

Figure 36:
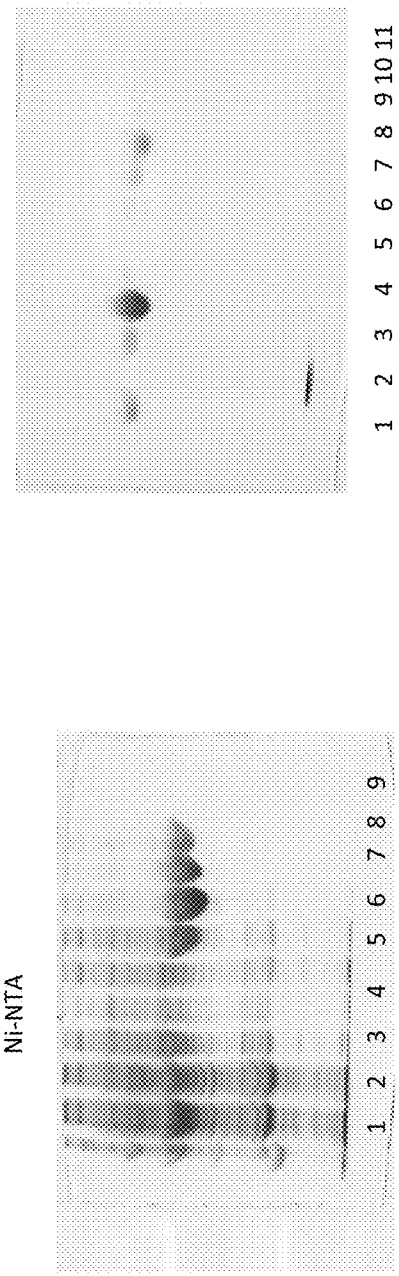
FIG. 36 shows the purification process of RAGE. The left diagram: a solution of a middle silk gland extract with sericin removed by freeze-thawing was bound to Ni-Agarose balanced with PBS, and the imidazole concentration in PBS was raised in stages to elute out sRAGE. Results are shown for a specimen subjected to SDS-PAGE at each stage and Coomassie staining. Lane 1: solution, 2: Ni-Agarose non-adsorption fraction, 3: Ni-Agarose adsorption fraction, 4: 20 mM imidazole elution fraction, 5: 100 mM imidazole elution fraction, 6: 250 mM imidazole elution fraction, 7: 500 mM imidazole elution fraction, 8: 1 M imidazole elution fraction, 9: non-elution fraction. An elution fraction was collected with 250 mM to 1M imidazole and dialyzed with PBS, and subjected to purification with TALON as needed. The right diagram: to increase the purification level of Ni-Agarose 250 mM to 1M elution fraction, it was bonded with TALON. The imidazole concentration was raised in steps to elute out sRAGE. Meanwhile, a tag for biotinylation, BIOEASE™ Tag biotin ligase birA substrate peptide (Life Technologies, Carlsbad, Calif.), was added to sRAGE. To confirm biotinylation, a bond to Streptavidin Mutein matrix was examined. Results are shown for the specimen at each stage subjected to SDS-PAGE and Coomassie staining. Lane 1: after Ni-Agarose purification (sufficient purification level was also confirmed even at this stage), 2: Mutein binding fraction, 3: Mutein non-adsorption fraction, 4: TALON adsorption fraction, 5: TALON non-adsorption fraction 6: 50 mM imidazole elution fraction, 7: 100 mM imidazole elution fraction, 8: 250 mM imidazole elution fraction, 9: 500 mM imidazole elution fraction, 10: 1M imidazole elution fraction, 11: TALON non-elution fraction. 100 mM to 1 M imidazole elution fractions were collected and dialyzed with PBS (−) to prepare purified sRAGE. This method resulted in 1.8 mg of purified protein from 13 ml solution (about 0.3 mg/silkworm in terms of one silkworm). Sufficiently usable sRAGE with a purity level of about 95% is obtained even if the binding/elution process to TALON is omitted. In this case, the yield would be 3-fold or greater.
Figure 37:
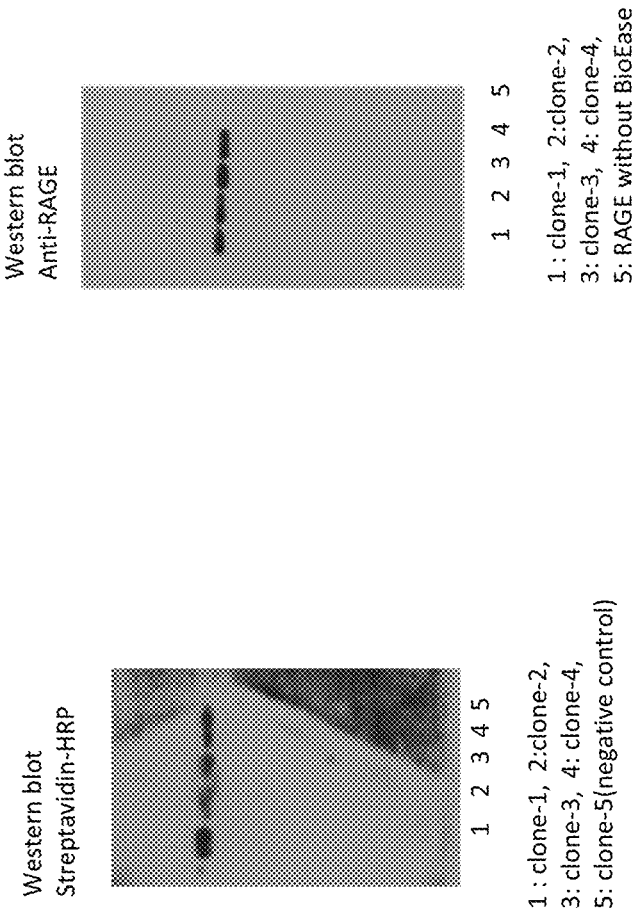
FIG. 37 shows a diagram confirming biotinylation of silkworm form sRAGE. The left diagram is the result of detecting biotinylation. Results are shown for a solution prepared from each line of genetically modified silkworms deployed in 12% SDS-PAGE and transcribed onto a PVDF film, and reacted with an HRP-labeled streptavidin, and then detecting a bond of streptavidin by ECL. Streptavidin specifically binds to biotin, such that biotinylation is confirmed by detecting streptavidin binding. Solutions prepared from lines 1, 2, 3, and 4 expressing sRAGE in the middle silk gland are subjected to each of Lanes 1 to 4. Lane 5 is a negative control (no expression of sRAGE). In lane 5, a signal was not observed, while a strong signal was observed in each of lanes 1 to 4 to which a specimen prepared from a middle silk gland of a genetically modified silkworm expressing sRAGE was added, demonstrating that a target protein can be biotinylated by adding and expressing a BIOEASE™ Tag biotin ligase birA substrate peptide (Life Technologies, Carlsbad, Calif.) in the body of a silkworm. The right diagram shows results of confirming that a protein confirmed to be biotinylated is RAGE. A solution prepared from each line of genetically modified silkworms, after deployment with 12% SDS-PAGE, was transcribed onto a PVDF film, and reacted with an anti-RAGE rabbit antibody as the primary antibody, and subsequently reacted with the secondary antibody HRP-modified anti-rabbit IgG. sRAGE was ultimately detected by ECL. Solutions prepared from lines 1, 2, 3, and 4 expressing sRAGE in the middle silk gland are subjected to each of Lanes 1 to 4. Lane 5 is a negative control (no expression of sRAGE). In lane 5, a signal was not observed, while a signal was observed in each of lanes 1 to 4. Furthermore, it was confirmed that signal positions matched with the diagram confirming biotinylation in the left diagram. This indicates that a protein confirmed to be biotinylated in the left diagram is sRAGE.

As shown in FIG. 36, silkworm form sRAGE was purified. 1.8 mg of purified protein was obtained from 13 ml of solution (about 0.3 mg/silkworm when calculated per silkworm). When process of binding to TALON and elution is omitted, sufficiently usable sRAGE with a purity of about 95% is obtained. In such a case, the yield is 3-fold or more (FIG. 36). As shown in FIG. 37, biotinylation of silkworm form sRAGE was examined. After Western blot, this was examined with an anti-RAGE antibody and HRP-labeled streptavidin. Biotinylation was confirmed in sRAGE from each line. Please also refer to FIG. 34.

(Sequence)

FIG. 34 shows a sequence of sRAGE manufactured in this Example. An N-linked sugar chain of a silkworm middle silk gland expressed protein has the following structure. sRAGE is specifically expressed in the silkworm middle silk gland. Sugar chains of a glycoprotein expressed in the middle silk gland are rarely a paucimannose type (with fucose) sugar chain or high mannose type sugar chain, which are found in sites other than the middle silk gland, and are complex type sugar chains, hybrid type sugar chains, or oligomannose type sugar chains. As a result of sugar chain analysis, glycosylation sites are determined to be aspartic acids at N-I-T and N-G-S. FIGS. 20 and 54 show examples of a structure of an N-linked sugar chain of a silkworm middle silk gland expressed protein.

(Sugar Chain Analysis)

Sugar chains were analyzed as discussed above. Glycosylation of silkworm derived sRAGE was examined to obtain results as disclosed in FIG. 39. As shown in FIG. 39, a molecular weight shift by removal of a sugar chain by PNGase F treatment was confirmed (FIG. 39 left). Further, it was no longer detected as a glycoprotein after PNGase F treatment as a result of glycoprotein staining before and after NGase F treatment (FIG. 39 middle). In addition, anti-RAGE antibodies were detected in each case as a result of detecting a specimen before and after PNGase F treatment with an anti-RAGE antibody after Western blot (FIG. 39 right).

(Sugar Chain Mass Spectrometry)

sRAGE with a silkworm form sugar chain contained in an electrophoresis gel fragment which was or was not treated with PNGase F was subjected to reductive alkylation and trypsin digestion. The resulting peptide was measured by a matrix assisted laser desorption ionization-time of flight (MALDI-TOF) mass spectrometer and a liquid chromatography (LC)-electrospray ionization Kingdon trap (ESI) mass spectrometer.

For MALDI-TOFMS, the following were used.
Apparatus: AB SCIEX 4800 plus TOF/TOF Analyzer
Matrix: α-cyano-4-hydroxy cinnamic acid
Laser: 337 nm nitrogen gas
MS/MS: MS/MS spectrum was collected from ions in the order of greater intensity.

LC-ESIMS used the following.
Apparatus (MS): Thermo Fischer Scientific's Orbitrap Veros Pro.
Apparatus (LC): Thermo Fischer Scientific's nano LC (EASY nLC)
Column: EASY Spray column (PepMapC18, 3 µm, 75 µm×15 cm, Thermo Fisher Scientific)
Solution: 300 nL/min, A) 0.1% formic acid, B) acetonitrile comprising 0.1% formic acid, gradient program which raises the concentration of B from 0% to 100% in 30 minutes and maintains the concentration for 10 minutes Subsequently, the mass spectra were compared for those with and without PNGase F treatment. Ions corresponding to two amino acid sequences comprising a region expected to have N-linked glycosylation were not or hardly observed in a specimen without PNGase treatment. Thus, it was understood that sugar chains were bound at two sites in sRAGE. After sugar chains were then cut out from silkworm form sRAGE and separated in an ODS column, the estimated sugar composition of 6 types of sugar chains was determined by MALDI-TOF-MS. Furthermore, the peak of each sugar chain whose sugar composition was estimated was separated by a normal phase Amido column. Furthermore, candidate sugar chains were narrowed down by GALAXY search from the molecular weight and Glucose unit (GU) value found with ODS and Amide columns. Finally, a specimen and a standard product of a sugar chain considered as a candidate were coninjected and separated by an ODS column to confirm a match between the candidate sugar chain and specimen to reveal that a sugar chain as shown in FIG. 54 is bound.

Example 17: Experiment of FIG. 38, Stability of sRAGE Comprising Silkworm Form Sugar Chain Next, the stability of *E. coli* form sRAGE manufactured in a comparative example and the sRAGE comprising a silkworm form sugar chain manufactured in Example 16 was examined. The procedure is shown below.

(Materials and Methods)
(Materials)

*E. coli* form and silkworm form sRAGE immediately after purification, *E. coli* form sRAGE stored for 40 days at 4° C. after purification, and silkworm form sRAGE stored for 90 days at 4° C. after purification were used.

(Methods)

10 µg (10 µl) of *E. coli* form and silkworm form sRAGE immediately after purification were treated with 5 µl of sample buffer for SDS-PAGE and stored at minus 20° C. *E. coli* form sRAGE stored for 40 days at 4° C. after purification, and silkworm form sRAGE stored for 90 days at 4° C. after purification were similarly treated. The specimens were subjected to electrophoresis in 12% SDS-PAGE and then Coomassie staining.

(Results)

The results are shown in FIG. 38. The stability of silkworm form sRAGE is shown. The left side shows *E. coli* form and the right side shows the silkworm form of the invention. 1 day and 40 day storage and 1 day and 90 day storage are shown, respectively. sRAGE comprising a silkworm form sugar chain is a very stable molecule, maintaining full length over a longer period in storage at 4° C. (confirmed up to half year as of the filing), while *E. coli* form is fragmented in 40 days.

The following Example 18 examines the retention of recognition ability using this molecule.

Example 18: Sandwich ELISA-Like Detection

Next, sandwich ELISA was used to confirm whether various AGESs can be detected using the sRAGE of the invention. The procedure thereof is shown below.

(Materials and Methods)
(Materials)

AGEs subjected to detection were prepared by maintaining BSA at a temperature at 37° C. for 12 weeks while aseptically maintaining the pH constant in the presence of ribose (R), fructose (F), and glucose (G). The control BSA (ctlBSA) was prepared by a similar reaction in the absence of sugar. As an antibody used in a sandwich-like detection system, an anti-BSA mouse monoclonal antibody (Abcam ab3781) was used, and an HRP-labeled anti-mouse IgG antibody (Merck Millipore AP192P) was used as the secondary antibody.

(Methods)

5 µg/ml/TBS of sRAGE (silkworm form or *E. coli* form) was added to a polystyrene 96-well microwell plate at 50 µl/well and allowed to adsorb overnight. The plate was washed three times with TBST (TBS, 0.05% Tween 20) at 200 µl/well. Protein free blocking buffer (Thermo Scientific) was added at 250 µl/well. The mixture was left standing for 2 hours at room temperature. After the plate was washed three times with TBST (200 µl/well), 0.01 to 8 µg/ml AGEs (R-AGEs, F-AGEs, G-AGEs, Ctl-AGEs) was added at 100 µl/well and reacted for 2 hour at room temperature. The plate was washed five times with TBST (200 µl/well) and anti-BSA mouse monoclonal antibody diluted 6000-fold with protein free blocking buffer was added at 100 µl/well and reacted for 1 hour at room temperature. The plate was washed five times with TBST (200 μl/well) and HRP-labeled anti-mouse IgG antibody diluted 5000-fold with protein free blocking buffer was added at 100 μl/well and reacted for 1 hour at room temperature. After washing the plate five times with TBST (200 μl/well), the luminescence was examined and 150 p/well of 1N HCl was added to suspend the reaction. Subsequently, the absorbance at 450 nm of each well of the plate was measured.

(Results)

Results are shown in FIG. 40. The left side shows recognition activity of *E. coli* form sRAGE after one week of storage after purification. The right side shows recognition activity of silkworm form sRAGE after 3 months of storage after purification. Since *E. coli* form is fragmented in about 40 days, AGE recognition ability is lost after 40 days such that AGE detection observed in the left diagram would be impossible. Meanwhile, the right diagram shows results of AGE detection by silkworm form sRAGE 90 days after purification. It was confirmed that recognition ability is maintained even after 90 days such that detection which is no different from the *E. coli* form in week 1 after purification is possible. In this manner, it is understood that sRAGE of the invention can be maintained extremely stably and is capable of highly sensitive detection.

Example 19: Production of Silkworm Form sRAGE and Silkworm Form CTLD14 by Silkworm Coexpressing Biotin Ligase This Example attempted production of a silkworm form sRAGE and silkworm form CTLD14 by a silkworm expressing a biotin ligase (BirA) specifically in the middle silk gland.

(Materials and Methods)

Figure 43:
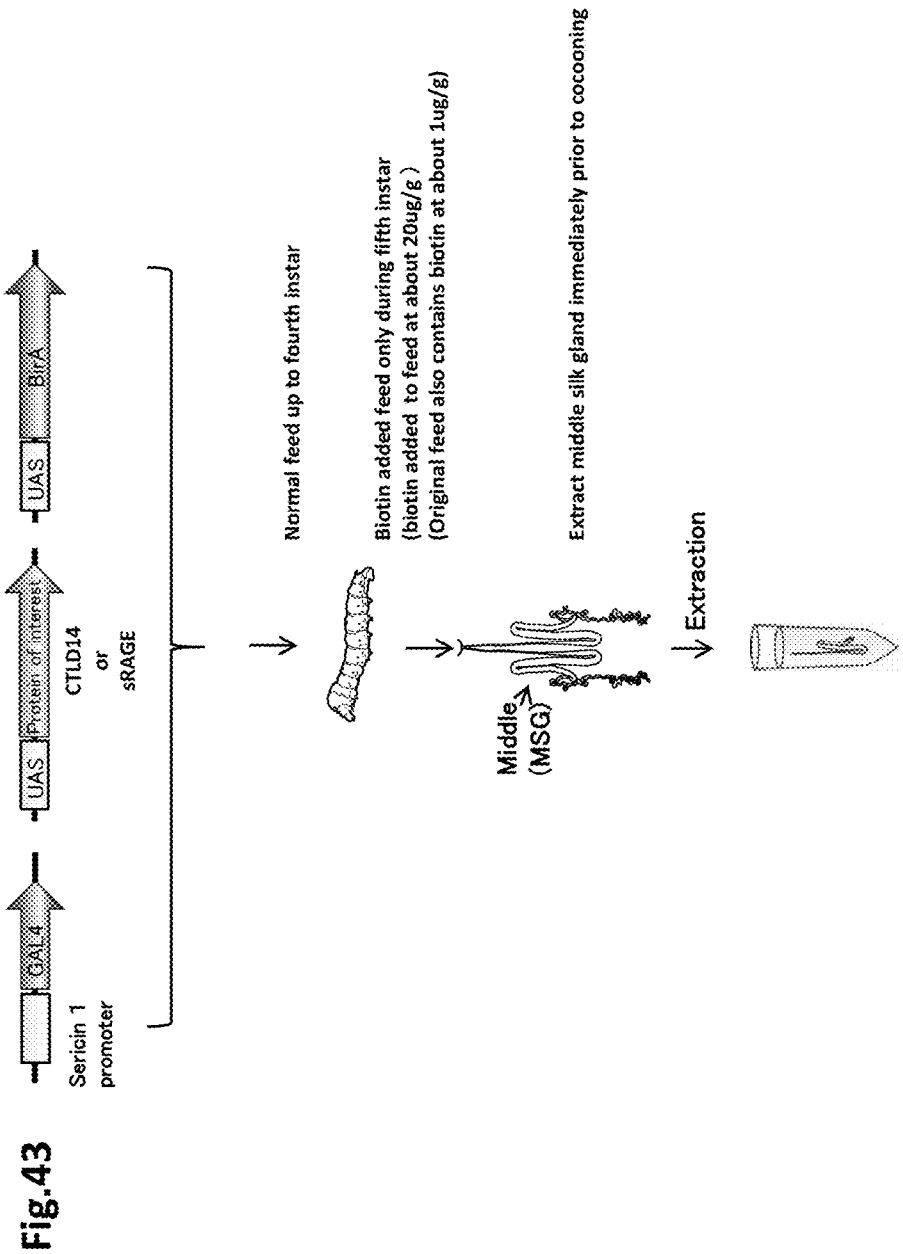
FIG. 43 shows a summary of silkworm form biotinylated protein production. As shown, three constructs were introduced into a single individual. Four lines were tested for BirA. A silkworm coexpressing a protein of interest and biotin ligase (BirA) was fed with biotin-added feed.

A genetically modified silkworm was created, which was introduced with three constructs: USA-Biotin tag CTLD14 (or USA-Biotin tag sRAGE) inserted with BIOEASE™ Tag biotin ligase birA substrate peptide (Life Technologies, Carlsbad, Calif.) CTLD14 (or BIOEASE™ tag sRAGE) downstream of the target sequence USA, USA-BirA inserted with a biotin ligase (BirA) downstream of the target sequence USA, and sericin 1 promotor (Ser1)-GAL which expresses GAL4 specifically in the middle silk gland. This silkworm expresses Biotin tag CTLD14 (or Biotin tag sRAGE) and BirA specifically in the middle silk gland. Furthermore, a larva in the $5^{th}$ instar was fed with feed supplemented with 20 μg of biotin per 1 g to supply biotin required for biotinylation of CTLD14 or sRAGE. Immediately prior to making a cocoon, the middle silk gland was extracted to extract a protein with TRITON® X-100 (Dow Chemical Co., Midland, Mich.)/PBS (−) (see FIG. 43).

(Examination of CTLD14 and sRAGE Expression)

Figure 44:
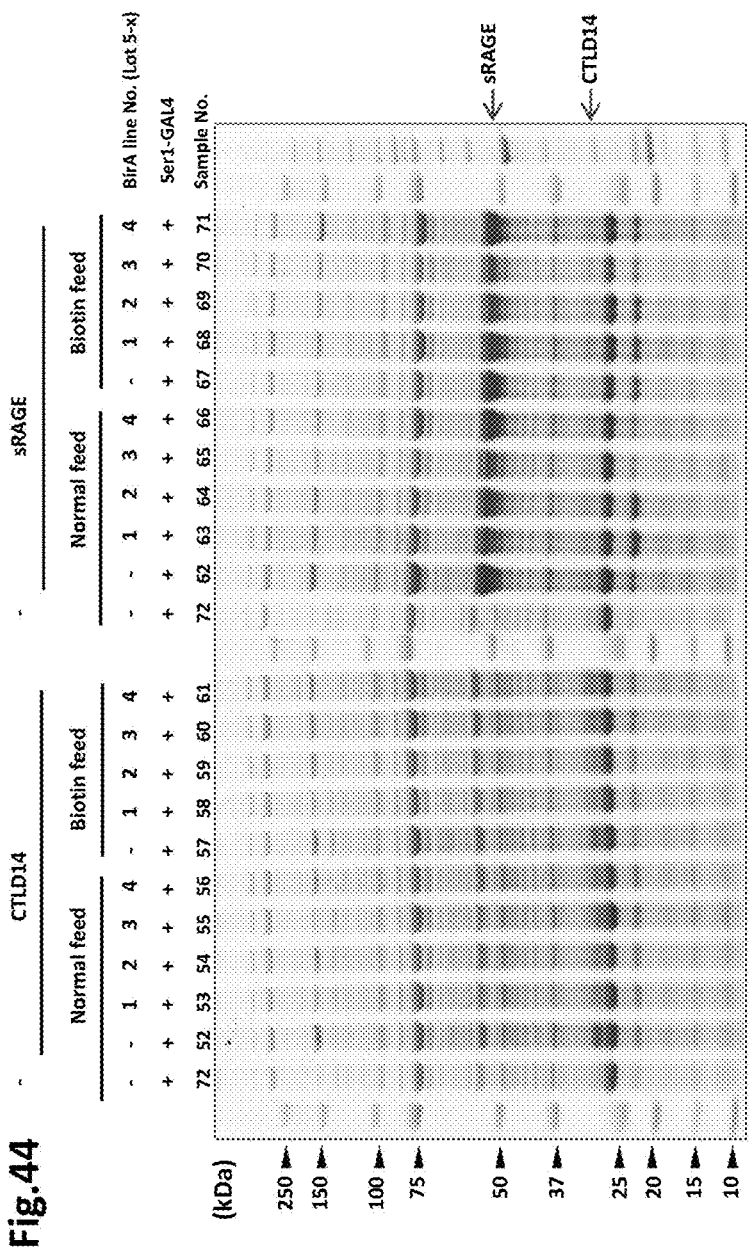
FIG. 44 shows results of Coomassie staining after SDS-PAGE of CTLD14 and sRAGE. "−" indicates a line that does not express BirA. Sample No. 72 is a negative control introduced with only Serl-GAL4.

FIG. 44 shows results of examining CTLD14 and sRAGE expression with Coomassie staining after SDS-PAGE. "−" is a line that does not express BirA. For each line, experimental sections for normal feed and biotin feed were provided. In the biotin feed section, feed supplemented with 20 μg of biotin per 1 g was given. Immediately prior to making a cocoon, the middle silk gland was extracted to prepare an extract solution treated with Triton X-100/PBS (−) and subjected to SDS-PAGE. Line 72 is a negative control introduced with only Ser1-GAL4 and no USB-CTLD14 (or USB-sRAGE). With regard to sRAGE, expression was confirmed at a position of the molecular weight of sRAGE (about 50 kDa) in lines 72 introduced with sRAGE. CTLD14 did not have expression as high as sRAGE.

(Examination of Biotinylation)

Figure 45:
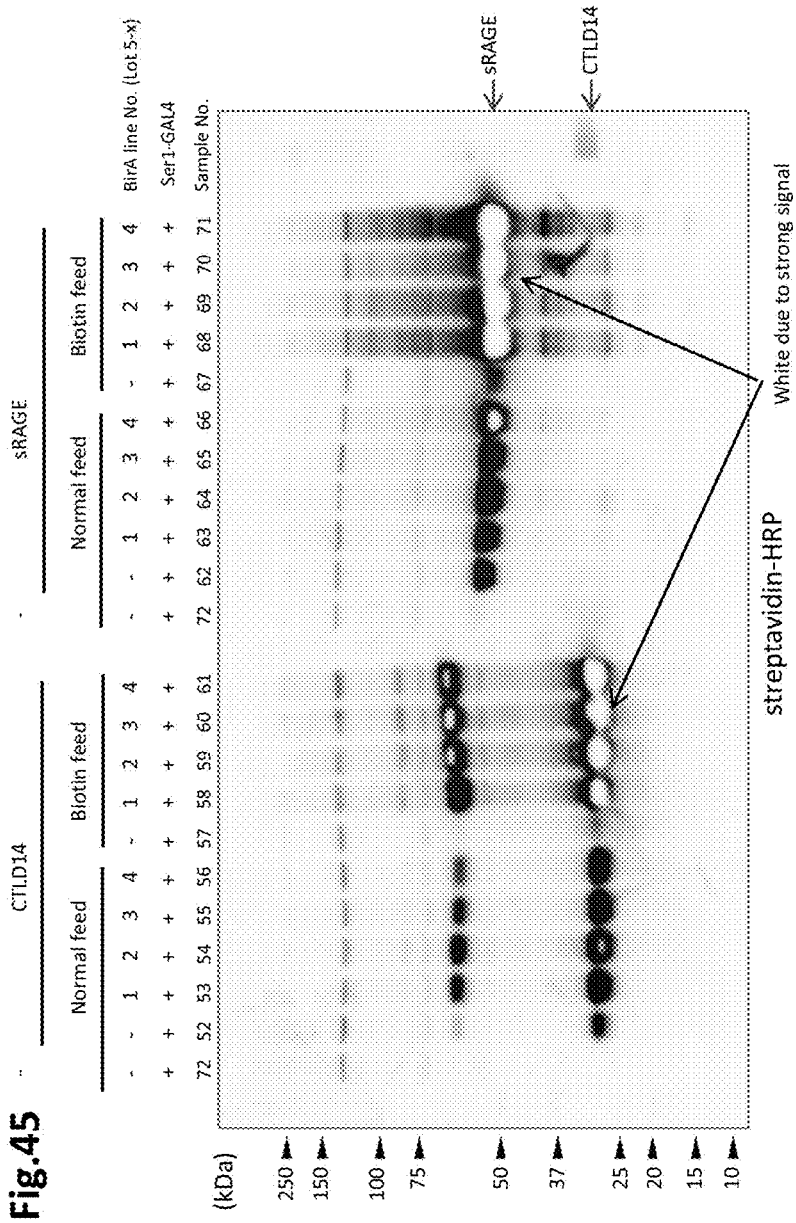
FIG. 45 shows results of Western blot for confirming biotinylation. The whited out band is due to a signal that is too strong. "-" indicates a line that does not express BirA. Sample No. 72 is a negative control introduced with only Serl-GAL4.

Next, biotinylation of each line was examined by Western blot (FIG. 45). The extract solution was deployed by SDS-PAGE and transcribed onto a PVDF film, and the solution was reacted with HRP-labeled streptavidin. Biotinylation was then confirmed by luminescence by ECL. Generally, a signal is obtained in black. What appears to be white is due to a luminescence signal being too strong (e.g., excessive biotinylation). A signal cannot be detected for a negative control (line 72). Meanwhile, although the signal is a very weak in the line of (−) BirA, a signal can be confirmed with coexpression of BirA (lines 1 to 4). A signal with a large molecular weight is simultaneously detected. This is considered a dimer of CTLD14. Furthermore, a very strong signal was observed by administration of a biotin feed. It was confirmed that biotinylation efficiency dramatically improves by BirA coexpression and biotin addition.

(Examination of Biotinylation Efficiency of sRAGE)

Figure 46:
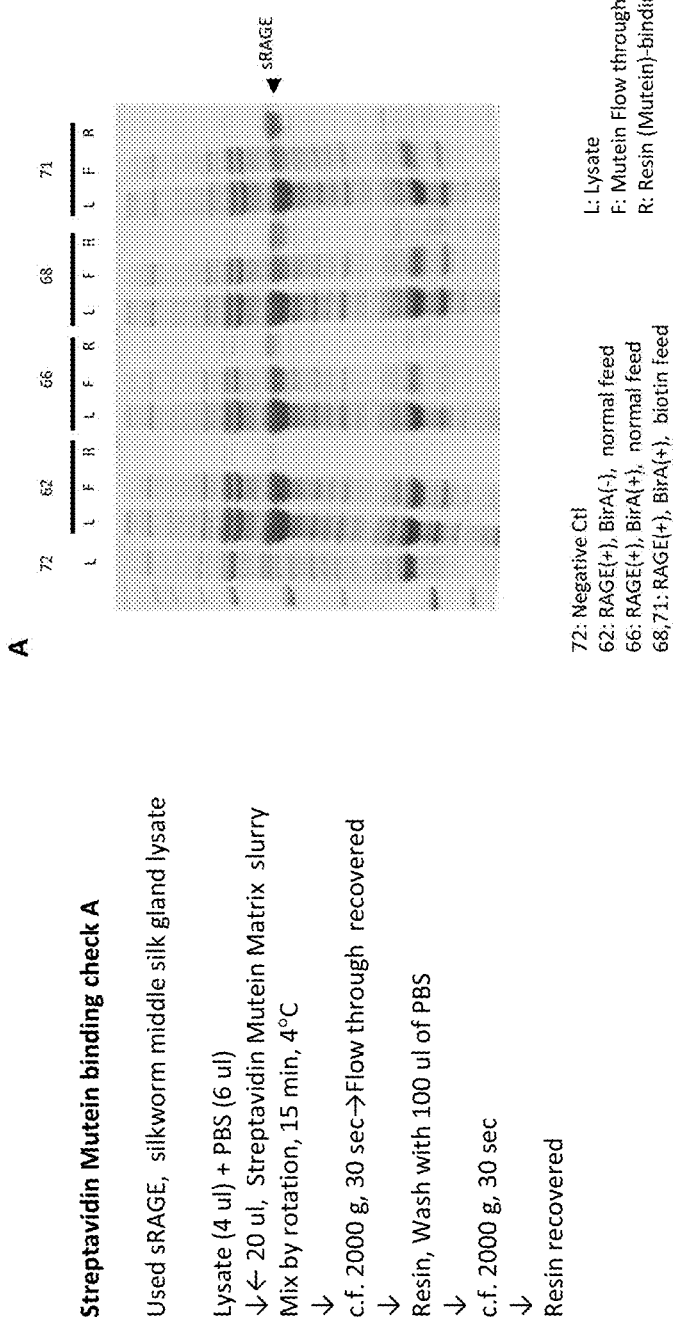
FIG. 46 shows a summary of an experiment for confirming biotinylation efficiency and results thereof. The L in the right diagram represents lysate before treatment, F represents a flow through fraction after treatment, and R represents a resin binding fraction. Sample No. 72 is a negative control introduced with only Serl-GAL4.

An extraction solution and a mutein matrix specifically binding to biotin were reacted, and Lysate prior to treatment (L), flow through fraction after treatment (F), and Resin binding fraction (R) were subjected to SDS-PAGE to estimate the biotinylation efficiency from the darkness of protein bands (arrow is position of sRAGE) by Coomassie staining (FIG. 46). Biotinylation efficiency of sRAGE is determined to be 60% (with no BirA coexpression, less than 1%). Biotinylation efficiency was calculated by the ratio of flow through fraction (F)/resin binding fraction (R).

(Examination of Biotinylation Efficiency of CTLD14)

Figure 47:
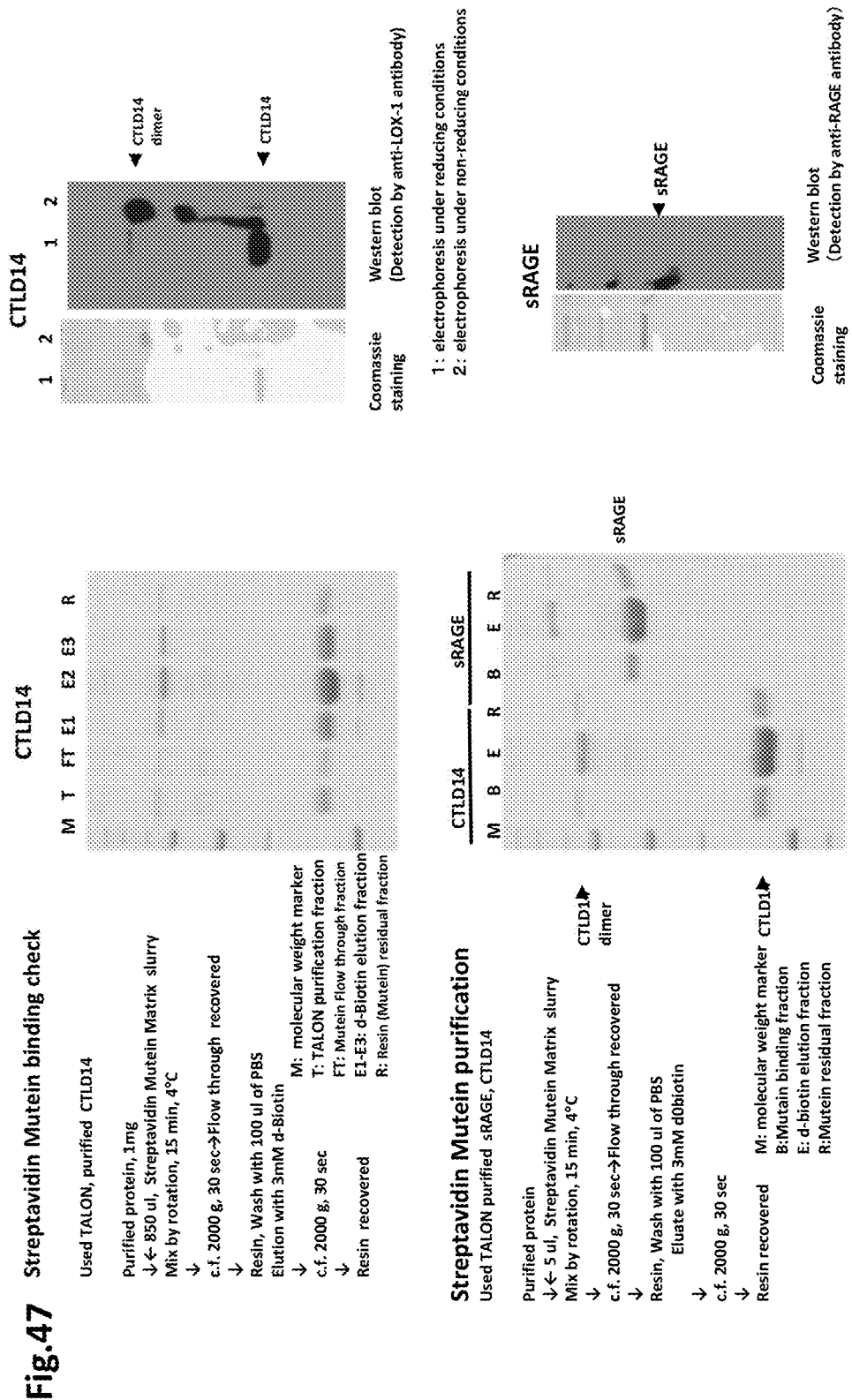
FIG. 47 shows a summary of yield and biotinylation efficiency of CTLD14 and sRAGE subjected to TALON and mutein column purification.

A lysate was purified by TALON (FIG. 47 left). Subsequently, CTLD14 purified by TALON was adsorbed to a mutein matrix and then eluted with 3 mM d-Biotin (sRAGE was similarly treated). The biotinylation efficiency was estimated as 30 to 40% from the ratio of flow through fraction (F) to Resin binding fraction (R) after MUTEIN treatment. Furthermore, it was revealed that 0.1 mg of biotinylated sRAGE and 0.04 mg of biotinylated CTLD14 is obtained per silkworm by TALON or MUTEIN column treatment. The right diagram is the result of Western blot on the resulting purified protein. The resulting protein was confirmed to be indeed CTLD14 or RAGE from chemiluminescence by ECL as a result of being deployed with SDS-PAGE, transcribed onto a PVDF film, and reacted with an anti-LOX-1 antibody (top right) or anti-RAGE antibody (bottom right), and then reacted with a secondary antibody HRP-labeled anti-rabbit IgG antibody. For CTLD14, a protein observed at the molecular weight of a dimer position stably detected in SDS-PAGE was confirmed to be a dimer of CTLD14, demonstrating that silkworm form CTLD14 is stably present as a dimer.

(Stability of Silkworm Form CTLD14)

*E. coli* form CTLD14 has characteristics that make metal colloid modification difficult, such as precipitation by desalination and precipitation by change in pH. Meanwhile, silkworm form CTLD14 did not precipitate and maintained the activity, even from a change to a salt-free phosphate buffer (PB) from PBS (−). Furthermore, silkworm form CTLD14 was also stable with Tris buffer, with which *E. coli* form tends to result in precipitation. Furthermore, the range of usable pH was wide at 7.4 to 9.2. *E. coli* form CTLD14 could not attain stable activity with Tris buffer (7.4 to 9.0). Thus, it was revealed that silkworm form CTLD14 is stable regardless of the presence/absence of salt, pH range, or buffer type (FIG. 48) and has a broad selection for utilization in detection/evaluation systems.

(Stability of Silkworm Form sRAGE)

As shown in FIG. 53, *E. coli* form sRAGE is fragmented in 1.5 months or less and loses the recognition ability, while silkworm form was stable after storage of nearly one year at 4° C.

Example 20: Detection of Oxidized LDL in Human Plasma by Silkworm Form CTLD14

This Example examined whether it is possible to detect a trace amount of oxidized LDL in human plasma by silkworm form CTLD14.

Detection was performed as follows with sandwich ELISA using CTLD14 and an anti-LDL chicken polyclonal antibody.

(1) 50 μg/ml/PBS of CTLD14 was added to a polystyrene 96-well microwell plate at 50 μl/well and allowed to adsorb overnight.

(2) The plate was washed three times with PBS (200 μl/well). Blocking buffer (0.25% BSA/PBS) was added at 250 μl/well. The mixture was left standing for 2 hours at room temperature.

(3) After the plate was washed three times with PBS (200 μl/well), a specimen was added at 100 μl/well and reacted for 2 hour at room temperature.

(4) The plate was washed five times with PBS (200 μl/well) and an anti-ApoB chicken polyclonal antibody diluted 6000-fold with blocking buffer or an anti-ApoB chicken monoclonal antibody diluted 8000-fold with blocking buffer was added at 100 μl/well and reacted for 1 hour at room temperature.

(5) The plate was washed five times with PBS (200 μl/well) and an anti-chicken IgY-HRP conjugate (Promega, G1351) diluted 2000-fold with blocking buffer was added at 100 μl/well and reacted for 1 hour at room temperature.

(6) The plate was washed five times with PBS (200 μl/well).

(7) TMB was added at 50 μl/well and the luminescence was examined. 50 p/well of 1N HCl was added to suspend the reaction.

(8) The absorbance at 450 nm was measured

In the detection, specimens (specimens 1 to 5) prepared from adding oxidized LDLs at the following concentrations to plasma derived from healthy individuals of Asian descent were used.

Specimen 1: no OxLDL added
Specimen 2: 1 ug/ml OxLDL
Specimen 3: 3 ug/ml OxLDL
Specimen 4: 6 ug/ml OxLDL
Specimen 5: 12 μg/ml OxLDL
Each were diluted 1/1000 with PBS (−)

Figure 49:
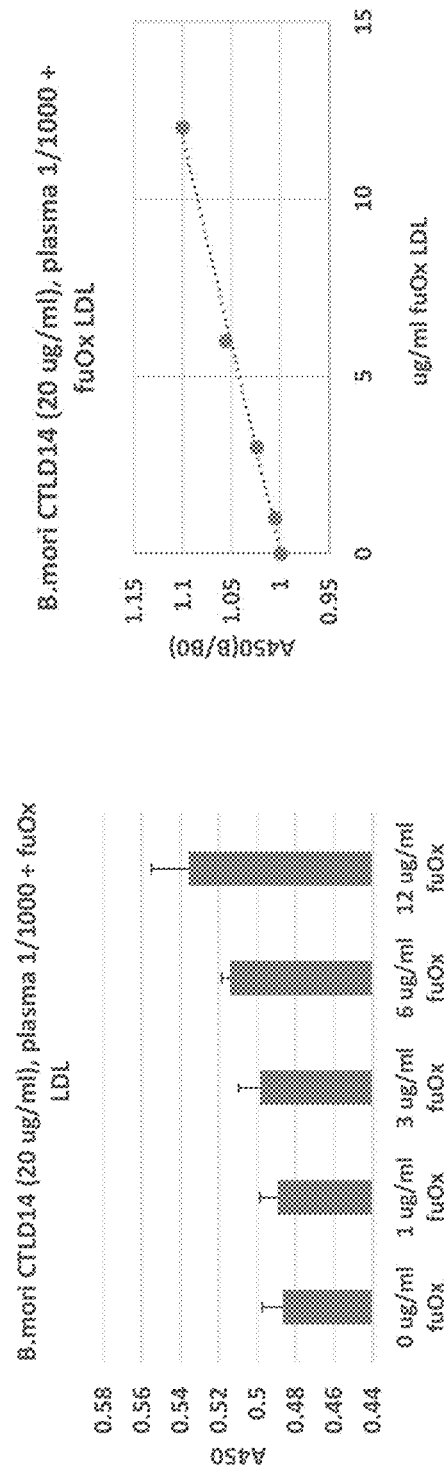
FIG. 49 shows results of detection of oxidized LDLs in human plasma diluted to 1/1000. The left graph shows, from the left, specimen 1 (OxLDL not added), specimen 2 (1 µg of OxLDL/ml added), specimen 3 (3 µg of OxLDL/ml added), specimen 4 (6 µg of OxLDL/ml added), and specimen 5 (12 µg of OxLDL/ml added). The right graph shows the relative absorbance while assuming specimen 1 (OxLDL not added) as 1.

FIG. 49 shows the results of detection. In view of the significant difference in specimens diluted 1000-fold and subjected to a detection system, it was revealed that a low concentration of oxidized LDLs can be detected with a detection limit of 1 ug/ml or 3 ug/ml in human plasma by sandwich ELISA utilizing silkworm form CTLD14. In human specimens, the oxidized LDL concentration is about 0.2% of LDLs (1.2 to 2.2 μg) with respect to excessive LDLs (600 to 1100 μg/ml) for healthy individuals. The ratio of oxidized LDLs increases with lipid abnormality, ischemic heart disease or the like. Since 1 to 3 ug/ml of oxidized LDL was able to be detected in human specimens with this approach, it was demonstrated that oxidized LDLs which are slightly elevated than those in healthy individuals can be detected or quantified.

Example 21: Oxidized LDL Detection System by Immunochromatography Based on Principle of Lateral Flow Assay Using Biotinylated CTLD14

Figure 50:
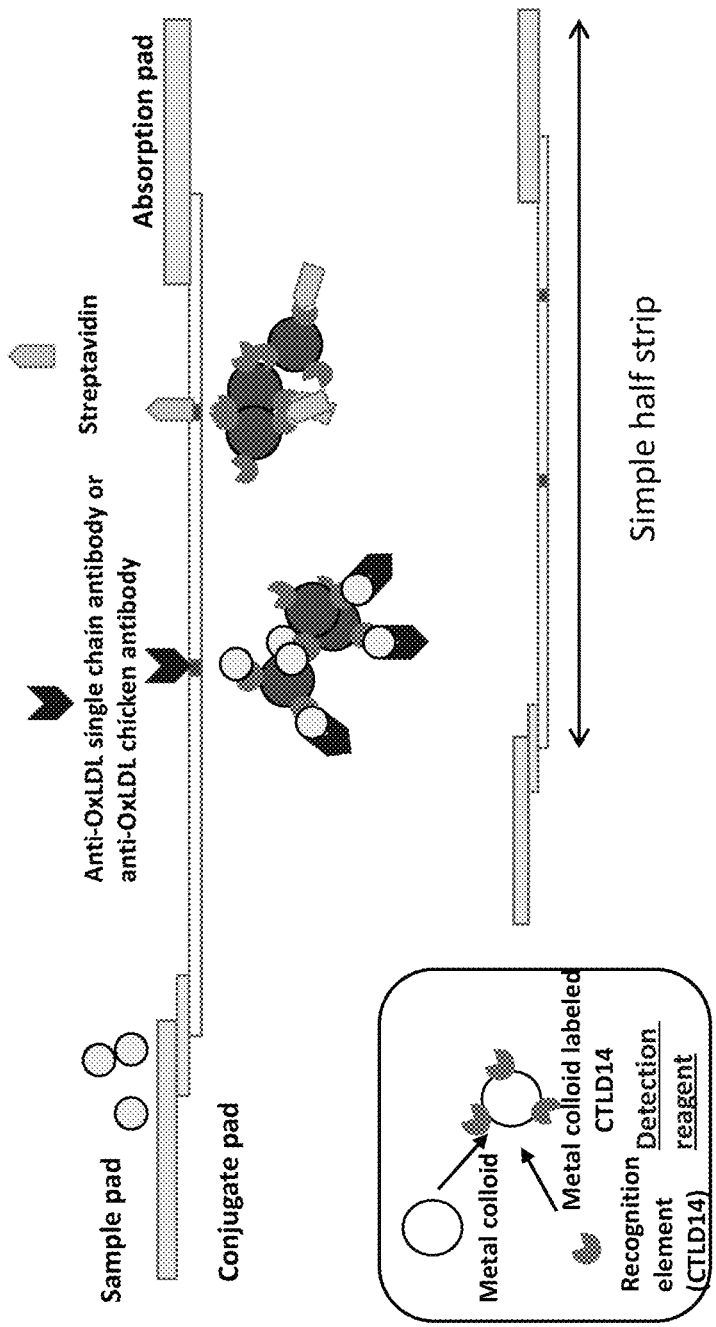
FIG. 50 shows a summary of an immonochromatographic detection system with a simple half strip using silkworm form biotinylated CTLD14.

This Example examined a detection system based on the principle of lateral flow assay using biotinylated CTLD14 (FIG. 50).

(Materials and Methods)

As a detect reagent, platinum colloid-labeled biotinylated CTLD14 was used. A half strip was made by applying a filter to one side of a nitrocellulose film. Furthermore, an anti-ApoB chicken monoclonal antibody or an anti-LDL chicken polyclonal antibody was applied to a test line, and streptavidin was applied to a control line. The strip was dried for 2 hours at 37° C. and stored at ambient temperature.

In addition to gold colloid that is commonly used as a metal colloid, platinum colloid and palladium colloid were also considered. As a result, platinum colloid-labeled CTLD14 was the best in terms of stability, detection sensitivity or the like of labeled CTLD14. Further, platinum colloid labeled CTLD14 was stable for several months at 4° C. Since platinum colloid aggregates and exhibits a black color, it was also detected in black in immunochromatography.

Figure 51:
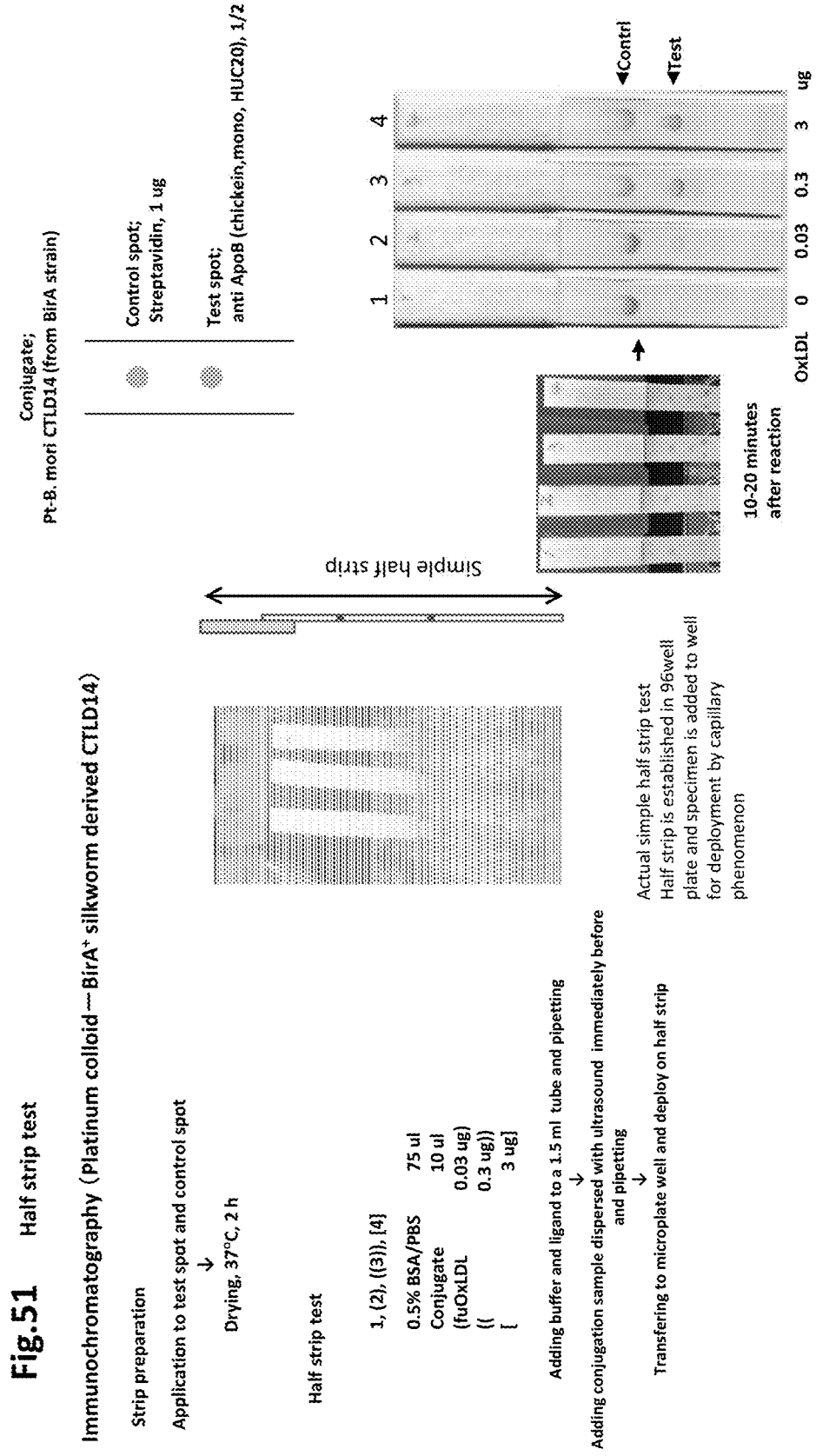
FIG. 51 shows results of immunochromatography using a simple half strip. Lane 1: 0 µg/well, lane 2: 0.03 µg/well, lane 3: 0.3 µg/well, and lane 4: 3 µg/well.

A 96-well plate was used. A specimen (oxidized LDL/PBS (−) platinum colloid-labeled biotinylated CTLD14 dispersed with ultrasound treatment was added and mixed immediately before) was placed in a well. A half strip was established and deployed by a capillary phenomenon (picture in the middle of FIG. 51). The reaction was ended in 10 to 20 minutes. Spots in the test line were visible even at oxidized LDL of 30 ng. This indicates that 30 ng/well of oxidized LDL can be detected in a short period of time of 20 minutes or less. Furthermore, the control line was shown to have a normal deployment. At the same time, the spot intensity of the test line increased depending on the specimen concentration, whereas the spot intensity of the control line decreased. Thus, it is expected that a certain degree of quantification or evaluation is possible with relative color of test line/relative color of control line.

Example 22: Identification of Sugar Chain Structure

This Example identified a sugar chain structure of silkworm form sRAGE.

After a sugar chain was cut out from silkworm form sRAGE and separated in an ODS column, estimated sugar composition of 6 types of sugar chains was determined by MALDI-TOF-MS. The peaks of each sugar chain whose sugar composition was estimated was separated with a normal phase Amido column to obtain sugar chains N1, N2, N3, N4-1, N4-2, and N4-3 (FIG. 54). A candidate sugar chain was narrowed down by GALAXY search from the molecular weight and Glucose unit (GU) value found by the ODS and Amide column. Finally, a specimen and a standard product of a sugar chain considered a candidate were con-injected and separated by an ODS column to confirm a match between the candidate sugar chain and specimen to identify a sugar chain.

FIG. 55 shows the composition ratio, quantitative value, and sugar composition of each identified sugar chain. It was found that oligomannose types of N1, N2, and N3 were present at composition ratios of 27.5%, 10.8%, and 51.4%, respectively. Thus, it was revealed that the oligomannose types account for 90% or greater.

Example 23: Analysis of Interaction with AGEs by Biotinylated sRAGE (Reaction Kinetics Analysis by Surface Plasmon Resonance Using Single Cycle Kinetics)

Figure 56:
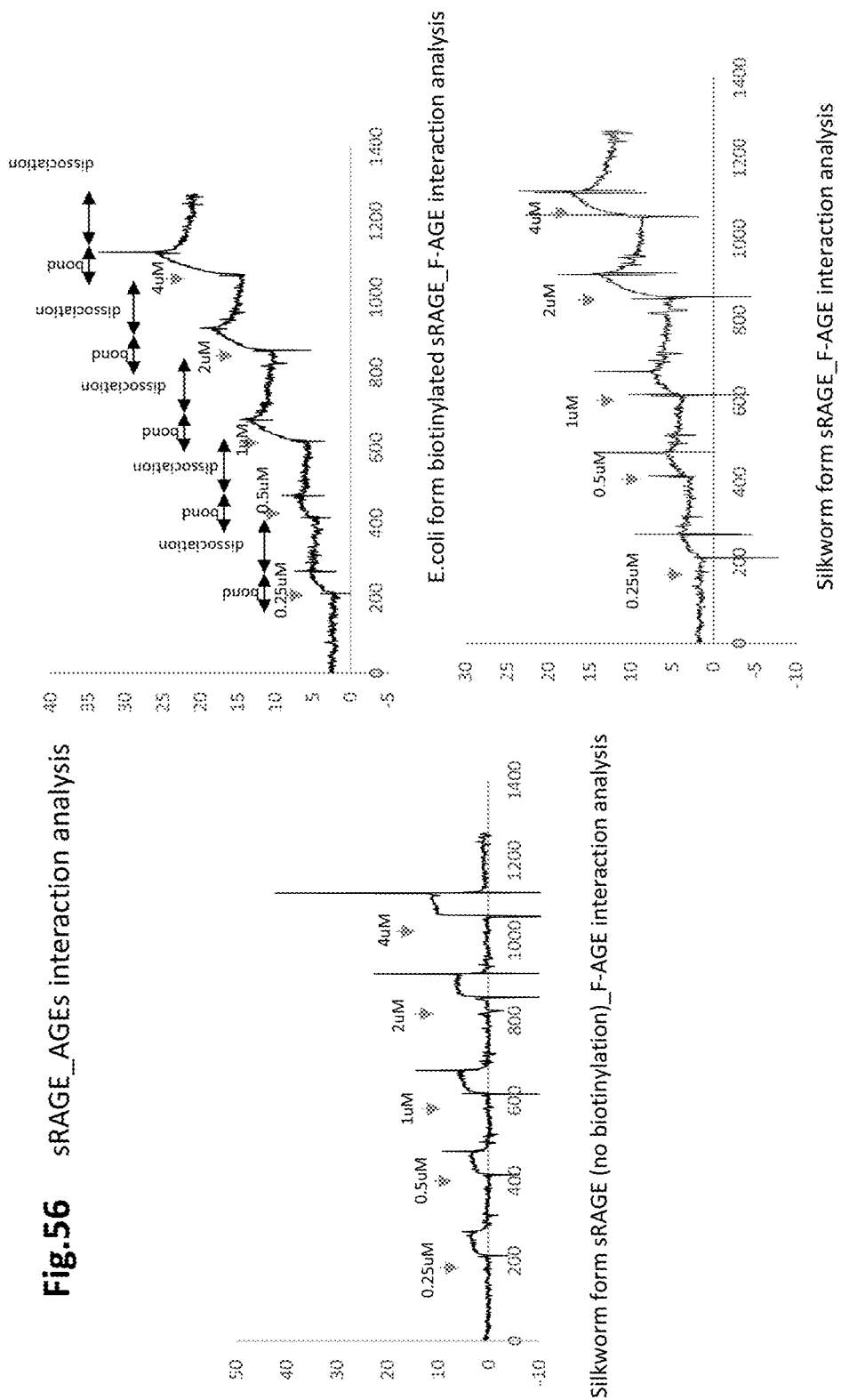
FIG. 56 shows results of measuring the interaction of AGEs with sRAGE without biotinylation or biotinylated sRAGE measured by surface plasmon resonance. The left diagram is a result of immobilizing silkworm form sRAGE without biotinylation to sensor chip CM5 by amine coupling and analyzing the interaction with typical AGEs, fructose treated BSA (F-AGE) by single cycle kinetics. The right diagram is a result of immobilizing biotinylated sRAGE with a single molecule of biotin added to the C-terminus side to sensor chip SA via the biotin and analyzing the interaction with typical AGEs, F-AGE, by single cycle kinetics. The top right diagram shows results of analyzing the interaction of *E.* *coli* form biotinylated sRAGE and F-AGE, and the bottom right diagram shows results of analyzing the interaction of silkworm form biotinylated sRAGE and AGEs. PBS (-) was used as the buffer, and the flow rate was 30 µl/min. 0.25, 0.5, 1, 2, and 4 µM of F-AGE were added at the arrows in the diagrams. Interaction was measured, with an addition time of 60 seconds and a dissociation time of 120 seconds. The interval between the times at which F-AGE of each concentration was added was 60 seconds. In each graph, the vertical axis indicates resonance units (RU), and the horizontal axis indicates time (second).

Without biotinylation, immobilization by amine coupling is common. Meanwhile, recognition ability is not maintained due to issues such as the possibility of Lys, which is important for recognition, being modified, possibility of losing activity in the process of immobilization, immobilization maintaining directionality being impossible or the like. Thus, a bond may be confirmed even when AGEs are added. The left diagram in FIG. 56 shows analysis of interaction between silkworm form sRAGE and AGEs (F-AGE) when immobilized on a CM5 chip by amine coupling. F-AGEs were added at a point indicated by the arrow, but the bond (vertical axis: increase in RU) was weak and the dissociation rate was high. It is unclear whether the original bonding ability is maintained. Interaction analysis was not possible. Meanwhile, when immobilized on a streptavidin chip via biotin of biotinylated sRAGE, the biotin is introduced at only one site on the C-terminus side. Thus, it is possible to immobilize while maintaining directionality. Further, immobilization can be performed while maintaining the activity of sRAGE by only adding an sRAGE solution under neutral conditions. As shown in the right diagram of FIG. 56, a bond-dissociation cycle was observed by adding AGEs (addition concentration is gradually raised as in 0.25 μg, 0.5 μg, 1 μg, 2 μg, and 4 μg). The kinetic analysis was performed with the resulting sensorgram using BIA evaluation software. As a result, it was binding rate constant: 7.25E+03, dissociation rate constant: 1.64E-03, and dissociation constant: 2.2e-7 for silkworm form sRAGE_F-AGE. Meanwhile for *E. coli* form, it was binding rate constant: 8.61E+03, dissociation rate constant: 2.41E-03, and dissociation constant: 2.8e-7 verb????. It was demonstrated that there is no significant difference in silkworm form and *E. coli* form in interaction with AGEs. Furthermore, the dissociation constant is close to the dissociation constant of RAGE_F-AGE in animal cells. It is demonstrated that the recognition ability of RAGE in cells is reproduced by silkworm form sRAGE.

Example 24: Production of Single Chain Antibody by Silkworm

This Example produced a single chain antibody γ+κ5 in a silkworm.

Figure 52:
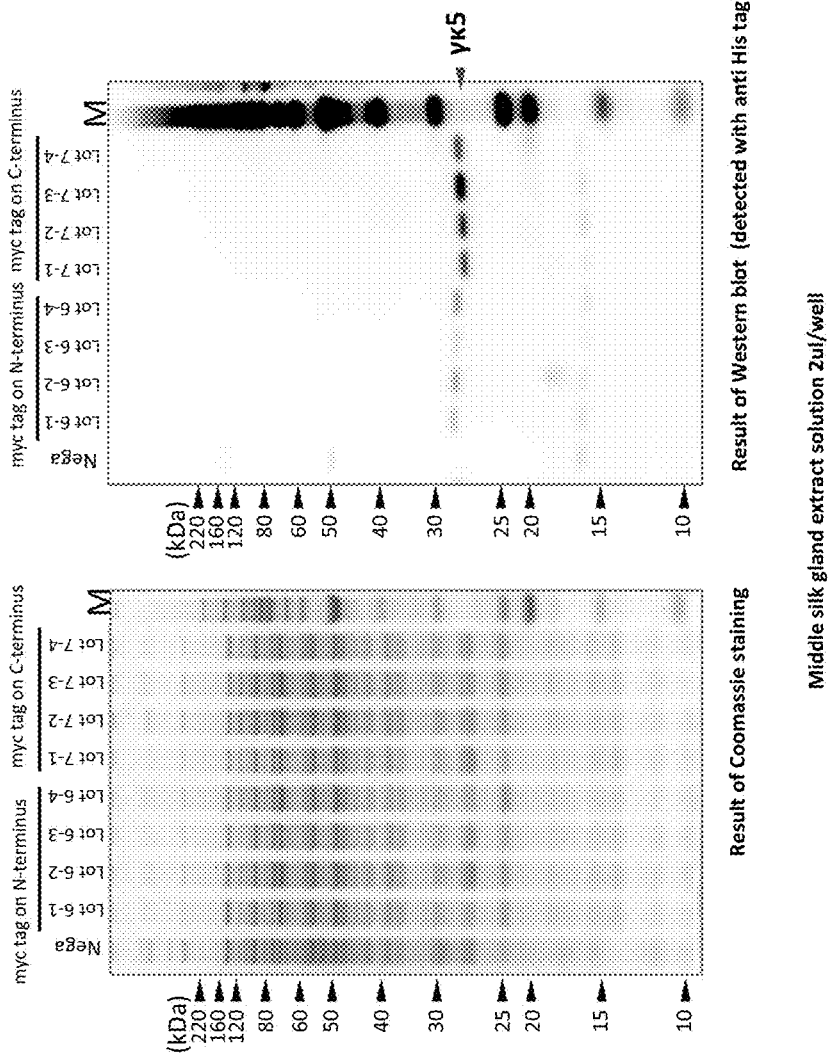
FIG. 52 shows results of having a single chain antibody γ+κ5 expressed in the middle silk gland of a genetically modified silkworm. Results are shown for middle silk grand extract prepared and subjected to SDS-PAGE for each of four clones of a line with an myc tag to add to the N-terminus and a line with that added to the C-terminus. The left diagram shows results of Coomassie staining and the right diagram shows results of detection with an anti-His antibody.

The results are shown in FIG. 52. A single chain antibody γ+κ5 was expressed in the middle silk gland of a genetically modified silkworm. A partial silk gland was extracted from each of four clones of a line with an added myc tag on the N-terminus and a line with that added to the C-terminus. An extract solution obtained by treating the gland with Triton X-100/PBS (−) was prepared and subjected to SDS-PAGE at 2 μl/lane. The left diagram of FIG. 52 shows results of Coomassie staining. The lane on the left end is the negative control not expressing γ+κ5. Meanwhile, a line expressing γ+κ5 at an amount that can be clearly confirmed with Coomassie staining could not be found. On the other hand, the right diagram is a result of detection with an anti-His antibody. Expression of γ+κ5 of interest was confirmed in all lines. It was shown that a line with an myc tag added to the C-terminus has more expression. Soluble γ+κ5 was obtained by purification utilizing an His tag and an myc tag. *E. coli* expressed γ+κ5 had issues such as the entire amount forming an inclusion body and requiring a process of complex refolding, and a purified product being prone to reaggregation. However, γ+κ5 can be produced as a soluble protein by a silkworm expression system.

As described above, the present invention is exemplified by the use of its preferred Embodiments. However, it is understood that the scope of the present invention should be interpreted solely based on the claims. It is also understood that any patent, any patent application, and any references cited herein should be incorporated by reference in the same manner as the contents are specifically described herein.

INDUSTRIAL APPLICABILITY

Fields such as the health industry (medical, pharmaceutical and the like) and food industry are presumed as the applicable filed. Evaluation of arteriosclerosis preventing effect of food, agricultural, forestry and fishery products and development of food expected to have a prophylactic effect are intended as the industrial applicability.

SEQUENCE LISTING FREE TEXT

SEQ ID NO: 1: sequencing primer M13forward used in plasmid pCR2.1-TOPO
SEQ ID NO: 2: sequencing primer M13reverse used in plasmid pCR2.1-TOPO
SEQ ID NO: 3: sequencing primer pCANTAB5-S1 used in plasmid pCANTAB-5E
SEQ ID NO: 4: sequencing primer pCANTAB5-S6 used in plasmid pCANTAB-5E
SEQ ID NO: 5: sequencing primer T7promoter used in plasmid pET-22b(+)
SEQ ID NO: 6: sequencing primer T7terminator used in plasmid pET-22b(+)
SEQ ID NO: 7: First-strand cDNA synthesis primer HIgG (gamma)
SEQ ID NO: 8: First-strand cDNA synthesis primer HIgM (mu)
SEQ ID NO: 9: First-strand cDNA synthesis primer Hkappa
SEQ ID NO: 10: First-strand cDNA synthesis primer Hlambda
SEQ ID NO: 11: reverse primer HVH1REV for amplifying γ chain and μ chain
SEQ ID NO: 12: reverse primer HVH2REV for amplifying γ chain and μ chain
SEQ ID NO: 13: reverse primer HVH3REV for amplifying γ chain and μ chain
SEQ ID NO: 14: reverse primer HVH4REV for amplifying γ chain and μ chain
SEQ ID NO: 15: reverse primer HVH5REV for amplifying γ chain and μ chain
SEQ ID NO: 16: reverse primer HVH6REV for amplifying γ chain and μ chain
SEQ ID NO: 17: forward primer HJH12FOR for amplifying γ chain and μ chain
SEQ ID NO: 18: forward primer HJH3 for amplifying γ chain and μ chain
SEQ ID NO: 19: forward primer HJH45FOR for amplifying γ chain and μ chain
SEQ ID NO: 20: forward primer HJH6FOR for amplifying γ chain and μ chain
SEQ ID NO: 21: reverse primer HV$_κ$1REV for amplifying κ chain SEQ ID NO: 22: reverse primer HV$_κ$2REV for amplifying κ chain
SEQ ID NO: 23: reverse primer HV$_κ$3REV for amplifying κ chain
SEQ ID NO: 24: reverse primer HV$_κ$4REV for amplifying κ chain
SEQ ID NO: 25: reverse primer HV$_κ$5REV for amplifying κ chain
SEQ ID NO: 26: reverse primer HV$_κ$6REV for amplifying κ chain
SEQ ID NO: 27: forward primer HJ$_κ$1FOR for amplifying κ chain
SEQ ID NO: 28: forward primer HJ$_κ$2FOR for amplifying κ chain
SEQ ID NO: 29: forward primer HJ$_κ$3FOR for amplifying κ chain
SEQ ID NO: 30: forward primer HJ$_κ$4FOR for amplifying κ chain
SEQ ID NO: 31: forward primer HJ$_κ$5FOR for amplifying κ chain
SEQ ID NO: 32: reverse primer HV$_λ$1REV for amplifying λ chain
SEQ ID NO: 33: reverse primer HV$_λ$2REV for amplifying λ chain
SEQ ID NO: 34: reverse primer HV$_λ$3aREV for amplifying λ chain
SEQ ID NO: 35: reverse primer HV$_λ$3bREV for amplifying λ chain
SEQ ID NO: 36: reverse primer HV$_λ$4REV for amplifying λ chain
SEQ ID NO: 37: reverse primer HV$_λ$5REV for amplifying λ chain
SEQ ID NO: 38: reverse primer HV$_λ$6REV for amplifying λ chain
SEQ ID NO: 39: forward primer HJ$_λ$1FOR for amplifying λ chain
SEQ ID NO: 40: forward primer HJ$_λ$2-3FOR for amplifying λ chain
SEQ ID NO: 41: forward primer HJ$_λ$4-5FOR for amplifying λ chain
SEQ ID NO: 42: forward primer HJH12FORLK for adding a linker sequence to γ chain and μ chain
SEQ ID NO: 43: forward primer HJH3 FORLK for adding a linker sequence to γ chain and μ chain
SEQ ID NO: 44: forward primer HJH45FORLK for adding a linker sequence to γ chain and μ chain
SEQ ID NO: 45: forward primer HJH6 FORLK for adding a linker sequence to γ chain and μ chain
SEQ ID NO: 46: reverse primer HV$_κ$1REVLK for adding a linker sequence to κ chain
SEQ ID NO: 47: reverse primer HV$_κ$2REVLK for adding a linker sequence to κ chain
SEQ ID NO: 48: reverse primer HV$_κ$3REVLK for adding a linker sequence to κ chain
SEQ ID NO: 49: reverse primer HV$_κ$4REVLK for adding a linker sequence to κ chain
SEQ ID NO: 50: reverse primer HVλ5REVLK for adding a linker sequence to κ chain
SEQ ID NO: 51: reverse primer HVλ6REVLK for adding a linker sequence to κ chain
SEQ ID NO: 52: reverse primer HV$_λ$1REVLK for adding a linker sequence to A chain
SEQ ID NO: 53: reverse primer HV$_λ$2REVLK for adding a linker sequence to A chain
SEQ ID NO: 54: reverse primer HV$_λ$3aREVLK for adding a linker sequence to A chain
SEQ ID NO: 55: reverse primer HV$_λ$3bREVLK for adding a linker sequence to A chain
SEQ ID NO: 56: reverse primer HV$_λ$4REVLK for adding a linker sequence to A chain
SEQ ID NO: 57: reverse primer HV$_λ$5REVLK for adding a linker sequence to A chain
SEQ ID NO: 58: reverse primer HV$_λ$6REVLK for adding a linker sequence to A chain
SEQ ID NO: 59: Human reverse SfiI primer HVH1REVSfiI for adding a restriction enzyme site
SEQ ID NO: 60: Human reverse SfiI primer HVH2REVSfiI for adding a restriction enzyme site
SEQ ID NO: 61: Human reverse SfiI primer HVH3REVSfiI for adding a restriction enzyme site
SEQ ID NO: 62: Human reverse SfiI primer HVH4REVSfiI for adding a restriction enzyme site
SEQ ID NO: 63: Human reverse SfiI primer HVH5REVSfiI for adding a restriction enzyme site
SEQ ID NO: 64: Human reverse SfiI primer HVH6REVSfiI for adding a restriction enzyme site
SEQ ID NO: 65: Human J$_κ$ forward NotI primer HJ$_κ$1FORNotI for adding a restriction enzyme site
SEQ ID NO: 66: Human J$_κ$ forward NotI primer HJ$_κ$2FORNotI for adding a restriction enzyme site
SEQ ID NO: 67: Human J$_κ$ forward NotI primer HJ$_κ$3FORNotI for adding a restriction enzyme site
SEQ ID NO: 68: Human J$_κ$ forward NotI primer HJ$_κ$4FORNotI for adding a restriction enzyme site
SEQ ID NO: 69: Human J$_κ$ forward NotI primer HJ$_κ$5FORNotI for adding a restriction enzyme site
SEQ ID NO: 70: Human J$_λ$ forward NotI primer HJ$_λ$1FORNotI for adding a restriction enzyme site
SEQ ID NO: 71: Human J$_λ$ forward NotI primer HJ$_λ$2-3FORNotI for adding a restriction enzyme site
SEQ ID NO: 72: Human J$_λ$ forward NotI primer HJ$_λ$4-5FORNotI for adding a restriction enzyme site
SEQ ID NO: 73: g+k a reverse primer
SEQ ID NO: 74: g+k b reverse primer
SEQ ID NO: 75: g+k a forward primer
SEQ ID NO: 76: amino acid sequence of single chain antibody γ+κ5
SEQ ID NO: 77: amino acid sequence of single chain antibody γ+κ12
SEQ ID NO: 78: amino acid sequence of single chain antibody γ+κ19
SEQ ID NO: 79: amino acid sequence of single chain antibody γ+κ40
SEQ ID NO: 80: amino acid sequence of single chain antibody γ+κ96
SEQ ID NO: 81: LOX-1 or nucleic acid sequence encoding LOX-1
SEQ ID NO: 82: LOX-1 or amino acid sequence of LOX-1
SEQ ID NO: 83: nucleic acid sequence encoding CTLD14
SEQ ID NO: 84: amino acid sequence encoding CTLD14
SEQ ID NO: 85: nucleic acid sequence encoding CTLD14 used in silkworm form
SEQ ID NO: 86: amino acid sequence encoding CTLD14 used in silkworm form
SEQ ID NO: 87: primer CTLD14-F: 5'-AATCTC-CAAGAAACACTGAAG-3'
SEQ ID NO: 88: primer CTLD14s-R: 5'-TCACTGTGCTCTTAGGTTTGC-3'
SEQ ID NO: 89: enterokinase recognition site (DDDDK)
SEQ ID NO: 90: partial sequence 1 of FIG. 29
SEQ ID NO: 91: partial sequence 2 of FIG. 29
SEQ ID NO: 92: partial sequence 3 of FIG. 29
SEQ ID NO: 93: partial sequence 4 of FIG. 29

SEQ ID NO: 94: partial sequence 5 of FIG. 29
SEQ ID NO: 95: partial sequence 6 of FIG. 29
SEQ ID NO: 96: nucleic acid sequence of sRAGE used in the present invention
SEQ ID NO: 97: amino acid sequence of sRAGE used in the present invention
SEQ ID NO: 98: biotinylated amino acid sequence "GLN-DIFEAQKIEWHE"
SEQ ID NO: 99: nucleic acid sequence of <Biotin-RAGE> (including fibroin H chain intron, signal peptide, BioEASE-tag&linker & FLAG and RAGE)
SEQ ID NO: 100: amino acid sequence of <Biotin-RAGE>
SEQ ID NO: 101: nucleic acid sequence of RAGE
SEQ ID NO: 102: amino acid sequence of RAGE
SEQ ID NO: 103: 1st partial sequence in the explanation in the bottom row of FIG. 41
SEQ ID NO: 104: 2nd partial sequence in the explanation in the bottom row of FIG. 41
SEQ ID NO: 105: 3rd partial sequence in the explanation in the bottom row of FIG. 41
SEQ ID NO: 106: nucleic acid sequence of biotin ligase (BirA)
SEQ ID NO: 107: amino acid sequence of biotin ligase (BirA)
SEQ ID NO: 108: amino acid sequence of γ+κ5 introduced with an Myc tag on N-terminus side
SEQ ID NO: 109: amino acid sequence of γ+κ5 introduced with an Myc tag on C-terminus side

The invention claimed is:

1. A silkworm, in which is coexpressably integrated into a genome of the silkworm a nucleic acid molecule encoding a target protein and a biotin ligase, wherein the biotin ligase ligates a biotin to the target protein when the biotin ligase and the target protein are expressed in the silkworm.

2. The silkworm of claim 1, wherein the biotin ligase is BirA.

3. The silkworm of claim 1, wherein the target protein is a C-type lectin-like domain (CTLD14) or a receptor for advanced glycation end products (sRAGE), or a variant thereof.

4. The silkworm of claim 3, wherein the CTLD14 is encoded by SEQ ID NO: 85, and the sRAGE is encoded by SEQ ID NO: 96.

5. The silkworm of claim 1 which comprises a tag sequence to be biotinylated.

6. The silkworm of claim 5, wherein the tag sequence to be biotinylated is one of GAGTPVTAPLAGTIWKVLASEGQTVAAGEVLLILEAMKMETEIRAAQAGTVRGIAVKA GDAVAVGDTLMTLA SEQ ID NO: 111 and GLNDIFEAQKIEWHE SEQ ID NO: 98.

* * * * *